(12) United States Patent
Shelton, IV et al.

(10) Patent No.: US 11,819,231 B2
(45) Date of Patent: Nov. 21, 2023

(54) ADAPTIVE CONTROL PROGRAMS FOR A SURGICAL SYSTEM COMPRISING MORE THAN ONE TYPE OF CARTRIDGE

(71) Applicant: Cilag GmbH International, Zug (CH)

(72) Inventors: Frederick E. Shelton, IV, Hillsboro, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 372 days.

(21) Appl. No.: 16/112,119

(22) Filed: Aug. 24, 2018

(65) Prior Publication Data
US 2019/0125338 A1    May 2, 2019

Related U.S. Application Data

(60) Provisional application No. 62/665,192, filed on May 1, 2018, provisional application No. 62/665,128, filed (Continued)

(51) Int. Cl.
*A61B 17/29* (2006.01)
*A61B 17/04* (2006.01)
(Continued)

(52) U.S. Cl.
CPC .......... *A61B 17/2909* (2013.01); *A61B 17/00* (2013.01); *A61B 17/105* (2013.01);
(Continued)

(58) Field of Classification Search
CPC .............. A61B 17/046; A61B 17/0491; A61B 17/06114; A61B 17/062; A61B 17/0625; A61B 17/2909
See application file for complete search history.

(56) References Cited

U.S. PATENT DOCUMENTS 1,853,416 A    4/1932  Hall
2,222,125 A   11/1940  Stehlik
(Continued)

FOREIGN PATENT DOCUMENTS

AU    2015201140 A1    3/2015
CA       2795323 A1    5/2014
(Continued)

OTHER PUBLICATIONS

US 10,504,709-B2, 8/23/2018, Karancsi et al. (withdrawn)
(Continued)

*Primary Examiner* — Martin T Ton

(57) ABSTRACT

A surgical suturing system is disclosed. The surgical suturing system comprises a shaft, a firing drive comprising a motor, and an end effector extending distally from the shaft. The end effector comprises a needle driver configured to be actuated by the motor, wherein the needle driver is configured to drive a needle installed within the end effector. The end effector further comprises a needle track configured to guide the needle installed within the end effector through a needle firing stroke, wherein the end effector is configured to accommodate suturing needles having different sizes. The surgical suturing system further comprises a control circuit configured to sense the size of the suturing needle installed within the end effector and adjust the actuation stroke of the motor to accommodate the size of the needle installed within the end effector.

18 Claims, 79 Drawing Sheets

Related U.S. Application Data on May 1, 2018, provisional application No. 62/665,129, filed on May 1, 2018, provisional application No. 62/665,177, filed on May 1, 2018, provisional application No. 62/665,139, filed on May 1, 2018, provisional application No. 62/665,134, filed on May 1, 2018, provisional application No. 62/578,855, filed on Oct. 30, 2017, provisional application No. 62/578,844, filed on Oct. 30, 2017, provisional application No. 62/578,817, filed on Oct. 30, 2017, provisional application No. 62/578,835, filed on Oct. 30, 2017, provisional application No. 62/578,804, filed on Oct. 30, 2017, provisional application No. 62/578,793, filed on Oct. 30, 2017.

(51) Int. Cl.

| | |
|---|---|
| *A61B 17/06* | (2006.01) |
| *A61B 17/00* | (2006.01) |
| *A61B 17/128* | (2006.01) |
| *A61B 17/28* | (2006.01) |
| *A61B 17/10* | (2006.01) |
| A61B 18/14 | (2006.01) |
| B33Y 80/00 | (2015.01) |
| A61B 90/00 | (2016.01) |
| A61B 17/32 | (2006.01) |
| A61B 18/00 | (2006.01) |
| A61B 18/12 | (2006.01) |
| F16D 27/00 | (2006.01) |
| F16D 27/108 | (2006.01) |
| F16D 27/12 | (2006.01) |
| G09G 3/34 | (2006.01) |
| G09G 3/36 | (2006.01) |
| G09G 3/38 | (2006.01) |
| A61B 34/30 | (2016.01) |
| A61B 17/3201 | (2006.01) |
| A61B 90/98 | (2016.01) |
| A61B 17/062 | (2006.01) |
| A61B 17/068 | (2006.01) |
| A61B 17/285 | (2006.01) |
| A61B 17/295 | (2006.01) |
| A61B 17/34 | (2006.01) |
| G06F 3/147 | (2006.01) |
| A61B 34/00 | (2016.01) |

(52) U.S. Cl.
CPC ........ *A61B 17/1285* (2013.01); *A61B 17/282* (2013.01); *A61B 17/2841* (2013.01); *A61B 17/29* (2013.01); A61B 17/0469 (2013.01); A61B 17/0482 (2013.01); A61B 17/0483 (2013.01); A61B 17/0491 (2013.01); A61B 17/062 (2013.01); A61B 17/06004 (2013.01); A61B 17/068 (2013.01); A61B 17/0625 (2013.01); A61B 17/06066 (2013.01); A61B 17/06114 (2013.01); A61B 17/06133 (2013.01); A61B 17/128 (2013.01); A61B 17/285 (2013.01); A61B 17/2833 (2013.01); A61B 17/295 (2013.01); A61B 17/3201 (2013.01); A61B 17/3421 (2013.01); A61B 17/3468 (2013.01); A61B 18/1206 (2013.01); A61B 18/1445 (2013.01); A61B 34/30 (2016.02); A61B 34/76 (2016.02); A61B 90/03 (2016.02); A61B 90/98 (2016.02); A61B 2017/0003 (2013.01); A61B 2017/00017 (2013.01); A61B 2017/00026 (2013.01); A61B 2017/00039 (2013.01); A61B 2017/0046 (2013.01); A61B 2017/00057 (2013.01); A61B 2017/00061 (2013.01); A61B 2017/00075 (2013.01); A61B 2017/00115 (2013.01); A61B 2017/00119 (2013.01); A61B 2017/00128 (2013.01); A61B 2017/00212 (2013.01); A61B 2017/00221 (2013.01); A61B 2017/00327 (2013.01); A61B 2017/00367 (2013.01); A61B 2017/00393 (2013.01); A61B 2017/00398 (2013.01); A61B 2017/00407 (2013.01); A61B 2017/00424 (2013.01); A61B 2017/00438 (2013.01); A61B 2017/00464 (2013.01); A61B 2017/00473 (2013.01); A61B 2017/00477 (2013.01); A61B 2017/00526 (2013.01); A61B 2017/00734 (2013.01); A61B 2017/06052 (2013.01); A61B 2017/06076 (2013.01); A61B 2017/2825 (2013.01); A61B 2017/2845 (2013.01); A61B 2017/2902 (2013.01); A61B 2017/2903 (2013.01); A61B 2017/2911 (2013.01); A61B 2017/2923 (2013.01); A61B 2017/2925 (2013.01); A61B 2017/2926 (2013.01); A61B 2017/2927 (2013.01); A61B 2017/2929 (2013.01); A61B 2017/2931 (2013.01); A61B 2017/2943 (2013.01); A61B 2017/2945 (2013.01); A61B 2017/320044 (2013.01); A61B 2018/0063 (2013.01); A61B 2018/0072 (2013.01); A61B 2018/00077 (2013.01); A61B 2018/00083 (2013.01); A61B 2018/00136 (2013.01); A61B 2018/00178 (2013.01); A61B 2018/00208 (2013.01); A61B 2018/00404 (2013.01); A61B 2018/00577 (2013.01); A61B 2018/00595 (2013.01); A61B 2018/00601 (2013.01); A61B 2018/00642 (2013.01); A61B 2018/00672 (2013.01); A61B 2018/00678 (2013.01); A61B 2018/00696 (2013.01); A61B 2018/00702 (2013.01); A61B 2018/00708 (2013.01); A61B 2018/00767 (2013.01); A61B 2018/00827 (2013.01); A61B 2018/00875 (2013.01); A61B 2018/00892 (2013.01); A61B 2018/126 (2013.01); A61B 2018/1253 (2013.01); A61B 2018/1266 (2013.01); A61B 2018/146 (2013.01); A61B 2018/1452 (2013.01); A61B 2018/1457 (2013.01); A61B 2090/035 (2016.02); A61B 2090/0811 (2016.02); B33Y 80/00 (2014.12); F16D 27/004 (2013.01); F16D 27/108 (2013.01); F16D 27/12 (2013.01); G06F 3/147 (2013.01); G09G 3/344 (2013.01); G09G 3/3648 (2013.01); G09G 3/38 (2013.01); G09G 2380/08 (2013.01)

(56) References Cited

U.S. PATENT DOCUMENTS

| | | |
|---|---|---|
| 3,082,426 A | 3/1963 | Miles |
| 3,503,396 A | 3/1970 | Pierie et al. |
| 3,584,628 A | 6/1971 | Green |
| 3,626,457 A | 12/1971 | Duerr et al. |
| 3,633,584 A | 1/1972 | Farrell |
| 3,759,017 A | 9/1973 | Young |
| 3,863,118 A | 1/1975 | Lander et al. |
| 3,898,545 A | 8/1975 | Coppa et al. |
| 3,912,121 A | 10/1975 | Steffen |
| 3,915,271 A | 10/1975 | Harper |
| 3,932,812 A | 1/1976 | Milligan |
| 4,041,362 A | 8/1977 | Ichiyanagi |
| 4,052,649 A | 10/1977 | Greenwell et al. |
| 4,087,730 A | 5/1978 | Goles |
| 4,157,859 A | 6/1979 | Terry |
| 4,171,700 A | 10/1979 | Farin |

(56) References Cited

U.S. PATENT DOCUMENTS

| | | |
|---|---|---|
| 4,202,722 A | 5/1980 | Paquin |
| 4,412,539 A | 11/1983 | Jarvik |
| 4,448,193 A | 5/1984 | Ivanov |
| 4,523,695 A | 6/1985 | Braun et al. |
| 4,608,160 A | 8/1986 | Zoch |
| 4,614,366 A | 9/1986 | North et al. |
| 4,633,874 A | 1/1987 | Chow et al. |
| 4,701,193 A | 10/1987 | Robertson et al. |
| 4,735,603 A | 4/1988 | Goodson et al. |
| 4,788,977 A | 12/1988 | Farin et al. |
| 4,827,911 A | 5/1989 | Broadwin et al. |
| 4,849,752 A | 7/1989 | Bryant |
| D303,787 S | 10/1989 | Messenger et al. |
| 4,892,244 A | 1/1990 | Fox et al. |
| 4,962,681 A | 10/1990 | Yang |
| 4,976,173 A | 12/1990 | Yang |
| 5,010,341 A | 4/1991 | Huntley et al. |
| 5,026,387 A | 6/1991 | Thomas |
| 5,035,692 A | 7/1991 | Lyon et al. |
| 5,042,460 A | 8/1991 | Sakurai et al. |
| 5,047,043 A | 9/1991 | Kubota et al. |
| 5,084,057 A | 1/1992 | Green et al. |
| 5,100,402 A | 3/1992 | Fan |
| D327,061 S | 6/1992 | Soren et al. |
| 5,129,570 A | 7/1992 | Schulze et al. |
| 5,151,102 A | 9/1992 | Kamiyama et al. |
| 5,156,315 A | 10/1992 | Green et al. |
| 5,158,585 A | 10/1992 | Saho et al. |
| 5,160,334 A | 11/1992 | Billings et al. |
| 5,171,247 A | 12/1992 | Hughett et al. |
| 5,189,277 A | 2/1993 | Boisvert et al. |
| 5,197,962 A | 3/1993 | Sansom et al. |
| 5,204,669 A | 4/1993 | Dorfe et al. |
| 5,217,003 A | 6/1993 | Wilk |
| 5,242,474 A | 9/1993 | Herbst et al. |
| 5,253,793 A | 10/1993 | Green et al. |
| 5,271,543 A | 12/1993 | Grant et al. |
| RE34,519 E | 1/1994 | Fox et al. |
| 5,275,323 A | 1/1994 | Schulze et al. |
| 5,318,516 A | 6/1994 | Cosmescu |
| 5,318,563 A | 6/1994 | Malis et al. |
| 5,322,055 A | 6/1994 | Davison et al. |
| 5,342,349 A | 8/1994 | Kaufman |
| 5,364,003 A | 11/1994 | Williamson, IV |
| 5,383,880 A | 1/1995 | Hooven |
| 5,385,544 A | 1/1995 | Edwards et al. |
| 5,391,144 A | 2/1995 | Sakurai et al. |
| 5,396,900 A | 3/1995 | Slater et al. |
| 5,397,046 A | 3/1995 | Savage et al. |
| 5,403,312 A | 4/1995 | Yates et al. |
| 5,403,327 A | 4/1995 | Thornton et al. |
| 5,413,267 A | 5/1995 | Solyntjes et al. |
| 5,415,335 A | 5/1995 | Knodell, Jr. |
| 5,417,699 A | 5/1995 | Klein et al. |
| 5,439,468 A | 8/1995 | Schulze et al. |
| 5,445,304 A | 8/1995 | Plyley et al. |
| 5,462,545 A | 10/1995 | Wang et al. |
| 5,465,895 A | 11/1995 | Knodel et al. |
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,496,317 A | 3/1996 | Goble et al. |
| 5,503,320 A | 4/1996 | Webster et al. |
| 5,507,773 A | 4/1996 | Huitema et al. |
| 5,529,235 A | 6/1996 | Boiarski et al. |
| 5,531,743 A | 7/1996 | Nettekoven et al. |
| 5,545,148 A | 8/1996 | Wurster |
| 5,552,685 A | 9/1996 | Young et al. |
| 5,560,372 A | 10/1996 | Cory |
| 5,584,425 A | 12/1996 | Savage et al. |
| 5,610,379 A | 3/1997 | Muz et al. |
| 5,610,811 A | 3/1997 | Honda |
| 5,613,966 A | 3/1997 | Makower et al. |
| 5,624,452 A | 4/1997 | Yates |
| D379,346 S | 5/1997 | Mieki |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,042 A | 12/1997 | Boiarski et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,720,287 A | 2/1998 | Chapelon et al. |
| 5,724,468 A | 3/1998 | Leone et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,458 A | 6/1998 | Wang et al. |
| 5,766,186 A | 6/1998 | Faraz et al. |
| 5,769,791 A | 6/1998 | Benaron et al. |
| 5,775,331 A | 7/1998 | Raymond et al. |
| 5,796,188 A | 8/1998 | Bays |
| 5,797,537 A | 8/1998 | Oberlin et al. |
| 5,800,350 A | 9/1998 | Coppleson et al. |
| 5,807,393 A | 9/1998 | Williamson, IV et al. |
| D399,561 S | 10/1998 | Ellingson |
| 5,817,093 A | 10/1998 | Williamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,869 A | 11/1998 | Kudo et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,004,269 A | 12/1999 | Crowley et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,102,907 A | 8/2000 | Smethers et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,139,561 A | 10/2000 | Shibata et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,283,960 B1 | 9/2001 | Ashley |
| 6,301,495 B1 | 10/2001 | Gueziec et al. |
| 6,302,881 B1 | 10/2001 | Farin |
| 6,308,089 B1 | 10/2001 | von der Ruhr et al. |

(56) References Cited

U.S. PATENT DOCUMENTS

| | | |
|---|---|---|
| 6,325,808 B1 | 12/2001 | Bernard et al. |
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 | 5/2002 | Bodden et al. |
| 6,423,057 B1 | 7/2002 | He et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,482,217 B1 | 11/2002 | Pintor et al. |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,628,989 B1 | 9/2003 | Penner et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,695,199 B2 | 2/2004 | Whitman |
| 6,699,187 B2 | 3/2004 | Webb et al. |
| 6,731,514 B2 | 5/2004 | Evans |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,652 B1 | 9/2004 | Whitman et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,071 B2 | 2/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,094,231 B1 | 8/2006 | Ellman et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,408,439 B2 | 8/2008 | Wang et al. |
| 7,413,541 B2 | 8/2008 | Konishi |
| 7,422,136 B1 | 9/2008 | Marczyk |
| 7,422,139 B2 | 9/2008 | Shelton, IV et al. |
| 7,422,586 B2 | 9/2008 | Morris et al. |
| 7,423,972 B2 | 9/2008 | Shaham et al. |
| D579,876 S | 11/2008 | Novotney et al. |
| 7,445,620 B2 | 11/2008 | Kefer |
| 7,457,804 B2 | 11/2008 | Uber, III et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,554,343 B2 | 6/2009 | Bromfield |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,637,907 B2 | 12/2009 | Blaha |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,772 B2 | 4/2010 | Pauker et al. |
| 7,699,860 B2 | 4/2010 | Huitema et al. |
| 7,717,312 B2 | 5/2010 | Beetel |
| 7,720,306 B2 | 5/2010 | Gardiner et al. |
| 7,721,934 B2 | 5/2010 | Shelton, IV et al. |

(56) References Cited

U.S. PATENT DOCUMENTS

| | | |
|---|---|---|
| 7,721,936 B2 | 5/2010 | Shalton, IV et al. |
| 7,722,603 B2 | 5/2010 | McPherson |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| D631,252 S | 1/2011 | Leslie |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,922,063 B2 | 4/2011 | Zemlok et al. |
| 7,927,014 B2 | 4/2011 | Dehler |
| 7,932,826 B2 | 4/2011 | Fritchie et al. |
| 7,942,300 B2 | 5/2011 | Rethy et al. |
| 7,945,065 B2 | 5/2011 | Menzl et al. |
| 7,945,342 B2 | 5/2011 | Tsai et al. |
| 7,950,560 B2 | 5/2011 | Zemlok et al. |
| 7,951,148 B2 | 5/2011 | McClurken |
| 7,954,682 B2 | 6/2011 | Giordano et al. |
| 7,954,687 B2 | 6/2011 | Zemlok et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,993,354 B1 | 8/2011 | Brecher et al. |
| 7,993,954 B2 | 8/2011 | Wieting |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,019,094 B2 | 9/2011 | Hsieh et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,075,571 B2 | 12/2011 | Vitali et al. |
| 8,095,327 B2 | 1/2012 | Tahara et al. |
| 8,096,459 B2 | 1/2012 | Ortiz et al. |
| 8,116,848 B2 | 2/2012 | Shahidi |
| 8,118,206 B2 | 2/2012 | Zand et al. |
| 8,120,301 B2 | 2/2012 | Goldberg et al. |
| 8,123,764 B2 | 2/2012 | Meade et al. |
| D655,678 S | 3/2012 | Kobayashi et al. |
| 8,128,625 B2 | 3/2012 | Odom |
| 8,131,565 B2 | 3/2012 | Dicks et al. |
| 8,136,712 B2 | 3/2012 | Zingman |
| 8,146,149 B2 | 3/2012 | Steinkogler et al. |
| D657,368 S | 4/2012 | Magee et al. |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,211,100 B2 | 7/2012 | Podhajsky et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,239,066 B2 | 8/2012 | Jennings et al. |
| 8,241,322 B2 | 8/2012 | Whitman et al. |
| 8,255,045 B2 | 8/2012 | Gharib et al. |
| D667,838 S | 9/2012 | Magee et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,639 B2 | 10/2012 | Achammer et al. |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,328,065 B2 | 12/2012 | Shah |
| 8,335,590 B2 | 12/2012 | Costa et al. |
| D675,164 S | 1/2013 | Kobayashi et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| D676,392 S | 2/2013 | Gassauer |
| 8,365,975 B1 | 2/2013 | Manoux et al. |
| D678,196 S | 3/2013 | Miyauchi et al. |
| D678,304 S | 3/2013 | Yakoub et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,429,153 B2 | 4/2013 | Birdwell et al. |
| 8,439,910 B2 | 5/2013 | Greep et al. |
| 8,444,663 B2 | 5/2013 | Houser et al. |

(56) References Cited

U.S. PATENT DOCUMENTS

| | | |
|---|---|---|
| 8,452,615 B2 | 5/2013 | Abri |
| 8,453,906 B2 | 6/2013 | Huang et al. |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,473,066 B2 | 6/2013 | Aghassian et al. |
| D687,146 S | 7/2013 | Juzkiw et al. |
| 8,476,227 B2 | 7/2013 | Kaplan et al. |
| 8,478,418 B2 | 7/2013 | Fahey |
| 8,489,235 B2 | 7/2013 | Moll et al. |
| 8,499,992 B2 | 8/2013 | Whitman et al. |
| 8,500,728 B2 | 8/2013 | Newton et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,517,239 B2 | 8/2013 | Scheib et al. |
| 8,521,331 B2 | 8/2013 | Itkowitz |
| 8,523,043 B2 | 9/2013 | Ullrich et al. |
| 8,533,475 B2 | 9/2013 | Frikart et al. |
| 8,540,709 B2 | 9/2013 | Allen |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,567,393 B2 | 10/2013 | Hickle et al. |
| 8,568,411 B2 | 10/2013 | Falkenstein et al. |
| 8,571,598 B2 | 10/2013 | Valavi |
| 8,573,459 B2 | 11/2013 | Smith et al. |
| 8,573,465 B2 | 11/2013 | Shelton, IV |
| 8,574,229 B2 | 11/2013 | Eder et al. |
| 8,585,631 B2 | 11/2013 | Dacquay |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,617,155 B2 | 12/2013 | Johnson et al. |
| 8,620,055 B2 | 12/2013 | Barratt et al. |
| 8,620,473 B2 | 12/2013 | Diolaiti et al. |
| 8,622,275 B2 | 1/2014 | Baxter, III et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,663,222 B2 | 3/2014 | Anderson et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| 8,708,213 B2 | 4/2014 | Shelton, IV et al. |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,795,001 B1 | 8/2014 | Lam et al. |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,819,581 B2 | 8/2014 | Nakamura et al. |
| 8,820,603 B2 | 9/2014 | Shelton, IV et al. |
| 8,820,607 B2 | 9/2014 | Marczyk |
| 8,820,608 B2 | 9/2014 | Miyamoto |
| 8,827,134 B2 | 9/2014 | Viola et al. |
| 8,827,136 B2 | 9/2014 | Hessler |
| 8,840,003 B2 | 9/2014 | Morgan et al. |
| D716,333 S | 10/2014 | Chotin et al. |
| 8,851,354 B2 | 10/2014 | Swensgard et al. |
| 8,852,174 B2 | 10/2014 | Burbank |
| 8,864,747 B2 | 10/2014 | Merchant et al. |
| 8,875,973 B2 | 11/2014 | Whitman |
| 8,876,857 B2 | 11/2014 | Burbank |
| 8,882,662 B2 | 11/2014 | Charles |
| 8,885,032 B2 | 11/2014 | Igarashi et al. |
| 8,886,790 B2 | 11/2014 | Harrang et al. |
| 8,893,946 B2 | 11/2014 | Boudreaux et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,917,513 B1 | 12/2014 | Hazzard |
| 8,918,207 B2 | 12/2014 | Prisco |
| 8,920,186 B2 | 12/2014 | Shishikura |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,934,684 B2 | 1/2015 | Mohamed |
| 8,936,614 B2 | 1/2015 | Allen, IV |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,296 B2 | 3/2015 | McPherson |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,288 B2 | 3/2015 | Konishi |
| 8,986,302 B2 | 3/2015 | Aldridge et al. |

(56) References Cited

U.S. PATENT DOCUMENTS

| | | |
|---|---|---|
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,608 B2 | 4/2015 | Casasanta, Jr. et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| D729,267 S | 5/2015 | Yoo et al. |
| 9,023,032 B2 | 5/2015 | Robinson |
| 9,023,071 B2 | 5/2015 | Miller et al. |
| 9,023,079 B2 | 5/2015 | Boulnois et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,055,870 B2 | 6/2015 | Meador et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,131,957 B2 | 9/2015 | Skarbnik et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,141,758 B2 | 9/2015 | Kress et al. |
| 9,149,322 B2 | 10/2015 | Knowlton |
| 9,155,503 B2 | 10/2015 | Cadwell |
| 9,160,853 B1 | 10/2015 | Daddi et al. |
| 9,161,803 B2 | 10/2015 | Yates et al. |
| 9,168,054 B2 | 10/2015 | Turner et al. |
| 9,168,091 B2 | 10/2015 | Janssen et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,198,711 B2 | 12/2015 | Joseph |
| 9,198,835 B2 | 12/2015 | Swisher et al. |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,211,120 B2 | 12/2015 | Scheib et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,259,282 B2 | 2/2016 | Azizian et al. |
| 9,265,429 B2 | 2/2016 | St. Pierre et al. |
| 9,265,585 B2 | 2/2016 | Wingardner et al. |
| 9,265,959 B2 | 2/2016 | Drew et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,974 B2 | 3/2016 | Shelton, IV |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,299,138 B2 | 3/2016 | Zellner et al. |
| 9,301,691 B2 | 4/2016 | Hufnagel et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,544 B2 | 5/2016 | Hourtash et al. |
| 9,345,546 B2 | 5/2016 | Toth et al. |
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,200 B2 | 6/2016 | Whitman et al. |
| 9,364,230 B2 | 6/2016 | Shelton, IV et al. |
| 9,364,231 B2 | 6/2016 | Wenchell |
| 9,364,249 B2 | 6/2016 | Kimball et al. |

(56) References Cited

U.S. PATENT DOCUMENTS

| | | |
|---|---|---|
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,404,868 B2 | 8/2016 | Yamanaka et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |
| 9,485,475 B2 | 11/2016 | Speier et al. |
| 9,486,271 B2 | 11/2016 | Dunning |
| 9,492,146 B2 | 11/2016 | Kostrzewski et al. |
| 9,492,237 B2 | 11/2016 | Kang et al. |
| 9,498,182 B2 | 11/2016 | Case et al. |
| 9,498,215 B2 | 11/2016 | Duque et al. |
| 9,498,219 B2 | 11/2016 | Moore et al. |
| 9,498,231 B2 | 11/2016 | Haider et al. |
| 9,498,291 B2 | 11/2016 | Balaji et al. |
| 9,509,566 B2 | 11/2016 | Chu et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,580 B2 | 12/2016 | Humayun et al. |
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,545,216 B2 | 1/2017 | D'Angelo et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,082 B2 | 2/2017 | Yen et al. |
| 9,561,982 B2 | 2/2017 | Enicks et al. |
| 9,566,708 B2 | 2/2017 | Kurnianto |
| 9,572,592 B2 | 2/2017 | Price et al. |
| 9,579,099 B2 | 2/2017 | Penna et al. |
| 9,579,503 B2 | 2/2017 | McKinney et al. |
| 9,585,657 B2 | 3/2017 | Shelton, IV et al. |
| 9,585,658 B2 | 3/2017 | Shelton, IV |
| 9,592,095 B2 | 3/2017 | Panescu et al. |
| 9,597,081 B2 | 3/2017 | Swayze et al. |
| 9,600,031 B2 | 3/2017 | Kaneko et al. |
| 9,600,138 B2 | 3/2017 | Thomas et al. |
| 9,603,024 B2 | 3/2017 | Wang et al. |
| 9,603,277 B2 | 3/2017 | Morgan et al. |
| 9,603,609 B2 | 3/2017 | Kawashima et al. |
| D783,675 S | 4/2017 | Yagisawa et al. |
| D784,270 S | 4/2017 | Bhattacharya |
| 9,610,114 B2 | 4/2017 | Baxter, III et al. |
| 9,610,412 B2 | 4/2017 | Zemlok et al. |
| 9,615,877 B2 | 4/2017 | Tyrrell et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,096 B1 | 5/2017 | Heaton, II et al. |
| 9,636,112 B2 | 5/2017 | Penna et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,089 B2 | 5/2017 | Smith et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,614 B2 | 5/2017 | Swensgard et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,713,503 B2 | 7/2017 | Goldschmidt |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,737,371 B2 | 8/2017 | Romo et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,750,560 B2 | 9/2017 | Ballakur et al. |
| 9,750,563 B2 | 9/2017 | Shikhman et al. |
| 9,753,135 B2 | 9/2017 | Bosch |
| 9,753,568 B2 | 9/2017 | McMillen |
| 9,757,126 B2 | 9/2017 | Cappola |

(56) References Cited

U.S. PATENT DOCUMENTS

| | | |
|---|---|---|
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,835 B2 | 10/2017 | Morgan et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,833,254 B1 | 12/2017 | Barral et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,467 B2 | 12/2017 | Harper et al. |
| 9,839,470 B2 | 12/2017 | Gilbert et al. |
| 9,839,487 B2 | 12/2017 | Dachs, II |
| 9,844,321 B1 | 12/2017 | Ekvall et al. |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,867,612 B2 | 1/2018 | Parihar et al. |
| 9,867,651 B2 | 1/2018 | Wham |
| 9,867,670 B2 | 1/2018 | Brannan et al. |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondoni et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,901,411 B2 | 2/2018 | Gombert et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,943,964 B2 | 4/2018 | Hares |
| 9,949,785 B2 | 4/2018 | Price et al. |
| 9,962,157 B2 | 5/2018 | Sapre |
| 9,968,355 B2 | 5/2018 | Shelton, IV et al. |
| 9,974,595 B2 | 5/2018 | Anderson et al. |
| 9,976,259 B2 | 5/2018 | Tan et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,016,538 B2 | 7/2018 | Locke et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |

(56) References Cited

U.S. PATENT DOCUMENTS

| | | |
|---|---|---|
| 10,039,564 B2 | 8/2018 | Hibner et al. |
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,111,703 B2 | 10/2018 | Cosman, Jr. et al. |
| D834,541 S | 11/2018 | You et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,130,373 B2 | 11/2018 | Castro et al. |
| 10,130,432 B2 | 11/2018 | Auld et al. |
| 10,133,248 B2 | 11/2018 | Fitzsimmons et al. |
| 10,135,242 B2 | 11/2018 | Baber et al. |
| 10,136,246 B2 | 11/2018 | Yamada |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |
| 10,137,245 B2 | 11/2018 | Melker et al. |
| 10,143,526 B2 | 12/2018 | Walker et al. |
| 10,143,948 B2 | 12/2018 | Bonifas et al. |
| 10,147,148 B2 | 12/2018 | Wu et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,891 B2 | 2/2019 | Jeong et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,254 B2 | 3/2019 | Cabrera et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,245,040 B2 | 4/2019 | Milliman |
| 10,251,661 B2 | 4/2019 | Collings et al. |
| 10,251,725 B2 | 4/2019 | Valentine et al. |
| 10,255,995 B2 | 4/2019 | Ingmanson |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,004 B2 | 4/2019 | Yamaguchi et al. |
| 10,265,035 B2 | 4/2019 | Fehre et al. |
| 10,265,066 B2 | 4/2019 | Measamer et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,282,963 B2 | 5/2019 | Fahey |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,610 B2 | 5/2019 | Srivastava |
| 10,292,704 B2 | 5/2019 | Harris et al. |
| 10,292,707 B2 | 5/2019 | Shelton, IV et al. |

(56) References Cited

U.S. PATENT DOCUMENTS

| | | |
|---|---|---|
| 10,292,758 B2 | 5/2019 | Boudreaux et al. |
| 10,292,769 B1 | 5/2019 | Yu |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,868 B2 | 5/2019 | Tsuboi et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,327,779 B2 | 6/2019 | Richard et al. |
| 10,335,042 B2 | 7/2019 | Schoenle et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,339,496 B2 | 7/2019 | Matson et al. |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,939 B2 | 7/2019 | Shelton, IV et al. |
| 10,349,941 B2 | 7/2019 | Marczyk et al. |
| 10,350,016 B2 | 7/2019 | Burbank et al. |
| 10,357,184 B2 | 7/2019 | Crawford et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,386,990 B2 | 8/2019 | Shikhman et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,281 B2 | 10/2019 | Shelton, IV et al. |
| 10,441,344 B2 | 10/2019 | Notz et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,684 B2 | 11/2019 | Toth et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,507,278 B2 | 12/2019 | Gao et al. |
| 10,510,267 B2 | 12/2019 | Jarc et al. |
| 10,512,413 B2 | 12/2019 | Schepis et al. |
| 10,512,461 B2 | 12/2019 | Gupta et al. |
| 10,512,499 B2 | 12/2019 | McHenry et al. |
| 10,512,509 B2 | 12/2019 | Bowling et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,537,396 B2 | 1/2020 | Zingaretti et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |

(56) References Cited

U.S. PATENT DOCUMENTS

| | | |
|---|---|---|
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,349 B2 | 2/2020 | Wedekind et al. |
| 10,561,422 B2 | 2/2020 | Schellin et al. |
| 10,561,470 B2 | 2/2020 | Hourtash et al. |
| 10,561,471 B2 | 2/2020 | Nichogi |
| 10,561,560 B2 | 2/2020 | Boutoussov et al. |
| 10,561,753 B2 | 2/2020 | Thompson et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savall et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,962 B2 | 3/2020 | Friedrichs et al. |
| 10,582,964 B2 | 3/2020 | Weinberg et al. |
| 10,586,074 B2 | 3/2020 | Rose et al. |
| 10,588,623 B2 | 3/2020 | Schmid et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,007 B2 | 3/2020 | Takano |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,413 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,667 B2 | 4/2020 | Faller et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,639,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,100 B2 | 6/2020 | Frushour |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,055 B2 | 6/2020 | Shelton, IV et al. |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,702,271 B2 | 7/2020 | Aranyi et al. |
| 10,709,446 B2 | 7/2020 | Harris et al. |
| 10,716,473 B2 | 7/2020 | Greiner |
| 10,716,489 B2 | 7/2020 | Kalvoy et al. |
| 10,716,583 B2 | 7/2020 | Look et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,498 B2 | 8/2020 | Watanabe et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,239 B2 | 8/2020 | Volek et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,673 B2 | 9/2020 | Allen, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |
| 10,786,327 B2 | 9/2020 | Anderson et al. |
| 10,792,038 B2 | 10/2020 | Becerra et al. |
| 10,792,118 B2 | 10/2020 | Prpa et al. |
| 10,792,422 B2 | 10/2020 | Douglas et al. |
| 10,799,304 B2 | 10/2020 | Kapadia et al. |

(56) References Cited

U.S. PATENT DOCUMENTS

| | | |
|---|---|---|
| 10,803,977 B2 | 10/2020 | Sanmugalingham |
| 10,806,445 B2 | 10/2020 | Penna et al. |
| 10,806,453 B2 | 10/2020 | Chen et al. |
| 10,806,454 B2 | 10/2020 | Kopp |
| 10,806,499 B2 | 10/2020 | Castaneda et al. |
| 10,806,506 B2 | 10/2020 | Gaspredes et al. |
| 10,806,532 B2 | 10/2020 | Grubbs et al. |
| 10,811,131 B2 | 10/2020 | Schneider et al. |
| 10,813,638 B2 | 10/2020 | Shelton, IV et al. |
| 10,813,703 B2 | 10/2020 | Swayze et al. |
| 10,818,383 B2 | 10/2020 | Sharifi Sedeh et al. |
| 10,828,028 B2 | 11/2020 | Harris et al. |
| 10,828,030 B2 | 11/2020 | Weir et al. |
| 10,835,206 B2 | 11/2020 | Bell et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,473 B2 | 11/2020 | Scheib et al. |
| 10,842,490 B2 | 11/2020 | DiNardo et al. |
| 10,842,492 B2 | 11/2020 | Shelton, IV et al. |
| 10,842,522 B2 | 11/2020 | Messerly et al. |
| 10,842,523 B2 | 11/2020 | Shelton, IV et al. |
| 10,842,575 B2 | 11/2020 | Panescu et al. |
| 10,842,897 B2 | 11/2020 | Schwartz et al. |
| D904,612 S | 12/2020 | Wynn et al. |
| 10,849,697 B2 | 12/2020 | Yates et al. |
| 10,849,700 B2 | 12/2020 | Kopp et al. |
| 10,856,768 B2 | 12/2020 | Osadchy et al. |
| 10,856,867 B2 | 12/2020 | Shelton, IV et al. |
| 10,856,868 B2 | 12/2020 | Shelton, IV et al. |
| 10,856,870 B2 | 12/2020 | Harris et al. |
| 10,863,984 B2 | 12/2020 | Shelton, IV et al. |
| 10,864,037 B2 | 12/2020 | Mun et al. |
| 10,864,050 B2 | 12/2020 | Tabandeh et al. |
| 10,872,684 B2 | 12/2020 | McNutt et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,881,464 B2 | 1/2021 | Odermatt et al. |
| 10,888,321 B2 | 1/2021 | Shelton, IV et al. |
| 10,888,322 B2 | 1/2021 | Morgan et al. |
| 10,892,899 B2 | 1/2021 | Shelton, IV et al. |
| 10,892,995 B2 | 1/2021 | Shelton, IV et al. |
| 10,893,863 B2 | 1/2021 | Shelton, IV et al. |
| 10,893,864 B2 | 1/2021 | Harris et al. |
| 10,893,884 B2 | 1/2021 | Stoddard et al. |
| 10,898,105 B2 | 1/2021 | Weprin et al. |
| 10,898,183 B2 | 1/2021 | Shelton, IV et al. |
| 10,898,186 B2 | 1/2021 | Bakos et al. |
| 10,898,189 B2 | 1/2021 | McDonald, II |
| 10,898,256 B2 | 1/2021 | Yates et al. |
| 10,898,280 B2 | 1/2021 | Kopp |
| 10,898,622 B2 | 1/2021 | Shelton, IV et al. |
| 10,902,944 B1 | 1/2021 | Casey et al. |
| 10,903,685 B2 | 1/2021 | Yates et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,912,559 B2 | 2/2021 | Harris et al. |
| 10,912,567 B2 | 2/2021 | Shelton, IV et al. |
| 10,912,580 B2 | 2/2021 | Green et al. |
| 10,912,619 B2 | 2/2021 | Jarc et al. |
| 10,916,415 B2 | 2/2021 | Karancsi et al. |
| 10,918,385 B2 | 2/2021 | Overmyer et al. |
| 10,930,400 B2 | 2/2021 | Robbins et al. |
| D914,878 S | 3/2021 | Shelton, IV et al. |
| 10,932,705 B2 | 3/2021 | Muhsin et al. |
| 10,932,772 B2 | 3/2021 | Shelton, IV et al. |
| 10,932,784 B2 | 3/2021 | Mozdzierz et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,939,313 B2 | 3/2021 | Eom et al. |
| 10,943,454 B2 | 3/2021 | Shelton, IV et al. |
| 10,944,728 B2 | 3/2021 | Wiener et al. |
| 10,945,727 B2 | 3/2021 | Shelton, IV et al. |
| 10,950,982 B2 | 3/2021 | Regnier et al. |
| 10,952,708 B2 | 3/2021 | Scheib et al. |
| 10,952,732 B2 | 3/2021 | Binmoeller et al. |
| 10,954,935 B2 | 3/2021 | O'Shea et al. |
| 10,959,727 B2 | 3/2021 | Hunter et al. |
| 10,959,729 B2 | 3/2021 | Ehrenfels et al. |
| 10,959,744 B2 | 3/2021 | Shelton, IV et al. |
| 10,959,788 B2 | 3/2021 | Grover et al. |
| 10,960,150 B2 | 3/2021 | Zergiebel et al. |
| 10,962,449 B2 | 3/2021 | Unuma et al. |
| 10,966,590 B2 | 4/2021 | Takahashi et al. |
| 10,966,791 B2 | 4/2021 | Harris et al. |
| 10,966,798 B2 | 4/2021 | Tesar et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,973,682 B2 | 4/2021 | Vezzu et al. |
| 10,980,536 B2 | 4/2021 | Weaner et al. |
| 10,980,537 B2 | 4/2021 | Shelton, IV et al. |
| 10,980,560 B2 | 4/2021 | Shelton, IV et al. |
| 10,980,595 B2 | 4/2021 | Wham |
| 10,980,610 B2 | 4/2021 | Rosenberg et al. |
| 11,000,276 B2 | 5/2021 | Shelton, IV et al. |
| 11,051,817 B2 | 7/2021 | Shelton, IV et al. |
| 11,051,902 B2 | 7/2021 | Kruecker et al. |
| 11,058,501 B2 | 7/2021 | Tokarchuk et al. |
| 11,071,595 B2 | 7/2021 | Johnson et al. |
| 11,103,246 B2 | 8/2021 | Marczyk et al. |
| 11,141,213 B2 | 10/2021 | Yates et al. |
| 11,183,293 B2 | 11/2021 | Lu et al. |
| 11,185,325 B2 | 11/2021 | Shelton, IV et al. |
| 11,273,290 B2 | 3/2022 | Kowshik |
| 11,289,188 B2 | 3/2022 | Mabotuwana et al. |
| D950,728 S | 5/2022 | Bakos et al. |
| D952,144 S | 5/2022 | Boudreaux |
| 11,322,248 B2 | 5/2022 | Grantcharov et al. |
| 11,350,932 B2 | 6/2022 | Shelton, IV et al. |
| 11,373,755 B2 | 6/2022 | Shelton, IV et al. |
| 11,376,098 B2 | 7/2022 | Shelton, IV et al. |
| 11,382,715 B2 | 7/2022 | Arai et al. |
| D964,564 S | 9/2022 | Boudreaux |
| 11,464,514 B2 | 10/2022 | Yates et al. |
| 11,504,191 B2 | 11/2022 | Mccloud et al. |
| 11,571,212 B2 | 2/2023 | Yates et al. |
| 2001/0056237 A1 | 12/2001 | Cane et al. |
| 2002/0049551 A1 | 4/2002 | Friedman et al. |
| 2002/0052616 A1 | 5/2002 | Wiener et al. |
| 2002/0072746 A1 | 6/2002 | Lingenfelder et al. |
| 2002/0138642 A1 | 9/2002 | Miyazawa et al. |
| 2002/0144147 A1 | 10/2002 | Basson et al. |
| 2002/0169584 A1 | 11/2002 | Fu et al. |
| 2002/0194023 A1 | 12/2002 | Turley et al. |
| 2003/0009111 A1 | 1/2003 | Cory et al. |
| 2003/0009154 A1 | 1/2003 | Whitman |
| 2003/0018329 A1 | 1/2003 | Hooven |
| 2003/0028183 A1 | 2/2003 | Sanchez et al. |
| 2003/0046109 A1 | 3/2003 | Uchikubo |
| 2003/0050654 A1 | 3/2003 | Whitman et al. |
| 2003/0069573 A1 | 4/2003 | Kadhiresan et al. |
| 2003/0093503 A1 | 5/2003 | Yamaki et al. |
| 2003/0114851 A1 | 6/2003 | Truckai et al. |
| 2003/0120284 A1 | 6/2003 | Palacios et al. |
| 2003/0130711 A1 | 7/2003 | Pearson et al. |
| 2003/0210812 A1 | 11/2003 | Khamene et al. |
| 2003/0223877 A1 | 12/2003 | Anstine et al. |
| 2004/0015053 A1 | 1/2004 | Bieger et al. |
| 2004/0078236 A1 | 4/2004 | Stoodley et al. |
| 2004/0082850 A1 | 4/2004 | Bonner et al. |
| 2004/0092992 A1 | 5/2004 | Adams et al. |
| 2004/0108825 A1 | 6/2004 | Lee et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0229496 A1 | 11/2004 | Robinson et al. |
| 2004/0243147 A1 | 12/2004 | Lipow |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |

(56) References Cited

U.S. PATENT DOCUMENTS

| | | |
|---|---|---|
| 2005/0020918 A1 | 1/2005 | Wilk et al. |
| 2005/0021027 A1 | 1/2005 | Shields et al. |
| 2005/0023324 A1 | 2/2005 | Doll et al. |
| 2005/0033108 A1 | 2/2005 | Sawyer |
| 2005/0063575 A1 | 3/2005 | Ma et al. |
| 2005/0065438 A1 | 3/2005 | Miller |
| 2005/0070800 A1 | 3/2005 | Takahashi |
| 2005/0100867 A1 | 5/2005 | Hilscher et al. |
| 2005/0131390 A1 | 6/2005 | Heinrich et al. |
| 2005/0139629 A1 | 6/2005 | Schwemberger et al. |
| 2005/0143759 A1 | 6/2005 | Kelly |
| 2005/0148854 A1 | 7/2005 | Ito et al. |
| 2005/0149001 A1 | 7/2005 | Uchikubo et al. |
| 2005/0149356 A1 | 7/2005 | Cyr et al. |
| 2005/0165390 A1 | 7/2005 | Mauti et al. |
| 2005/0182655 A1 | 8/2005 | Merzlak et al. |
| 2005/0192633 A1* | 9/2005 | Montpetit .......... A61B 17/0469 606/232 |
| 2005/0203380 A1 | 9/2005 | Sauer et al. |
| 2005/0203384 A1 | 9/2005 | Sati et al. |
| 2005/0203504 A1 | 9/2005 | Wham et al. |
| 2005/0213832 A1 | 9/2005 | Schofield et al. |
| 2005/0222631 A1 | 10/2005 | Dalal et al. |
| 2005/0228246 A1 | 10/2005 | Lee et al. |
| 2005/0228425 A1 | 10/2005 | Boukhny et al. |
| 2005/0236474 A1 | 10/2005 | Onuma et al. |
| 2005/0251233 A1 | 11/2005 | Kanzius |
| 2005/0277913 A1 | 12/2005 | McCary |
| 2005/0288425 A1 | 12/2005 | Lee et al. |
| 2006/0020272 A1* | 1/2006 | Gildenberg ............. A61B 17/29 606/144 |
| 2006/0025816 A1 | 2/2006 | Shelton |
| 2006/0039105 A1 | 2/2006 | Smith et al. |
| 2006/0059018 A1 | 3/2006 | Shiobara et al. |
| 2006/0069388 A1 | 3/2006 | Truckai et al. |
| 2006/0079872 A1 | 4/2006 | Eggleston |
| 2006/0079874 A1 | 4/2006 | Faller et al. |
| 2006/0116908 A1 | 6/2006 | Dew et al. |
| 2006/0122558 A1 | 6/2006 | Sherman et al. |
| 2006/0136622 A1 | 6/2006 | Rouvelin et al. |
| 2006/0142739 A1 | 6/2006 | DiSilestro et al. |
| 2006/0184160 A1 | 8/2006 | Ozaki et al. |
| 2006/0241399 A1 | 10/2006 | Fabian |
| 2006/0282009 A1 | 12/2006 | Oberg et al. |
| 2006/0282096 A1* | 12/2006 | Papa .................... A61B 1/2736 606/144 |
| 2006/0287645 A1 | 12/2006 | Tashiro et al. |
| 2007/0010838 A1 | 1/2007 | Shelton et al. |
| 2007/0016235 A1 | 1/2007 | Tanaka et al. |
| 2007/0016979 A1 | 1/2007 | Damaj et al. |
| 2007/0027459 A1 | 2/2007 | Horvath et al. |
| 2007/0038080 A1 | 2/2007 | Salisbury et al. |
| 2007/0049947 A1 | 3/2007 | Menn et al. |
| 2007/0066970 A1 | 3/2007 | Ineson |
| 2007/0078678 A1 | 4/2007 | DiSilvestro et al. |
| 2007/0084896 A1 | 4/2007 | Doll et al. |
| 2007/0085528 A1 | 4/2007 | Govari et al. |
| 2007/0156019 A1 | 7/2007 | Larkin et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175951 A1 | 8/2007 | Shelton et al. |
| 2007/0175955 A1 | 8/2007 | Shelton et al. |
| 2007/0179482 A1 | 8/2007 | Anderson |
| 2007/0179508 A1 | 8/2007 | Arndt |
| 2007/0191713 A1 | 8/2007 | Eichmann et al. |
| 2007/0192139 A1 | 8/2007 | Cookson et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0239028 A1 | 10/2007 | Houser et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282195 A1 | 12/2007 | Masini et al. |
| 2007/0282321 A1 | 12/2007 | Shah et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0019393 A1 | 1/2008 | Yamaki |
| 2008/0033404 A1 | 2/2008 | Romoda et al. |
| 2008/0039742 A1 | 2/2008 | Hashimshony et al. |
| 2008/0040151 A1 | 2/2008 | Moore |
| 2008/0058593 A1 | 3/2008 | Gu et al. |
| 2008/0059658 A1 | 3/2008 | Williams |
| 2008/0077158 A1 | 3/2008 | Haider et al. |
| 2008/0083414 A1 | 4/2008 | Messerges |
| 2008/0091071 A1 | 4/2008 | Kumar et al. |
| 2008/0114212 A1 | 5/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0164296 A1 | 7/2008 | Shelton et al. |
| 2008/0167644 A1 | 7/2008 | Shelton et al. |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0223904 A1 | 9/2008 | Marczyk |
| 2008/0234708 A1 | 9/2008 | Houser et al. |
| 2008/0235052 A1 | 9/2008 | Node-Langlois et al. |
| 2008/0245841 A1 | 10/2008 | Smith et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0048595 A1 | 2/2009 | Mihori et al. |
| 2009/0048611 A1 | 2/2009 | Funda et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0114699 A1 | 5/2009 | Viola |
| 2009/0128084 A1 | 5/2009 | Johnson et al. |
| 2009/0157072 A1 | 6/2009 | Wham et al. |
| 2009/0182577 A1 | 7/2009 | Squilla et al. |
| 2009/0188094 A1 | 7/2009 | Cunningham et al. |
| 2009/0192591 A1 | 7/2009 | Ryan et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0259489 A1 | 10/2009 | Kimura et al. |
| 2009/0270678 A1 | 10/2009 | Scott et al. |
| 2009/0281541 A1 | 11/2009 | Ibrahim et al. |
| 2009/0299214 A1 | 12/2009 | Wu et al. |
| 2009/0306581 A1 | 12/2009 | Claus |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0036374 A1 | 2/2010 | Ward |
| 2010/0036405 A1 | 2/2010 | Giordano et al. |
| 2010/0038403 A1 | 2/2010 | D'Arcangelo |
| 2010/0057106 A1 | 3/2010 | Sorrentino et al. |
| 2010/0065604 A1 | 3/2010 | Weng |
| 2010/0069939 A1 | 3/2010 | Konishi |
| 2010/0069942 A1 | 3/2010 | Shelton, IV |
| 2010/0070417 A1 | 3/2010 | Flynn et al. |
| 2010/0108741 A1 | 5/2010 | Hessler et al. |
| 2010/0120266 A1 | 5/2010 | Rimborg |
| 2010/0132334 A1 | 6/2010 | Duclos et al. |
| 2010/0137845 A1 | 6/2010 | Ramstein et al. |

(56) References Cited

U.S. PATENT DOCUMENTS

| | | |
|---|---|---|
| 2010/0137886 A1 | 6/2010 | Zergiebel et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0193570 A1 | 8/2010 | Ehrenfels et al. |
| 2010/0194574 A1 | 8/2010 | Monk et al. |
| 2010/0198200 A1 | 8/2010 | Horvath |
| 2010/0198248 A1 | 8/2010 | Vakharia |
| 2010/0204717 A1 | 8/2010 | Knodel |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0258327 A1 | 10/2010 | Esenwein et al. |
| 2010/0280247 A1 | 11/2010 | Mutti et al. |
| 2010/0292535 A1 | 11/2010 | Paskar |
| 2010/0292684 A1 | 11/2010 | Cybulski et al. |
| 2010/0301095 A1 | 12/2010 | Shelton, IV et al. |
| 2011/0006876 A1 | 1/2011 | Moberg et al. |
| 2011/0022032 A1 | 1/2011 | Zemlok et al. |
| 2011/0036890 A1 | 2/2011 | Ma |
| 2011/0043612 A1 | 2/2011 | Keller et al. |
| 2011/0046618 A1 | 2/2011 | Minar et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0087502 A1 | 4/2011 | Yelton et al. |
| 2011/0089220 A1 | 4/2011 | Ingmanson et al. |
| 2011/0095070 A1 | 4/2011 | Patel et al. |
| 2011/0105277 A1 | 5/2011 | Shauli |
| 2011/0105895 A1 | 5/2011 | Kornblau et al. |
| 2011/0112569 A1 | 5/2011 | Friedman et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0152712 A1 | 6/2011 | Cao et al. |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0218526 A1 | 9/2011 | Mathur |
| 2011/0237883 A1 | 9/2011 | Chun |
| 2011/0238079 A1 | 9/2011 | Hannaford et al. |
| 2011/0251612 A1 | 10/2011 | Faller et al. |
| 2011/0264000 A1 | 10/2011 | Paul et al. |
| 2011/0264078 A1 | 10/2011 | Lipow et al. |
| 2011/0264086 A1 | 10/2011 | Ingle |
| 2011/0265311 A1 | 11/2011 | Kondo et al. |
| 2011/0273465 A1 | 11/2011 | Konishi et al. |
| 2011/0278343 A1 | 11/2011 | Knodel et al. |
| 2011/0290024 A1 | 12/2011 | Lefler |
| 2011/0295270 A1 | 12/2011 | Giordano et al. |
| 2011/0306840 A1 | 12/2011 | Allen et al. |
| 2011/0307284 A1 | 12/2011 | Thompson et al. |
| 2012/0012638 A1 | 1/2012 | Huang et al. |
| 2012/0021684 A1 | 1/2012 | Schultz et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0100517 A1 | 4/2012 | Bowditch et al. |
| 2012/0101488 A1 | 4/2012 | Aldridge et al. |
| 2012/0116265 A1 | 5/2012 | Houser et al. |
| 2012/0116381 A1 | 5/2012 | Houser et al. |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203067 A1 | 8/2012 | Higgins et al. |
| 2012/0203785 A1 | 8/2012 | Awada |
| 2012/0211542 A1 | 8/2012 | Racenet |
| 2012/0226150 A1 | 9/2012 | Balicki et al. |
| 2012/0232549 A1 | 9/2012 | Willyard et al. |
| 2012/0245958 A1 | 9/2012 | Lawrence et al. |
| 2012/0253329 A1 | 10/2012 | Zemlok et al. |
| 2012/0253847 A1 | 10/2012 | Dell'Anno et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0001121 A1 | 1/2013 | Metzger |
| 2013/0006241 A1 | 1/2013 | Takashino |
| 2013/0008677 A1 | 1/2013 | Huifu |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0046295 A1 | 2/2013 | Kerr et al. |
| 2013/0066647 A1 | 3/2013 | Andrie et al. |
| 2013/0090526 A1 | 4/2013 | Suzuki et al. |
| 2013/0090755 A1 | 4/2013 | Kiryu et al. |
| 2013/0093829 A1 | 4/2013 | Rosenblatt et al. |
| 2013/0096597 A1 | 4/2013 | Anand et al. |
| 2013/0116218 A1 | 5/2013 | Kaplan et al. |
| 2013/0131845 A1 | 5/2013 | Guilleminot |
| 2013/0144284 A1 | 6/2013 | Behnke, II et al. |
| 2013/0146643 A1 | 6/2013 | Schmid et al. |
| 2013/0153635 A1 | 6/2013 | Hodgkinson |
| 2013/0165776 A1 | 6/2013 | Blomqvist |
| 2013/0168435 A1 | 7/2013 | Huang et al. |
| 2013/0178853 A1 | 7/2013 | Hyink et al. |
| 2013/0190755 A1 | 7/2013 | Deborski et al. |
| 2013/0191647 A1 | 7/2013 | Ferrara, Jr. et al. |
| 2013/0193188 A1 | 8/2013 | Shelton, IV et al. |
| 2013/0196703 A1 | 8/2013 | Masoud et al. |
| 2013/0197531 A1 | 8/2013 | Boukhny et al. |
| 2013/0201356 A1 | 8/2013 | Kennedy et al. |
| 2013/0206813 A1 | 8/2013 | Nalagatla |
| 2013/0214025 A1 | 8/2013 | Zemlok et al. |
| 2013/0240623 A1 | 9/2013 | Baym et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0268283 A1 | 10/2013 | Vann et al. |
| 2013/0277410 A1 | 10/2013 | Fernandez et al. |
| 2013/0313130 A1 | 11/2013 | Little et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005668 A1 | 1/2014 | Rhee et al. |
| 2014/0006132 A1 | 1/2014 | Barker |
| 2014/0009894 A1 | 1/2014 | Yu |
| 2014/0013565 A1 | 1/2014 | MacDonald et al. |
| 2014/0018788 A1 | 1/2014 | Engelman et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0039491 A1 | 2/2014 | Bakos et al. |
| 2014/0058407 A1 | 2/2014 | Tsekos et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William R et al. |
| 2014/0117256 A1 | 5/2014 | Mueller et al. |
| 2014/0121669 A1 | 5/2014 | Claus |
| 2014/0142963 A1 | 5/2014 | Hill et al. |
| 2014/0148729 A1 | 5/2014 | Schmitz et al. |
| 2014/0148803 A1 | 5/2014 | Taylor |

(56) References Cited

U.S. PATENT DOCUMENTS

| | | |
|---|---|---|
| 2014/0151430 A1 | 6/2014 | Scheib et al. |
| 2014/0160015 A1* | 6/2014 | Ogawa .................. B25J 13/02 |
| | | 345/156 |
| 2014/0163359 A1 | 6/2014 | Sholev et al. |
| 2014/0166724 A1 | 6/2014 | Schellin et al. |
| 2014/0171778 A1 | 6/2014 | Tsusaka et al. |
| 2014/0171787 A1 | 6/2014 | Garbey et al. |
| 2014/0176576 A1 | 6/2014 | Spencer |
| 2014/0187856 A1 | 7/2014 | Holoien et al. |
| 2014/0188440 A1 | 7/2014 | Donhowe et al. |
| 2014/0194864 A1 | 7/2014 | Martin et al. |
| 2014/0195052 A1 | 7/2014 | Tsusaka et al. |
| 2014/0204190 A1 | 7/2014 | Rosenblatt, III et al. |
| 2014/0226572 A1 | 8/2014 | Thota et al. |
| 2014/0243799 A1 | 8/2014 | Parihar |
| 2014/0243809 A1 | 8/2014 | Gelfand et al. |
| 2014/0243811 A1 | 8/2014 | Reschke et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0275760 A1 | 9/2014 | Lee et al. |
| 2014/0276748 A1 | 9/2014 | Ku et al. |
| 2014/0276749 A1 | 9/2014 | Johnson |
| 2014/0278219 A1 | 9/2014 | Canavan et al. |
| 2014/0287393 A1 | 9/2014 | Kumar et al. |
| 2014/0296694 A1 | 10/2014 | Jaworski |
| 2014/0303660 A1 | 10/2014 | Boyden et al. |
| 2014/0303990 A1 | 10/2014 | Schoenefeld et al. |
| 2014/0336943 A1 | 11/2014 | Pellini et al. |
| 2014/0337052 A1 | 11/2014 | Pellini et al. |
| 2014/0364691 A1 | 12/2014 | Krivopisk et al. |
| 2015/0006201 A1 | 1/2015 | Pait et al. |
| 2015/0012010 A1 | 1/2015 | Adler et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051598 A1 | 2/2015 | Orszulak et al. |
| 2015/0051617 A1 | 2/2015 | Takemura et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0053749 A1 | 2/2015 | Shelton, IV et al. |
| 2015/0057675 A1 | 2/2015 | Akeel et al. |
| 2015/0062316 A1 | 3/2015 | Haraguchi et al. |
| 2015/0066000 A1 | 3/2015 | An et al. |
| 2015/0070187 A1 | 3/2015 | Wiesner et al. |
| 2015/0073400 A1 | 3/2015 | Sverdlik et al. |
| 2015/0077528 A1 | 3/2015 | Awdeh |
| 2015/0083774 A1 | 3/2015 | Measamer et al. |
| 2015/0099458 A1 | 4/2015 | Weisner et al. |
| 2015/0108198 A1 | 4/2015 | Estrella |
| 2015/0133945 A1 | 5/2015 | Dushyant et al. |
| 2015/0136833 A1 | 5/2015 | Shelton, IV et al. |
| 2015/0140982 A1 | 5/2015 | Postrel |
| 2015/0141980 A1 | 5/2015 | Jadhav et al. |
| 2015/0145682 A1 | 5/2015 | Harris |
| 2015/0148830 A1 | 5/2015 | Stulen et al. |
| 2015/0157354 A1 | 6/2015 | Bales, Jr. et al. |
| 2015/0168126 A1 | 6/2015 | Nevet et al. |
| 2015/0173673 A1 | 6/2015 | Toth et al. |
| 2015/0173756 A1 | 6/2015 | Baxter, III et al. |
| 2015/0173757 A1 | 6/2015 | Williams et al. |
| 2015/0182220 A1 | 7/2015 | Yates et al. |
| 2015/0196295 A1 | 7/2015 | Shelton, IV et al. |
| 2015/0199109 A1 | 7/2015 | Lee |
| 2015/0201918 A1 | 7/2015 | Kumar et al. |
| 2015/0202014 A1 | 7/2015 | Kim et al. |
| 2015/0208934 A1 | 7/2015 | Sztrubel et al. |
| 2015/0209035 A1* | 7/2015 | Zemlok ................ G01D 18/008 |
| | | 73/1.01 |
| 2015/0223725 A1 | 8/2015 | Engel et al. |
| 2015/0223868 A1 | 8/2015 | Brandt et al. |
| 2015/0237502 A1 | 8/2015 | Schmidt et al. |
| 2015/0257783 A1 | 9/2015 | Levine et al. |
| 2015/0272557 A1* | 10/2015 | Overmyer .......... A61B 17/07207 |
| | | 606/1 |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0282733 A1 | 10/2015 | Fielden et al. |
| 2015/0282821 A1 | 10/2015 | Look et al. |
| 2015/0289925 A1 | 10/2015 | Voegele et al. |
| 2015/0296042 A1 | 10/2015 | Aoyama |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1* | 10/2015 | Collar .................... G16H 40/63 |
| | | 382/128 |
| 2015/0305735 A1* | 10/2015 | Gorek ................... A61B 46/23 |
| | | 606/147 |
| 2015/0305828 A1 | 10/2015 | Park et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0320423 A1 | 11/2015 | Aranyi |
| 2015/0324114 A1 | 11/2015 | Hurley et al. |
| 2015/0328474 A1 | 11/2015 | Flyash et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2015/0374259 A1 | 12/2015 | Garbey et al. |
| 2016/0000437 A1 | 1/2016 | Giordano et al. |
| 2016/0001411 A1 | 1/2016 | Alberti |
| 2016/0005169 A1 | 1/2016 | Sela et al. |
| 2016/0015471 A1 | 1/2016 | Piron et al. |
| 2016/0019346 A1 | 1/2016 | Boston et al. |
| 2016/0022374 A1 | 1/2016 | Haider et al. |
| 2016/0034648 A1 | 2/2016 | Mohlenbrock et al. |
| 2016/0038224 A1 | 2/2016 | Couture et al. |
| 2016/0038253 A1 | 2/2016 | Piron et al. |
| 2016/0048780 A1 | 2/2016 | Sethumadhavan et al. |
| 2016/0051315 A1 | 2/2016 | Boudreaux |
| 2016/0058439 A1 | 3/2016 | Shelton, IV et al. |
| 2016/0058440 A1 | 3/2016 | Dinardo et al. |
| 2016/0066913 A1 | 3/2016 | Swayze et al. |
| 2016/0078190 A1 | 3/2016 | Greene et al. |
| 2016/0100837 A1 | 4/2016 | Huang et al. |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0143659 A1 | 5/2016 | Glutz et al. |
| 2016/0157717 A1 | 6/2016 | Gaster |
| 2016/0158468 A1 | 6/2016 | Tang et al. |
| 2016/0166336 A1 | 6/2016 | Razzaque et al. |
| 2016/0174998 A1 | 6/2016 | Lal et al. |
| 2016/0175025 A1 | 6/2016 | Strobl |
| 2016/0180045 A1 | 6/2016 | Syed |
| 2016/0182637 A1 | 6/2016 | Adriaens et al. |
| 2016/0184054 A1 | 6/2016 | Lowe |
| 2016/0192960 A1 | 7/2016 | Bueno et al. |
| 2016/0203599 A1 | 7/2016 | Gillies et al. |
| 2016/0206202 A1 | 7/2016 | Frangioni |
| 2016/0206362 A1 | 7/2016 | Mehta et al. |
| 2016/0224760 A1 | 8/2016 | Petak et al. |
| 2016/0225551 A1 | 8/2016 | Shedletsky |
| 2016/0228061 A1 | 8/2016 | Kallback et al. |
| 2016/0228204 A1 | 8/2016 | Quaid et al. |
| 2016/0235303 A1 | 8/2016 | Fleming et al. |
| 2016/0242836 A1 | 8/2016 | Eggers et al. |
| 2016/0249910 A1 | 9/2016 | Shelton, IV et al. |
| 2016/0249920 A1 | 9/2016 | Gupta et al. |
| 2016/0270732 A1 | 9/2016 | Källbäck et al. |
| 2016/0270842 A1 | 9/2016 | Strobl |
| 2016/0270861 A1 | 9/2016 | Guru et al. |
| 2016/0275259 A1 | 9/2016 | Nolan et al. |
| 2016/0278841 A1 | 9/2016 | Panescu et al. |
| 2016/0287312 A1 | 10/2016 | Tegg et al. |
| 2016/0287316 A1 | 10/2016 | Worrell et al. |
| 2016/0287337 A1 | 10/2016 | Aram et al. |

(56) References Cited

U.S. PATENT DOCUMENTS

| | | |
|---|---|---|
| 2016/0287912 A1 | 10/2016 | Warnking |
| 2016/0292456 A1 | 10/2016 | Dubey et al. |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0310204 A1 | 10/2016 | Mchenry et al. |
| 2016/0314716 A1 | 10/2016 | Grubbs |
| 2016/0314717 A1 | 10/2016 | Grubbs |
| 2016/0321400 A1 | 11/2016 | Durrant et al. |
| 2016/0323283 A1 | 11/2016 | Kang et al. |
| 2016/0331460 A1 | 11/2016 | Cheatham, III et al. |
| 2016/0331473 A1 | 11/2016 | Yamamura |
| 2016/0338685 A1 | 11/2016 | Nawana et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0345976 A1 | 12/2016 | Gonzalez et al. |
| 2016/0350490 A1 | 12/2016 | Martinez et al. |
| 2016/0354160 A1 | 12/2016 | Crowley et al. |
| 2016/0354162 A1 | 12/2016 | Yen et al. |
| 2016/0361070 A1 | 12/2016 | Ardel et al. |
| 2016/0367305 A1 | 12/2016 | Hareland |
| 2016/0367401 A1 | 12/2016 | Claus |
| 2016/0374710 A1 | 12/2016 | Sinelnikov et al. |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0000516 A1 | 1/2017 | Stulen et al. |
| 2017/0000553 A1 | 1/2017 | Wiener et al. |
| 2017/0005911 A1 | 1/2017 | Kasargod et al. |
| 2017/0007247 A1 | 1/2017 | Shelton, IV et al. |
| 2017/0027603 A1 | 2/2017 | Pandey |
| 2017/0042604 A1 | 2/2017 | McFarland et al. |
| 2017/0049522 A1 | 2/2017 | Kapadia |
| 2017/0068792 A1 | 3/2017 | Reiner |
| 2017/0079530 A1 | 3/2017 | DiMaio et al. |
| 2017/0079730 A1 | 3/2017 | Azizian et al. |
| 2017/0086829 A1 | 3/2017 | Vendely et al. |
| 2017/0086906 A1 | 3/2017 | Tsuruta |
| 2017/0086930 A1 | 3/2017 | Thompson et al. |
| 2017/0105754 A1 | 4/2017 | Boudreaux et al. |
| 2017/0105787 A1 | 4/2017 | Witt et al. |
| 2017/0116873 A1 | 4/2017 | Lendvay et al. |
| 2017/0119477 A1 | 5/2017 | Amiot et al. |
| 2017/0127499 A1 | 5/2017 | Unoson et al. |
| 2017/0132374 A1 | 5/2017 | Lee et al. |
| 2017/0132385 A1 | 5/2017 | Hunter et al. |
| 2017/0132785 A1 | 5/2017 | Wshah et al. |
| 2017/0143284 A1 | 5/2017 | Sehnert et al. |
| 2017/0143366 A1 | 5/2017 | Groene et al. |
| 2017/0154156 A1 | 6/2017 | Sevenster et al. |
| 2017/0164996 A1 | 6/2017 | Honda et al. |
| 2017/0164997 A1 | 6/2017 | Johnson et al. |
| 2017/0165008 A1 | 6/2017 | Finley |
| 2017/0165012 A1 | 6/2017 | Chaplin et al. |
| 2017/0172550 A1 | 6/2017 | Mukherjee et al. |
| 2017/0172565 A1 | 6/2017 | Heneveld |
| 2017/0172614 A1 | 6/2017 | Scheib et al. |
| 2017/0172674 A1 | 6/2017 | Hanuschik et al. |
| 2017/0172676 A1 | 6/2017 | Itkowitz et al. |
| 2017/0173262 A1 | 6/2017 | Veltz |
| 2017/0177807 A1 | 6/2017 | Fabian |
| 2017/0178069 A1 | 6/2017 | Paterra et al. |
| 2017/0185732 A1 | 6/2017 | Niklewski et al. |
| 2017/0196583 A1 | 7/2017 | Sugiyama |
| 2017/0196637 A1 | 7/2017 | Shelton, IV et al. |
| 2017/0202591 A1 | 7/2017 | Shelton, IV et al. |
| 2017/0202595 A1 | 7/2017 | Shelton, IV |
| 2017/0202607 A1 | 7/2017 | Shelton, IV et al. |
| 2017/0202608 A1 | 7/2017 | Shelton, IV et al. |
| 2017/0209145 A1 | 7/2017 | Swayze et al. |
| 2017/0215944 A1 | 8/2017 | Keffeler |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231553 A1 | 8/2017 | Igarashi et al. |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249431 A1 | 8/2017 | Shelton, IV et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0265943 A1 | 9/2017 | Sela et al. |
| 2017/0273715 A1 | 9/2017 | Piron et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281189 A1 | 10/2017 | Nalagatla et al. |
| 2017/0289617 A1 | 10/2017 | Song et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304007 A1 | 10/2017 | Piron et al. |
| 2017/0304020 A1 | 10/2017 | Ng et al. |
| 2017/0311777 A1 | 11/2017 | Hirayama et al. |
| 2017/0312456 A1 | 11/2017 | Phillips |
| 2017/0319268 A1 | 11/2017 | Akagane |
| 2017/0325876 A1 | 11/2017 | Nakadate et al. |
| 2017/0325878 A1 | 11/2017 | Messerly et al. |
| 2017/0333147 A1 | 11/2017 | Bernstein |
| 2017/0333152 A1 | 11/2017 | Wade |
| 2017/0337043 A1 | 11/2017 | Brincat et al. |
| 2017/0348047 A1 | 12/2017 | Reiter et al. |
| 2017/0360358 A1 | 12/2017 | Amiot et al. |
| 2017/0360499 A1 | 12/2017 | Greep et al. |
| 2017/0367583 A1 | 12/2017 | Black et al. |
| 2017/0367695 A1 | 12/2017 | Shelton, IV et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0014764 A1 | 1/2018 | Bechtel et al. |
| 2018/0021058 A1 | 1/2018 | Meglan |
| 2018/0042659 A1 | 2/2018 | Rupp et al. |
| 2018/0050196 A1 | 2/2018 | Pawsey et al. |
| 2018/0052971 A1 | 2/2018 | Hanina et al. |
| 2018/0055529 A1 | 3/2018 | Messerly et al. |
| 2018/0056496 A1 | 3/2018 | Rubens et al. |
| 2018/0065248 A1 | 3/2018 | Barral et al. |
| 2018/0078170 A1 | 3/2018 | Panescu et al. |
| 2018/0082480 A1 | 3/2018 | White et al. |
| 2018/0085102 A1 | 3/2018 | Kikuchi |
| 2018/0098049 A1 | 4/2018 | Sugano et al. |
| 2018/0098816 A1 | 4/2018 | Govari et al. |
| 2018/0108438 A1 | 4/2018 | Ryan et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0144243 A1 | 5/2018 | Hsieh et al. |
| 2018/0144314 A1 | 5/2018 | Miller |
| 2018/0153436 A1 | 6/2018 | Olson |
| 2018/0153574 A1 | 6/2018 | Faller et al. |
| 2018/0153632 A1 | 6/2018 | Tokarchuk et al. |
| 2018/0154297 A1 | 6/2018 | Maletich et al. |
| 2018/0161062 A1 | 6/2018 | Kaga et al. |
| 2018/0161716 A1 | 6/2018 | Li et al. |
| 2018/0165780 A1 | 6/2018 | Romeo |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168590 A1 | 6/2018 | Overmyer et al. |
| 2018/0168592 A1 | 6/2018 | Overmyer et al. |

(56) References Cited

U.S. PATENT DOCUMENTS

| | | |
|---|---|---|
| 2018/0168597 A1 | 6/2018 | Fanelli et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0172420 A1 | 6/2018 | Hein et al. |
| 2018/0177383 A1 | 6/2018 | Noonan et al. |
| 2018/0182475 A1 | 6/2018 | Cossler et al. |
| 2018/0183684 A1 | 6/2018 | Jacobson et al. |
| 2018/0193579 A1 | 7/2018 | Hanrahan et al. |
| 2018/0206884 A1 | 7/2018 | Beaupre |
| 2018/0206905 A1 | 7/2018 | Batchelor et al. |
| 2018/0211726 A1 | 7/2018 | Courtemanche et al. |
| 2018/0214025 A1 | 8/2018 | Homyk et al. |
| 2018/0221005 A1 | 8/2018 | Hamel et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0233235 A1 | 8/2018 | Angelides |
| 2018/0235719 A1 | 8/2018 | Jarc |
| 2018/0235722 A1 | 8/2018 | Baghdadi et al. |
| 2018/0242967 A1* | 8/2018 | Meade ............... A61B 17/0482 |
| 2018/0247128 A1 | 8/2018 | Alvi et al. |
| 2018/0247711 A1 | 8/2018 | Terry |
| 2018/0250086 A1 | 9/2018 | Grubbs |
| 2018/0250825 A1 | 9/2018 | Hashimoto et al. |
| 2018/0263699 A1 | 9/2018 | Murphy et al. |
| 2018/0263710 A1 | 9/2018 | Sakaguchi et al. |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0289427 A1 | 10/2018 | Griffiths et al. |
| 2018/0294060 A1 | 10/2018 | Kassab |
| 2018/0296286 A1 | 10/2018 | Peine et al. |
| 2018/0296289 A1 | 10/2018 | Rodriguez-Navarro et al. |
| 2018/0300506 A1 | 10/2018 | Kawakami et al. |
| 2018/0303552 A1 | 10/2018 | Ryan et al. |
| 2018/0304471 A1 | 10/2018 | Tokuchi |
| 2018/0310986 A1 | 11/2018 | Batchelor et al. |
| 2018/0315492 A1 | 11/2018 | Bishop et al. |
| 2018/0317916 A1 | 11/2018 | Wixey |
| 2018/0325619 A1 | 11/2018 | Rauniyar et al. |
| 2018/0333188 A1 | 11/2018 | Nott et al. |
| 2018/0333207 A1 | 11/2018 | Moctezuma De la Barrera |
| 2018/0333209 A1 | 11/2018 | Frushour et al. |
| 2018/0351987 A1 | 12/2018 | Patel et al. |
| 2018/0353186 A1 | 12/2018 | Mozdzierz et al. |
| 2018/0357383 A1 | 12/2018 | Allen et al. |
| 2018/0360456 A1 | 12/2018 | Shelton, IV et al. |
| 2018/0366213 A1 | 12/2018 | Fidone et al. |
| 2018/0368930 A1 | 12/2018 | Esterberg et al. |
| 2019/0000478 A1 | 1/2019 | Messerly et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0045515 A1 | 2/2019 | Kwasnick et al. |
| 2019/0046198 A1 | 2/2019 | Stokes et al. |
| 2019/0053801 A1 | 2/2019 | Wixey et al. |
| 2019/0053866 A1 | 2/2019 | Seow et al. |
| 2019/0059986 A1 | 2/2019 | Shelton, IV et al. |
| 2019/0059997 A1 | 2/2019 | Frushour |
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0087544 A1 | 3/2019 | Peterson |
| 2019/0099221 A1 | 4/2019 | Schmidt et al. |
| 2019/0099226 A1 | 4/2019 | Hallen |
| 2019/0104919 A1 | 4/2019 | Shelton, IV et al. |
| 2019/0110828 A1 | 4/2019 | Despatie |
| 2019/0110855 A1 | 4/2019 | Barral et al. |
| 2019/0110856 A1 | 4/2019 | Barral et al. |
| 2019/0115108 A1 | 4/2019 | Hegedus et al. |
| 2019/0122330 A1 | 4/2019 | Saget et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125339 A1 | 5/2019 | Shelton, IV et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125384 A1 | 5/2019 | Scheib et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0163875 A1 | 5/2019 | Allen et al. |
| 2019/0167296 A1 | 6/2019 | Tsubuku et al. |
| 2019/0192044 A1 | 6/2019 | Ravi et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |

(56) References Cited

U.S. PATENT DOCUMENTS

| | | |
|---|---|---|
| 2019/0200998 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201076 A1 | 7/2019 | Honda et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0208641 A1 | 7/2019 | Yates et al. |
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cuti et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0307520 A1 | 10/2019 | Peine et al. |
| 2019/0311802 A1 | 10/2019 | Kokubo et al. |
| 2019/0314015 A1 | 10/2019 | Shelton, IV et al. |
| 2019/0314016 A1 | 10/2019 | Huitema et al. |
| 2019/0314081 A1 | 10/2019 | Brogna |
| 2019/0320929 A1 | 10/2019 | Spencer et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0365569 A1 | 12/2019 | Skovgaard et al. |
| 2019/0374140 A1 | 12/2019 | Tucker et al. |
| 2019/0374292 A1 | 12/2019 | Barral et al. |
| 2019/0378610 A1 | 12/2019 | Barral et al. |
| 2020/0000470 A1 | 1/2020 | Du et al. |
| 2020/0000509 A1 | 1/2020 | Hayashida et al. |
| 2020/0038120 A1 | 2/2020 | Ziraknejad et al. |
| 2020/0046353 A1 | 2/2020 | Deck et al. |

(56) References Cited

U.S. PATENT DOCUMENTS

| | | |
|---|---|---|
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054326 A1 | 2/2020 | Harris et al. |
| 2020/0054328 A1 | 2/2020 | Harris et al. |
| 2020/0054330 A1 | 2/2020 | Harris et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0193600 A1 | 6/2020 | Shameli et al. |
| 2020/0197027 A1 | 6/2020 | Hershberger et al. |
| 2020/0203004 A1 | 6/2020 | Shanbhag et al. |
| 2020/0214699 A1 | 7/2020 | Shelton, IV et al. |
| 2020/0222149 A1 | 7/2020 | Valentine et al. |
| 2020/0226751 A1 | 7/2020 | Jin et al. |
| 2020/0230803 A1 | 7/2020 | Yamashita et al. |
| 2020/0237372 A1 | 7/2020 | Park |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0314569 A1 | 10/2020 | Morgan et al. |
| 2020/0348662 A1 | 11/2020 | Cella et al. |
| 2020/0352664 A1 | 11/2020 | King et al. |
| 2020/0388385 A1 | 12/2020 | De Los Reyes et al. |
| 2020/0405304 A1 | 12/2020 | Mozdzierz et al. |
| 2020/0405375 A1 | 12/2020 | Shelton, IV et al. |
| 2021/0000555 A1 | 1/2021 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0068834 A1 | 3/2021 | Shelton, IV et al. |
| 2021/0076966 A1 | 3/2021 | Grantcharov et al. |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0177489 A1 | 6/2021 | Yates et al. |
| 2021/0186454 A1 | 6/2021 | Behzadi et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |
| 2021/0212717 A1 | 7/2021 | Yates et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0219976 A1 | 7/2021 | DiNardo et al. |
| 2021/0220058 A1 | 7/2021 | Messerly et al. |
| 2021/0240852 A1 | 8/2021 | Shelton, IV et al. |
| 2021/0241898 A1 | 8/2021 | Shelton, IV et al. |
| 2021/0249125 A1 | 8/2021 | Morgan et al. |
| 2021/0251487 A1 | 8/2021 | Shelton, IV et al. |
| 2021/0259687 A1 | 8/2021 | Gonzalez et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |
| 2021/0282781 A1 | 9/2021 | Shelton, IV et al. |
| 2021/0306176 A1 | 9/2021 | Park et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |
| 2021/0336939 A1 | 10/2021 | Wiener et al. |
| 2021/0353287 A1 | 11/2021 | Shelton, IV et al. |
| 2021/0353288 A1 | 11/2021 | Shelton, IV et al. |
| 2021/0358599 A1 | 11/2021 | Alvi et al. |
| 2021/0361284 A1 | 11/2021 | Shelton, IV et al. |
| 2022/0000484 A1 | 1/2022 | Shelton, IV et al. |
| 2022/0054158 A1 | 2/2022 | Shelton, IV et al. |
| 2022/0079591 A1 | 3/2022 | Bakos et al. |
| 2022/0157306 A1 | 5/2022 | Albrecht et al. |
| 2022/0160438 A1 | 5/2022 | Shelton, IV et al. |
| 2022/0175374 A1 | 6/2022 | Shelton, IV et al. |
| 2022/0230738 A1 | 7/2022 | Shelton, IV et al. |
| 2022/0241027 A1 | 8/2022 | Shelton, IV et al. |
| 2022/0249097 A1 | 8/2022 | Shelton, IV et al. |
| 2022/0323092 A1 | 10/2022 | Shelton, IV et al. |
| 2022/0323095 A1 | 10/2022 | Nott et al. |
| 2022/0323150 A1 | 10/2022 | Yates et al. |
| 2022/0331011 A1 | 10/2022 | Shelton, IV et al. |
| 2022/0331018 A1 | 10/2022 | Parihar et al. |
| 2022/0346792 A1 | 11/2022 | Shelton, IV et al. |
| 2022/0370117 A1 | 11/2022 | Messerly et al. |
| 2022/0370126 A1 | 11/2022 | Shelton, IV et al. |
| 2022/0374414 A1 | 11/2022 | Shelton, IV et al. |
| 2022/0395276 A1 | 12/2022 | Yates et al. |
| 2022/0401099 A1 | 12/2022 | Shelton, IV et al. |
| 2022/0406452 A1 | 12/2022 | Shelton, IV |

(56) References Cited

U.S. PATENT DOCUMENTS

| | | | |
|---|---|---|---|
| 2022/0409302 | A1 | 12/2022 | Shelton, IV et al. |
| 2023/0000518 | A1 | 1/2023 | Nott et al. |
| 2023/0037577 | A1 | 2/2023 | Kimball et al. |
| 2023/0064821 | A1 | 3/2023 | Shelton, IV |
| 2023/0092371 | A1 | 3/2023 | Yates et al. |
| 2023/0098870 | A1 | 3/2023 | Harris et al. |
| 2023/0116571 | A1 | 4/2023 | Shelton, IV et al. |
| 2023/0146947 | A1 | 5/2023 | Shelton, IV et al. |
| 2023/0165642 | A1 | 6/2023 | Shelton, IV et al. |

FOREIGN PATENT DOCUMENTS

| | | |
|---|---|---|
| CN | 101617950 A | 1/2010 |
| CN | 106413578 A | 2/2017 |
| CN | 104490448 B | 3/2017 |
| CN | 206097107 U | 4/2017 |
| CN | 107811710 A | 3/2018 |
| CN | 108652695 A | 10/2018 |
| DE | 3016131 A1 | 10/1981 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 0408160 A1 | 1/1991 |
| EP | 0473987 A1 | 3/1992 |
| EP | 0929263 B1 | 7/1999 |
| EP | 1214913 A2 | 6/2002 |
| EP | 2730209 A1 | 5/2014 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| FR | 2838234 A1 | 10/2003 |
| GB | 2037167 A1 | 7/1980 |
| GB | 2509523 A | 7/2014 |
| JP | S5191993 U | 7/1976 |
| JP | S5373315 A | 6/1978 |
| JP | S57185848 A | 11/1982 |
| JP | S58207752 A | 12/1983 |
| JP | S63315049 A | 12/1988 |
| JP | H06142113 A | 5/1994 |
| JP | H06178780 A | 6/1994 |
| JP | H06209902 A | 8/1994 |
| JP | H07132122 A | 5/1995 |
| JP | H08071072 A | 3/1996 |
| JP | H08332169 A | 12/1996 |
| JP | H0928663 A | 2/1997 |
| JP | H09154850 A | 6/1997 |
| JP | H11151247 A | 6/1999 |
| JP | H11197159 A | 7/1999 |
| JP | H11309156 A | 11/1999 |
| JP | 2000058355 A | 2/2000 |
| JP | 2001029353 A | 2/2001 |
| JP | 2001195686 A | 7/2001 |
| JP | 2001314411 A | 11/2001 |
| JP | 2001340350 A | 12/2001 |
| JP | 2002272758 A | 9/2002 |
| JP | 2003061975 A | 3/2003 |
| JP | 2003070921 A | 3/2003 |
| JP | 2003153918 A | 5/2003 |
| JP | 2004118664 A | 4/2004 |
| JP | 2005111080 A | 4/2005 |
| JP | 2005309702 A | 11/2005 |
| JP | 2005348797 A | 12/2005 |
| JP | 2006077626 A | 3/2006 |
| JP | 2006117143 A | 5/2006 |
| JP | 2006164251 A | 6/2006 |
| JP | 2006280804 A | 10/2006 |
| JP | 2006288431 A | 10/2006 |
| JP | 2007123394 A | 5/2007 |
| JP | 2007139822 A | 6/2007 |
| JP | 2007300312 A | 11/2007 |
| JP | 2009039515 A | 2/2009 |
| JP | 2010057642 A | 3/2010 |
| JP | 2010131265 A | 6/2010 |
| JP | 2010269067 A | 12/2010 |
| JP | 2012065698 A | 4/2012 |
| JP | 2012239669 A | 12/2012 |
| JP | 2012533346 A | 12/2012 |
| JP | 2013044303 A | 3/2013 |
| JP | 2013081282 A | 5/2013 |
| JP | 2013135738 A | 7/2013 |
| JP | 2013144057 A | 7/2013 |
| JP | 2014155207 A | 8/2014 |
| JP | 2015085454 A | 5/2015 |
| JP | 2016514017 A | 5/2016 |
| JP | 2016528010 A | 9/2016 |
| JP | 2016174836 A | 10/2016 |
| JP | 2016214553 A | 12/2016 |
| JP | 2017047022 A | 3/2017 |
| JP | 2017513561 A | 6/2017 |
| JP | 2017526510 A | 9/2017 |
| JP | 2017532168 A | 11/2017 |
| KR | 20140104587 A | 8/2014 |
| KR | 101587721 B1 | 1/2016 |
| WO | WO-9734533 A1 | 9/1997 |
| WO | WO-9808449 A1 | 3/1998 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2006001264 A1 | 1/2006 |
| WO | WO-2007137304 A2 | 11/2007 |
| WO | WO-2008053485 A1 | 5/2008 |
| WO | WO-2008056618 A2 | 5/2008 |
| WO | WO-2008069816 A1 | 6/2008 |
| WO | WO-2008076079 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014031800 A1 | 2/2014 |
| WO | WO-2014071184 A1 | 5/2014 |
| WO | WO-2014116961 A1 | 7/2014 |
| WO | WO-2014134196 A1 | 9/2014 |
| WO | WO-2015030157 A1 | 3/2015 |
| WO | WO-2015054665 A1 | 4/2015 |
| WO | WO-2015129395 A1 | 9/2015 |
| WO | WO-2016093049 A1 | 6/2016 |
| WO | WO-2016100719 A1 | 6/2016 |
| WO | WO-2016118752 A1 | 7/2016 |
| WO | WO-2016206015 A1 | 12/2016 |
| WO | WO-2017011382 A1 | 1/2017 |
| WO | WO-2017011646 A1 | 1/2017 |
| WO | WO-2017058617 | 4/2017 |
| WO | WO-2017058695 A1 | 4/2017 |
| WO | WO-2017151996 A1 | 9/2017 |
| WO | WO-2017183353 A1 | 10/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018116247 A1 | 6/2018 |
| WO | WO-2018152141 A1 | 8/2018 |
| WO | WO-2018176414 A1 | 10/2018 |

OTHER PUBLICATIONS

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

(56) References Cited

OTHER PUBLICATIONS

Yuyi Mao et al., "A Survey on Mobile Edge Computing: The Communication Perspective," IEEE Communications Surveys & Tutorials, pp. 2322-2358, Jun. 13, 2017.

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Yang et al., "A dynamic stategy for packet scheduling and band-width allocation based on channel quality in IEEE 802.16e OFDMA system," Journal of Network and Computer Applications, vol. 39, pp. 52-60, May 2, 2013.

Takahashi et al., "Automatic smoke evacuation in laparoscopic surgery: a simplified method for objective evaluation," Surgical Endoscopy, vol. 27, No. 8, pp. 2980-2987, Feb. 23, 2013.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trend-based methods," Computers in Biology and Medic, New York, NY, vol. 27, No. 5, pp. 389-409 (1997).

Stacey et al., "Temporal abstraction in intelligent clinical data analysis: A survey," Artificial Intelligence in Medicine, vol. 39, No. 1, pp. 1-24 (2006).

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Slocinski et al., "Distance measure for impedance spectra for quantified evaluations," Lecture Notes on Impedance Spectroscopy, vol. 3, Taylor and Francis Group (Jul. 2012)—Book Not Attached.

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.

Phumzile Malindi, "5. QoS in Telemedicine," "Telemedicine," Jun. 20, 2011, IntechOpen, pp. 119-138.

Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.

Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.

Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.

Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.

Altenberg et al., "Genes of Glycolysis are Ubiquitously Overexpressed in 24 Cancer Classes," Genomics, vol. 84, pp. 1014-1020 (2004).

Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).

Marshall Brain, How Microcontrollers Work, 2006, retrieved from the internet <https://web.archive.org/web/20060221235221/http://electronics.howstuffworks.com/microcontroller.htm/printable> (Year: 2006).

CRC Press, "The Measurement, Instrumentation and Sensors Handbook," 1999, Section VII, Chapter 41, Peter O'Shea, "Phase Measurement," pp. 1303-1321, ISBN 0-8493-2145-X.

Jiang, "'Sound of Silence' : a secure indoor wireless ultrasonic communication system," Article, 2014, pp. 46-50, Snapshots of Doctoral Research at University College Cork, School of Engineering—Electrical & Electronic Engineering, UCC, Cork, Ireland.

Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.

Salamon, "AI Detects Polyps Better Than Colonoscopists" Online Article, Jun. 3, 2018, Medscape Medical News, Digestive Disease Week (DDW) 2018: Presentation 133.

Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.

Dottorato, "Analysis and Design of the Rectangular Microstrip Patch Antennas for TM0n0 operating mode," Article, Oct. 8, 2010, pp. 1-9, Microwave Journal.

Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.

Hsiao-Wei Tang, "ARCM", Video, Sep. 2012, YouTube, 5 screenshots, Retrieved from internet: <https://www.youtube.com/watch?v=UIdQaxb3fRw&feature=youtu.be>.

Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.

Vander Heiden, et al., "Understanding the Warburg effect: the metabolic requirements of cell proliferation," Article, May 22, 2009, pp. 1-12, vol. 324, Issue 5930, Science.

Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.

Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.

Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.

"ATM-MPLS Network Interworking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

IEEE Std No. 177, "Standard Definitions and Methods of Measurement for Piezoelectric Vibrators," published May 1966, The Institute of Electrical and Electronics Engineers, Inc., New York, N.Y.

Shi et al., An intuitive control console for robotic syrgery system, 2014, IEEE, p. 404-407 (Year: 2014).

Choi et al., A haptic augmented reality surgeon console for a laparoscopic surgery robot system, 2013, IEEE, p. 355-357 (Year: 2013).

(56) References Cited

OTHER PUBLICATIONS

Xie et al., Development of stereo vision and master-slave controller for a compact surgical robot system, 2015, IEEE, p. 403-407 (Year: 2015).

Sun et al., Innovative effector design for simulation training in robotic surgery, 2010, IEEE, p. 1735-1759 (Year: 2010).

Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.

Draijer, Matthijs et al., "Review of laser speckle contrast techniques for visualizing tissue perfusion," Lasers in Medical Science, Springer-Verlag, LO, vol. 24, No. 4, Dec. 3, 2008, pp. 639-651.

Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.

"Surgical instrumentation: the true cost of instrument trays and a potential strategy for optimization"; Mhlaba et al.; Sep. 23, 2015 (Year: 2015).

Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.

Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.

Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].

Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.

Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

Lalys, et al., "Automatic knowledge-based recognition of low-level tasks in ophthalmological procedures", Int J CARS, vol. 8, No. 1, pp. 1-49, Apr. 19, 2012.

Hu, Jinwen, Stimulations of adaptive temperature control with self-focused hyperthermia system for tumor treatment, Jan. 9, 2012, Ultrasonics 53, pp. 171-177, (Year: 2012).

Hussain et al., "A survey on resource allocation in high performance distributed computing systems", Parallel Computing, vol. 39, No. 11, pp. 709-736 (2013).

Anonymous: "Quality of service—Wikipedia", Dec. 7, 2017, Retrieved from the Internet: URL:https://en.wikipedia.org/w/index.php?title=Quality_of_service&oldid=814298744#Applications [retrieved on Feb. 14, 2023], pp. 1-12.

Anonymous: "Differentiated services—Wikipedia", Dec. 14, 2017, Retrieved from the Internet: URL:https://en.wikipedia.org/w/index.php?title=Differentiated_services&oldid=815415620 [retrieved on Feb. 14, 2023], pp. 1-7.

Anonymous: "Cloud computing—Wikipedia", Dec. 19, 2017, Retrieved from the Internet: URL:https://en.wikipedia.org/w/index.php?title=Cloud_computing&oldid=816206558 [retrieved Feb. 14, 2023], pp. 1-21.

* cited by examiner

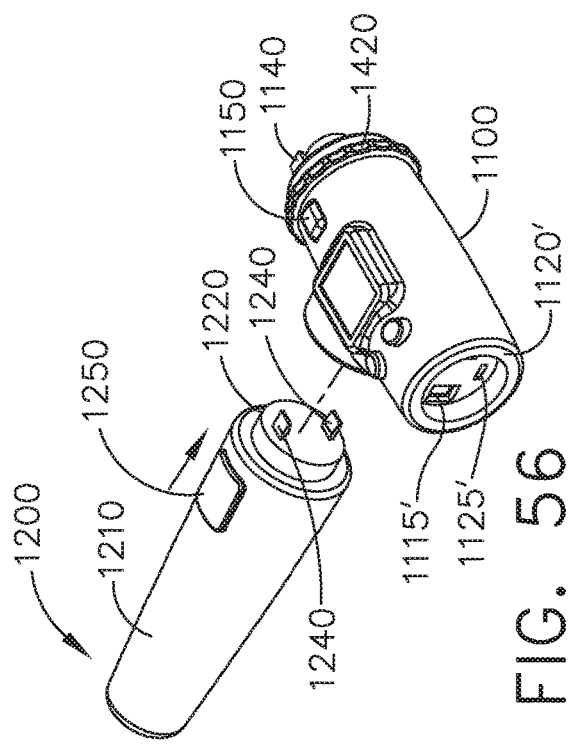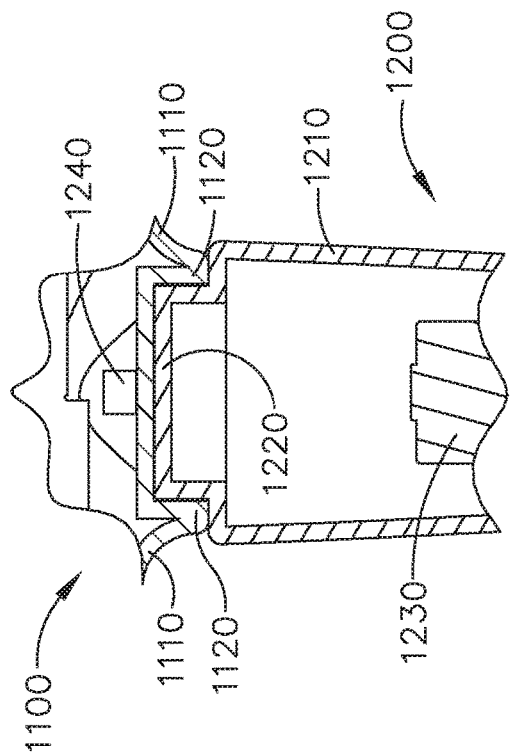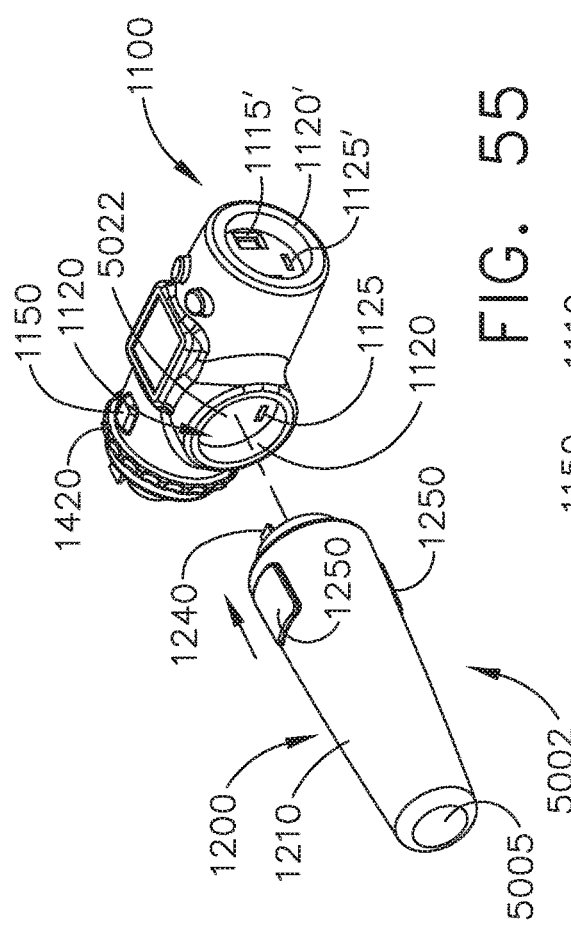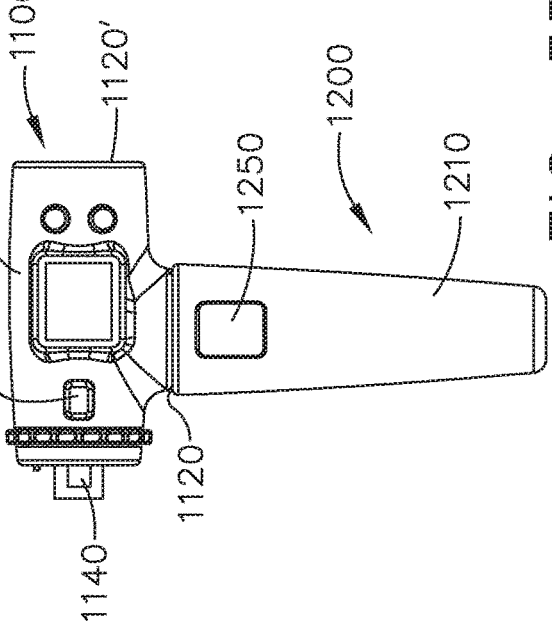

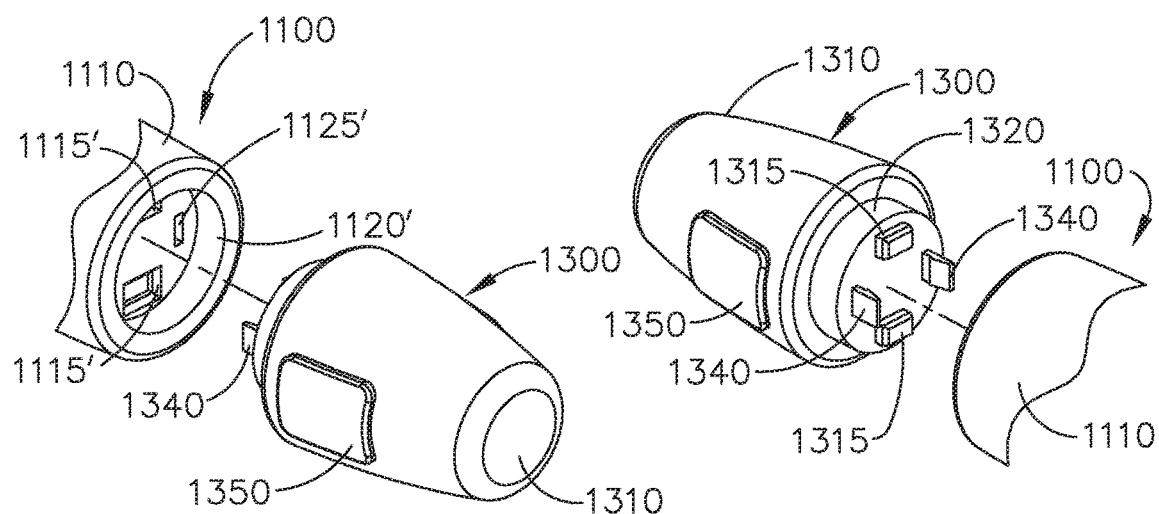
FIG. 63
FIG. 64
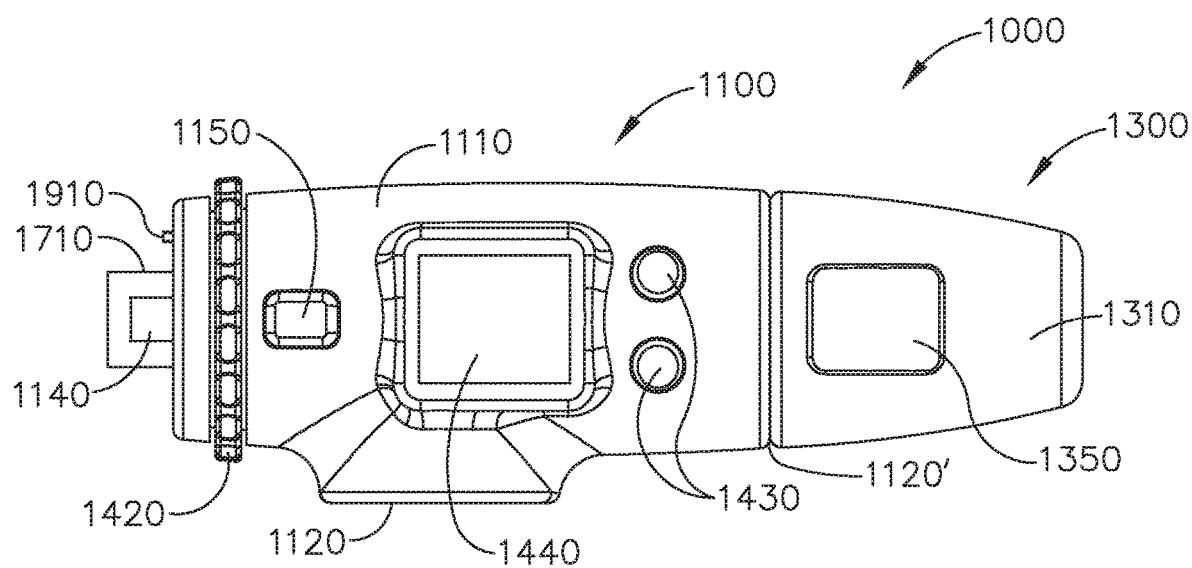
FIG. 65

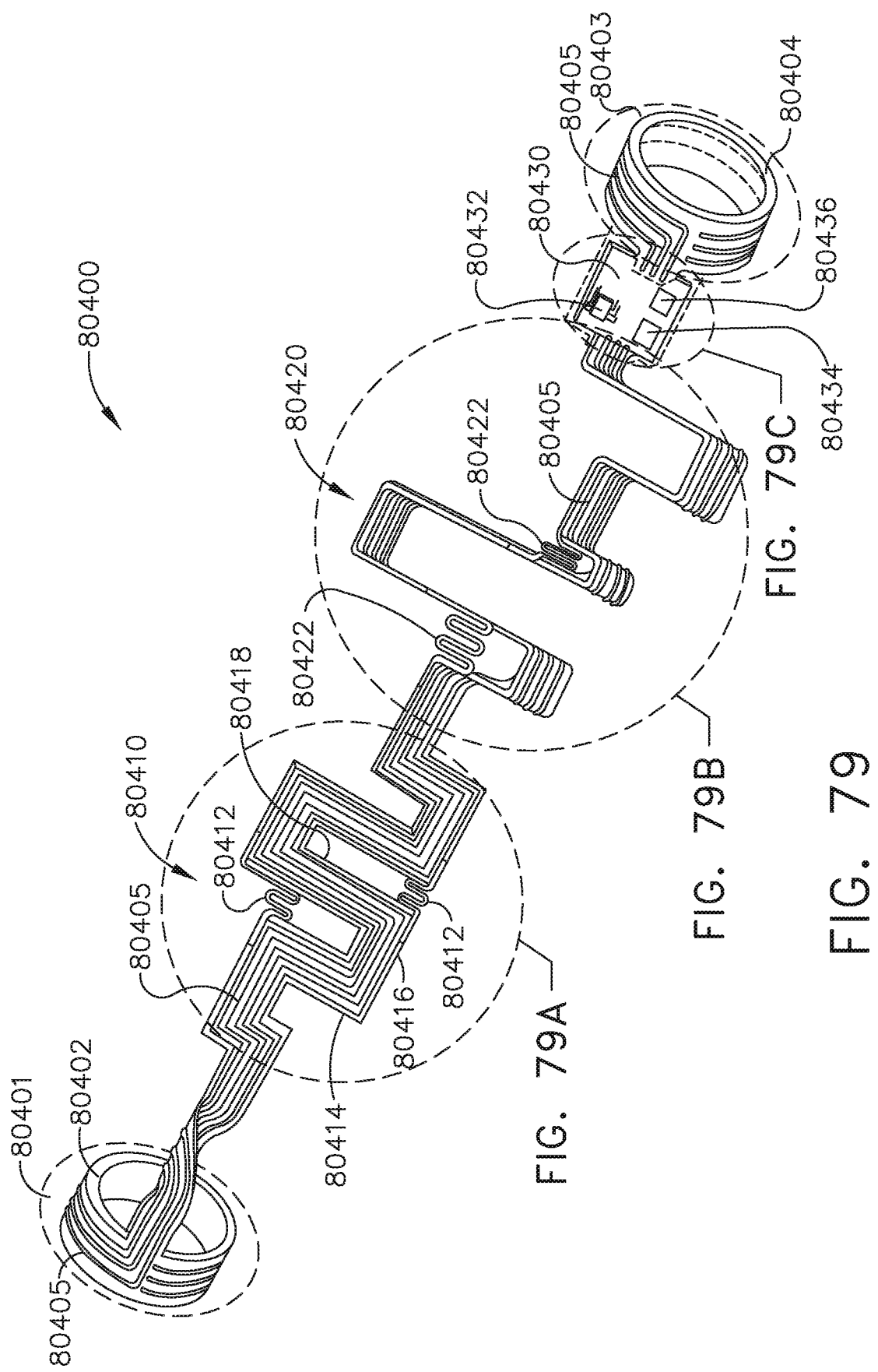

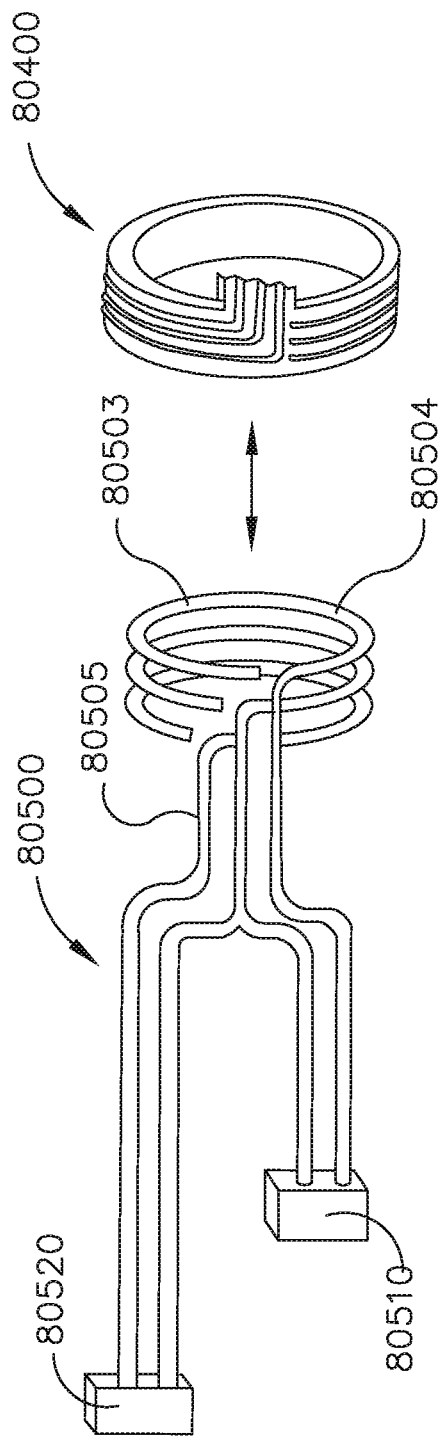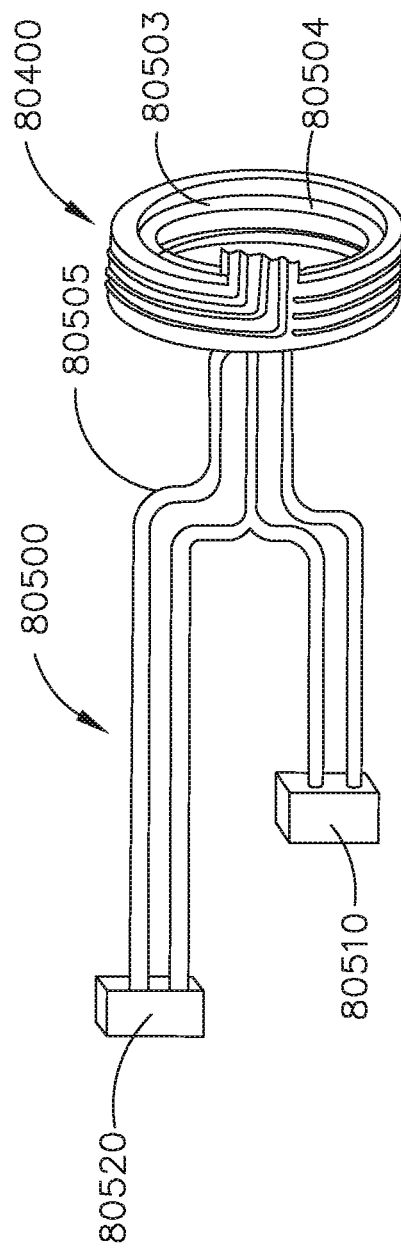
FIG. 81A
FIG. 81B

ADAPTIVE CONTROL PROGRAMS FOR A SURGICAL SYSTEM COMPRISING MORE THAN ONE TYPE OF CARTRIDGE

CROSS-REFERENCE TO RELATED APPLICATIONS

This non-provisional application claims the benefit under 35 U.S.C. § 119(e) of U.S. Provisional Patent Application Ser. No. 62/578,793, entitled SURGICAL INSTRUMENT WITH REMOTE RELEASE, filed Oct. 30, 2017, of U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT, filed Oct. 30, 2017, of U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,844, entitled SURGICAL INSTRUMENT WITH MODULAR POWER SOURCES, filed Oct. 30, 2017, and of U.S. Provisional Patent Application Ser. No. 62/578,855, entitled SURGICAL INSTRUMENT WITH SENSOR AND/OR CONTROL SYSTEMS, filed Oct. 30, 2017, the disclosures of which are incorporated by reference herein in their entirety. This non-provisional application claims the benefit under 35 U.S.C. § 119(e) of U.S. Provisional Patent Application Ser. No. 62/665,129, entitled SURGICAL SUTURING SYSTEMS, filed May 1, 2018, of U.S. Provisional Patent Application Ser. No. 62/665,139, entitled SURGICAL INSTRUMENTS COMPRISING CONTROL SYSTEMS, filed May 1, 2018, of U.S. Provisional Patent Application Ser. No. 62/665,177, entitled SURGICAL INSTRUMENTS COMPRISING HANDLE ARRANGEMENTS, filed May 1, 2018, of U.S. Provisional Patent Application Ser. No. 62/665,128, entitled MODULAR SURGICAL INSTRUMENTS, filed May 1, 2018, of U.S. Provisional Patent Application Ser. No. 62/665,192, entitled SURGICAL DISSECTORS, filed May 1, 2018, and of U.S. Provisional Patent Application Ser. No. 62/665,134, entitled SURGICAL CLIP APPLIER, filed May 1, 2018, the disclosures of which are incorporated by reference herein in their entirety.

BACKGROUND

The present disclosure relates to surgical systems and, in various arrangements, to grasping instruments that are designed to grasp the tissue of a patient, dissecting instruments configured to manipulate the tissue of a patient, clip appliers configured to clip the tissue of a patient, and suturing instruments configured to suture the tissue of a patient, among others.

BRIEF DESCRIPTION OF THE DRAWINGS

Various features of the embodiments described herein, together with advantages thereof, may be understood in accordance with the following description taken in conjunction with the accompanying drawings as follows:

FIG. 55 is a perspective view of the drive module of FIG. 7 and a power module of FIG. 1;

FIG. 56 is a perspective view of the drive module of FIG. 7 and the power module of FIG. 55;

FIG. 57 is an elevational view of the drive module of FIG. 7 and the power module of FIG. 55 attached to a side battery port of the drive module;

FIG. 58 is a partial cross-sectional view of the connection between the side battery port of the drive module of FIG. 7 and the power module of FIG. 55;

FIG. 63 is a perspective view of the power module of FIG. 45 detached from the drive module of FIG. 7;

FIG. 64 is another perspective view of the power module of FIG. 45 detached from the drive module of FIG. 7;

FIG. 65 is an elevational view of the power module of FIG. 45 attached to the proximal battery port of the drive module of FIG. 7;

FIG. 79 is a perspective view of a flex circuit for use in the surgical instrument of FIG. 73 in accordance with at least one aspect of the present disclosure;

FIG. 81A is a perspective view of the flex circuit of FIG. 79 prior to being electrically coupled with the flex circuit of FIG. 80 in accordance with at least one aspect of the present disclosure;

FIG. 81B is a perspective view of the flex circuit of FIG. 79 electrically coupled to the flex circuit of FIG. 80 in accordance with at least one aspect of the present disclosure;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
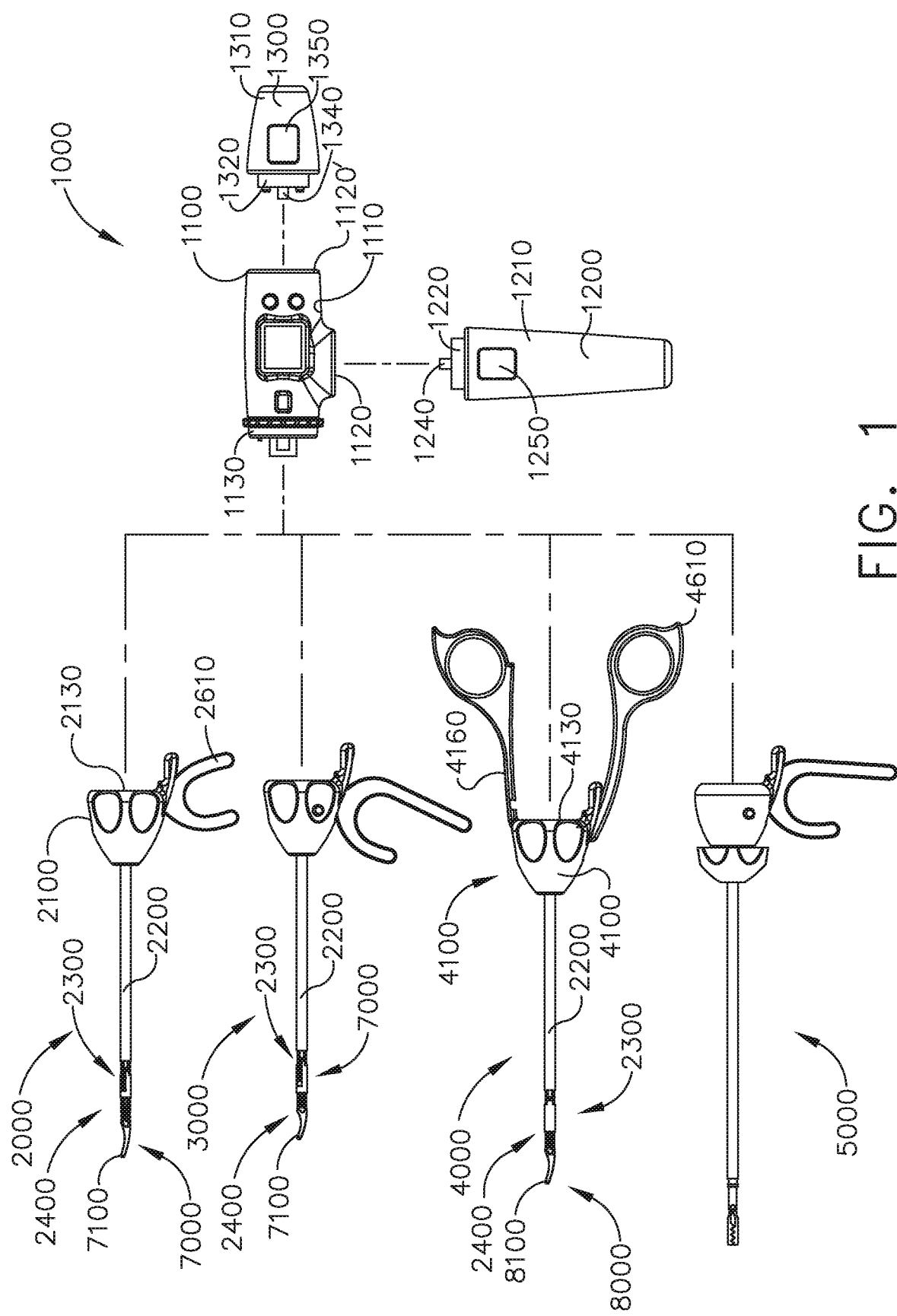
FIG. 1 illustrates a surgical system comprising a handle and several shaft assemblies—each of which are selectively attachable to the handle in accordance with at least one embodiment.

Applicant of the present application owns the following U.S. Patent Applications that were filed on Aug. 24, 2018 and which are each herein incorporated by reference in their respective entireties:

U.S. patent application Ser. No. 16/112,129, entitled SURGICAL SUTURING INSTRUMENT CONFIGURED TO MANIPULATE TISSUE USING MECHANICAL AND ELECTRICAL POWER, now U.S. Pat. No. 11,602,366;

U.S. patent application Ser. No. 16/112,155, entitled SURGICAL SUTURING INSTRUMENT COMPRISING A CAPTURE WIDTH WHICH IS LARGER THAN TROCAR DIAMETER, now U.S. Pat. No. 11,564,703;

U.S. patent application Ser. No. 16/112,168, entitled SURGICAL SUTURING INSTRUMENT COMPRISING A NON-CIRCULAR NEEDLE, now U.S. Patent Application Publication No. 2019/0125336;

U.S. patent application Ser. No. 16/112,180, entitled ELECTRICAL POWER OUTPUT CONTROL BASED ON MECHANICAL FORCES, now U.S. Patent Application Publication No. 2019/0125432;

U.S. patent application Ser. No. 16/112,193, entitled REACTIVE ALGORITHM FOR SURGICAL SYSTEM, now U.S. Pat. No. 10,932,806;

U.S. patent application Ser. No. 16/112,099, entitled SURGICAL INSTRUMENT COMPRISING AN ADAPTIVE ELECTRICAL SYSTEM, now U.S. Patent Application Publication No. 2019/0125378;

U.S. patent application Ser. No. 16/112,112, entitled CONTROL SYSTEM ARRANGEMENTS FOR A MODULAR SURGICAL INSTRUMENT, now U.S. Patent Appliction Publication No. 2019/0125320;

U.S. patent application Ser. No. 16/112,097, entitled SURGICAL INSTRUMENT SYSTEMS COMPRISING BATTERY ARRANGEMENTS, now U.S. Pat. No. 11,648,022;

U.S. patent application Ser. No. 16/112,109, entitled SURGICAL INSTRUMENT SYSTEMS COMPRISING HANDLE ARRANGEMENTS, now U.S. Patent Application Publication No. 2019/0125388;

U.S. patent application Ser. No. 16/112,114, entitled SURGICAL INSTRUMENT SYSTEMS COMPRISING FEEDBACK MECHANISMS, now U.S. Pat. No. 10,980,560;

U.S. patent application Ser. No. 16/112,117, entitled SURGICAL INSTRUMENT SYSTEMS COMPRISING LOCKOUT MECHANISMS, now U.S. Patent Application Publication No. 2019/0125476;

U.S. patent application Ser. No. 16/112,095, entitled SURGICAL INSTRUMENTS COMPRISING A LOCKABLE END EFFECTOR SOCKET, now U.S. Pat. No. 11,291,465;

U.S. patent application Ser. No. 16/112,121, entitled SURGICAL INSTRUMENTS COMPRISING A SHIFTING MECHANISM, now U.S. Pat. No. 11,026,712;

U.S. patent application Ser. No. 16/112,151, entitled SURGICAL INSTRUMENTS COMPRISING A SYSTEM FOR ARTICULATION AND ROTATION COMPENSATION, now U.S. Pat. No. 10,772,651;

U.S. patent application Ser. No. 16/112,151, entitled SURGICAL INSTRUMENTS COMPRISING A BIASED SHIFTING MECHANISM, now U.S. Pat. No. 10,772,651;

U.S. patent application Ser. No. 16/112,226, entitled SURGICAL INSTRUMENTS COMPRISING AN ARTICULATION DRIVE THAT PROVIDES FOR HIGH ARTICULATION ANGLES, now U.S. Pat. No. 11,129,636;

U.S. patent application Ser. No. 16/112,062, entitled SURGICAL DISSECTORS AND MANUFACTURING TECHNIQUES, now U.S. Pat. No. 10,959,744;

U.S. patent application Ser. No. 16/112,098, entitled SURGICAL DISSECTORS CONFIGURED TO APPLY MECHANICAL AND ELECTRICAL ENERGY, now U.S. Pat. No. 11,696,778;

U.S. patent application Ser. No. 16/112,237, entitled SURGICAL CLIP APPLIER CONFIGURED TO STORE CLIPS IN A STORED STATE now U.S. Pat. No. 11,026,713;

U.S. patent application Ser. No. 16/112,245, entitled SURGICAL CLIP APPLIER COMPRISING AN EMPTY CLIP CARTRIDGE LOCKOUT, now U.S. Pat. No. 11,051,836;

U.S. patent application Ser. No. 16/112,249, entitled SURGICAL CLIP APPLIER COMPRISING AN AUTOMATIC CLIP FEEDING SYSTEM, now U.S. Pat. No. 11,109,878;

U.S. patent application Ser. No. 16/112,253, entitled SURGICAL CLIP APPLIER COMPRISING ADAPTIVE FIRING CONTROL, now U.S. Pat. No. 11,103,268; and U.S. patent application Ser. No. 16/112,257, entitled SURGICAL CLIP APPLIER COMPRISING ADAPTIVE CONTROL IN RESPONSE TO A STRAIN GAUGE CIRCUIT, now U.S. Pat. No. 11,071,560;

Applicant of the present application owns the following U.S. Patent Applications that were filed on May 1, 2018 and which are each herein incorporated by reference in their respective entireties:

U.S. Patent Application Ser. No. 62/665,129, entitled SURGICAL SUTURING SYSTEMS;

U.S. Provisional Patent Application Ser. No. 62/665,139, entitled SURGICAL INSTRUMENTS COMPRISING CONTROL SYSTEMS;

U.S. Patent Application Ser. No. 62/665,177, entitled SURGICAL INSTRUMENTS COMPRISING HANDLE ARRANGEMENTS;

U.S. Patent Application Ser. No. 62/665,128, entitled MODULAR SURGICAL INSTRUMENTS;

U.S. Patent Application Ser. No. 62/665,192, entitled SURGICAL DISSECTORS; and

U.S. Patent Application Ser. No. 62/665,134, entitled SURGICAL CLIP APPLIER.

Applicant of the present application owns the following U.S. Patent Applications that were filed on Feb. 28, 2018 and which are each herein incorporated by reference in their respective entireties:

U.S. patent application Ser. No. 15/908,021, entitled SURGICAL INSTRUMENT WITH REMOTE RELEASE;

U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT;

U.S. patent application Ser. No. 15/908,040, entitled SURGICAL INSTRUMENT WITH ROTARY DRIVE SELECTIVELY ACTUATING MULTIPLE END EFFECTOR FUNCTIONS;

U.S. patent application Ser. No. 15/908,057, entitled SURGICAL INSTRUMENT WITH ROTARY DRIVE SELECTIVELY ACTUATING MULTIPLE END EFFECTOR FUNCTIONS;

U.S. patent application Ser. No. 15/908,058, entitled SURGICAL INSTRUMENT WITH MODULAR POWER SOURCES; and U.S. patent application Ser. No. 15/908,143, entitled SURGICAL INSTRUMENT WITH SENSOR AND/OR CONTROL SYSTEMS.

Applicant of the present application owns the following U.S. Patent Applications that were filed on Oct. 30, 2017 and which are each herein incorporated by reference in their respective entireties:

U.S. Provisional Patent Application Ser. No. 62/578,793, entitled SURGICAL INSTRUMENT WITH REMOTE RELEASE;

U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT;

U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,844, entitled SURGICAL INSTRUMENT WITH MODULAR POWER SOURCES; and U.S. Provisional Patent Application Ser. No. 62/578,855, entitled SURGICAL INSTRUMENT WITH SENSOR AND/OR CONTROL SYSTEMS.

Applicant of the present application owns the following U.S. Provisional Patent Applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Patent Applications, filed on Mar. 29, 2018, each of which is herein incorporated by reference in its entirety:

U.S. patent application Ser. No. 15/940,641, entitled INTERACTIVE SURGICAL SYSTEMS WITH ENCRYPTED COMMUNICATION CAPABILITIES;

U.S. patent application Ser. No. 15/940,648, entitled INTERACTIVE SURGICAL SYSTEMS WITH CONDITION HANDLING OF DEVICES AND DATA CAPABILITIES;

U.S. patent application Ser. No. 15/940,656, entitled SURGICAL HUB COORDINATION OF CONTROL AND COMMUNICATION OF OPERATING ROOM DEVICES;

U.S. patent application Ser. No. 15/940,666, entitled SPATIAL AWARENESS OF SURGICAL HUBS IN OPERATING ROOMS;

U.S. patent application Ser. No. 15/940,670, entitled COOPERATIVE UTILIZATION OF DATA DERIVED FROM SECONDARY SOURCES BY INTELLIGENT SURGICAL HUBS;

U.S. patent application Ser. No. 15/940,677, entitled SURGICAL HUB CONTROL ARRANGEMENTS;

U.S. patent application Ser. No. 15/940,632, entitled DATA STRIPPING METHOD TO INTERROGATE PATIENT RECORDS AND CREATE ANONYMIZED RECORD;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, entitled SELF DESCRIBING DATA PACKETS GENERATED AT AN ISSUING INSTRUMENT;

U.S. patent application Ser. No. 15/940,649, entitled DATA PAIRING TO INTERCONNECT A DEVICE MEASURED PARAMETER WITH AN OUTCOME;

U.S. patent application Ser. No. 15/940,654, entitled SURGICAL HUB SITUATIONAL AWARENESS;

U.S. patent application Ser. No. 15/940,663, entitled SURGICAL SYSTEM DISTRIBUTED PROCESSING;

U.S. patent application Ser. No. 15/940,668, entitled AGGREGATION AND REPORTING OF SURGICAL HUB DATA;

U.S. patent application Ser. No. 15/940,671, entitled SURGICAL HUB SPATIAL AWARENESS TO DETERMINE DEVICES IN OPERATING THEATER;

U.S. patent application Ser. No. 15/940,686, entitled DISPLAY OF ALIGNMENT OF STAPLE CARTRIDGE TO PRIOR LINEAR STAPLE LINE;

U.S. patent application Ser. No. 15/940,700, entitled STERILE FIELD INTERACTIVE CONTROL DISPLAYS;

U.S. patent application Ser. No. 15/940,629, entitled COMPUTER IMPLEMENTED INTERACTIVE SURGICAL SYSTEMS;

U.S. patent application Ser. No. 15/940,704, entitled USE OF LASER LIGHT AND RED-GREEN-BLUE COLORATION TO DETERMINE PROPERTIES OF BACK SCATTERED LIGHT;

U.S. patent application Ser. No. 15/940,722, entitled CHARACTERIZATION OF TISSUE IRREGULARITIES THROUGH THE USE OF MONO-CHROMATIC LIGHT REFRACTIVITY; and U.S. patent application Ser. No. 15/940,742, entitled DUAL CMOS ARRAY IMAGING.

Applicant of the present application owns the following U.S. Patent Applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES;

U.S. patent application Ser. No. 15/940,653, entitled ADAPTIVE CONTROL PROGRAM UPDATES FOR SURGICAL HUBS;

U.S. patent application Ser. No. 15/940,660, entitled CLOUD-BASED MEDICAL ANALYTICS FOR CUSTOMIZATION AND RECOMMENDATIONS TO A USER;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, entitled CLOUD-BASED MEDICAL ANALYTICS FOR SECURITY AND AUTHENTICATION TRENDS AND REACTIVE MEASURES;

U.S. patent application Ser. No. 15/940,706, entitled DATA HANDLING AND PRIORITIZATION IN A CLOUD ANALYTICS NETWORK; and U.S. patent application Ser. No. 15/940,675, entitled CLOUD INTERFACE FOR COUPLED SURGICAL DEVICES.

Applicant of the present application owns the following U.S. Patent Applications, filed on Mar. 29, 2018, each of which is herein incorporated by reference in its entirety:

U.S. patent application Ser. No. 15/940,627, entitled DRIVE ARRANGEMENTS FOR ROBOT-ASSISTED SURGICAL PLATFORMS;

U.S. patent application Ser. No. 15/940,637, entitled COMMUNICATION ARRANGEMENTS FOR ROBOT-ASSISTED SURGICAL PLATFORMS;

U.S. patent application Ser. No. 15/940,642, entitled CONTROLS FOR ROBOT-ASSISTED SURGICAL PLATFORMS;

U.S. patent application Ser. No. 15/940,676, entitled AUTOMATIC TOOL ADJUSTMENTS FOR ROBOT-ASSISTED SURGICAL PLATFORMS;

U.S. patent application Ser. No. 15/940,680, entitled CONTROLLERS FOR ROBOT-ASSISTED SURGICAL PLATFORMS;

U.S. patent application Ser. No. 15/940,683, entitled COOPERATIVE SURGICAL ACTIONS FOR ROBOT-ASSISTED SURGICAL PLATFORMS;

U.S. patent application Ser. No. 15/940,690, entitled DISPLAY ARRANGEMENTS FOR ROBOT-ASSISTED SURGICAL PLATFORMS; and U.S. patent application Ser. No. 15/940,711, entitled SENSING ARRANGEMENTS FOR ROBOT-ASSISTED SURGICAL PLATFORMS.

Applicant of the present application owns the following U.S. Provisional Patent Applications, filed on Mar. 30, 2018, each of which is herein incorporated by reference in its entirety:

U.S. Provisional Patent Application Ser. No. 62/650,887, entitled SURGICAL SYSTEMS WITH OPTIMIZED SENSING CAPABILITIES;

U.S. Provisional Patent Application Ser. No. 62/650,877, entitled SURGICAL SMOKE EVACUATION SENSING AND CONTROLS;

U.S. Provisional Patent Application Ser. No. 62/650,882, entitled SMOKE EVACUATION MODULE FOR INTERACTIVE SURGICAL PLATFORM; and U.S. Provisional Patent Application Ser. No. 62/650,898, entitled CAPACITIVE COUPLED RETURN PATH PAD WITH SEPARABLE ARRAY ELEMENTS.

Applicant of the present application owns the following U.S. Provisional Patent Application, filed on Apr. 19, 2018, which is herein incorporated by reference in its entirety:

U.S. Provisional Patent Application Ser. No. 62/659,900, entitled METHOD OF HUB COMMUNICATION.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a surgical system, device, or apparatus that "comprises," "has," "includes", or "contains" one or more elements possesses those one or more elements, but is not limited to possessing only those one or more elements. Likewise, an element of a system, device, or apparatus that "comprises," "has," "includes", or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical instrument, such as a grasper, for example, can comprise a handle, a shaft extending from the handle, and an end effector extending from the shaft. In various instances, the end effector comprises a first jaw and a second jaw, wherein one or both of the jaws are movable relative to the other to grasp the tissue of a patient. That said, an end effector of a surgical instrument can comprise any suitable arrangement and can perform any suitable function. For instance, an end effector can comprise first and second jaws configured to dissect or separate the tissue of a patient. Also, for instance, an end effector can be configured to suture and/or clip the tissue of a patient. In various instances, the end effector and/or shaft of the surgical instrument are configured to be inserted into a patient through a trocar, or cannula, and can have any suitable diameter, such as approximately 5 mm, 8 mm, and/or 12 mm, for example. U.S. patent application Ser. No. 11/013,924, entitled TROCAR SEAL ASSEMBLY, now U.S. Pat. No. 7,371,227, is incorporated by reference in its entirety. The shaft can define a longitudinal axis and at least a portion of the end effector can be rotatable about the longitudinal axis. Moreover, the surgical instrument can further comprise an articulation joint which can permit at least a portion of the end effector to be articulated relative to the shaft. In use, a clinician can rotate and/or articulate the end effector in order to maneuver the end effector within the patient.

Figure 2:
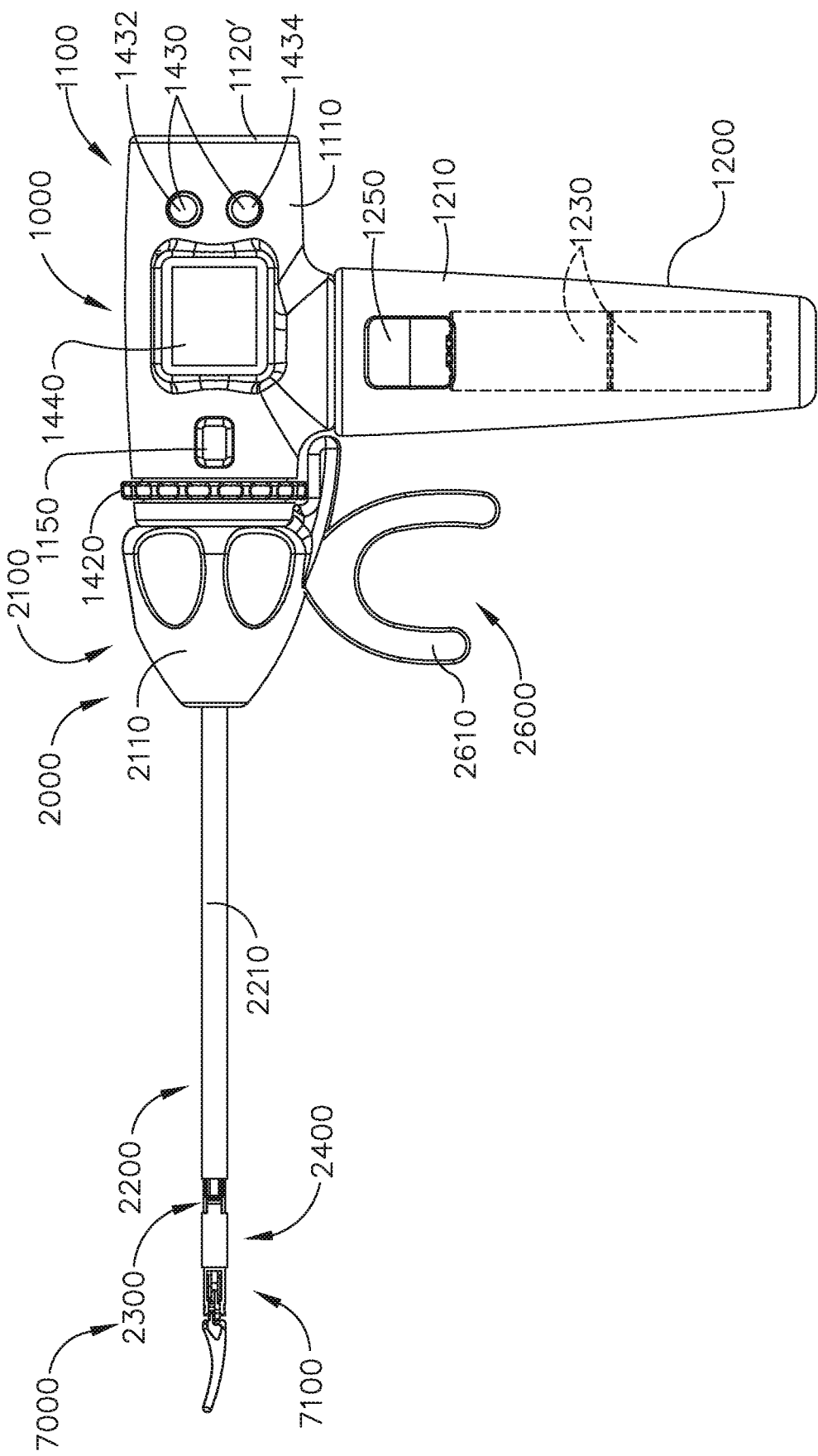
FIG. 2 is an elevational view of the handle and one of the shaft assemblies of the surgical system of FIG. 1.
Figure 3:
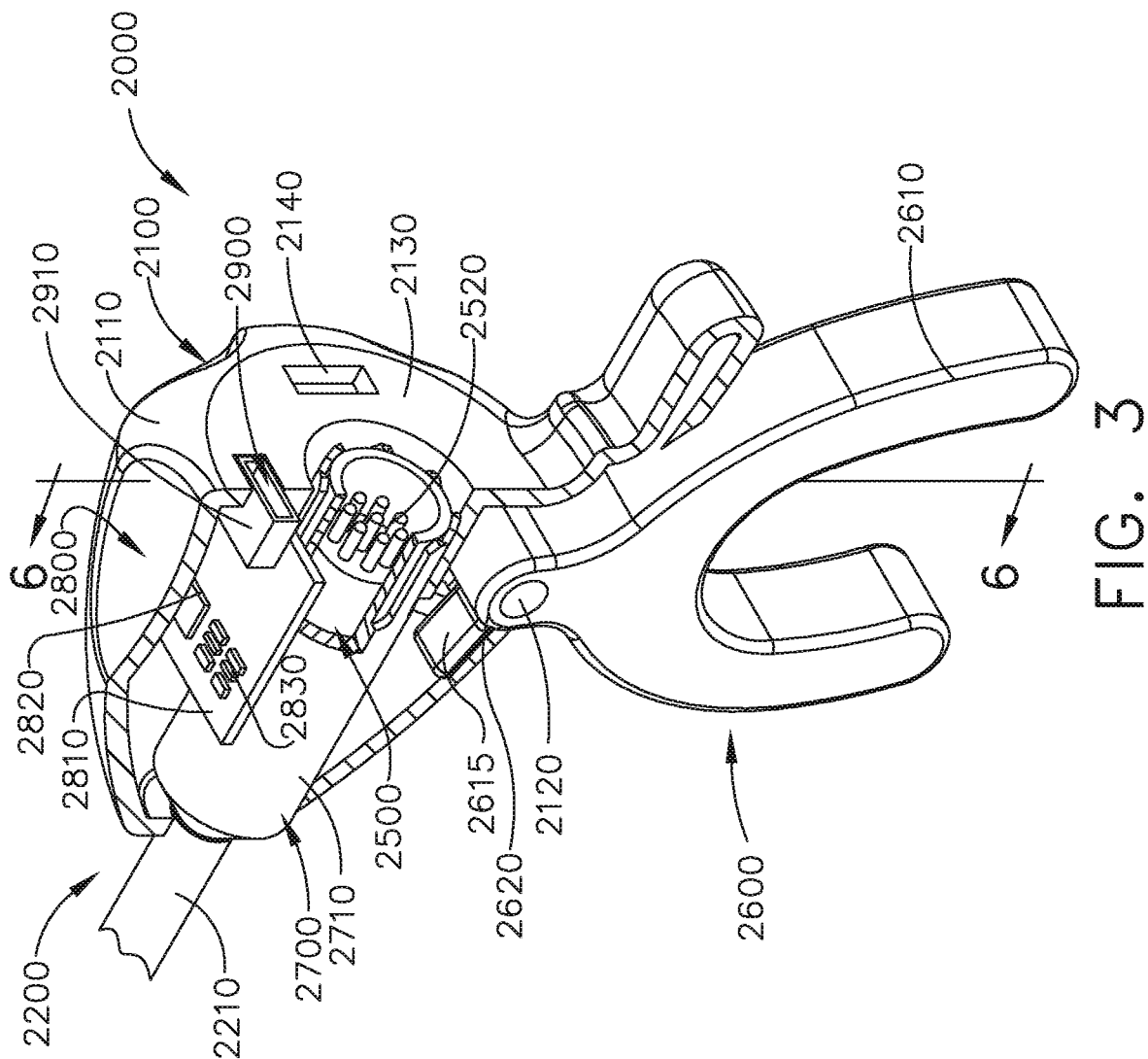
FIG. 3 is a partial cross-sectional perspective view of the shaft assembly of FIG. 2.
Figure 4:
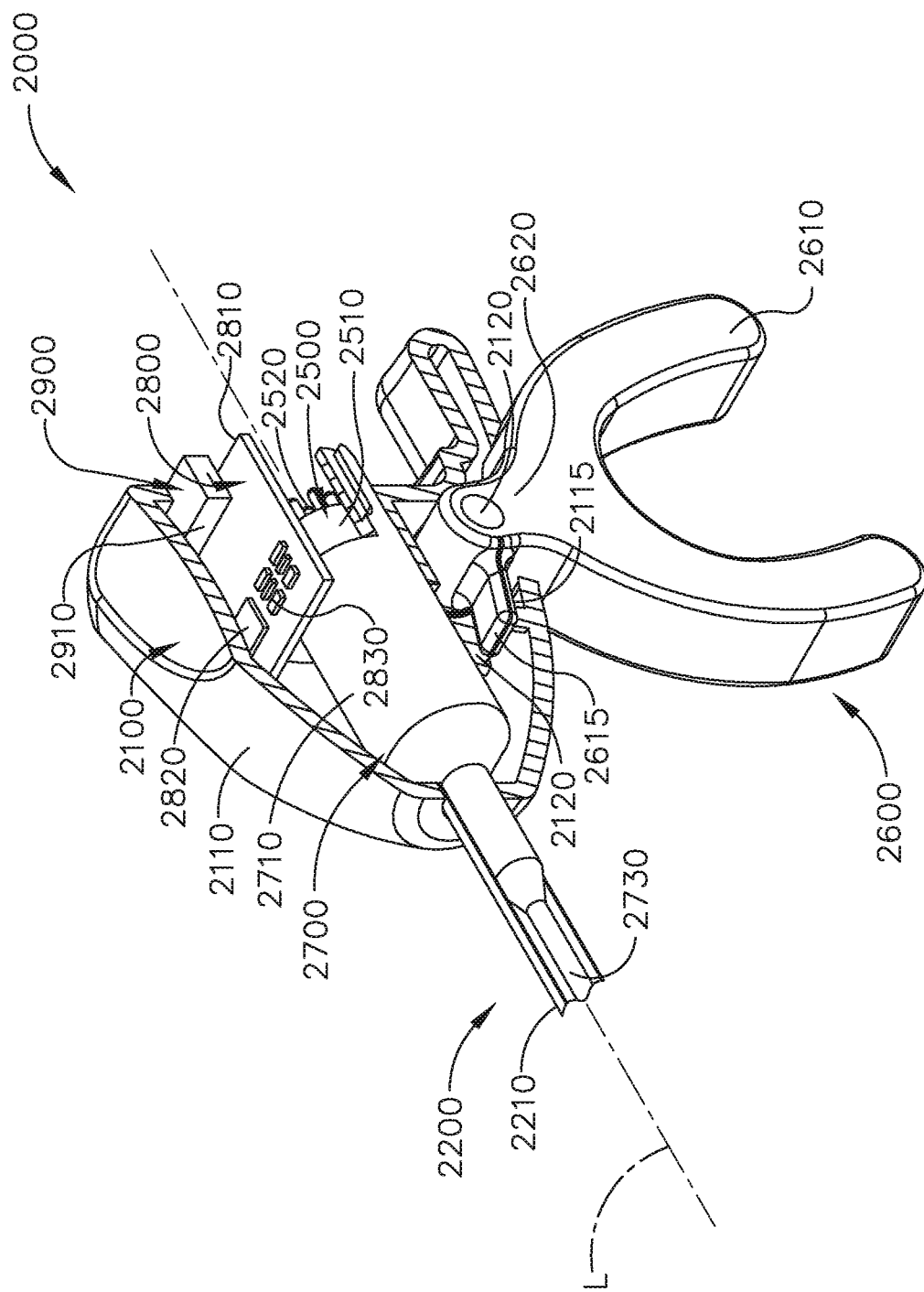
FIG. 4 is another partial cross-sectional perspective view of the shaft assembly of FIG. 2.
Figure 45:
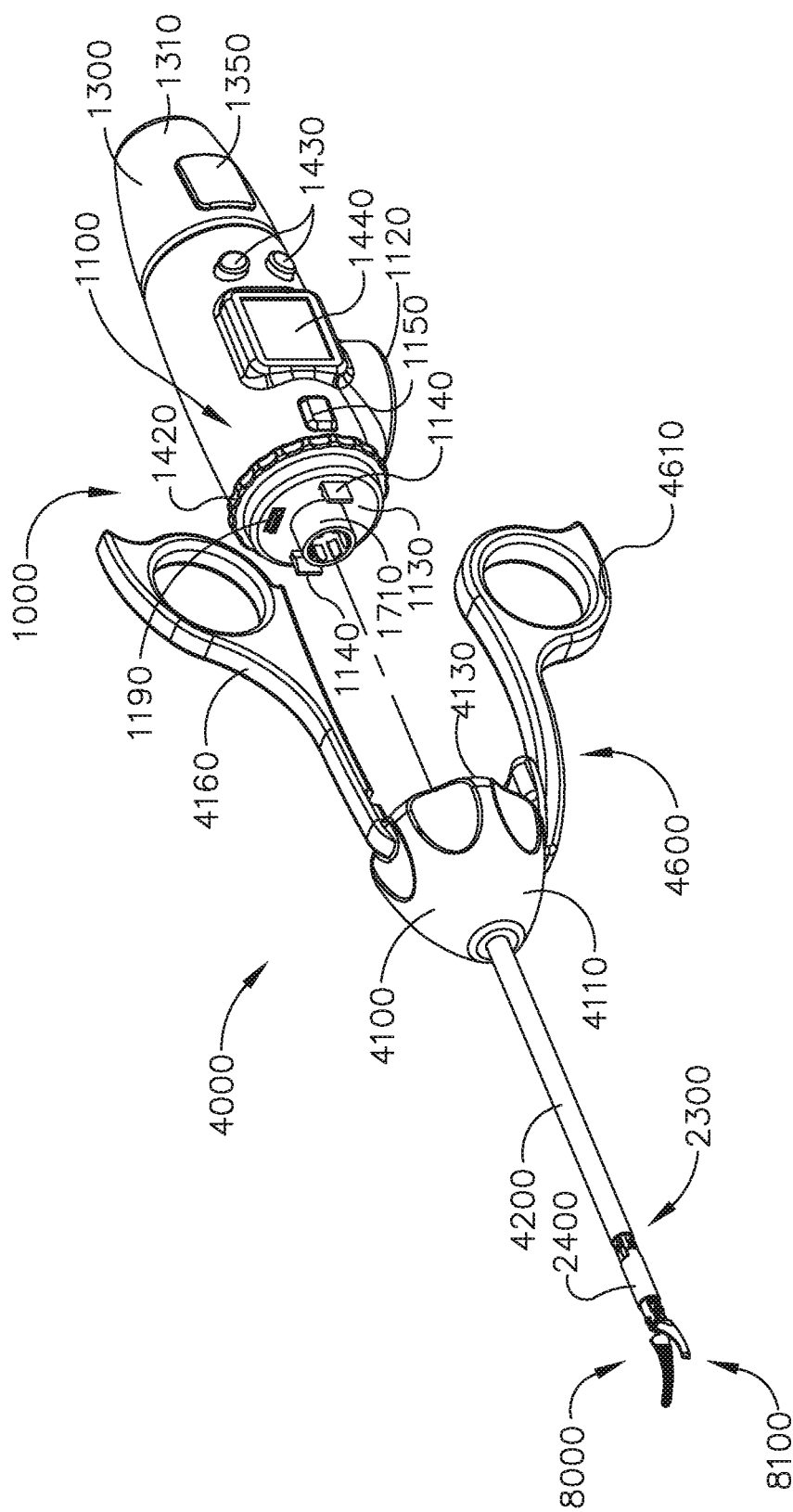
FIG. 45 is a perspective view of the handle drive module of FIG. 7 and one of the shaft assemblies of the surgical system of FIG. 1.
Figure 46:
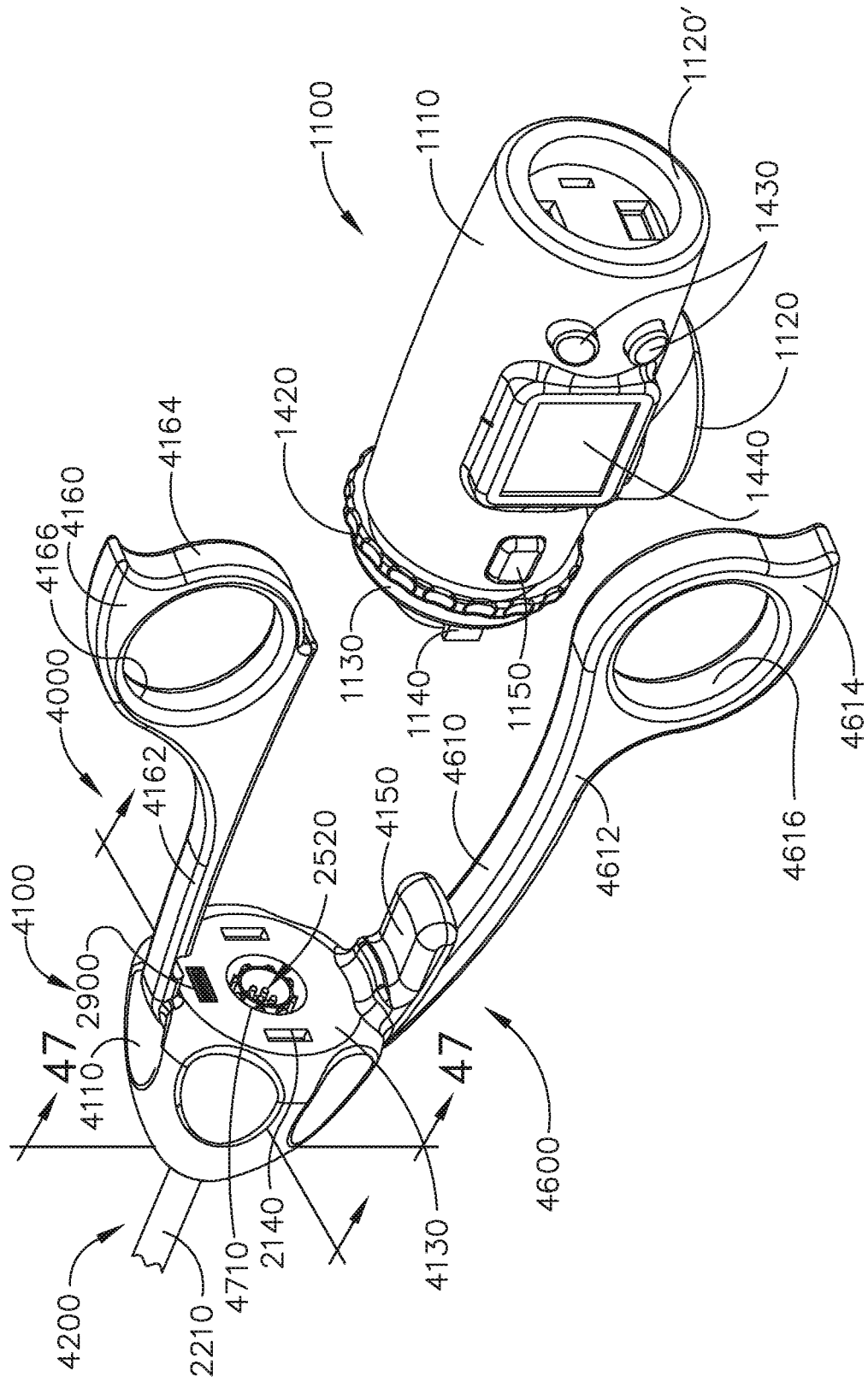
FIG. 46 is another perspective view of the handle drive module of FIG. 7 and the shaft assembly of FIG. 45.

A surgical instrument system is depicted in FIG. 1. The surgical instrument system comprises a handle assembly 1000 which is selectively usable with a shaft assembly 2000, a shaft assembly 3000, a shaft assembly 4000, a shaft assembly 5000, and/or any other suitable shaft assembly. The shaft assembly 2000 is attached to the handle assembly 1000 in FIG. 2 and the shaft assembly 4000 is attached to the handle assembly 1000 in FIG. 45. The shaft assembly 2000 comprises a proximal portion 2100, an elongate shaft 2200 extending from the proximal portion 2100, a distal attachment portion 2400, and an articulation joint 2300 rotatably connecting the distal attachment portion 2400 to the elongate shaft 2200. The shaft assembly 2000 further comprises a replaceable end effector assembly 7000 attached to the distal attachment portion 2400. The replaceable end effector assembly 7000 comprises a jaw assembly 7100 configured to be opened and closed to clamp and/or manipulate the tissue of a patient. In use, the end effector assembly 7000 can be articulated about the articulation joint 2300 and/or rotated relative to the distal attachment portion 2400 about a longitudinal axis to better position the jaw assembly 7100 within the patient, as described in greater detail further below.

Referring again to FIG. 1, the handle assembly 1000 comprises, among other things, a drive module 1100. As described in greater detail below, the drive module 1100 comprises a distal mounting interface which permits a clinician to selectively attach one of the shaft assemblies 2000, 3000, 4000, and 5000, for example, to the drive module 1100. Thus, each of the shaft assemblies 2000, 3000, 4000, and 5000 comprises an identical, or an at least similar, proximal mounting interface which is configured to engage the distal mounting interface of the drive module 1100. As also described in greater detail below, the mounting interface of the drive module 1100 mechanically secures and electrically couples the selected shaft assembly to the drive module 1100. The drive module 1100 further comprises at least one electric motor, one or more controls and/or displays, and a controller configured to operate the electric motor—the rotational output of which is transmitted to a drive system of the shaft assembly attached to the drive module 1100. Moreover, the drive module 1100 is usable with one ore more power modules, such as power modules 1200 and 1300, for example, which are operably attachable to the drive module 1100 to supply power thereto.

Further to the above, referring again to FIGS. 1 and 2, the handle drive module 1100 comprises a housing 1110, a first module connector 1120, and a second module connector 1120'. The power module 1200 comprises a housing 1210, a connector 1220, one or more release latches 1250, and one or more batteries 1230. The connector 1220 is configured to be engaged with the first module connector 1120 of the drive module 1100 in order to attach the power module 1200 to the drive module 1100. The connector 1220 comprises one or more latches 1240 which mechanically couple and fixedly secure the housing 1210 of the power module 1200 to the housing 1110 of the drive module 1100. The latches 1240 are movable into disengaged positions when the release latches 1250 are depressed so that the power module 1200 can be detached from the drive module 1100. The connector 1220 also comprises one or more electrical contacts which place the batteries 1230, and/or an electrical circuit including the batteries 1230, in electrical communication with an electrical circuit in the drive module 1100.

Figure 47:
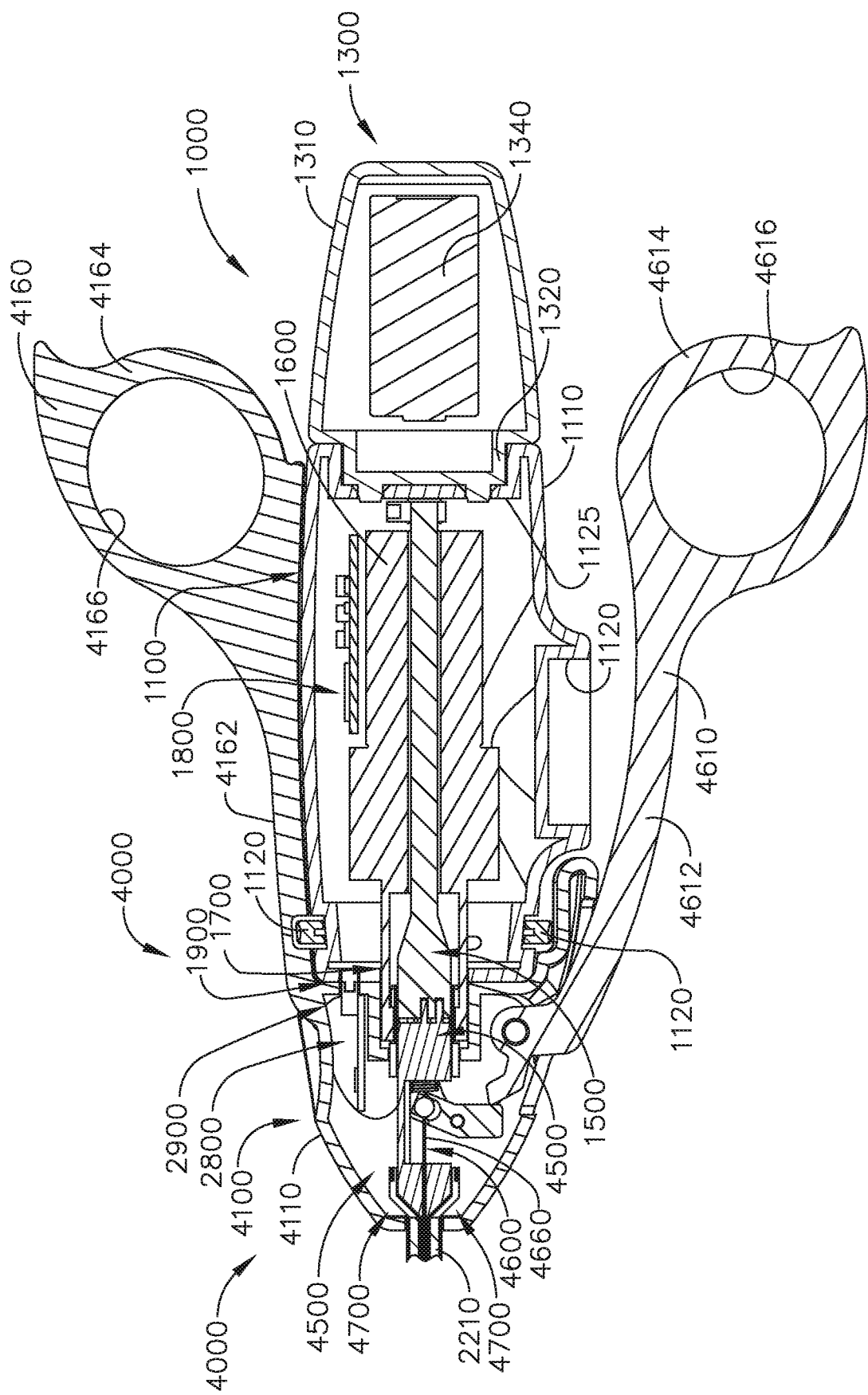
FIG. 47 is a partial cross-sectional view of the shaft assembly of FIG. 45 attached to the handle of FIG. 1.

Further to the above, referring again to FIGS. 1 and 2, the power module 1300 comprises a housing 1310, a connector 1320, one or more release latches 1350, and one or more batteries 1330 (FIG. 47). The connector 1320 is configured to be engaged with the second module connector 1120' of the drive module 1100 to attach the power module 1300 to the drive module 1100. The connector 1320 comprises one or more latches 1340 which mechanically couple and fixedly secure the housing 1310 of the power module 1300 to the housing 1110 of the drive module 1100. The latches 1340 are movable into disengaged positions when the release latches 1350 are depressed so that the power module 1300 can be detached from the drive module 1100. The connector 1320 also comprises one or more electrical contacts which place the batteries 1330 of the power module 1300, and/or an electrical power circuit including the batteries 1330, in electrical communication with an electrical power circuit in the drive module 1100.

Further to the above, the power module 1200, when attached to the drive module 1100, comprises a pistol grip which can allow a clinician to hold the handle 1000 in a manner which places the drive module 1100 on top of the clinician's hand. The power module 1300, when attached to the drive module 1100, comprises an end grip which allows a clinician to hold the handle 1000 like a wand. The power module 1200 is longer than the power module 1300, although the power modules 1200 and 1300 can comprise any suitable length. The power module 1200 has more battery cells than the power module 1300 and can suitably accommodate these additional battery cells owing to its length. In various instances, the power module 1200 can provide more power to the drive module 1100 than the power module 1300 while, in some instances, the power module 1200 can provide power for a longer period of time. In some instances, the housing 1110 of the drive module 1100 comprises keys, and/or any other suitable features, which prevent the power module 1200 from being connected to the second module connector 1120' and, similarly, prevent the power module 1300 from being connected to the first module connector 1120. Such an arrangement can assure that the longer power module 1200 is used in the pistol grip arrangement and that the shorter power module 1300 is used in the wand grip arrangement. In alternative embodiments, the power module 1200 and the power module 1300 can be selectively coupled to the drive module 1100 at either the first module connector 1120 or the second module connector 1120'. Such embodiments provide a clinician with more options to customize the handle 1000 in a manner suitable to them.

In various instances, further to the above, only one of the power modules 1200 and 1300 is coupled to the drive module 1100 at a time. In certain instances, the power module 1200 can be in the way when the shaft assembly 4000, for example, is attached to the drive module 1100. Alternatively, both of the power modules 1200 and 1300 can be operably coupled to the drive module 1100 at the same time. In such instances, the drive module 1100 can have access to power provided by both of the power modules 1200 and 1300. Moreover, a clinician can switch between a pistol grip and a wand grip when both of the power modules 1200 and 1300 are attached to the drive module 1100. Moreover, such an arrangement allows the power module 1300 to act as a counterbalance to a shaft assembly, such as shaft assemblies 2000, 3000, 4000, or 5000, for example, attached to the drive module 1100.

Figure 7:
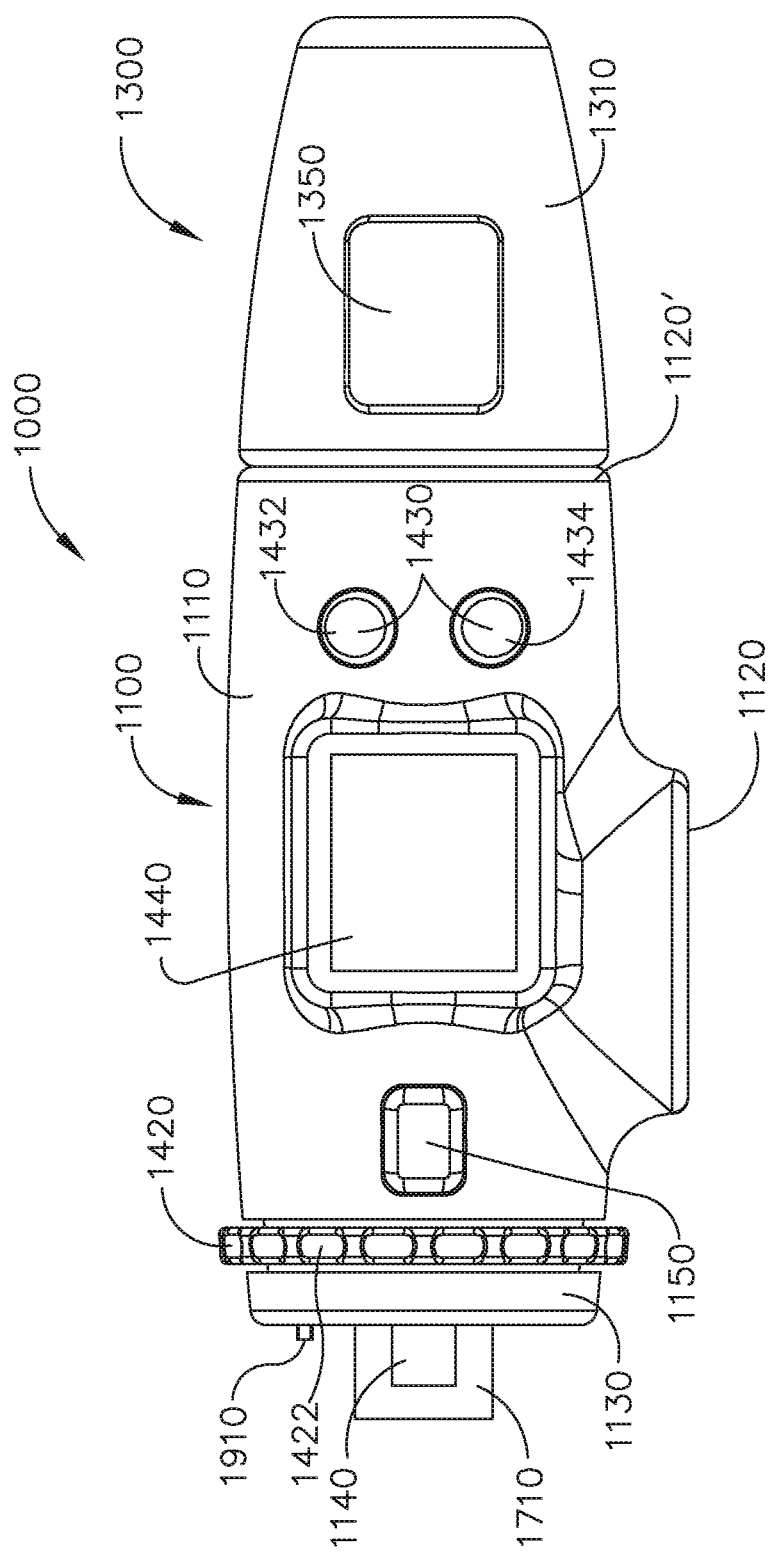
FIG. 7 is an elevational view of a drive module of the handle of FIG. 1.
Figure 8:
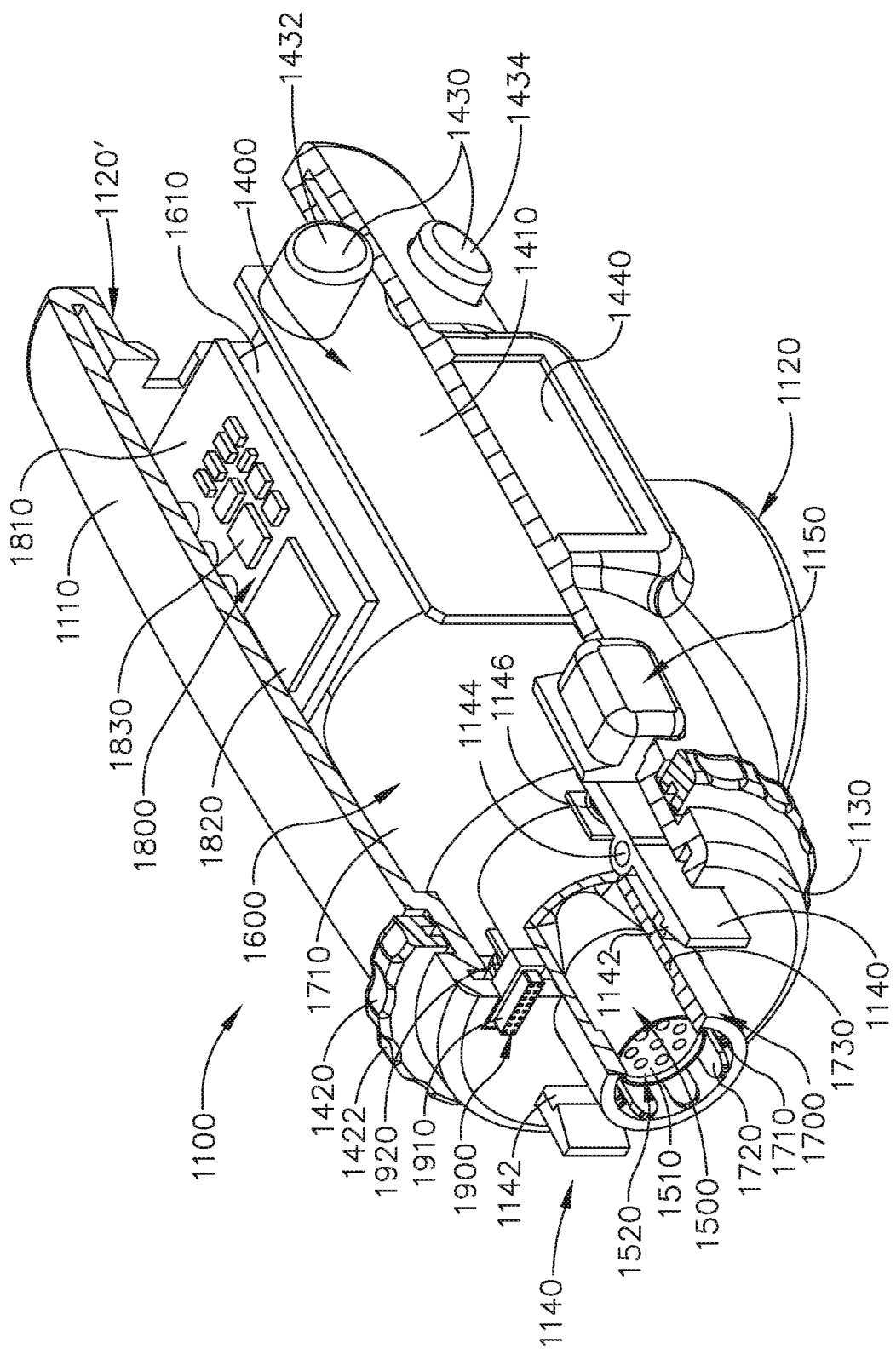
FIG. 8 is a cross-sectional perspective view of the drive module of FIG. 7.
Figure 9:
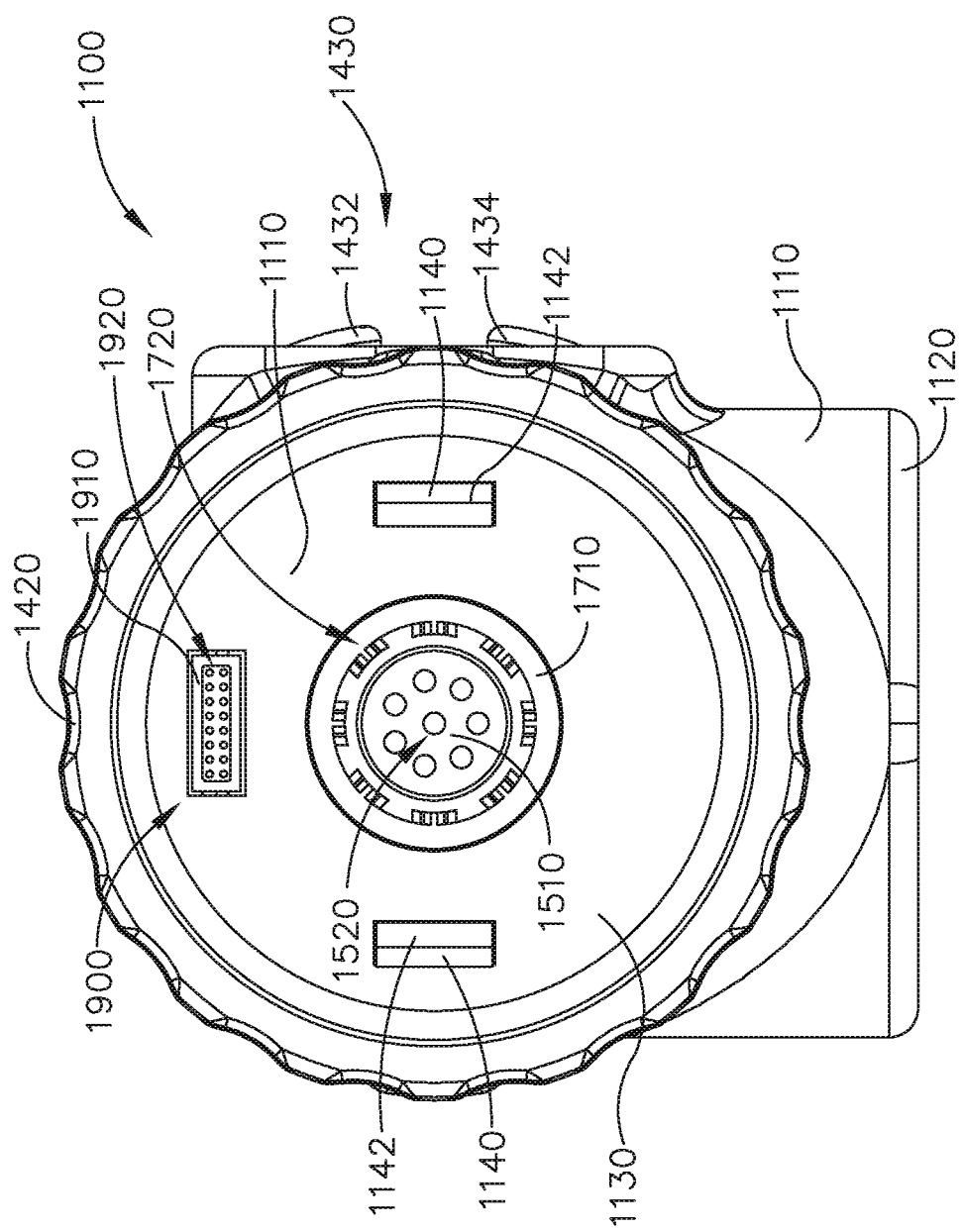
FIG. 9 is an end view of the drive module of FIG. 7.

Referring to FIGS. 7 and 8, the handle drive module 1100 further comprises a frame 1500, a motor assembly 1600, a drive system 1700 operably engaged with the motor assembly 1600, and a control system 1800. The frame 1500 comprises an elongate shaft that extends through the motor assembly 1600. The elongate shaft comprises a distal end 1510 and electrical contacts, or sockets, 1520 defined in the distal end 1510. The electrical contacts 1520 are in electrical communication with the control system 1800 of the drive module 1100 via one or more electrical circuits and are configured to convey signals and/or power between the control system 1800 and the shaft assembly, such as the shaft assembly 2000, 3000, 4000, or 5000, for example, attached to the drive module 1100. The control system 1800 comprises a printed circuit board (PCB) 1810, at least one microprocessor 1820, and at least one memory device 1830. The board 1810 can be rigid and/or flexible and can comprise any suitable number of layers. The microprocessor 1820 and the memory device 1830 are part of a control circuit defined on the board 1810 which controls the operation of the motor assembly 1600, as described in greater detail below.

Figure 12:
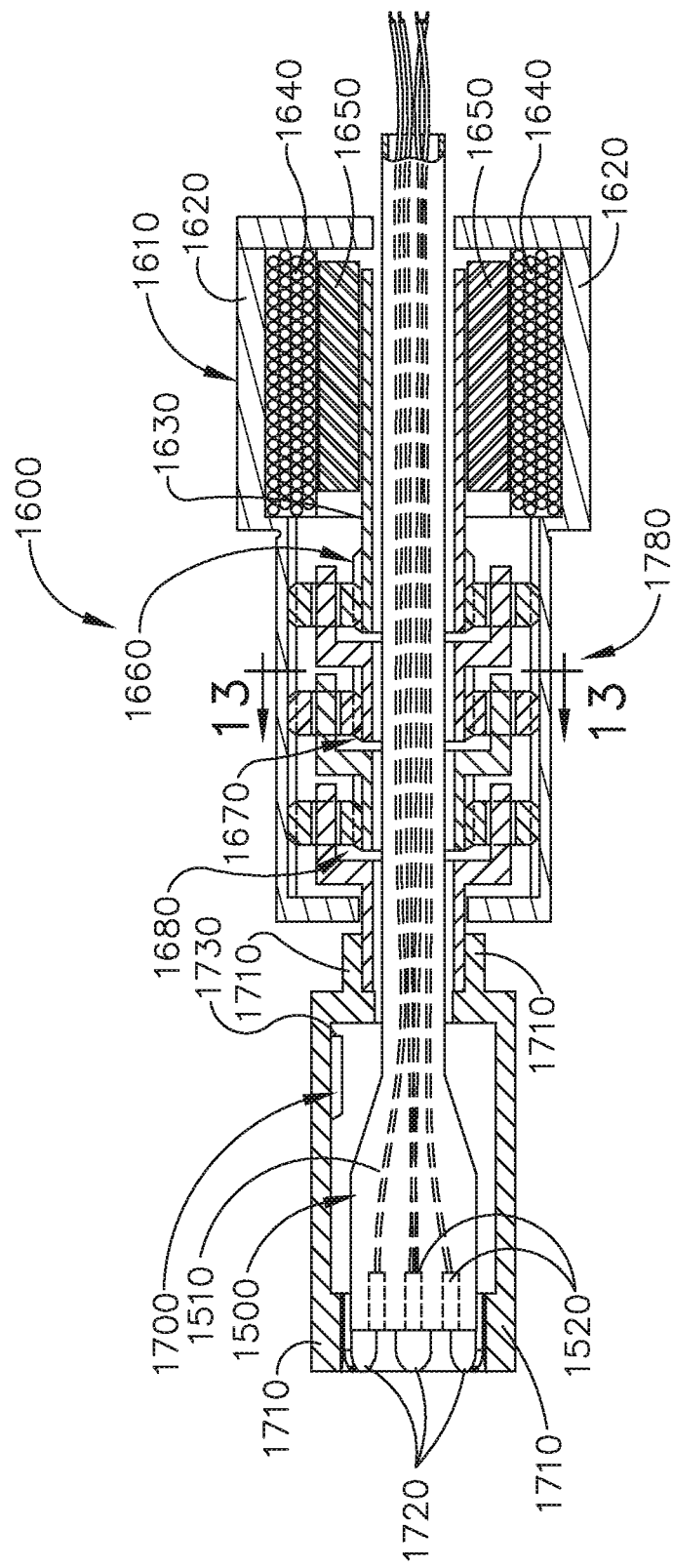
FIG. 12 is a cross-sectional perspective view of a motor and a speed reduction gear assembly of the drive module of FIG. 7.
Figure 13:
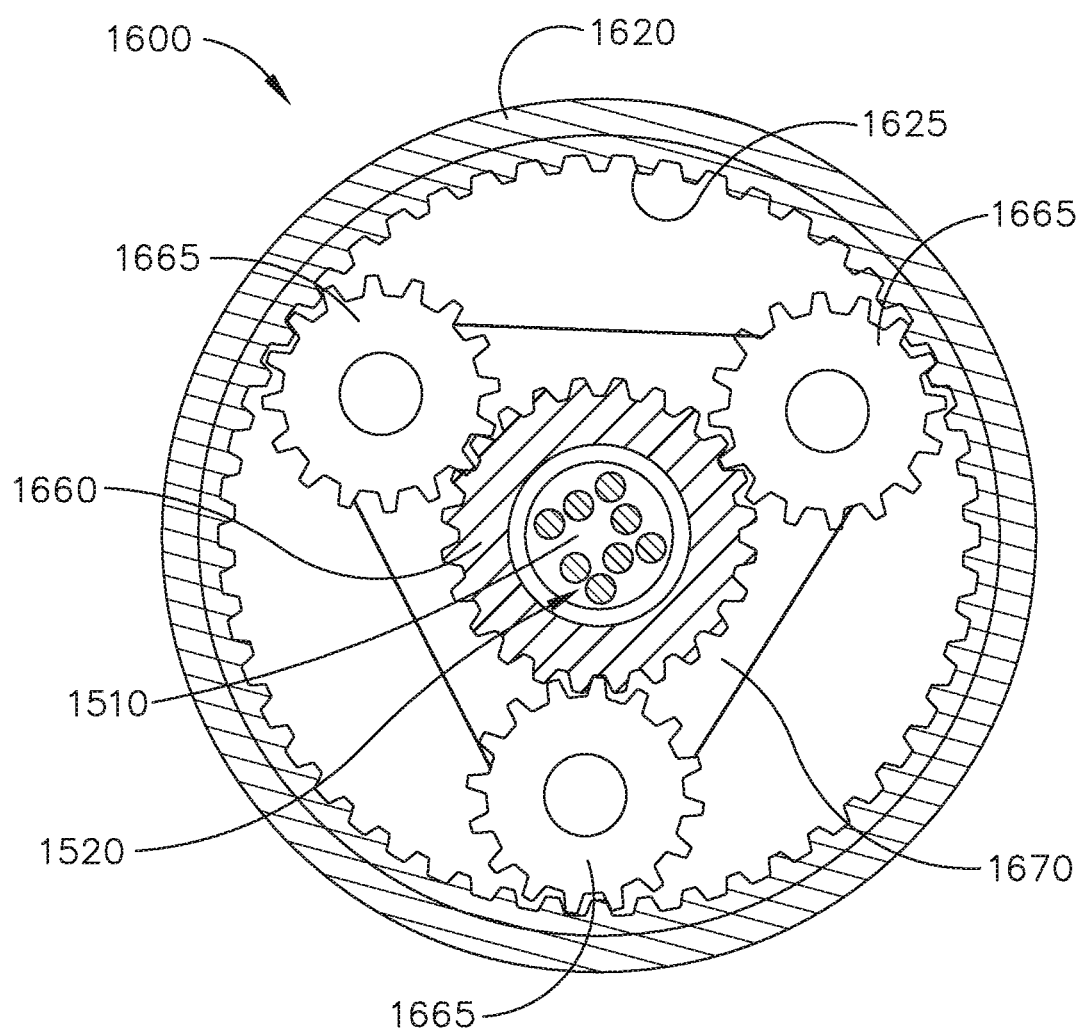
FIG. 13 is an end view of the speed reduction gear assembly of FIG. 12.
Figure 14:
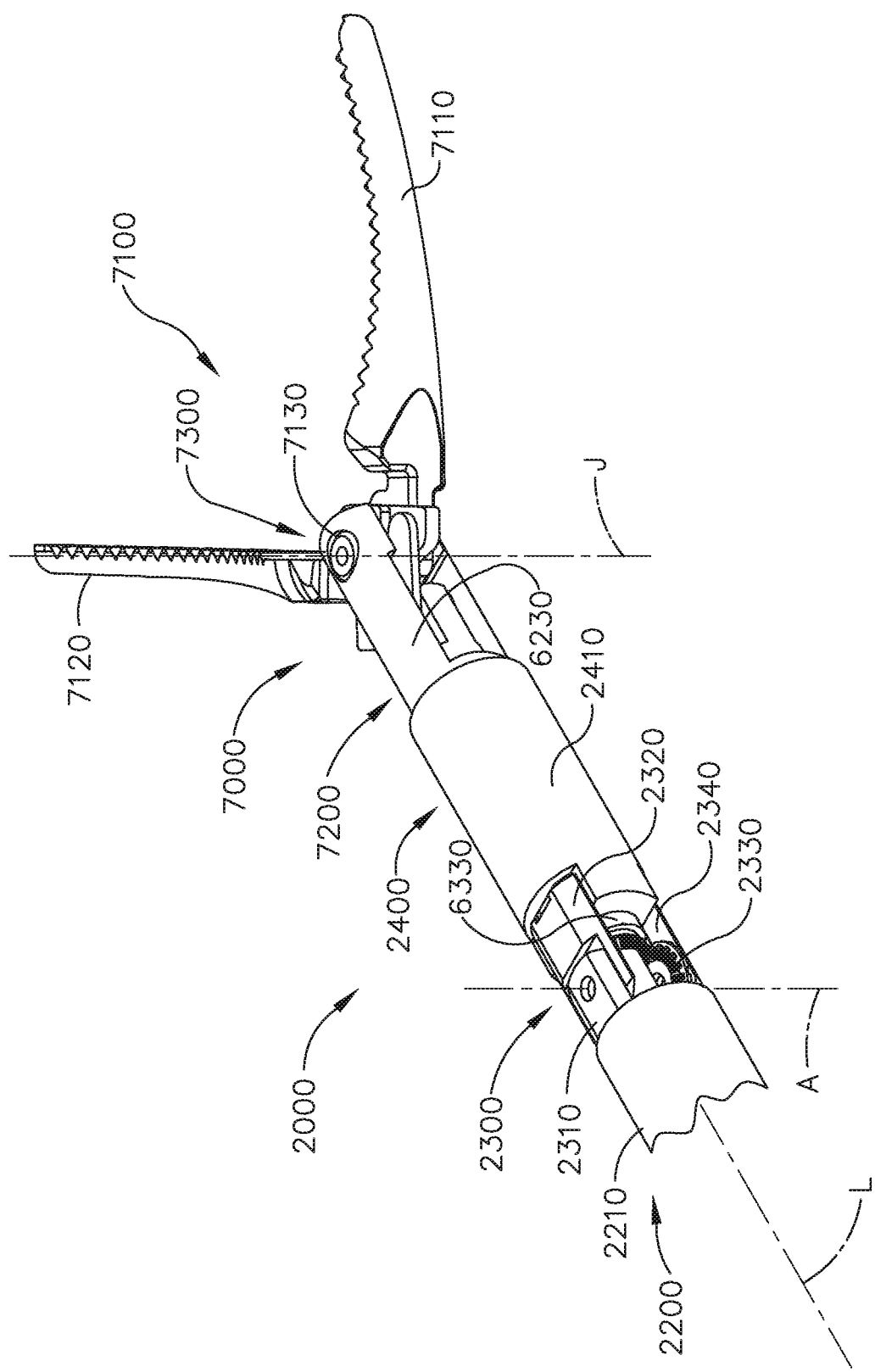
FIG. 14 is a partial perspective view of an end effector of the shaft assembly of FIG. 2 in an open configuration.

Referring to FIGS. 12 and 13, the motor assembly 1600 comprises an electric motor 1610 including a housing 1620, a drive shaft 1630, and a gear reduction system. The electric motor 1610 further comprises a stator including windings 1640 and a rotor including magnetic elements 1650. The stator windings 1640 are supported in the housing 1620 and the rotor magnetic elements 1650 are mounted to the drive shaft 1630. When the stator windings 1640 are energized with an electric current controlled by the control system 1800, the drive shaft 1630 is rotated about a longitudinal axis. The drive shaft 1630 is operably engaged with a first planetary gear system 1660 which includes a central sun gear and several planetary gears operably intermeshed with the sun gear. The sun gear of the first planetary gear system 1660 is fixedly mounted to the drive shaft 1630 such that it rotates with the drive shaft 1630. The planetary gears of the first planetary gear system 1660 are rotatably mounted to the sun gear of a second planetary gear system 1670 and, also, intermeshed with a geared or splined inner surface 1625 of the motor housing 1620. As a result of the above, the rotation of the first sun gear rotates the first planetary gears which rotate the second sun gear. Similar to the above, the second planetary gear system 1670 further comprises planetary gears 1665 (FIG. 13) which drive a third planetary gear system and, ultimately, the drive shaft 1710. The planetary gear systems 1660, 1670, and 1680 co-operate to gear down the speed applied to the drive shaft 1710 by the motor shaft 1620. Various alternative embodiments are envisioned without a speed reduction system. Such embodiments are suitable when it is desirable to drive the end effector functions quickly. Notably, the drive shaft 1630 comprises an aperture, or hollow core, extending therethrough through which wires and/or electrical circuits can extend.

The control system 1800 is in communication with the motor assembly 1600 and the electrical power circuit of the drive module 1100. The control system 1800 is configured to control the power delivered to the motor assembly 1600 from the electrical power circuit. The electrical power circuit is configured to supply a constant, or at least nearly constant, direct current (DC) voltage. In at least one instance, the electrical power circuit supplies 3 VDC to the control system 1800. The control system 1800 comprises a pulse width modulation (PWM) circuit which is configured to deliver voltage pulses to the motor assembly 1600. The duration or width of the voltage pulses, and/or the duration or width between the voltage pulses, supplied by the PWM circuit can be controlled in order to control the power applied to the motor assembly 1600. By controlling the power applied to the motor assembly 1600, the PWM circuit can control the speed of the output shaft of the motor assembly 1600. In addition to or in lieu of a PWM circuit, the control system 1800 can include a frequency modulation (FM) circuit. As discussed in greater detail below, the control system 1800 is operable in more than one operating mode and, depending on the operating mode being used, the control system 1800 can operate the motor assembly 1600 at a speed, or a range of speeds, which is determined to be appropriate for that operating mode.

Further to the above, referring again to FIGS. 7 and 8, the drive system 1700 comprises a rotatable shaft 1710 comprising a splined distal end 1720 and a longitudinal aperture 1730 defined therein. The rotatable shaft 1710 is operably mounted to the output shaft of the motor assembly 1600 such that the rotatable shaft 1710 rotates with the motor output shaft. The handle frame 1510 extends through the longitudinal aperture 1730 and rotatably supports the rotatable shaft 1710. As a result, the handle frame 1510 serves as a bearing for the rotatable shaft 1710. The handle frame 1510 and the rotatable shaft 1710 extend distally from a mounting interface 1130 of the drive module 1110 and are coupled with corresponding components on the shaft assembly 2000 when the shaft assembly 2000 is assembled to the drive module 1100. Referring primarily to FIGS. 3-6, the shaft assembly 2000 further comprises a frame 2500 and a drive system 2700. The frame 2500 comprises a longitudinal shaft 2510 extending through the shaft assembly 2000 and a plurality of electrical contacts, or pins, 2520 extending proximally from the shaft 2510. When the shaft assembly 2000 is attached to the drive module 1100, the electrical contacts 2520 on the shaft frame 2510 engage the electrical contacts 1520 on the handle frame 1510 and create electrical pathways therebetween.

Similar to the above, the drive system 2700 comprises a rotatable drive shaft 2710 which is operably coupled to the rotatable drive shaft 1710 of the handle 1000 when the shaft assembly 2000 is assembled to the drive module 1100 such that the drive shaft 2710 rotates with the drive shaft 1710. To this end, the drive shaft 2710 comprises a splined proximal end 2720 which mates with the splined distal end 1720 of the drive shaft 1710 such that the drive shafts 1710 and 2710 rotate together when the drive shaft 1710 is rotated by the motor assembly 1600. Given the nature of the splined interconnection between the drive shafts 1710 and 2710 and the electrical interconnection between the frames 1510 and 2510, the shaft assembly 2000 is assembled to the handle 1000 along a longitudinal axis; however, the operable interconnection between the drive shafts 1710 and 2710 and the electrical interconnection between the frames 1510 and 2510 can comprise any suitable configuration which can allow a shaft assembly to be assembled to the handle 1000 in any suitable manner.

Figure 10:
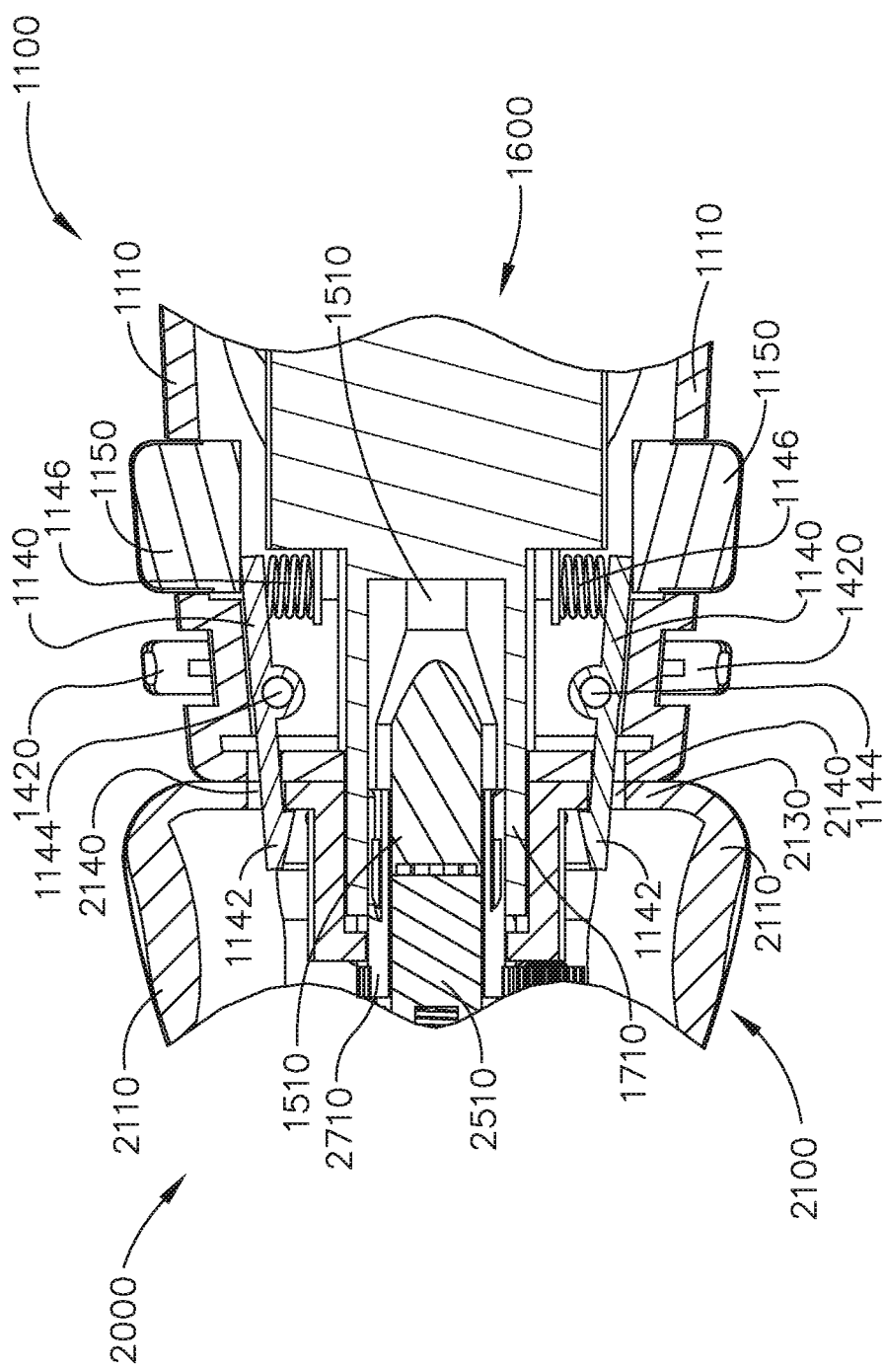
FIG. 10 is a partial cross-sectional view of the interconnection between the handle and shaft assembly of FIG. 2 in a locked configuration.
Figure 11:
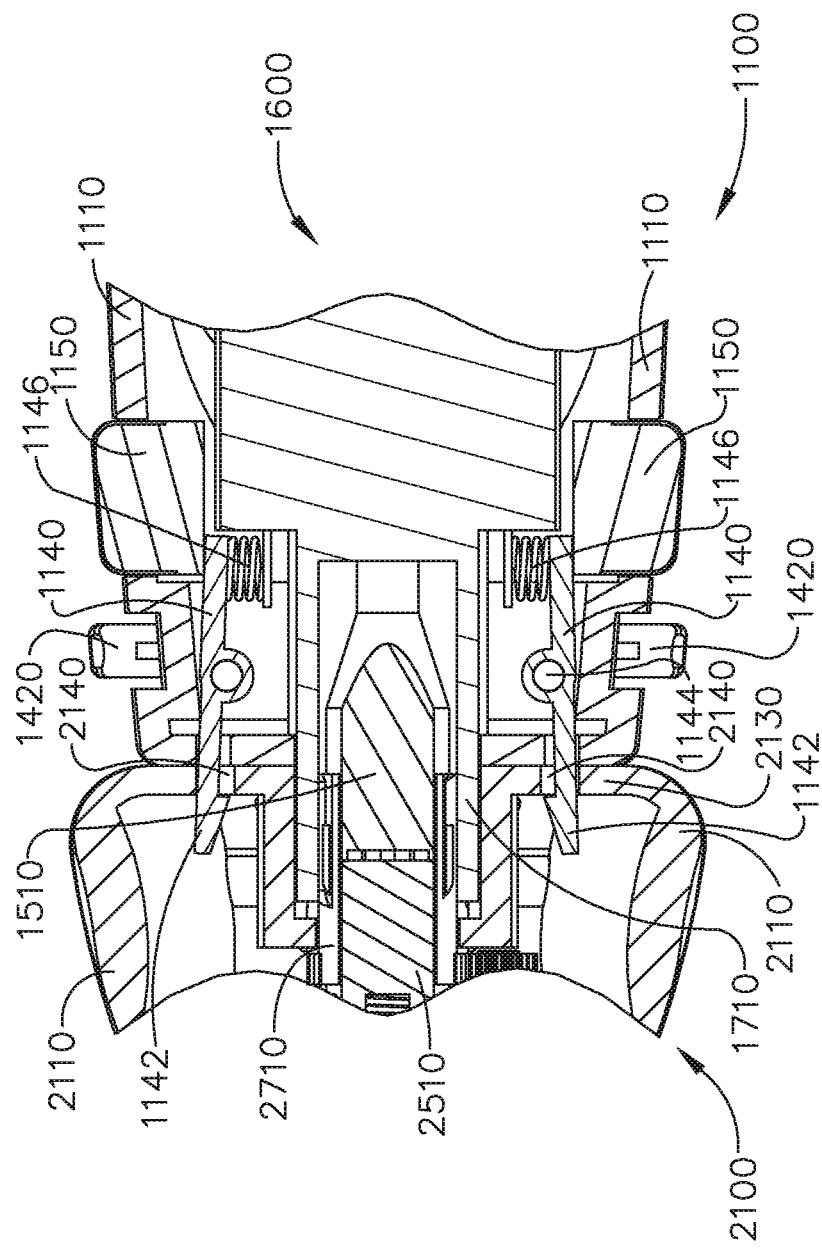
FIG. 11 is a partial cross-sectional view of the interconnection between the handle and shaft assembly of FIG. 2 in an unlocked configuration.

As discussed above, referring to FIGS. 3-8, the mounting interface 1130 of the drive module 1110 is configured to be coupled to a corresponding mounting interface on the shaft assemblies 2000, 3000, 4000, and 5000, for example. For instance, the shaft assembly 2000 comprises a mounting interface 2130 configured to be coupled to the mounting interface 1130 of the drive module 1100. More specifically, the proximal portion 2100 of the shaft assembly 2000 comprises a housing 2110 which defines the mounting interface 2130. Referring primarily to FIG. 8, the drive module 1100 comprises latches 1140 which are configured to releasably hold the mounting interface 2130 of the shaft assembly 2000 against the mounting interface 1130 of the drive module 1100. When the drive module 1100 and the shaft assembly 2000 are brought together along a longitudinal axis, as described above, the latches 1140 contact the mounting interface 2130 and rotate outwardly into an unlocked position. Referring primarily to FIGS. 8, 10, and 11, each latch 1140 comprises a lock end 1142 and a pivot portion 1144. The pivot portion 1144 of each latch 1140 is rotatably coupled to the housing 1110 of the drive module 1100 and, when the latches 1140 are rotated outwardly, as mentioned above, the latches 1140 rotate about the pivot portions 1144. Notably, each latch 1140 further comprises a biasing spring 1146 configured to bias the latches 1140 inwardly into a locked position. Each biasing spring 1146 is compressed between a latch 1140 and the housing 1110 of the drive module 1100 such that the biasing springs 1146 apply biasing forces to the latches 1140; however, such biasing forces are overcome when the latches 1140 are rotated outwardly into their unlocked positions by the shaft assembly 2000. That said, when the latches 1140 rotate outwardly after contacting the mounting interface 2130, the lock ends 1142 of the latches 1140 can enter into latch windows 2140 defined in the mounting interface 2130. Once the lock ends 1142 pass through the latch windows 2140, the springs 1146 can bias the latches 1140 back into their locked positions. Each lock end 1142 comprises a lock shoulder, or surface, which securely holds the shaft assembly 2000 to the drive module 1100.

Further to the above, the biasing springs 1146 hold the latches 1140 in their locked positions. The distal ends 1142 are sized and configured to prevent, or at least inhibit, relative longitudinal movement, i.e., translation along a longitudinal axis, between the shaft assembly 2000 and the drive module 1100 when the latches 1140 are in their locked positions. Moreover, the latches 1140 and the latch windows 1240 are sized and configured to prevent relative lateral movement, i.e., translation transverse to the longitudinal axis, between the shaft assembly 2000 and the drive module 1100. In addition, the latches 1140 and the latch windows 2140 are sized and configured to prevent the shaft assembly 2000 from rotating relative to the drive module 1100. The drive module 1100 further comprises release actuators 1150 which, when depressed by a clinician, move the latches 1140 from their locked positions into their unlocked positions. The drive module 1100 comprises a first release actuator 1150 slideably mounted in an opening defined in the first side of the handle housing 1110 and a second release actuator 1150 slideably mounted in an opening defined in a second, or opposite, side of the handle housing 1110. Although the release actuators 1150 are actuatable separately, both release actuators 1150 typically need to be depressed to completely unlock the shaft assembly 2000 from the drive module 1100 and allow the shaft assembly 2000 to be detached from the drive module 1100. That said, it is possible that the shaft assembly 2000 could be detached from the drive module 1100 by depressing only one release actuator 1150.

Once the shaft assembly 2000 has been secured to the handle 1000 and the end effector 7000, for example, has been assembled to the shaft 2000, the clinician can maneuver the handle 1000 to insert the end effector 7000 into a patient. In at least one instance, the end effector 7000 is inserted into the patient through a trocar and then manipulated in order to position the jaw assembly 7100 of the end effector assembly 7000 relative to the patient's tissue. Oftentimes, the jaw assembly 7100 must be in its closed, or clamped, configuration in order to fit through the trocar. Once through the trocar, the jaw assembly 7100 can be opened so that the patient tissue fit between the jaws of the jaw assembly 7100. At such point, the jaw assembly 7100 can be returned to its closed configuration to clamp the patient tissue between the jaws. The clamping force applied to the patient tissue by the jaw assembly 7100 is sufficient to move or otherwise manipulate the tissue during a surgical procedure. Thereafter, the jaw assembly 7100 can be re-opened to release the patient tissue from the end effector 7000. This process can be repeated until it is desirable to remove the end effector 7000 from the patient. At such point, the jaw assembly 7100 can be returned to its closed configuration and retracted through the trocar. Other surgical techniques are envisioned in which the end effector 7000 is inserted into a patient through an open incision, or without the use of the trocar. In any event, it is envisioned that the jaw assembly 7100 may have to be opened and closed several times throughout a surgical technique.

Referring again to FIGS. 3-6, the shaft assembly 2000 further comprises a clamping trigger system 2600 and a control system 2800. The clamping trigger system 2600 comprises a clamping trigger 2610 rotatably connected to the proximal housing 2110 of the shaft assembly 2000. As discussed below, the clamping trigger 2610 actuates the motor 1610 to operate the jaw drive of the end effector 7000 when the clamping trigger 2610 is actuated. The clamping trigger 2610 comprises an elongate portion which is graspable by the clinician while holding the handle 1000. The clamping trigger 2610 further comprises a mounting portion 2620 which is pivotably connected to a mounting portion 2120 of the proximal housing 2110 such that the clamping trigger 2610 is rotatable about a fixed, or an at least substantially fixed, axis. The closure trigger 2610 is rotatable between a distal position and a proximal position, wherein the proximal position of the closure trigger 2610 is closer to the pistol grip of the handle 1000 than the distal position. The closure trigger 2610 further comprises a tab 2615 extending therefrom which rotates within the proximal housing 2110. When the closure trigger 2610 is in its distal position, the tab 2615 is positioned above, but not in contact with, a switch 2115 mounted on the proximal housing 2110. The switch 2115 is part of an electrical circuit configured to detect the actuation of the closure trigger 2610 which is in an open condition the closure trigger 2610 is in its open position. When the closure trigger 2610 is moved into its proximal position, the tab 2615 comes into contact with the switch 2115 and closes the electrical circuit. In various instances, the switch 2115 can comprise a toggle switch, for example, which is mechanically switched between open and closed states when contacted by the tab 2615 of the closure trigger 2610. In certain instances, the switch 2115 can comprise a proximity sensor, for example, and/or any suitable type of sensor. In at least one instance, the switch 2115 comprises a Hall Effect sensor which can detect the amount in which the closure trigger 2610 has been rotated and, based on the amount of rotation, control the speed in which the motor 1610 is operated. In such instances, larger rotations of the closure trigger 2610 result in faster speeds of the motor 1610 while smaller rotations result in slower speeds, for example. In any event, the electrical circuit is in communication with the control system 2800 of the shaft assembly 2000, which is discussed in greater detail below.

Further to the above, the control system 2800 of the shaft assembly 2000 comprises a printed circuit board (PCB) 2810, at least one microprocessor 2820, and at least one memory device 2830. The board 2810 can be rigid and/or flexible and can comprise any suitable number of layers. The microprocessor 2820 and the memory device 2830 are part of a control circuit defined on the board 2810 which communicates with the control system 1800 of the handle 1000. The shaft assembly 2000 further comprises a signal communication system 2900 and the handle 1000 further comprises a signal communication system 1900 which are configured to convey data between the shaft control system 2800 and the handle control system 1800. The signal communication system 2900 is configured to transmit data to the signal communication system 1900 utilizing any suitable analog and/or digital components. In various instances, the communication systems 2900 and 1900 can communicate using a plurality of discrete channels which allows the input gates of the microprocessor 1820 to be directly controlled, at least in part, by the output gates of the microprocessor 2820. In some instances, the communication systems 2900 and 1900 can utilize multiplexing. In at least one such instance, the control system 2900 includes a multiplexing device that sends multiple signals on a carrier channel at the same time in the form of a single, complex signal to a multiplexing device of the control system 1900 that recovers the separate signals from the complex signal.

The communication system 2900 comprises an electrical connector 2910 mounted to the circuit board 2810. The electrical connector 2910 comprises a connector body and a plurality of electrically-conductive contacts mounted to the connector body. The electrically-conductive contacts comprise male pins, for example, which are soldered to electrical traces defined in the circuit board 2810. In other instances, the male pins can be in communication with circuit board traces through zero-insertion-force (ZIF) sockets, for example. The communication system 1900 comprises an electrical connector 1910 mounted to the circuit board 1810. The electrical connector 1910 comprises a connector body and a plurality of electrically-conductive contacts mounted to the connector body. The electrically-conductive contacts comprise female pins, for example, which are soldered to electrical traces defined in the circuit board 1810. In other instances, the female pins can be in communication with circuit board traces through zero-insertion-force (ZIF) sockets, for example. When the shaft assembly 2000 is assembled to the drive module 1100, the electrical connector 2910 is operably coupled to the electrical connector 1910 such that the electrical contacts form electrical pathways therebetween. The above being said, the connectors 1910 and 2910 can comprise any suitable electrical contacts. Moreover, the communication systems 1900 and 2900 can communicate with one another in any suitable manner. In various instances, the communication systems 1900 and 2900 communicate wirelessly. In at least one such instance, the communication system 2900 comprises a wireless signal transmitter and the communication system 1900 comprises a wireless signal receiver such that the shaft assembly 2000 can wirelessly communicate data to the handle 1000. Likewise, the communication system 1900 can comprise a wireless signal transmitter and the communication system 2900 can comprise a wireless signal receiver such that the handle 1000 can wirelessly communicate data to the shaft assembly 2000.

As discussed above, the control system 1800 of the handle 1000 is in communication with, and is configured to control, the electrical power circuit of the handle 1000. The handle control system 1800 is also powered by the electrical power circuit of the handle 1000. The handle communication system 1900 is in signal communication with the handle control system 1800 and is also powered by the electrical power circuit of the handle 1000. The handle communication system 1900 is powered by the handle electrical power circuit via the handle control system 1800, but could be directly powered by the electrical power circuit. As also discussed above, the handle communication system 1900 is in signal communication with the shaft communication system 2900. That said, the shaft communication system 2900 is also powered by the handle electrical power circuit via the handle communication system 1900. To this end, the electrical connectors 1910 and 2010 connect both one or more signal circuits and one or more power circuits between the handle 1000 and the shaft assembly 2000. Moreover, the shaft communication system 2900 is in signal communication with the shaft control system 2800, as discussed above, and is also configured to supply power to the shaft control system 2800. Thus, the control systems 1800 and 2800 and the communication systems 1900 and 2900 are all powered by the electrical power circuit of the handle 1000; however, alternative embodiments are envisioned in which the shaft assembly 2000 comprises its own power source, such as one or more batteries, for example, an and electrical power circuit configured to supply power from the batteries to the handle systems 2800 and 2900. In at least one such embodiment, the handle control system 1800 and the handle communication system 1900 are powered by the handle electrical power system and the shaft control system 2800 and the handle communication system 2900 are powered by the shaft electrical power system.

Further to the above, the actuation of the clamping trigger 2610 is detected by the shaft control system 2800 and communicated to the handle control system 1800 via the communication systems 2900 and 1900. Upon receiving a signal that the clamping trigger 2610 has been actuated, the handle control system 1800 supplies power to the electric motor 1610 of the motor assembly 1600 to rotate the drive shaft 1710 of the handle drive system 1700, and the drive shaft 2710 of the shaft drive system 2700, in a direction which closes the jaw assembly 7100 of the end effector 7000. The mechanism for converting the rotation of the drive shaft 2710 to a closure motion of the jaw assembly 7100 is discussed in greater detail below. So long as the clamping trigger 2610 is held in its actuated position, the electric motor 1610 will rotate the drive shaft 1710 until the jaw assembly 7100 reaches its fully-clamped position. When the jaw assembly 7100 reaches its fully-clamped position, the handle control system 1800 cuts the electrical power to the electric motor 1610. The handle control system 1800 can determine when the jaw assembly 7100 has reached its fully-clamped position in any suitable manner. For instance, the handle control system 1800 can comprise an encoder system which monitors the rotation of, and counts the rotations of, the output shaft of the electric motor 1610 and, once the number of rotations reaches a predetermined threshold, the handle control system 1800 can discontinue supplying power to the electric motor 1610. In at least one instance, the end effector assembly 7000 can comprise one or more sensors configured to detect when the jaw assembly 7100 has reached its fully-clamped position. In at least one such instance, the sensors in the end effector 7000 are in signal communication with the handle control system 1800 via electrical circuits extending through the shaft assembly 2000 which can include the electrical contacts 1520 and 2520, for example.

When the clamping trigger 2610 is rotated distally out of its proximal position, the switch 2115 is opened which is detected by the shaft control system 2800 and communicated to the handle control system 1800 via the communication systems 2900 and 1900. Upon receiving a signal that the clamping trigger 2610 has been moved out of its actuated position, the handle control system 1800 reverses the polarity of the voltage differential being applied to the electric motor 1610 of the motor assembly 1600 to rotate the drive shaft 1710 of the handle drive system 1700, and the drive shaft 2710 of the shaft drive system 2700, in an opposite direction which, as a result, opens the jaw assembly 7100 of the end effector 7000. When the jaw assembly 7100 reaches its fully-open position, the handle control system 1800 cuts the electrical power to the electric motor 1610. The handle control system 1800 can determine when the jaw assembly 7100 has reached its fully-open position in any suitable manner. For instance, the handle control system 1800 can utilize the encoder system and/or the one or more sensors described above to determine the configuration of the jaw assembly 7100. In view of the above, the clinician needs to be mindful about holding the clamping trigger 2610 in its actuated position in order to maintain the jaw assembly 7100 in its clamped configuration as, otherwise, the control system 1800 will open jaw assembly 7100. With this in mind, the shaft assembly 2000 further comprises an actuator latch 2630 configured to releasably hold the clamping trigger 2610 in its actuated position to prevent the accidental opening of the jaw assembly 7100. The actuator latch 2630 can be manually released, or otherwise defeated, by the clinician to allow the clamping trigger 2610 to be rotated distally and open the jaw assembly 7100.

The clamping trigger system 2600 further comprises a resilient biasing member, such as a torsion spring, for example, configured to resist the closure of the clamping trigger system 2600. The torsion spring can also assist in reducing and/or mitigating sudden movements and/or jitter of the clamping trigger 2610. Such a torsion spring can also automatically return the clamping trigger 2610 to its unactuated position when the clamping trigger 2610 is released. The actuator latch 2630 discussed above can suitably hold the clamping trigger 2610 in its actuated position against the biasing force of the torsion spring.

As discussed above, the control system 1800 operates the electric motor 1610 to open and close the jaw assembly 7100. The control system 1800 is configured to open and close the jaw assembly 7100 at the same speed. In such instances, the control system 1800 applies the same voltage pulses to the electric motor 1610, albeit with different voltage polarities, when opening and closing the jaw assembly 7100. That said, the control system 1800 can be configured to open and close the jaw assembly 7100 at different speeds. For instance, the jaw assembly 7100 can be closed at a first speed and opened at a second speed which is faster than the first speed. In such instances, the slower closing speed affords the clinician an opportunity to better position the jaw assembly 7100 while clamping the tissue. Alternatively, the control system 1800 can open the jaw assembly 7100 at a slower speed. In such instances, the slower opening speed reduces the possibility of the opening jaws colliding with adjacent tissue. In either event, the control system 1800 can decrease the duration of the voltage pulses and/or increase the duration between the voltage pulses to slow down and/or speed up the movement of the jaw assembly 7100.

As discussed above, the control system 1800 is configured to interpret the position of the clamping trigger 2610 as a command to position the jaw assembly 7100 in a specific configuration. For instance, the control system 1800 is configured to interpret the proximal-most position of the clamping trigger 2610 as a command to close the jaw assembly 7100 and any other position of the clamping trigger as a command to open the jaw assembly 7100. That said, the control system 1800 can be configured to interpret the position of the clamping trigger 2610 in a proximal range of positions, instead of a single position, as a command to close the jaw assembly 7100. Such an arrangement can allow the jaw assembly 7000 to be better responsive to the clinician's input. In such instances, the range of motion of the clamping trigger 2610 is divided into ranges—a proximal range which is interpreted as a command to close the jaw assembly 7100 and a distal range which is interpreted as a command to open the jaw assembly 7100. In at least one instance, the range of motion of the clamping trigger 2610 can have an intermediate range between the proximal range and the distal range. When the clamping trigger 2610 is in the intermediate range, the control system 1800 can interpret the position of the clamping trigger 2610 as a command to neither open nor close the jaw assembly 7100. Such an intermediate range can prevent, or reduce the possibility of, jitter between the opening and closing ranges. In the instances described above, the control system 1800 can be configured to ignore cumulative commands to open or close the jaw assembly 7100. For instance, if the closure trigger 2610 has already been fully retracted into its proximal-most position, the control assembly 1800 can ignore the motion of the clamping trigger 2610 in the proximal, or clamping, range until the clamping trigger 2610 enters into the distal, or opening, range wherein, at such point, the control system 1800 can then actuate the electric motor 1610 to open the jaw assembly 7100.

In certain instances, further to the above, the position of the clamping trigger 2610 within the clamping trigger range, or at least a portion of the clamping trigger range, can allow the clinician to control the speed of the electric motor 1610 and, thus, the speed in which the jaw assembly 7100 is being opened or closed by the control assembly 1800. In at least one instance, the sensor 2115 comprises a Hall Effect sensor, and/or any other suitable sensor, configured to detect the position of the clamping trigger 2610 between its distal, unactuated position and its proximal, fully-actuated position. The Hall Effect sensor is configured to transmit a signal to the handle control system 1800 via the shaft control system 2800 such that the handle control system 1800 can control the speed of the electric motor 1610 in response to the position of the clamping trigger 2610. In at least one instance, the handle control system 1800 controls the speed of the electric motor 1610 proportionately, or in a linear manner, to the position of the clamping trigger 2610. For example, if the clamping trigger 2610 is moved half way through its range, then the handle control system 1800 will operate the electric motor 1610 at half of the speed in which the electric motor 1610 is operated when the clamping trigger 2610 is fully-retracted. Similarly, if the clamping trigger 2610 is moved a quarter way through its range, then the handle control system 1800 will operate the electric motor 1610 at a quarter of the speed in which the electric motor 1610 is operated when the clamping trigger 2610 is fully-retracted. Other embodiments are envisioned in which the handle control system 1800 controls the speed of the electric motor 1610 in a non-linear manner to the position of the clamping trigger 2610. In at least one instance, the control system 1800 operates the electric motor 1610 slowly in the distal portion of the clamping trigger range while quickly accelerating the speed of the electric motor 1610 in the proximal portion of the clamping trigger range.

As described above, the clamping trigger 2610 is movable to operate the electric motor 1610 to open or close the jaw assembly 7100 of the end effector 7000. The electric motor 1610 is also operable to rotate the end effector 7000 about a longitudinal axis and articulate the end effector 7000 relative to the elongate shaft 2200 about the articulation joint 2300 of the shaft assembly 2000. Referring primarily to FIGS. 7 and 8, the drive module 1100 comprises an input system 1400 including a rotation actuator 1420 and an articulation actuator 1430. The input system 1400 further comprises a printed circuit board (PCB) 1410 which is in signal communication with the printed circuit board (PCB) 1810 of the control system 1800. The drive module 1100 comprises an electrical circuit, such as a flexible wiring harness or ribbon, for example, which permits the input system 1400 to communicate with the control system 1800. The rotation actuator 1420 is rotatably supported on the housing 1110 and is in signal communication with the input board 1410 and/or control board 1810, as described in greater detail below. The articulation actuator 1430 is supported by and in signal communication with the input board 1410 and/or control board 1810, as also described in greater detail below.

Referring primarily to FIGS. 8, 10, and 11, further to the above, the handle housing 1110 comprises an annular groove or slot defined therein adjacent the distal mounting interface 1130. The rotation actuator 1420 comprises an annular ring 1422 rotatably supported within the annular groove and, owing to the configuration of the sidewalls of the annular groove, the annular ring 1422 is constrained from translating longitudinally and/or laterally with respect to the handle housing 1110. The annular ring 1422 is rotatable in a first, or clockwise, direction and a second, or counter-clockwise direction, about a longitudinal axis extending through the frame 1500 of the drive module 1100. The rotation actuator 1420 comprises one or more sensors configured to detect the rotation of the annular ring 1422. In at least one instance, the rotation actuator 1420 comprises a first sensor positioned on a first side of the drive module 1100 and a second sensor positioned on a second, or opposite, side of the drive module 1100 and the annular ring 1422 comprises a detectable element which is detectable by the first and second sensors. The first sensor is configured to detect when the annular ring 1422 is rotated in the first direction and the second sensor is configured to detect when the annular ring 1422 is rotated in the second direction. When the first sensor detects that the annular ring 1422 is rotated in the first direction, the handle control system 1800 rotates the handle drive shaft 1710, the drive shaft 2710, and the end effector 7000 in the first direction, as described in greater detail below. Similarly, the handle control system 1800 rotates the handle drive shaft 1710, the drive shaft 2710, and the end effector 7000 in the second direction when the second sensor detects that the annular ring 1422 is rotated in the second direction. In view of the above, the reader should appreciate that the clamping trigger 2610 and the rotation actuator 1420 are both operable to rotate the drive shaft 2710.

In various embodiments, further to the above, the first and second sensors comprise switches which are mechanically closable by the detectable element of the annular ring 1422. When the annular ring 1422 is rotated in the first direction from a center position, the detectable element closes the switch of the first sensor. When the switch of the first sensor is closed, the control system 1800 operates the electric motor 1610 to rotate the end effector 7000 in the first direction. When the annular ring 1422 is rotated in the second direction toward the center position, the detectable element is disengaged from the first switch and the first switch is re-opened. Once the first switch is re-opened, the control system 1800 cuts the power to the electric motor 1610 to stop the rotation of the end effector 7000. Similarly, the detectable element closes the switch of the second sensor when the annular ring 1422 is rotated in the second direction from the center position. When the switch of the second sensor is closed, the control system 1800 operates the electric motor 1610 to rotate the end effector 7000 in the second direction. When the annular ring 1422 is rotated in the first direction toward the center position, the detectable element is disengaged from the second switch and the second switch is re-opened. Once the second switch is re-opened, the control system 1800 cuts the power to the electric motor 1610 to stop the rotation of the end effector 7000.

In various embodiments, further to the above, the first and second sensors of the rotation actuator 1420 comprise proximity sensors, for example. In certain embodiments, the first and second sensors of the rotation actuator 1420 comprise Hall Effect sensors, and/or any suitable sensors, configured to detect the distance between the detectable element of the annular ring 1422 and the first and second sensors. If the first Hall Effect sensor detects that the annular ring 1422 has been rotated in the first direction, then, as discussed above, the control system 1800 will rotate the end effector 7000 in the first direction. In addition, the control system 1800 can rotate the end effector 7000 at a faster speed when the detectable element is closer to the first Hall Effect sensor than when the detectable element is further away from the first Hall Effect sensor. If the second Hall Effect sensor detects that the annular ring 1422 has been rotated in the second direction, then, as discussed above, the control system 1800 will rotate the end effector 7000 in the second direction. In addition, the control system 1800 can rotate the end effector 7000 at a faster speed when the detectable element is closer to the second Hall Effect sensor than when the detectable element is further away from the second Hall Effect sensor. As a result, the speed in which the end effector 7000 is rotated is a function of the amount, or degree, in which the annular ring 1422 is rotated. The control system 1800 is further configured to evaluate the inputs from both the first and second Hall Effect sensors when determining the direction and speed in which to rotate the end effector 7000. In various instances, the control system 1800 can use the closest Hall Effect sensor to the detectable element of the annular ring 1422 as a primary source of data and the Hall Effect sensor furthest away from the detectable element as a confirmational source of data to double-check the data provided by the primary source of data. The control system 1800 can further comprise a data integrity protocol to resolve situations in which the control system 1800 is provided with conflicting data. In any event, the handle control system 1800 can enter into a neutral state in which the handle control system 1800 does not rotate the end effector 7000 when the Hall Effect sensors detect that the detectable element is in its center position, or in a position which is equidistant between the first Hall Effect sensor and the second Hall Effect sensor. In at least one such instance, the control system 1800 can enter into its neutral state when the detectable element is in a central range of positions. Such an arrangement would prevent, or at least reduce the possibility of, rotational jitter when the clinician is not intending to rotate the end effector 7000.

Further to the above, the rotation actuator 1420 can comprise one or more springs configured to center, or at least substantially center, the rotation actuator 1420 when it is released by the clinician. In such instances, the springs can act to shut off the electric motor 1610 and stop the rotation of the end effector 7000. In at least one instance, the rotation actuator 1420 comprises a first torsion spring configured to rotate the rotation actuator 1420 in the first direction and a second torsion spring configured to rotate the rotation actuator 1420 in the second direction. The first and second torsion springs can have the same, or at least substantially the same, spring constant such that the forces and/or torques applied by the first and second torsion springs balance, or at least substantially balance, the rotation actuator 1420 in its center position.

In view of the above, the reader should appreciate that the clamping trigger 2610 and the rotation actuator 1420 are both operable to rotate the drive shaft 2710 and either, respectively, operate the jaw assembly 7100 or rotate the end effector 7000. The system that uses the rotation of the drive shaft 2710 to selectively perform these functions is described in greater detail below.

Referring to FIGS. 7 and 8, the articulation actuator 1430 comprises a first push button 1432 and a second push button 1434. The first push button 1432 is part of a first articulation control circuit and the second push button 1434 is part of a second articulation circuit of the input system 1400. The first push button 1432 comprises a first switch that is closed when the first push button 1432 is depressed. The handle control system 1800 is configured to sense the closure of the first switch and, moreover, the closure of the first articulation control circuit. When the handle control system 1800 detects that the first articulation control circuit has been closed, the handle control system 1800 operates the electric motor 1610 to articulate the end effector 7000 in a first articulation direction about the articulation joint 2300. When the first push button 1432 is released by the clinician, the first articulation control circuit is opened which, once detected by the control system 1800, causes the control system 1800 to cut the power to the electric motor 1610 to stop the articulation of the end effector 7000.

In various instances, further to the above, the articulation range of the end effector 7000 is limited and the control system 1800 can utilize the encoder system discussed above for monitoring the rotational output of the electric motor 1610, for example, to monitor the amount, or degree, in which the end effector 7000 is rotated in the first direction. In addition to or in lieu of the encoder system, the shaft assembly 2000 can comprise a first sensor configured to detect when the end effector 7000 has reached the limit of its articulation in the first direction. In any event, when the control system 1800 determines that the end effector 7000 has reached the limit of articulation in the first direction, the control system 1800 can cut the power to the electric motor 1610 to stop the articulation of the end effector 7000.

Similar to the above, the second push button 1434 comprises a second switch that is closed when the second push button 1434 is depressed. The handle control system 1800 is configured to sense the closure of the second switch and, moreover, the closure of the second articulation control circuit. When the handle control system 1800 detects that the second articulation control circuit has been closed, the handle control system 1800 operates the electric motor 1610 to articulate the end effector 7000 in a second direction about the articulation joint 2300. When the second push button 1434 is released by the clinician, the second articulation control circuit is opened which, once detected by the control system 1800, causes the control system 1800 to cut the power to the electric motor 1610 to stop the articulation of the end effector 7000.

In various instances, the articulation range of the end effector 7000 is limited and the control system 1800 can utilize the encoder system discussed above for monitoring the rotational output of the electric motor 1610, for example, to monitor the amount, or degree, in which the end effector 7000 is rotated in the second direction. In addition to or in lieu of the encoder system, the shaft assembly 2000 can comprise a second sensor configured to detect when the end effector 7000 has reached the limit of its articulation in the second direction. In any event, when the control system 1800 determines that the end effector 7000 has reached the limit of articulation in the second direction, the control system 1800 can cut the power to the electric motor 1610 to stop the articulation of the end effector 7000.

Figure 15:
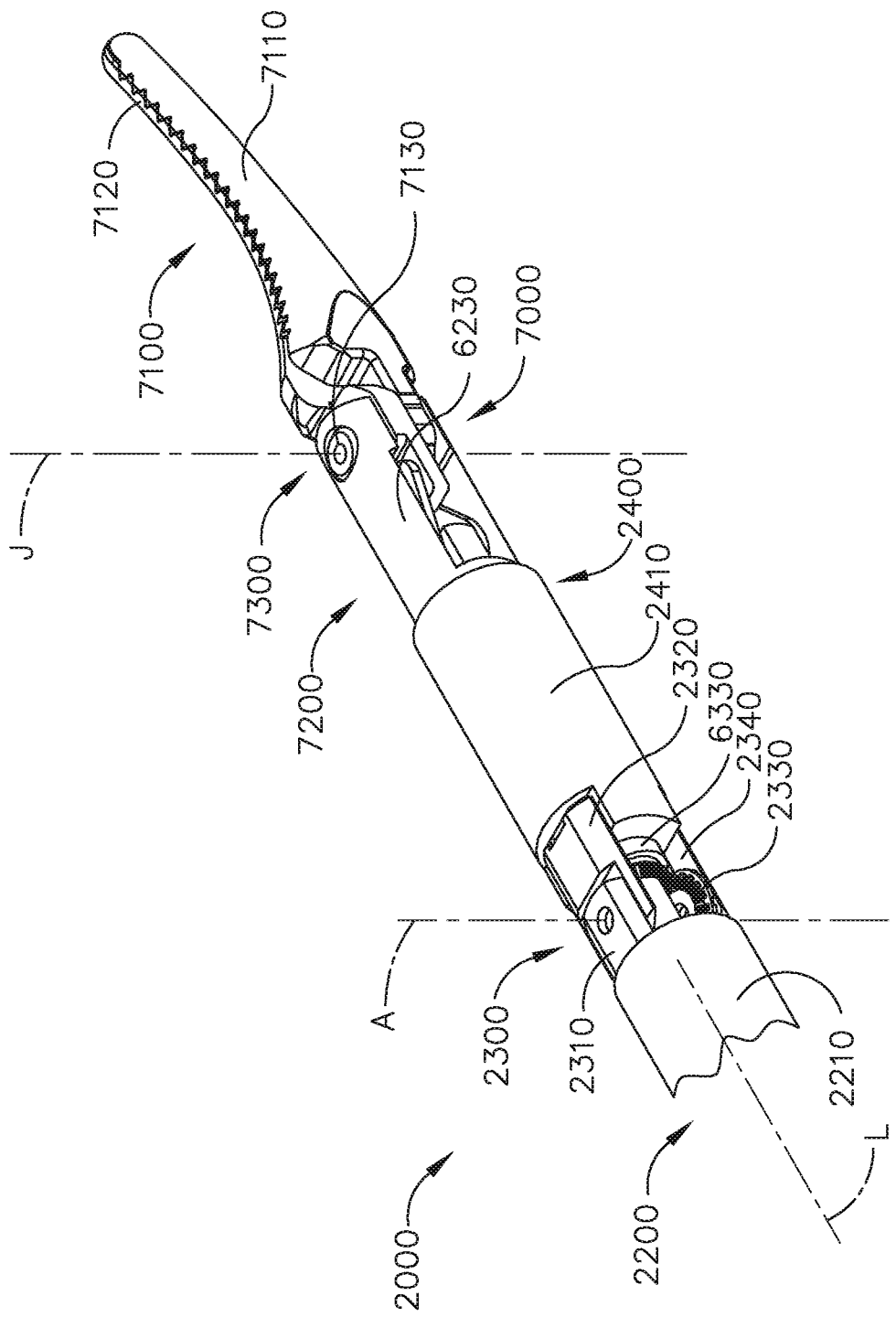
FIG. 15 is a partial perspective view of the end effector of FIG. 14 in a closed configuration.

As described above, the end effector 7000 is articulatable in a first direction (FIG. 16) and/or a second direction (FIG. 17) from a center, or unarticulated, position (FIG. 15). Once the end effector 7000 has been articulated, the clinician can attempt to re-center the end effector 7000 by using the first and second articulation push buttons 1432 and 1434. As the reader can appreciate, the clinician may struggle to re-center the end effector 7000 as, for instance, the end effector 7000 may not be entirely visible once it is positioned in the patient. In some instances, the end effector 7000 may not fit back through a trocar if the end effector 7000 is not re-centered, or at least substantially re-centered. With that in mind, the control system 1800 is configured to provide feedback to the clinician when the end effector 7000 is moved into its unarticulated, or centered, position. In at least one instance, the feedback comprises audio feedback and the handle control system 1800 can comprise a speaker which emits a sound, such as a beep, for example, when the end effector 7000 is centered. In certain instances, the feedback comprises visual feedback and the handle control system 1800 can comprise a light emitting diode (LED), for example, positioned on the handle housing 1110 which flashes when the end effector 7000 is centered. In various instances, the feedback comprises haptic feedback and the handle control system 1800 can comprise an electric motor comprising an eccentric element which vibrates the handle 1000 when the end effector 7000 is centered. Manually re-centering the end effector 7000 in this way can be facilitated by the control system 1800 slowing the motor 1610 when the end effector 7000 is approaching its centered position. In at least one instance, the control system 1800 slows the articulation of the end effector 7000 when the end effector 7000 is within approximately 5 degrees of center in either direction, for example.

In addition to or in lieu of the above, the handle control system 1800 can be configured to re-center the end effector 7000. In at least one such instance, the handle control system 1800 can re-center the end effector 7000 when both of the articulation buttons 1432 and 1434 of the articulation actuator 1430 are depressed at the same time. When the handle control system 1800 comprises an encoder system configured to monitor the rotational output of the electric motor 1610, for example, the handle control system 1800 can determine the amount and direction of articulation needed to re-center, or at least substantially re-center, the end effector 7000. In various instances, the input system 1400 can comprise a home button, for example, which, when depressed, automatically centers the end effector 7000.

Figure 5:
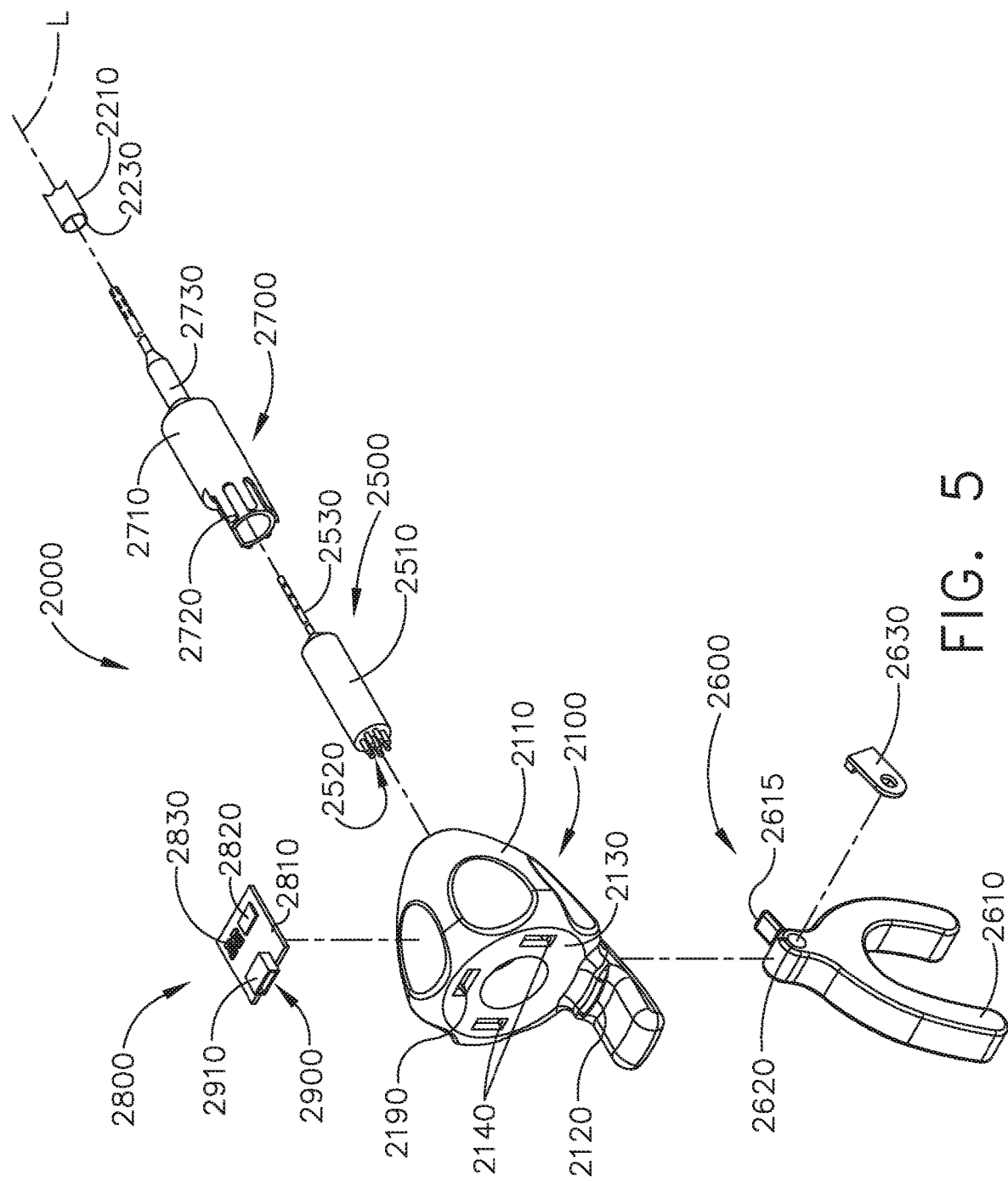
FIG. 5 is a partial exploded view of the shaft assembly of FIG. 2.
Figure 6:
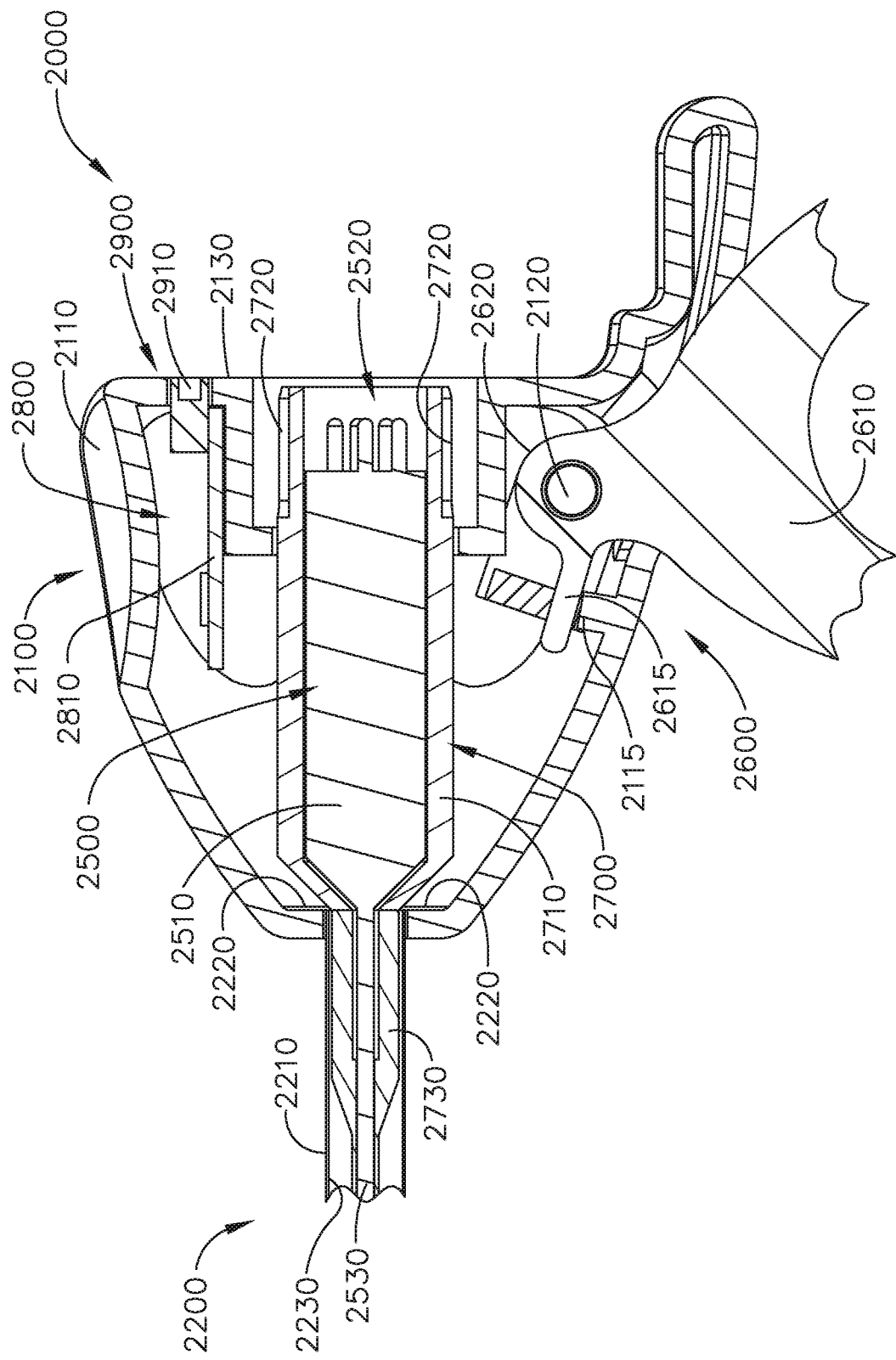
FIG. 6 is a partial cross-sectional elevational view of the shaft assembly of FIG. 2.

Referring primarily to FIGS. 5 and 6, the elongate shaft 2200 of the shaft assembly 2000 comprises an outer housing, or tube, 2210 mounted to the proximal housing 2110 of the proximal portion 2100. The outer housing 2210 comprises a longitudinal aperture 2230 extending therethrough and a proximal flange 2220 which secures the outer housing 2210 to the proximal housing 2110. The frame 2500 of the shaft assembly 2000 extends through the longitudinal aperture 2230 of the elongate shaft 2200. More specifically, the shaft 2510 of the shaft frame 2500 necks down into a smaller shaft 2530 which extends through the longitudinal aperture 2230. That said, the shaft frame 2500 can comprise any suitable arrangement. The drive system 2700 of the shaft assembly 2000 also extends through the longitudinal aperture 2230 of the elongate shaft 2200. More specifically, the drive shaft 2710 of the shaft drive system 2700 necks down into a smaller drive shaft 2730 which extends through the longitudinal aperture 2230. That said, the shaft drive system 2700 can comprise any suitable arrangement.

Figure 20:
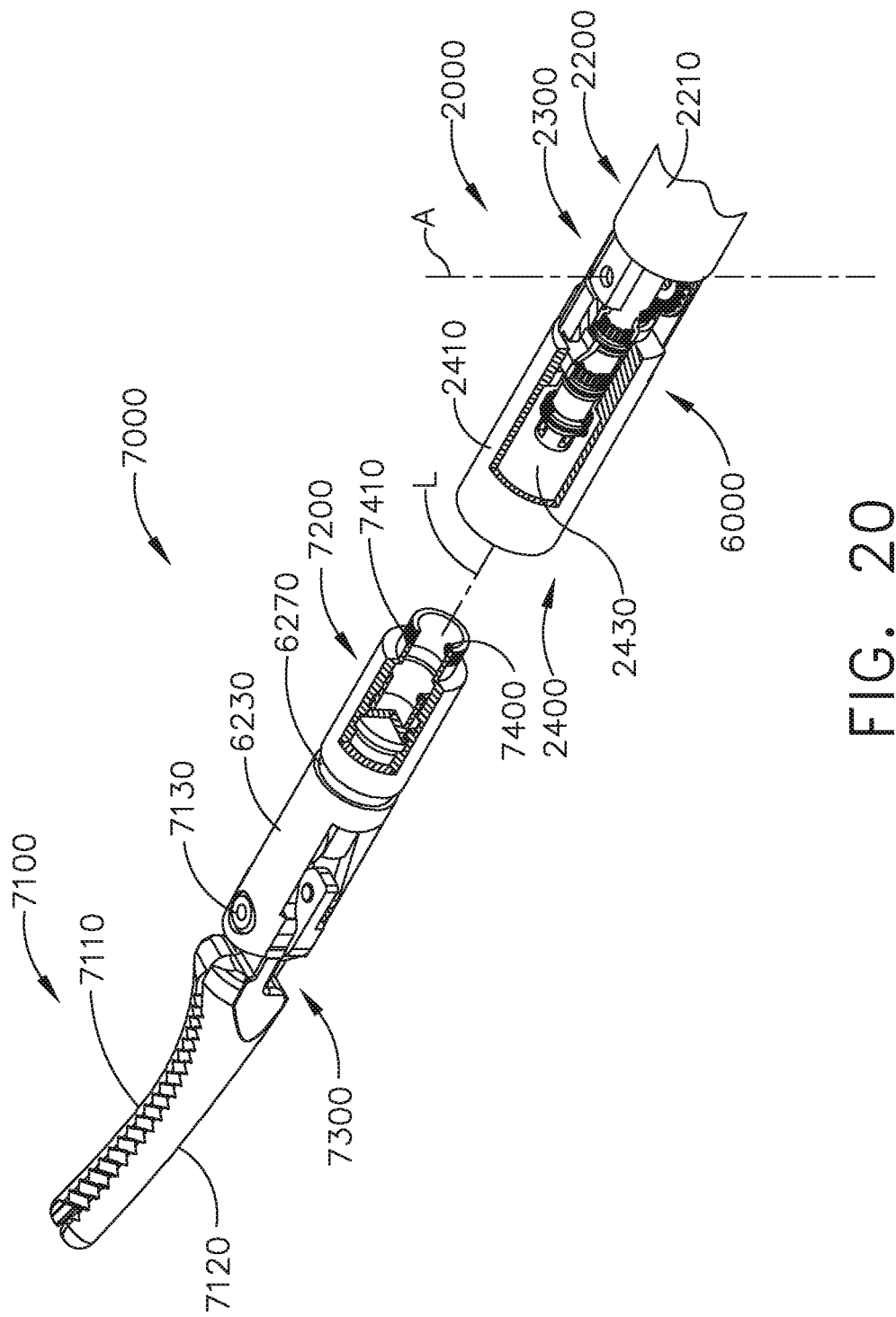
FIG. 20 is a partial cross-sectional perspective view of the end effector of FIG. 14 detached from the shaft assembly of FIG. 2.
Figure 22:
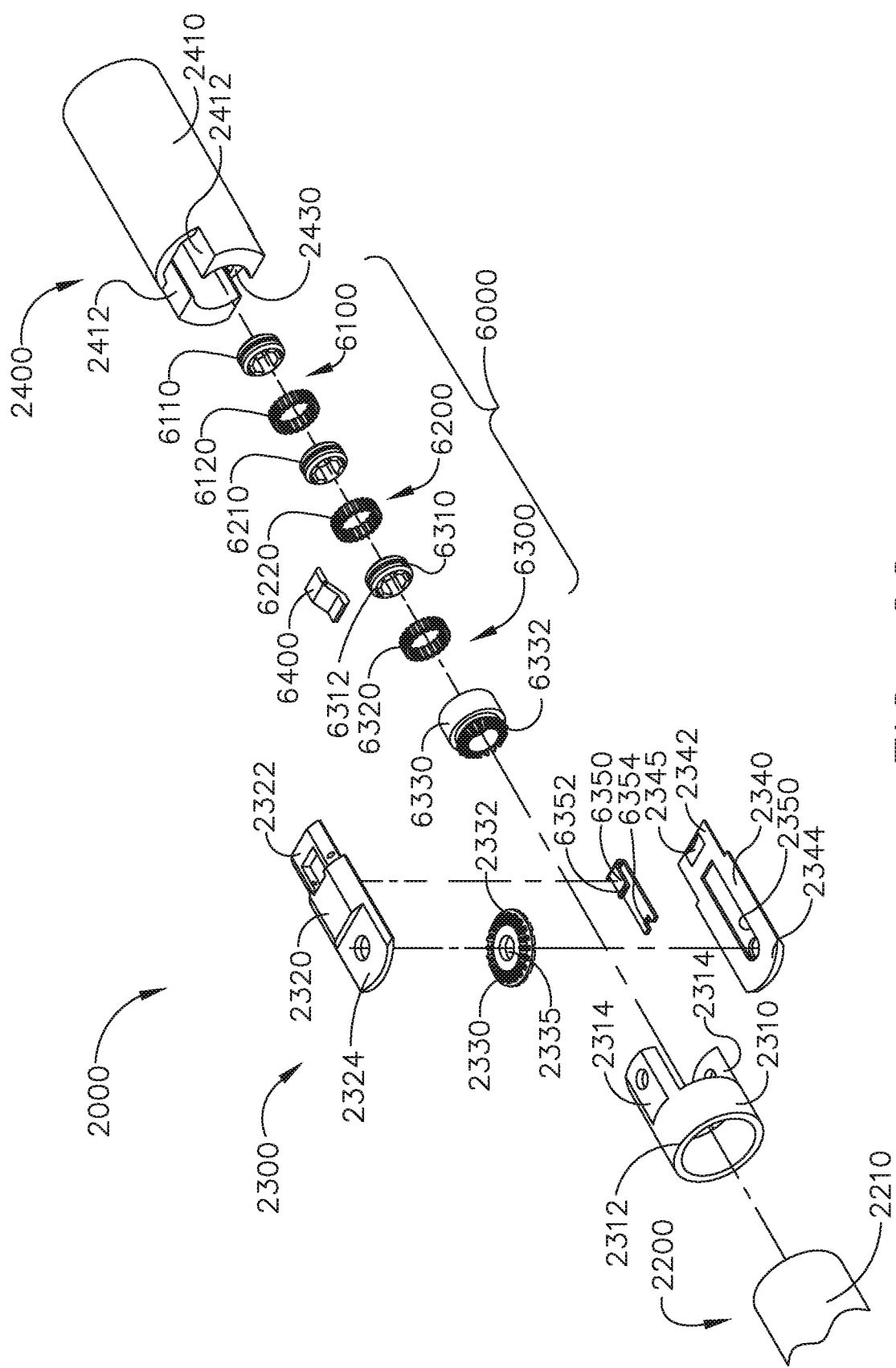
FIG. 22 is an exploded view of a distal attachment portion of the shaft assembly of FIG. 2.
Figure 23:
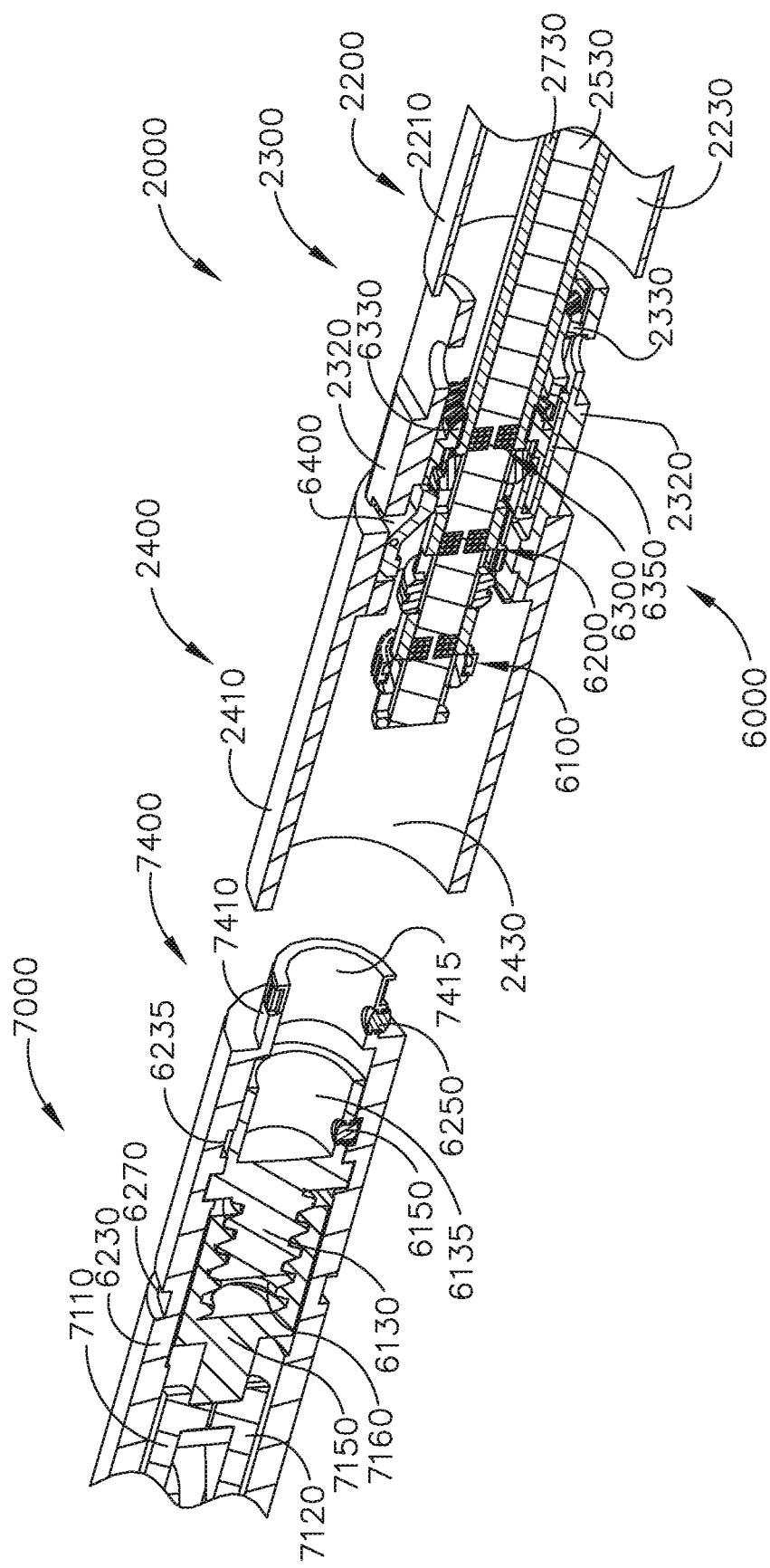
FIG. 23 is another partial cross-sectional perspective view of the end effector of FIG. 14 detached from the shaft assembly of FIG. 2.
Figure 24:
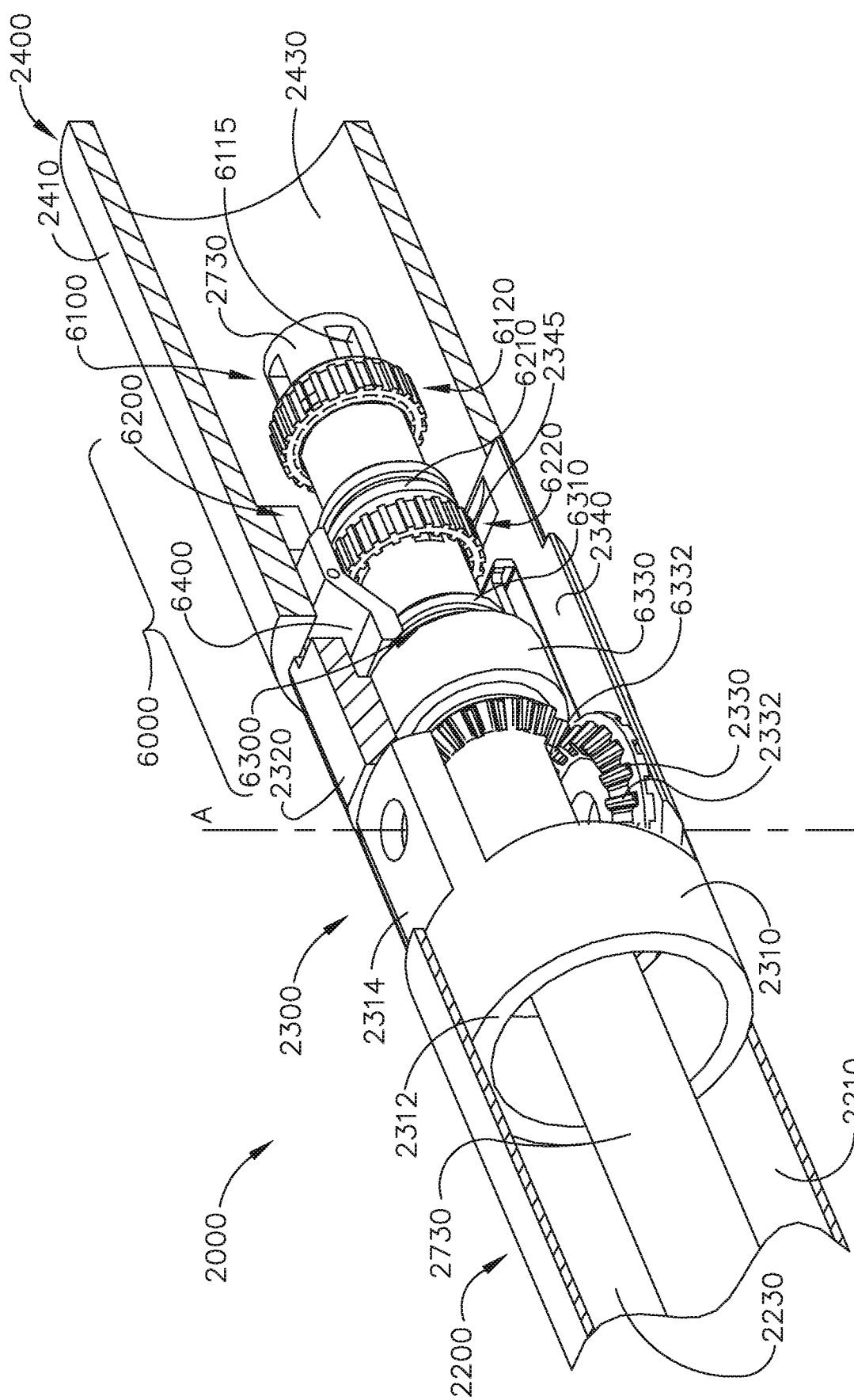
FIG. 24 is a partial cross-sectional perspective view of the end effector of FIG. 14 attached to the shaft assembly of FIG. 2.

Referring primarily to FIGS. 20, 23, and 24, the outer housing 2210 of the elongate shaft 2200 extends to the articulation joint 2300. The articulation joint 2300 comprises a proximal frame 2310 mounted to the outer housing 2210 such that there is little, if any, relative translation and/or rotation between the proximal frame 2310 and the outer housing 2210. Referring primarily to FIG. 22, the proximal frame 2310 comprises an annular portion 2312 mounted to the sidewall of the outer housing 2210 and tabs 2314 extending distally from the annular portion 2312. The articulation joint 2300 further comprises links 2320 and 2340 which are rotatably mounted to the frame 2310 and mounted to an outer housing 2410 of the distal attachment portion 2400. The link 2320 comprises a distal end 2322 mounted to the outer housing 2410. More specifically, the distal end 2322 of the link 2320 is received and fixedly secured within a mounting slot 2412 defined in the outer housing 2410. Similarly, the link 2340 comprises a distal end 2342 mounted to the outer housing 2410. More specifically, the distal end 2342 of the link 2340 is received and fixedly secured within a mounting slot defined in the outer housing 2410. The link 2320 comprises a proximal end 2324 rotatably coupled to a tab 2314 of the proximal articulation frame 2310. Although not illustrated in FIG. 22, a pin extends through apertures defined in the proximal end 2324 and the tab 2314 to define a pivot axis therebetween. Similarly, the link 2340 comprises a proximal end 2344 rotatably coupled to a tab 2314 of the proximal articulation frame 2310. Although not illustrated in FIG. 22, a pin extends through apertures defined in the proximal end 2344 and the tab 2314 to define a pivot axis therebetween. These pivot axes are collinear, or at least substantially collinear, and define an articulation axis A of the articulation joint 2300.

Referring primarily to FIGS. 20, 23, and 24, the outer housing 2410 of the distal attachment portion 2400 comprises a longitudinal aperture 2430 extending therethrough. The longitudinal aperture 2430 is configured to receive a proximal attachment portion 7400 of the end effector 7000. The end effector 7000 comprises an outer housing 6230 which is closely received within the longitudinal aperture 2430 of the distal attachment portion 2400 such that there is little, if any, relative radial movement between the proximal attachment portion 7400 of the end effector 7000 and the distal attachment portion 2400 of the shaft assembly 2000. The proximal attachment portion 7400 further comprises an annular array of lock notches 7410 defined on the outer housing 6230 which is releasably engaged by an end effector lock 6400 in the distal attachment portion 2400 of the shaft assembly 2000. When the end effector lock 6400 is engaged with the array of lock notches 7410, the end effector lock 6400 prevents, or at least inhibits, relative longitudinal movement between the proximal attachment portion 7400 of the end effector 7000 and the distal attachment portion 2400 of the shaft assembly 2000. As a result of the above, only relative rotation between the proximal attachment portion 7400 of the end effector 7000 and the distal attachment portion 2400 of the shaft assembly 2000 is permitted. To this end, the outer housing 6230 of the end effector 7000 is closely received within the longitudinal aperture 2430 defined in the distal attachment portion 2400 of the shaft assembly 2000.

Figure 21:
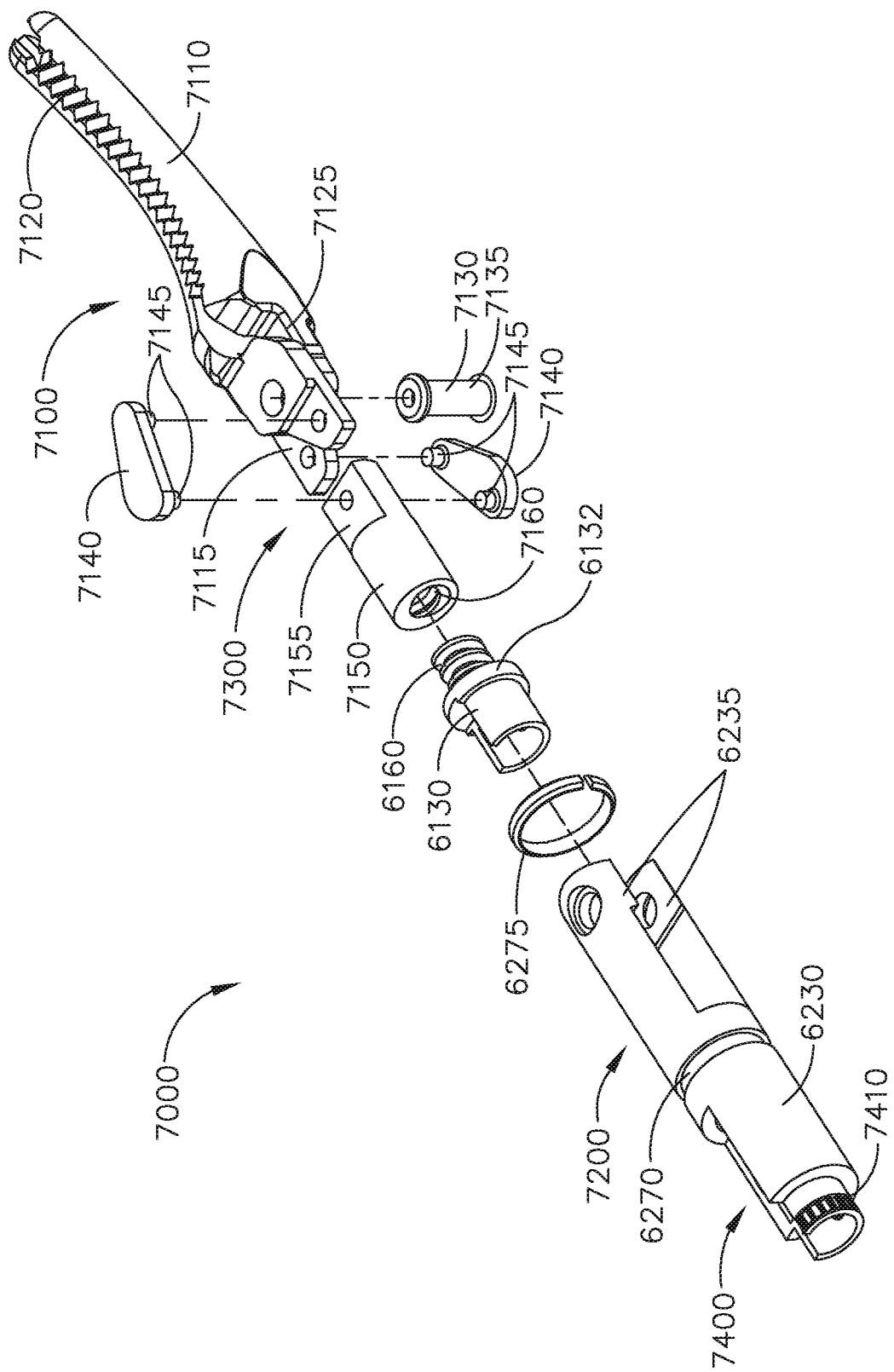
FIG. 21 is an exploded view of the end effector of FIG. 14 illustrated with some components removed.

Further to the above, referring to FIG. 21, the outer housing 6230 further comprises an annular slot, or recess, 6270 defined therein which is configured to receive an O-ring 6275 therein. The O-ring 6275 is compressed between the outer housing 6230 and the sidewall of the longitudinal aperture 2430 when the end effector 7000 is inserted into the distal attachment portion 2400. The O-ring 6275 is configured to resist, but permit, relative rotation between the end effector 7000 and the distal attachment portion 2400 such that the O-ring 6275 can prevent, or reduce the possibility of, unintentional relative rotation between the end effector 7000 and the distal attachment portion 2400. In various instances, the O-ring 6275 can provide a seal between the end effector 7000 and the distal attachment portion 2400 to prevent, or at least reduce the possibility of, fluid ingress into the shaft assembly 2000, for example.

Referring to FIGS. 14-21, the jaw assembly 7100 of the end effector 7000 comprises a first jaw 7110 and a second jaw 7120. Each jaw 7110, 7120 comprises a distal end which is configured to assist a clinician in dissecting tissue with the end effector 7000. Each jaw 7110, 7120 further comprises a plurality of teeth which are configured to assist a clinician in grasping and holding onto tissue with the end effector 7000. Moreover, referring primarily to FIG. 21, each jaw 7110, 7120 comprises a proximal end, i.e., proximal ends 7115, 7125, respectively, which rotatably connect the jaws 7110, 7120 together. Each proximal end 7115, 7125 comprises an aperture extending therethrough which is configured to closely receive a pin 7130 therein. The pin 7130 comprises a central body 7135 closely received within the apertures defined in the proximal ends 7115, 7125 of the jaws 7110, 7120 such that there is little, if any, relative translation between the jaws 7110, 7120 and the pin 7130. The pin 7130 defines a jaw axis J about which the jaws 7110, 7120 can be rotated and, also, rotatably mounts the jaws 7110, 7120 to the outer housing 6230 of the end effector 7000. More specifically, the outer housing 6230 comprises distally-extending tabs 6235 having apertures defined therein which are also configured to closely receive the pin 7130 such that the jaw assembly 7100 does not translate relative to a shaft portion 7200 of the end effector 7000. The pin 7130 further comprises enlarged ends which prevent the jaws 7110, 7120 from becoming detached from the pin 7130 and also prevents the jaw assembly 7100 from becoming detached from the shaft portion 7200. This arrangement defines a rotation joint 7300.

Referring primarily to FIGS. 21 and 23, the jaws 7110 and 7120 are rotatable between their open and closed positions by a jaw assembly drive including drive links 7140, a drive nut 7150, and a drive screw 6130. As described in greater detail below, the drive screw 6130 is selectively rotatable by the drive shaft 2730 of the shaft drive system 2700. The drive screw 6130 comprises an annular flange 6132 which is closely received within a slot, or groove, 6232 (FIG. 25) defined in the outer housing 6230 of the end effector 7000. The sidewalls of the slot 6232 are configured to prevent, or at least inhibit, longitudinal and/or radial translation between the drive screw 6130 and the outer housing 6230, but yet permit relative rotational motion between the drive screw 6130 and the outer housing 6230. The drive screw 6130 further comprises a threaded end 6160 which is threadably engaged with a threaded aperture 7160 defined in the drive nut 7150. The drive nut 7150 is constrained from rotating with the drive screw 6130 and, as a result, the drive nut 7150 is translated when the drive screw 6130 is rotated. In use, the drive screw 6130 is rotated in a first direction to displace the drive nut 7150 proximally and in a second, or opposite, direction to displace the drive nut 7150 distally. The drive nut 7150 further comprises a distal end 7155 comprising an aperture defined therein which is configured to closely receive pins 7145 extending from the drive links 7140. Referring primarily to FIG. 21, a first drive link 7140 is attached to one side of the distal end 7155 and a second drive link 7140 is attached to the opposite side of the distal end 7155. The first drive link 7140 comprises another pin 7145 extending therefrom which is closely received in an aperture defined in the proximal end 7115 of the first jaw 7110 and, similarly, the second drive link 7140 comprises another pin extending therefrom which is closely received in an aperture defined in the proximal end 7125 of the second jaw 7120. As a result of the above, the drive links 7140 operably connect the jaws 7110 and 7120 to the drive nut 7150. When the drive nut 7150 is driven proximally by the drive screw 6130, as described above, the jaws 7110, 7120 are rotated into the closed, or clamped, configuration. Correspondingly, the jaws 7110, 7120 are rotated into their open configuration when the drive nut 7150 is driven distally by the drive screw 6130.

Figure 16:
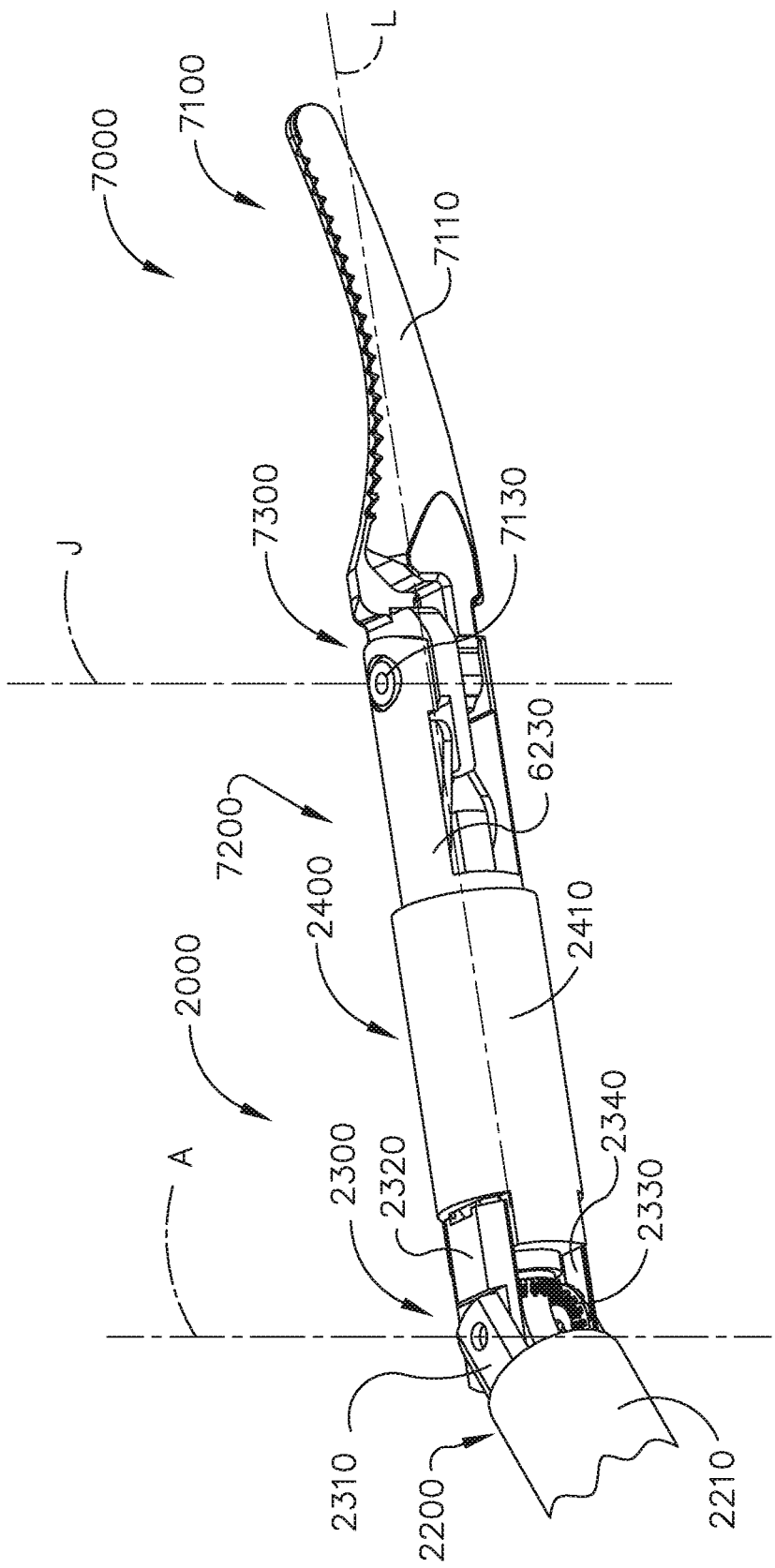
FIG. 16 is a partial perspective view of the end effector of FIG. 14 articulated in a first direction.
Figure 17:
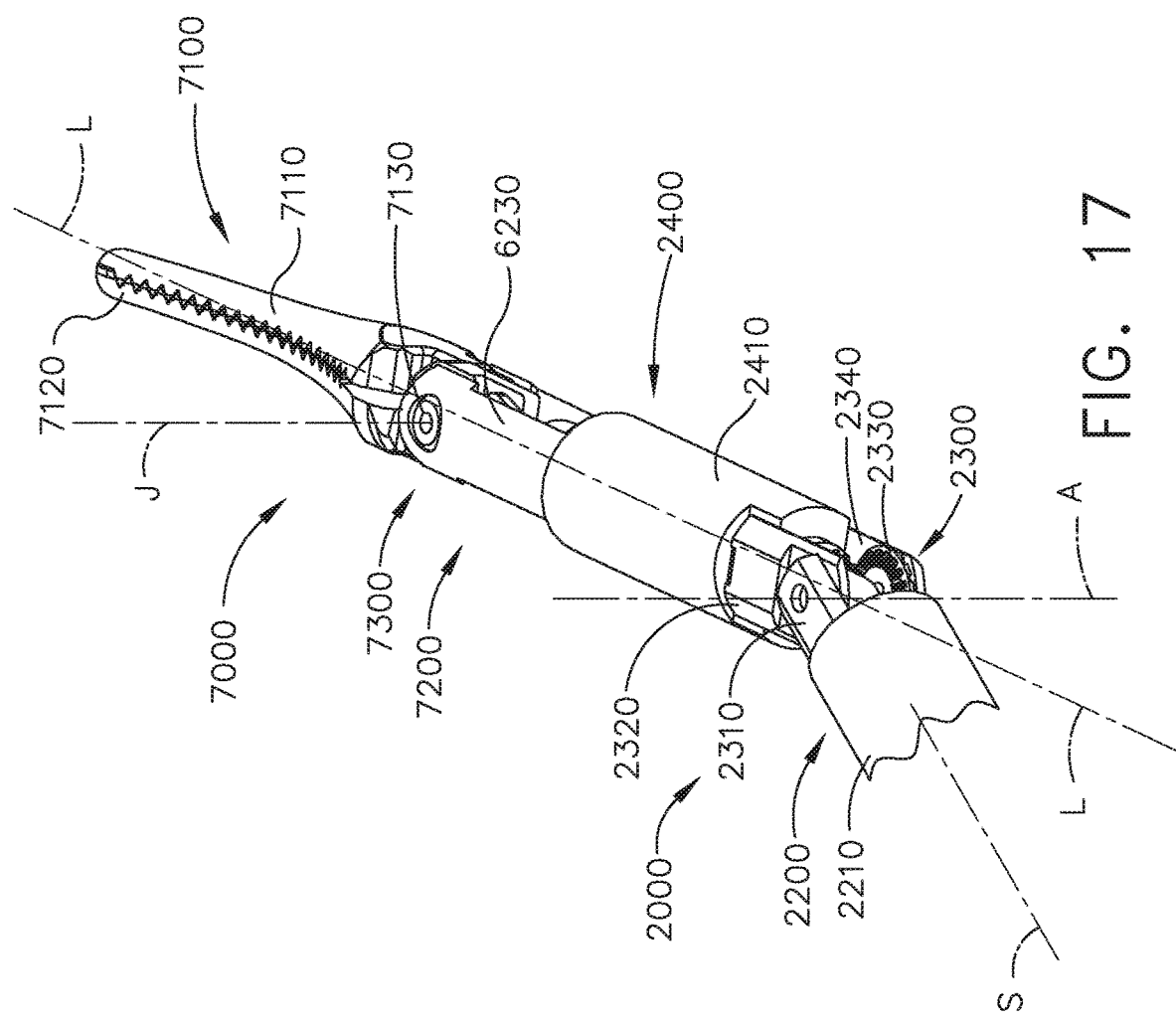
FIG. 17 is a partial perspective view of the end effector of FIG. 14 articulated in a second direction.
Figure 18:
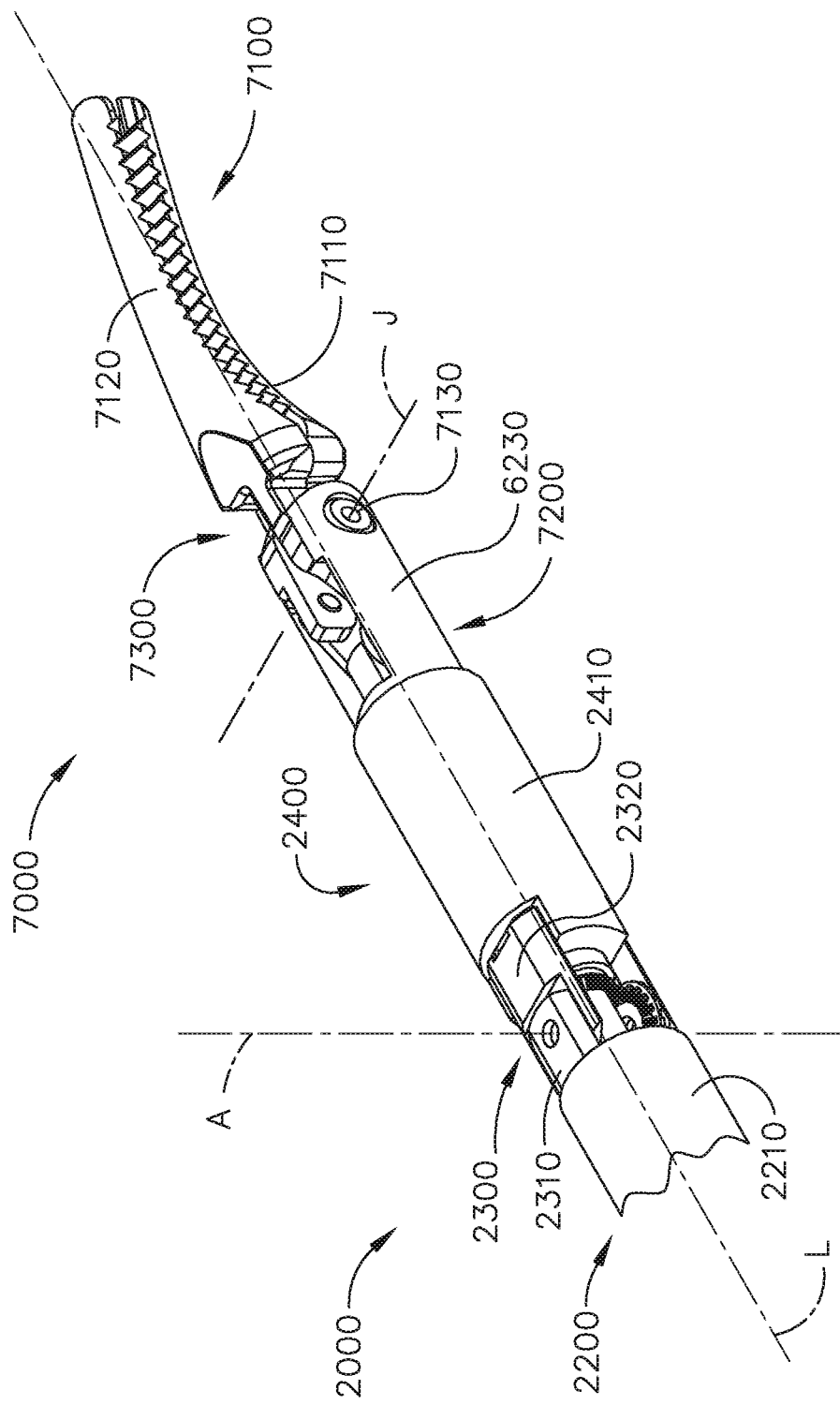
FIG. 18 is a partial perspective view of the end effector of FIG. 14 rotated in a first direction.
Figure 19:
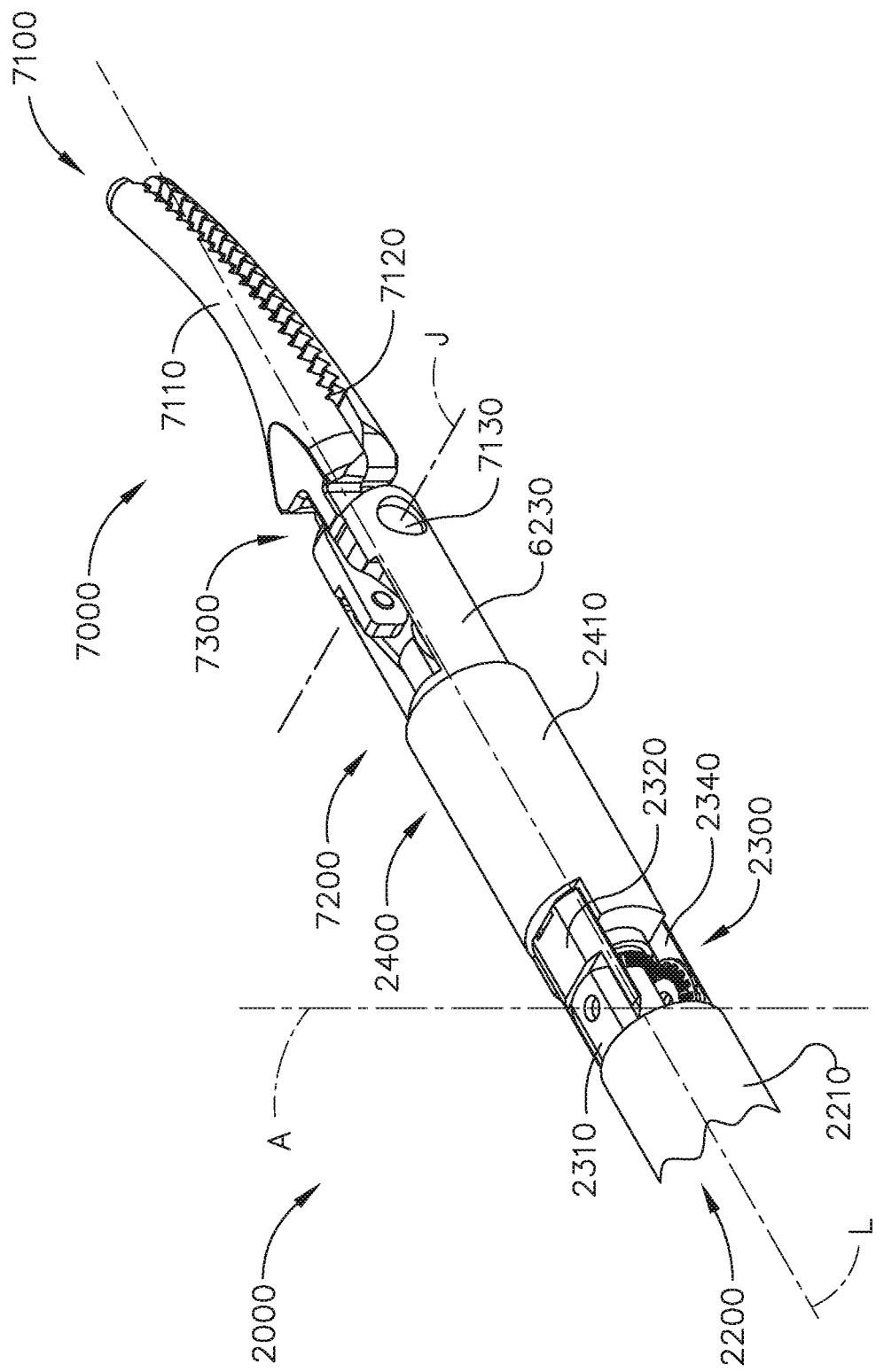
FIG. 19 is a partial perspective view of the end effector of FIG. 14 rotated in a second direction.
Figure 26:
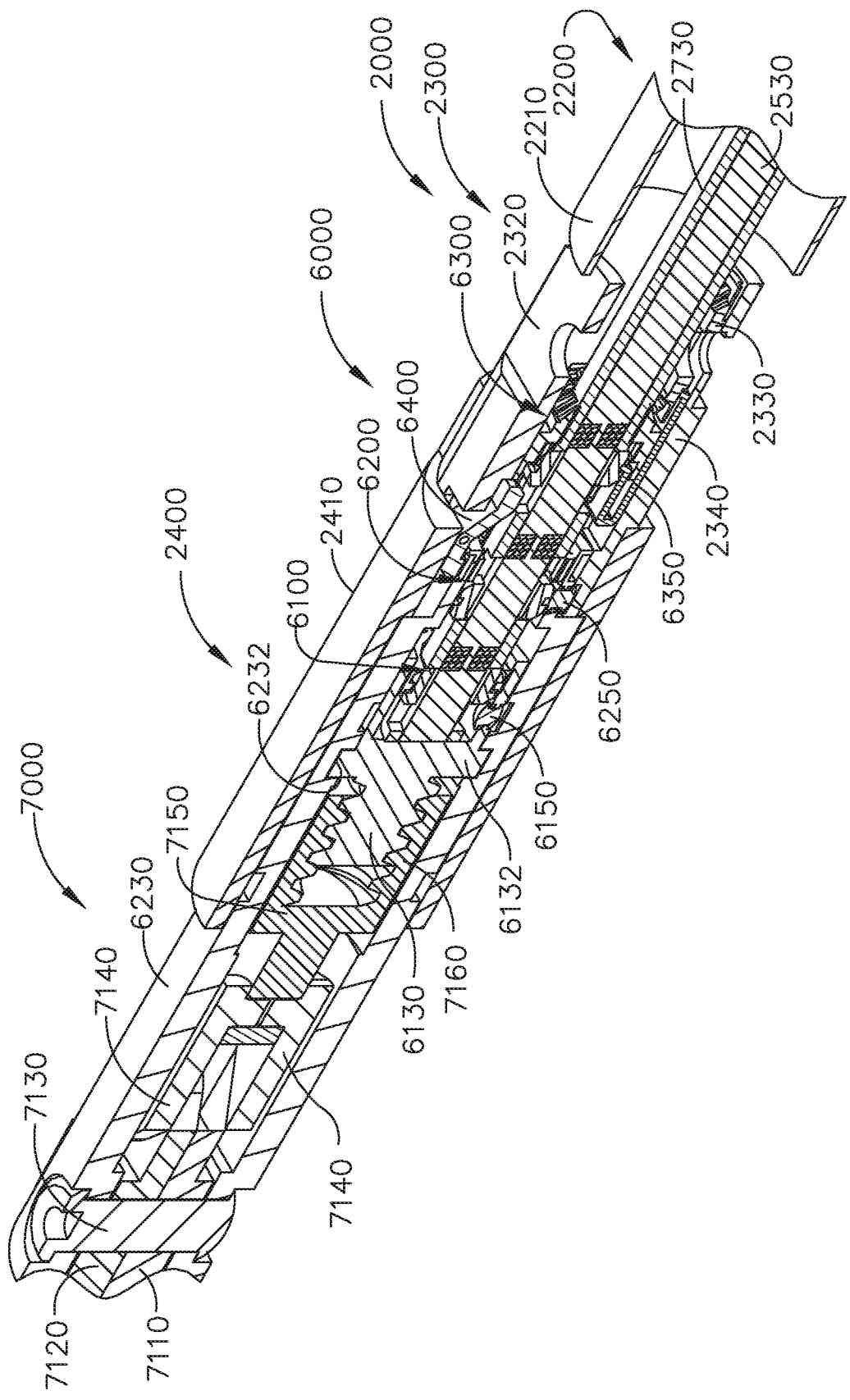
FIG. 26 is another partial cross-sectional perspective view of the end effector of FIG. 14 attached to the shaft assembly of FIG. 2.
Figure 27:
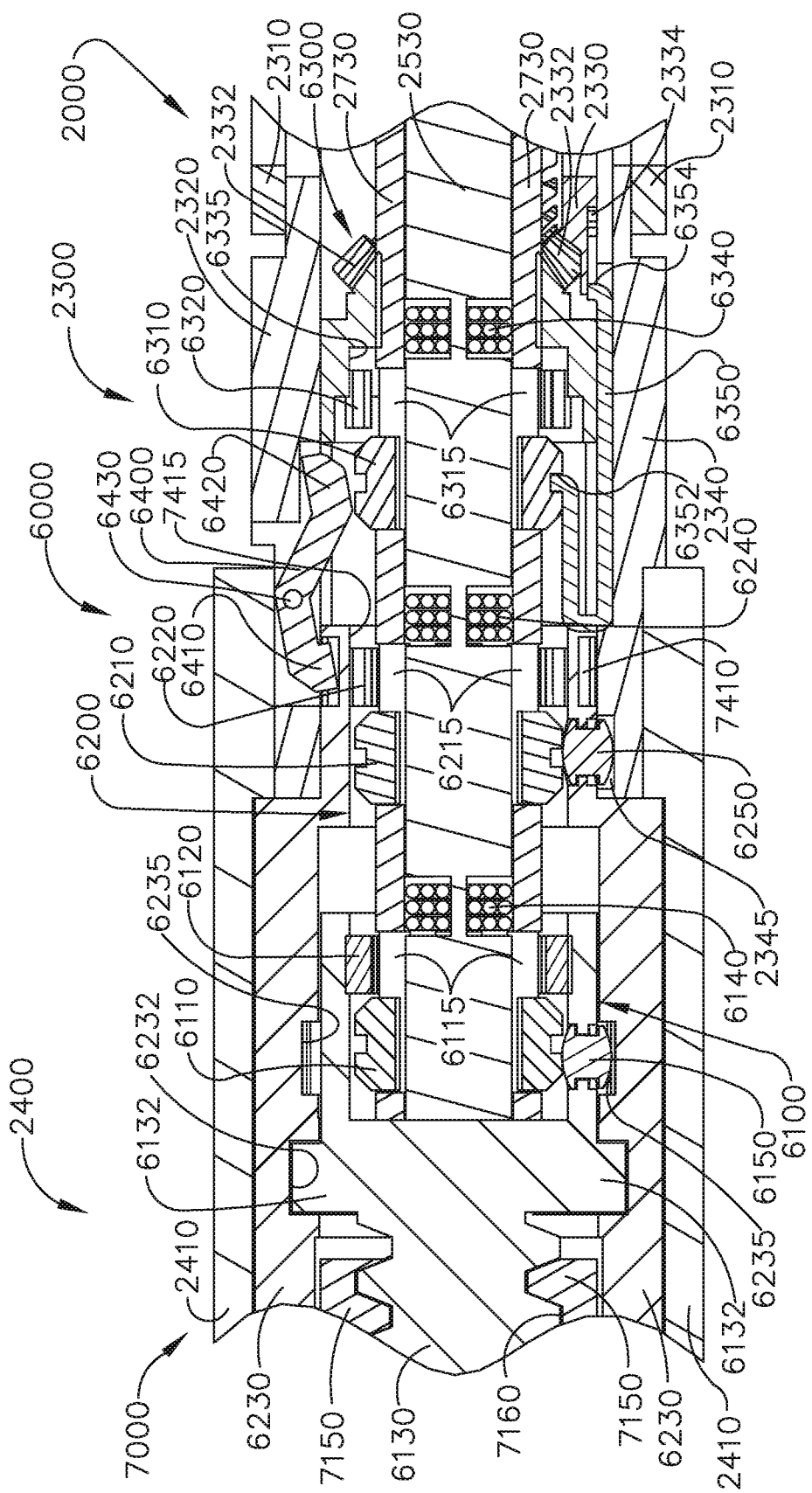
FIG. 27 is a partial cross-sectional view of the end effector of FIG. 14 attached to the shaft assembly of FIG. 2 depicting a first, second, and third clutch of the end effector.

As discussed above, the control system 1800 is configured to actuate the electric motor 1610 to perform three different end effector functions—clamping/opening the jaw assembly 7100 (FIGS. 14 and 15), rotating the end effector 7000 about a longitudinal axis (FIGS. 18 and 19), and articulating the end effector 7000 about an articulation axis (FIGS. 16 and 17). Referring primarily to FIGS. 26 and 27, the control system 1800 is configured to operate a transmission 6000 to selectively perform these three end effector functions. The transmission 6000 comprises a first clutch system 6100 configured to selectively transmit the rotation of the drive shaft 2730 to the drive screw 6130 of the end effector 7000 to open or close the jaw assembly 7100, depending on the direction in which the drive shaft 2730 is rotated. The transmission 6000 further comprises a second clutch system 6200 configured to selectively transmit the rotation of the drive shaft 2730 to the outer housing 6230 of the end effector 7000 to rotate the end effector 7000 about the longitudinal axis L. The transmission 6000 also comprises a third clutch system 6300 configured to selectively transmit the rotation of the drive shaft 2730 to the articulation joint 2300 to articulate the distal attachment portion 2400 and the end effector 7000 about the articulation axis A. The clutch systems 6100, 6200, and 6300 are in electrical communication with the control system 1800 via electrical circuits extending through the shaft 2510, the connector pins 2520, the connector pins 1520, and the shaft 1510, for example. In at least one instance, each of these clutch control circuits comprises two connector pins 2520 and two connector pins 1520, for example.

In various instances, further to the above, the shaft 2510 and/or the shaft 1510 comprise a flexible circuit including electrical traces which form part of the clutch control circuits. The flexible circuit can comprise a ribbon, or substrate, with conductive pathways defined therein and/or thereon. The flexible circuit can also comprise sensors and/or any solid state component, such as signal smoothing capacitors, for example, mounted thereto. In at least one instance, each of the conductive pathways can comprise one or more signal smoothing capacitors which can, among other things, even out fluctuations in signals transmitted through the conductive pathways. In various instances, the flexible circuit can be coated with at least one material, such as an elastomer, for example, which can seal the flexible circuit against fluid ingress.

Figure 22A:
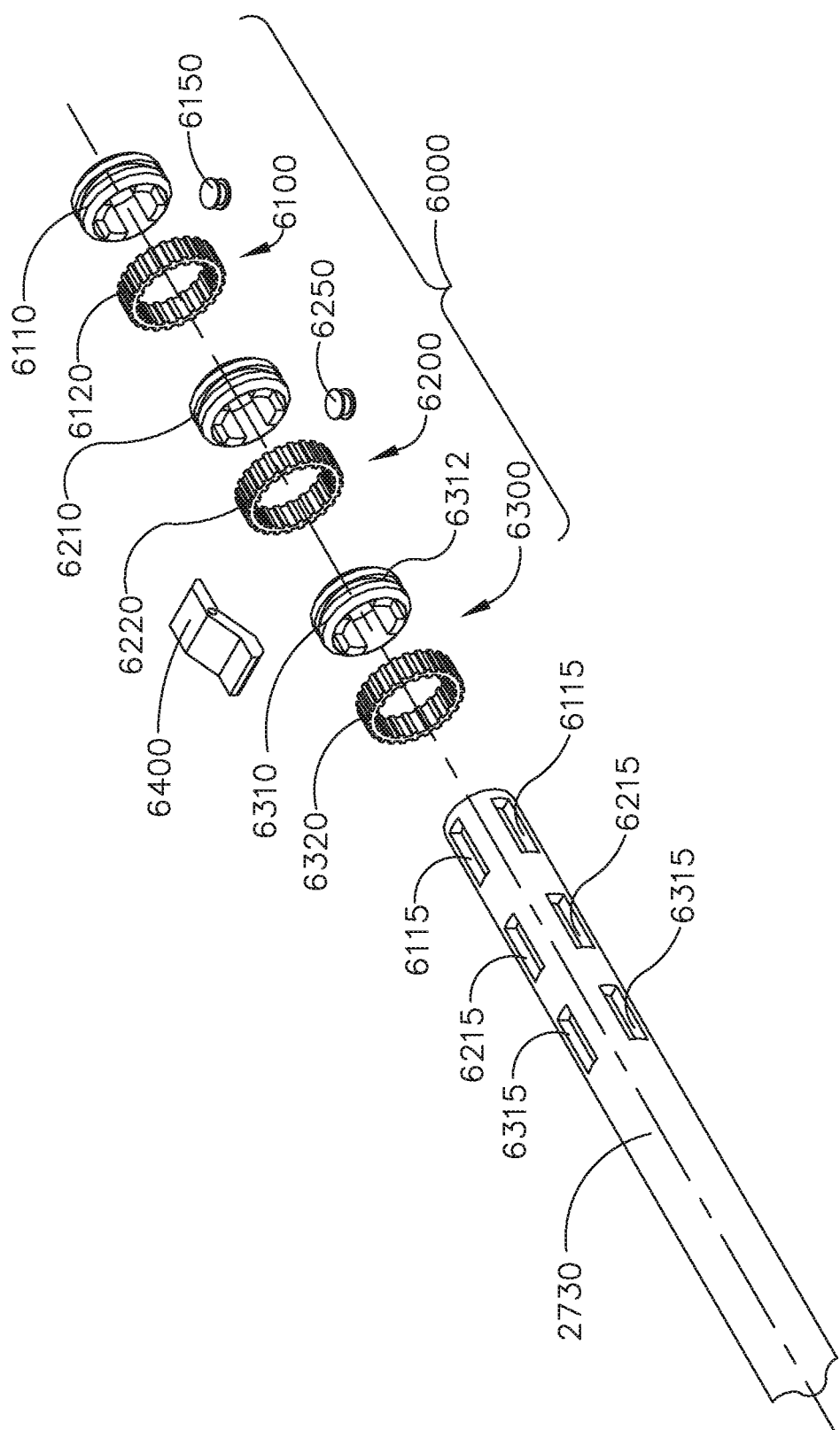
FIG. 22A is an exploded view of the distal portion of the shaft assembly of FIG. 2 illustrated with some components removed.
Figure 28:
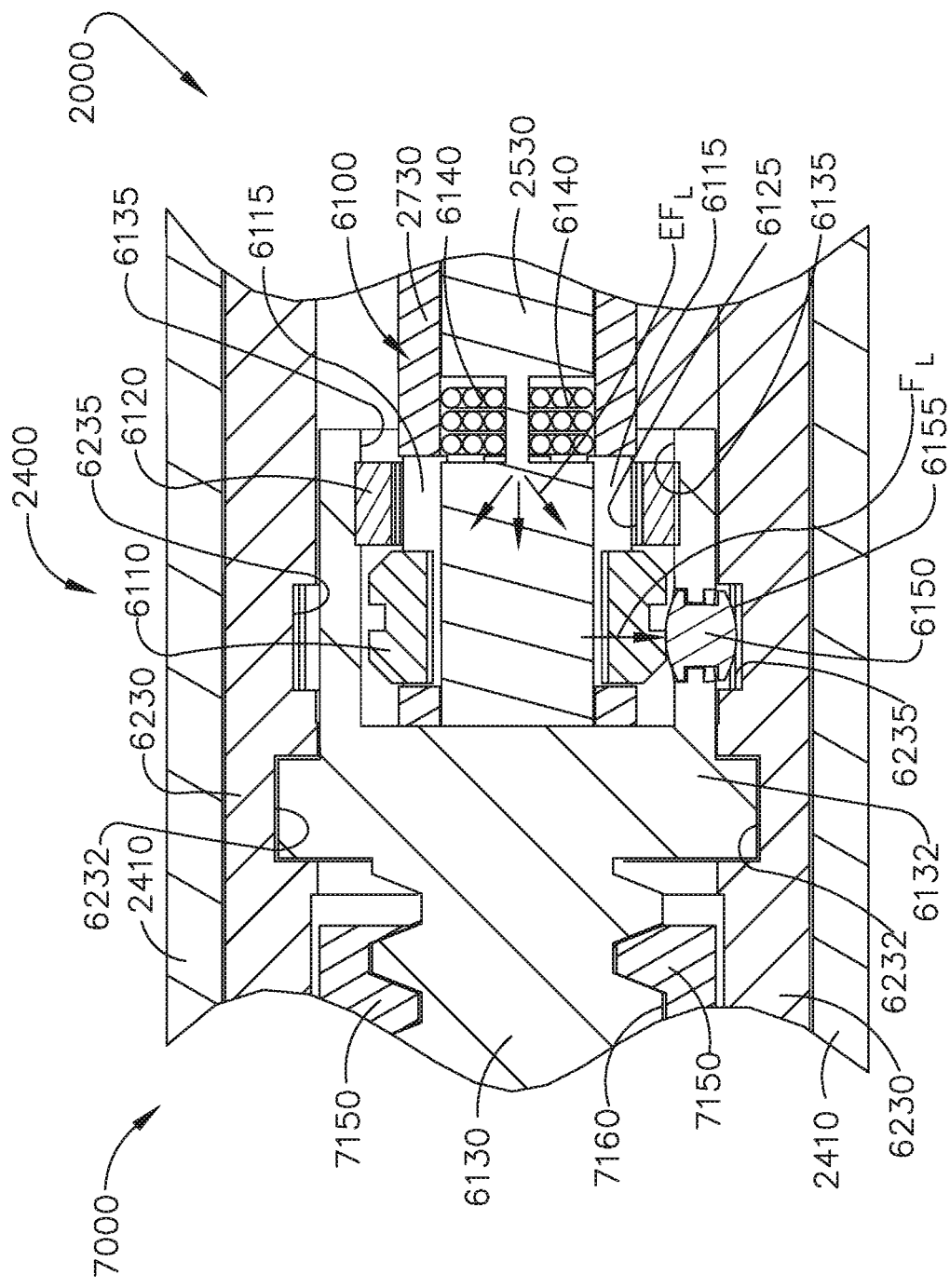
FIG. 28 depicts the first clutch of FIG. 27 in an unactuated condition.

Referring primarily to FIG. 28, the first clutch system 6100 comprises a first clutch 6110, an expandable first drive ring 6120, and a first electromagnetic actuator 6140. The first clutch 6110 comprises an annular ring and is slideably disposed on the drive shaft 2730. The first clutch 6110 is comprised of a magnetic material and is movable between a disengaged, or unactuated, position (FIG. 28) and an engaged, or actuated, position (FIG. 29) by electromagnetic fields EF generated by the first electromagnetic actuator 6140. In various instances, the first clutch 6110 is at least partially comprised of iron and/or nickel, for example. In at least one instance, the first clutch 6110 comprises a permanent magnet. As illustrated in FIG. 22A, the drive shaft 2730 comprises one or more longitudinal key slots 6115 defined therein which are configured to constrain the longitudinal movement of the clutch 6110 relative to the drive shaft 2730. More specifically, the clutch 6110 comprises one or more keys extending into the key slots 6115 such that the distal ends of the key slots 6115 stop the distal movement of the clutch 6110 and the proximal ends of the key slots 6115 stop the proximal movement of the clutch 6110.

Figure 29:
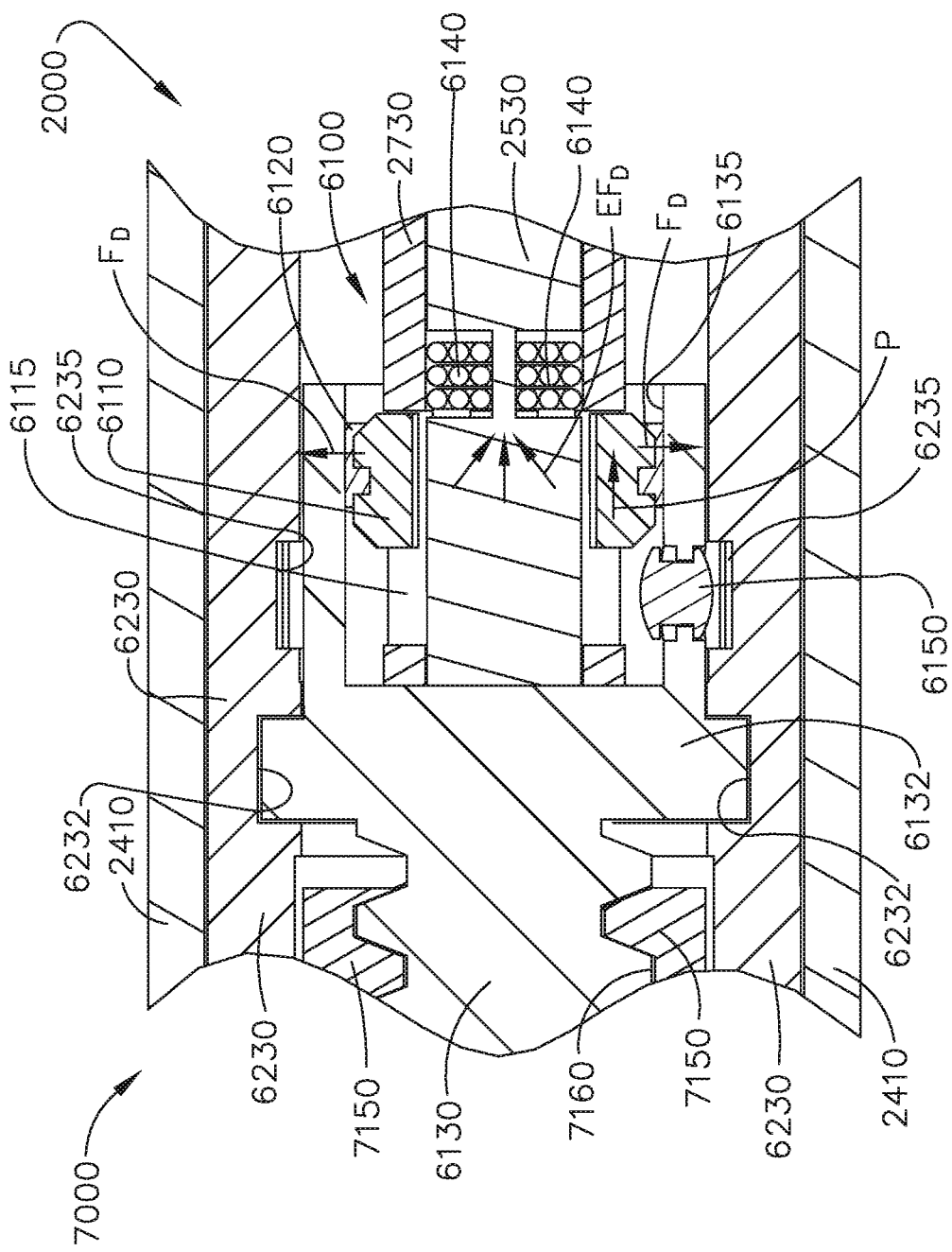
FIG. 29 depicts the first clutch of FIG. 27 in an actuated condition.

When the first clutch 6110 is in its disengaged position (FIG. 28), the first clutch 6110 rotates with the drive shaft 2130 but does not transmit rotational motion to the first drive ring 6120. As can be seen in FIG. 28, the first clutch 6110 is separated from, or not in contact with, the first drive ring 6120. As a result, the rotation of the drive shaft 2730 and the first clutch 6110 is not transmitted to the drive screw 6130 when the first clutch assembly 6100 is in its disengaged state. When the first clutch 6110 is in its engaged position (FIG. 29), the first clutch 6110 is engaged with the first drive ring 6120 such that the first drive ring 6120 is expanded, or stretched, radially outwardly into contact with the drive screw 6130. In at least one instance, the first drive ring 6120 comprises an elastomeric band, for example. As can be seen in FIG. 29, the first drive ring 6120 is compressed against an annular inner sidewall 6135 of the drive screw 6130. As a result, the rotation of the drive shaft 2730 and the first clutch 6110 is transmitted to the drive screw 6130 when the first clutch assembly 6100 is in its engaged state. Depending on the direction in which the drive shaft 2730 is rotated, the first clutch assembly 6100 can move the jaw assembly 7100 into its open and closed configurations when the first clutch assembly 6100 is in its engaged state.

As described above, the first electromagnetic actuator 6140 is configured to generate magnetic fields to move the first clutch 6110 between its disengaged (FIG. 28) and engaged (FIG. 29) positions. For instance, referring to FIG. 28, the first electromagnetic actuator 6140 is configured to emit a magnetic field $EF_L$ which repulses, or drives, the first clutch 6110 away from the first drive ring 6120 when the first clutch assembly 6100 is in its disengaged state. The first electromagnetic actuator 6140 comprises one or more wound coils in a cavity defined in the shaft frame 2530 which generate the magnetic field $EF_L$ when current flows in a first direction through a first electrical clutch circuit including the wound coils. The control system 1800 is configured to apply a first voltage polarity to the first electrical clutch circuit to create the current flowing in the first direction. The control system 1800 can continuously apply the first voltage polarity to the first electric shaft circuit to continuously hold the first clutch 6110 in its disengaged position. While such an arrangement can prevent the first clutch 6110 from unintentionally engaging the first drive ring 6120, such an arrangement can also consume a lot of power. Alternatively, the control system 1800 can apply the first voltage polarity to the first electrical clutch circuit for a sufficient period of time to position the first clutch 6110 in its disengaged position and then discontinue applying the first voltage polarity to the first electric clutch circuit, thereby resulting in a lower consumption of power. That being said, the first clutch assembly 6100 further comprises a first clutch lock 6150 mounted in the drive screw 6130 which is configured to releasably hold the first clutch 6110 in its disengaged position. The first clutch lock 6150 is configured to prevent, or at least reduce the possibility of, the first clutch 6110 from becoming unintentionally engaged with the first drive ring 6120. When the first clutch 6110 is in its disengaged position, as illustrated in FIG. 28, the first clutch lock 6150 interferes with the free movement of the first clutch 6110 and holds the first clutch 6110 in position via a friction force and/or an interference force therebetween. In at least one instance, the first clutch lock 6150 comprises an elastomeric plug, seat, or detent, comprised of rubber, for example. In certain instances, the first clutch lock 6150 comprises a permanent magnet which holds the first clutch 6110 in its disengaged position by an electromagnetic force. In any event, the first electromagnetic actuator 6140 can apply an electromagnetic pulling force to the first clutch 6110 that overcomes these forces, as described in greater detail below.

Further to the above, referring to FIG. 29, the first electromagnetic actuator 6140 is configured to emit a magnetic field $EF_D$ which pulls, or drives, the first clutch 6110 toward the first drive ring 6120 when the first clutch assembly 6100 is in its engaged state. The coils of the first electromagnetic actuator 6140 generate the magnetic field $EF_D$ when current flows in a second, or opposite, direction through the first electrical clutch circuit. The control system 1800 is configured to apply an opposite voltage polarity to the first electrical clutch circuit to create the current flowing in the opposite direction. The control system 1800 can continuously apply the opposite voltage polarity to the first electrical clutch circuit to continuously hold the first clutch 6110 in its engaged position and maintain the operable engagement between the first drive ring 6120 and the drive screw 6130. Alternatively, the first clutch 6110 can be configured to become wedged within the first drive ring 6120 when the first clutch 6110 is in its engaged position and, in such instances, the control system 1800 may not need to continuously apply a voltage polarity to the first electrical clutch circuit to hold the first clutch assembly 6100 in its engaged state. In such instances, the control system 1800 can discontinue applying the voltage polarity once the first clutch 6110 has been sufficiently wedged in the first drive ring 6120.

Notably, further to the above, the first clutch lock 6150 is also configured to lockout the jaw assembly drive when the first clutch 6110 is in its disengaged position. More specifically, referring again to FIG. 28, the first clutch 6110 pushes the first clutch lock 6150 in the drive screw 6130 into engagement with the outer housing 6230 of the end effector 7000 when the first clutch 6110 is in its disengaged position such that the drive screw 6130 does not rotate, or at least substantially rotate, relative to the outer housing 6230. The outer housing 6230 comprises a slot 6235 defined therein which is configured to receive the first clutch lock 6150. When the first clutch 6110 is moved into its engaged position, referring to FIG. 29, the first clutch 6110 is no longer engaged with the first clutch lock 6150 and, as a result, the first clutch lock 6150 is no longer biased into engagement with the outer housing 6230 and the drive screw 6130 can rotate freely with respect to the outer housing 6230. As a result of the above, the first clutch 6110 can do at least two things—operate the jaw drive when the first clutch 6110 is in its engaged position and lock out the jaw drive when the first clutch 6110 is in its disengaged position.

Moreover, further to the above, the threads of the threaded portions 6160 and 7160 can be configured to prevent, or at least resist, backdriving of the jaw drive. In at least one instance, the thread pitch and/or angle of the threaded portions 6160 and 7160, for example, can be selected to prevent the backdriving, or unintentional opening, of the jaw assembly 7100. As a result of the above, the possibility of the jaw assembly 7100 unintentionally opening or closing is prevented, or at least reduced.

Figure 30:
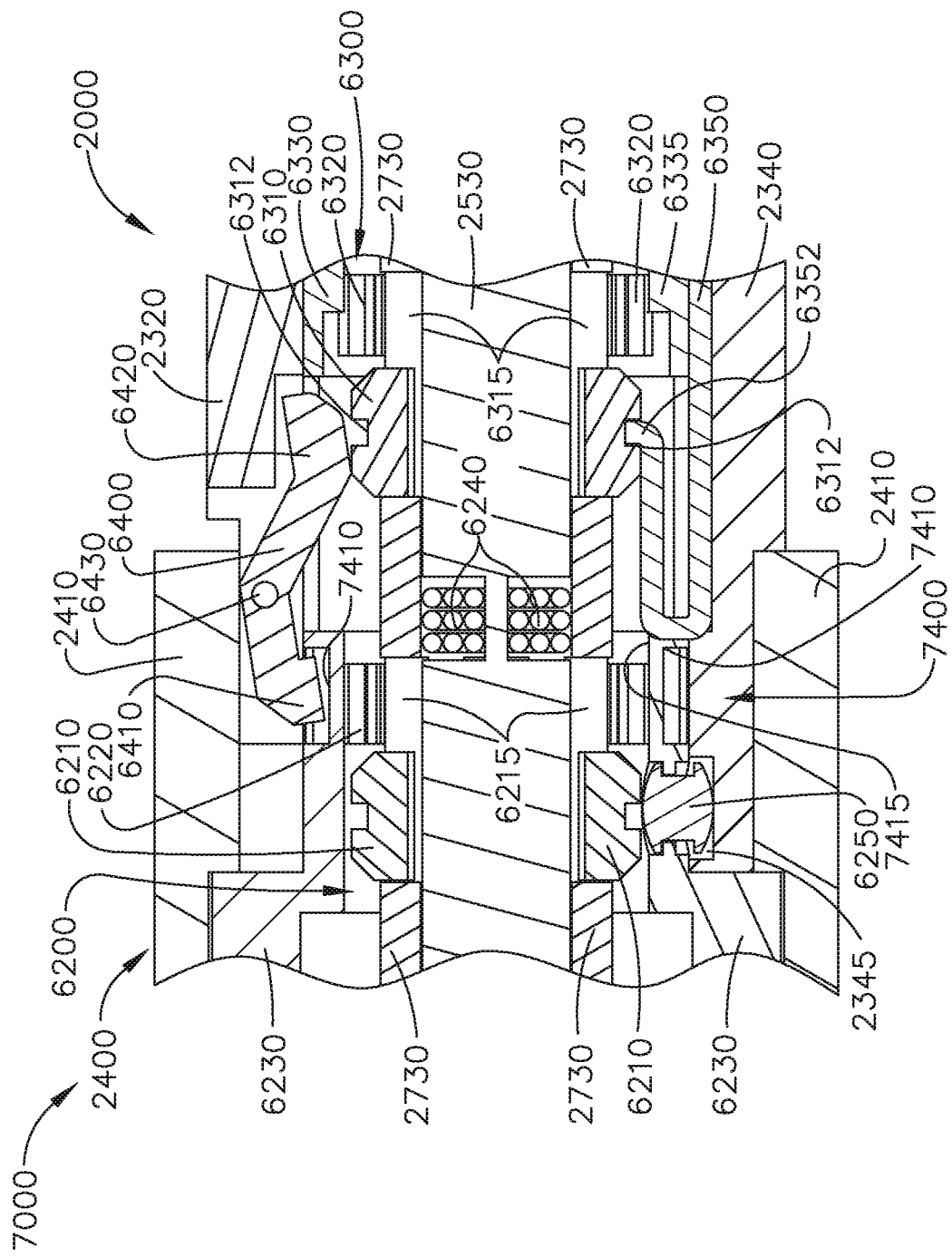
FIG. 30 depicts the second clutch of FIG. 27 in an unactuated condition.

Referring primarily to FIG. 30, the second clutch system 6200 comprises a second clutch 6210, an expandable second drive ring 6220, and a second electromagnetic actuator 6240. The second clutch 6210 comprises an annular ring and is slideably disposed on the drive shaft 2730. The second clutch 6210 is comprised of a magnetic material and is movable between a disengaged, or unactuated, position (FIG. 30) and an engaged, or actuated, position (FIG. 31) by electromagnetic fields EF generated by the second electromagnetic actuator 6240. In various instances, the second clutch 6210 is at least partially comprised of iron and/or nickel, for example. In at least one instance, the second clutch 6210 comprises a permanent magnet. As illustrated in FIG. 22A, the drive shaft 2730 comprises one or more longitudinal key slots 6215 defined therein which are configured to constrain the longitudinal movement of the second clutch 6210 relative to the drive shaft 2730. More specifically, the second clutch 6210 comprises one or more keys extending into the key slots 6215 such that the distal ends of the key slots 6215 stop the distal movement of the second clutch 6210 and the proximal ends of the key slots 6215 stop the proximal movement of the second clutch 6210.

Figure 31:
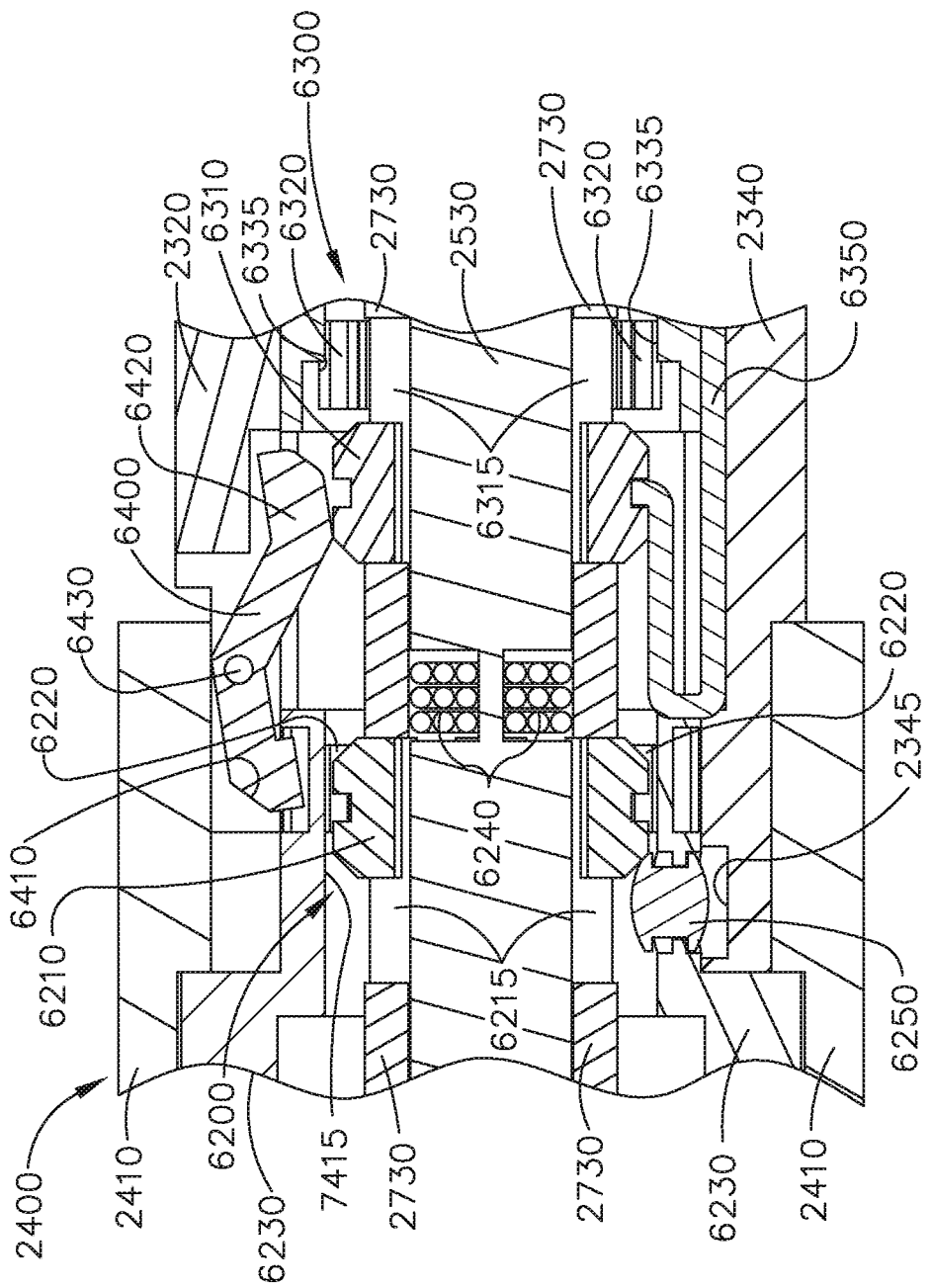
FIG. 31 depicts the second clutch of FIG. 27 in an actuated condition.

When the second clutch 6210 is in its disengaged position, referring to FIG. 30, the second clutch 6210 rotates with the drive shaft 2730 but does not transmit rotational motion to the second drive ring 6220. As can be seen in FIG. 30, the second clutch 6210 is separated from, or not in contact with, the second drive ring 6220. As a result, the rotation of the drive shaft 2730 and the second clutch 6210 is not transmitted to the outer housing 6230 of the end effector 7000 when the second clutch assembly 6200 is in its disengaged state. When the second clutch 6210 is in its engaged position (FIG. 31), the second clutch 6210 is engaged with the second drive ring 6220 such that the second drive ring 6220 is expanded, or stretched, radially outwardly into contact with the outer housing 6230. In at least one instance, the second drive ring 6220 comprises an elastomeric band, for example. As can be seen in FIG. 31, the second drive ring 6220 is compressed against an annular inner sidewall 7415 of the outer housing 6230. As a result, the rotation of the drive shaft 2730 and the second clutch 6210 is transmitted to the outer housing 6230 when the second clutch assembly 6200 is in its engaged state. Depending on the direction in which the drive shaft 2730 is rotated, the second clutch assembly 6200 can rotate the end effector 7000 in a first direction or a second direction about the longitudinal axis L when the second clutch assembly 6200 is in its engaged state.

As described above, the second electromagnetic actuator 6240 is configured to generate magnetic fields to move the second clutch 6210 between its disengaged (FIG. 30) and engaged (FIG. 31) positions. For instance, the second electromagnetic actuator 6240 is configured to emit a magnetic field $EF_L$ which repulses, or drives, the second clutch 6210 away from the second drive ring 6220 when the second clutch assembly 6200 is in its disengaged state. The second electromagnetic actuator 6240 comprises one or more wound coils in a cavity defined in the shaft frame 2530 which generate the magnetic field $EF_L$ when current flows in a first direction through a second electrical clutch circuit including the wound coils. The control system 1800 is configured to apply a first voltage polarity to the second electrical clutch circuit to create the current flowing in the first direction. The control system 1800 can continuously apply the first voltage polarity to the second electric clutch circuit to continuously hold the second clutch 6120 in its disengaged position. While such an arrangement can prevent the second clutch 6210 from unintentionally engaging the second drive ring 6220, such an arrangement can also consume a lot of power. Alternatively, the control system 1800 can apply the first voltage polarity to the second electrical clutch circuit for a sufficient period of time to position the second clutch 6210 in its disengaged position and then discontinue applying the first voltage polarity to the second electric clutch circuit, thereby resulting in a lower consumption of power. That being said, the second clutch assembly 6200 further comprises a second clutch lock 6250 mounted in the outer housing 6230 which is configured to releasably hold the second clutch 6210 in its disengaged position. Similar to the above, the second clutch lock 6250 can prevent, or at least reduce the possibility of, the second clutch 6210 from becoming unintentionally engaged with the second drive ring 6220. When the second clutch 6210 is in its disengaged position, as illustrated in FIG. 30, the second clutch lock 6250 interferes with the free movement of the second clutch 6210 and holds the second clutch 6210 in position via a friction and/or interference force therebetween. In at least one instance, the second clutch lock 6250 comprises an elastomeric plug, seat, or detent, comprised of rubber, for example. In certain instances, the second clutch lock 6250 comprises a permanent magnet which holds the second clutch 6210 in its disengaged position by an electromagnetic force. That said, the second electromagnetic actuator 6240 can apply an electromagnetic pulling force to the second clutch 6210 that overcomes these forces, as described in greater detail below.

Further to the above, referring to FIG. 31, the second electromagnetic actuator 6240 is configured to emit a magnetic field $EF_D$ which pulls, or drives, the second clutch 6210 toward the second drive ring 6220 when the second clutch assembly 6200 is in its engaged state. The coils of the second electromagnetic actuator 6240 generate the magnetic field $EF_D$ when current flows in a second, or opposite, direction through the second electrical shaft circuit. The control system 1800 is configured to apply an opposite voltage polarity to the second electrical shaft circuit to create the current flowing in the opposite direction. The control system 1800 can continuously apply the opposite voltage polarity to the second electric shaft circuit to continuously hold the second clutch 6210 in its engaged position and maintain the operable engagement between the second drive ring 6220 and the outer housing 6230. Alternatively, the second clutch 6210 can be configured to become wedged within the second drive ring 6220 when the second clutch 6210 is in its engaged position and, in such instances, the control system 1800 may not need to continuously apply a voltage polarity to the second shaft electrical circuit to hold the second clutch assembly 6200 in its engaged state. In such instances, the control system 1800 can discontinue applying the voltage polarity once the second clutch 6210 has been sufficiently wedged in the second drive ring 6220.

Notably, further to the above, the second clutch lock 6250 is also configured to lockout the rotation of the end effector 7000 when the second clutch 6210 is in its disengaged position. More specifically, referring again to FIG. 30, the second clutch 6210 pushes the second clutch lock 6250 in the outer shaft 6230 into engagement with the articulation link 2340 when the second clutch 6210 is in its disengaged position such that the end effector 7000 does not rotate, or at least substantially rotate, relative to the distal attachment portion 2400 of the shaft assembly 2000. As illustrated in FIG. 27, the second clutch lock 6250 is positioned or wedged within a slot, or channel, 2345 defined in the articulation link 2340 when the second clutch 6210 is in its disengaged position. As a result of the above, the possibility of the end effector 7000 unintentionally rotating is prevented, or at least reduced. Moreover, as a result of the above, the second clutch 6210 can do at least two things—operate the end effector rotation drive when the second clutch 6210 is in its engaged position and lock out the end effector rotation drive when the second clutch 6210 is in its disengaged position.

Figure 25:
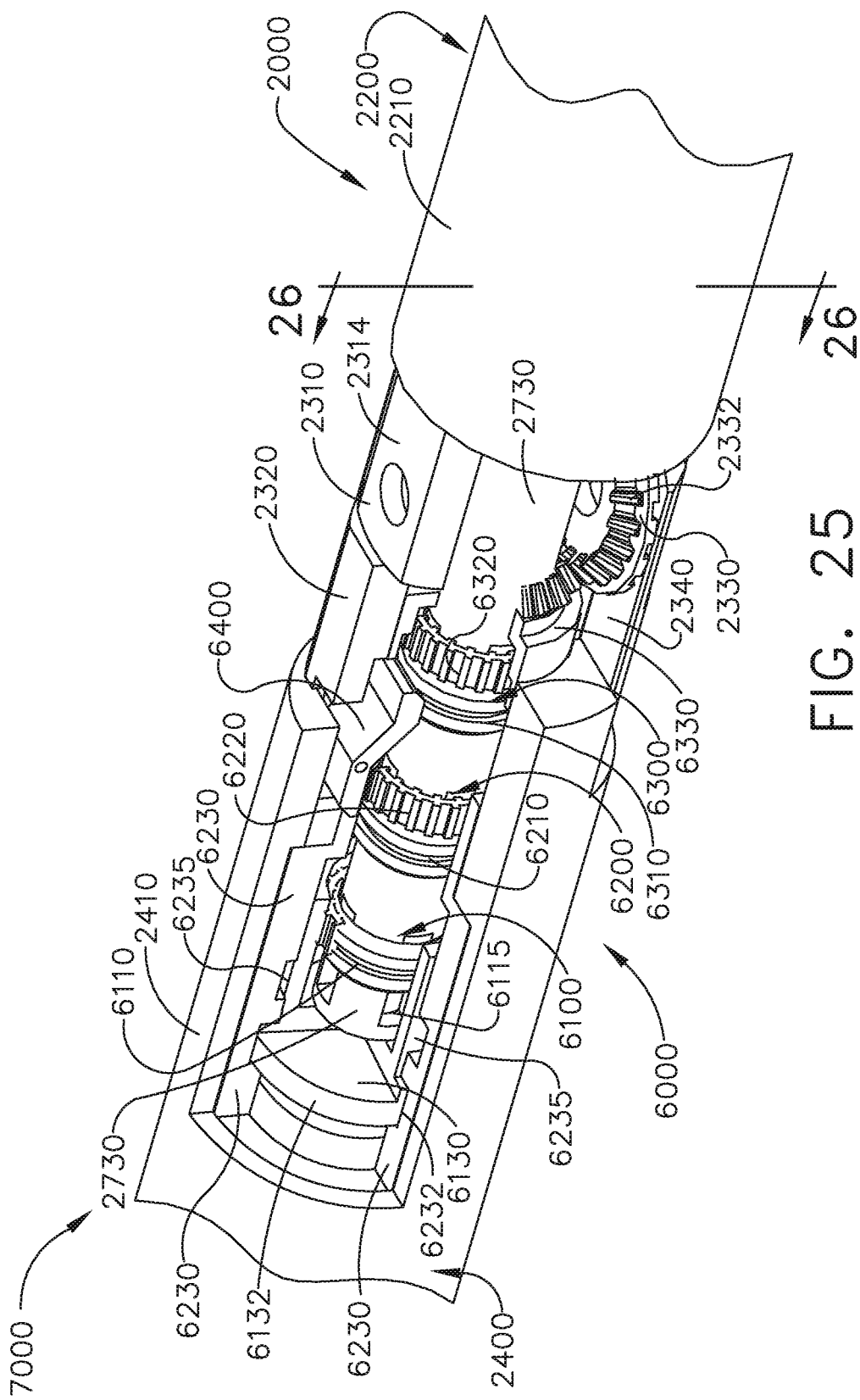
FIG. 25 is a partial cross-sectional perspective view of the end effector of FIG. 14 attached to the shaft assembly of FIG. 2.

Referring primarily to FIGS. 22, 24, and 25, the shaft assembly 2000 further comprises an articulation drive system configured to articulate the distal attachment portion 2400 and the end effector 7000 about the articulation joint 2300. The articulation drive system comprises an articulation drive 6330 rotatably supported within the distal attachment portion 2400. That said, the articulation drive 6330 is closely received within the distal attachment portion 2400 such that the articulation drive 6330 does not translate, or at least substantially translate, relative to the distal attachment portion 2400. The articulation drive system of the shaft assembly 2000 further comprises a stationary gear 2330 fixedly mounted to the articulation frame 2310. More specifically, the stationary gear 2330 is fixedly mounted to a pin connecting a tab 2314 of the articulation frame 2310 and the articulation link 2340 such that the stationary gear 2330 does not rotate relative to the articulation frame 2310. The stationary gear 2330 comprises a central body 2335 and an annular array of stationary teeth 2332 extending around the perimeter of the central body 2335. The articulation drive 6330 comprises an annular array of drive teeth 6332 which is meshingly engaged with the stationary teeth 2332. When the articulation drive 6330 is rotated, the articulation drive 6330 pushes against the stationary gear 2330 and articulates the distal attachment portion 2400 of the shaft assembly 2000 and the end effector 7000 about the articulation joint 2300.

Figure 32:
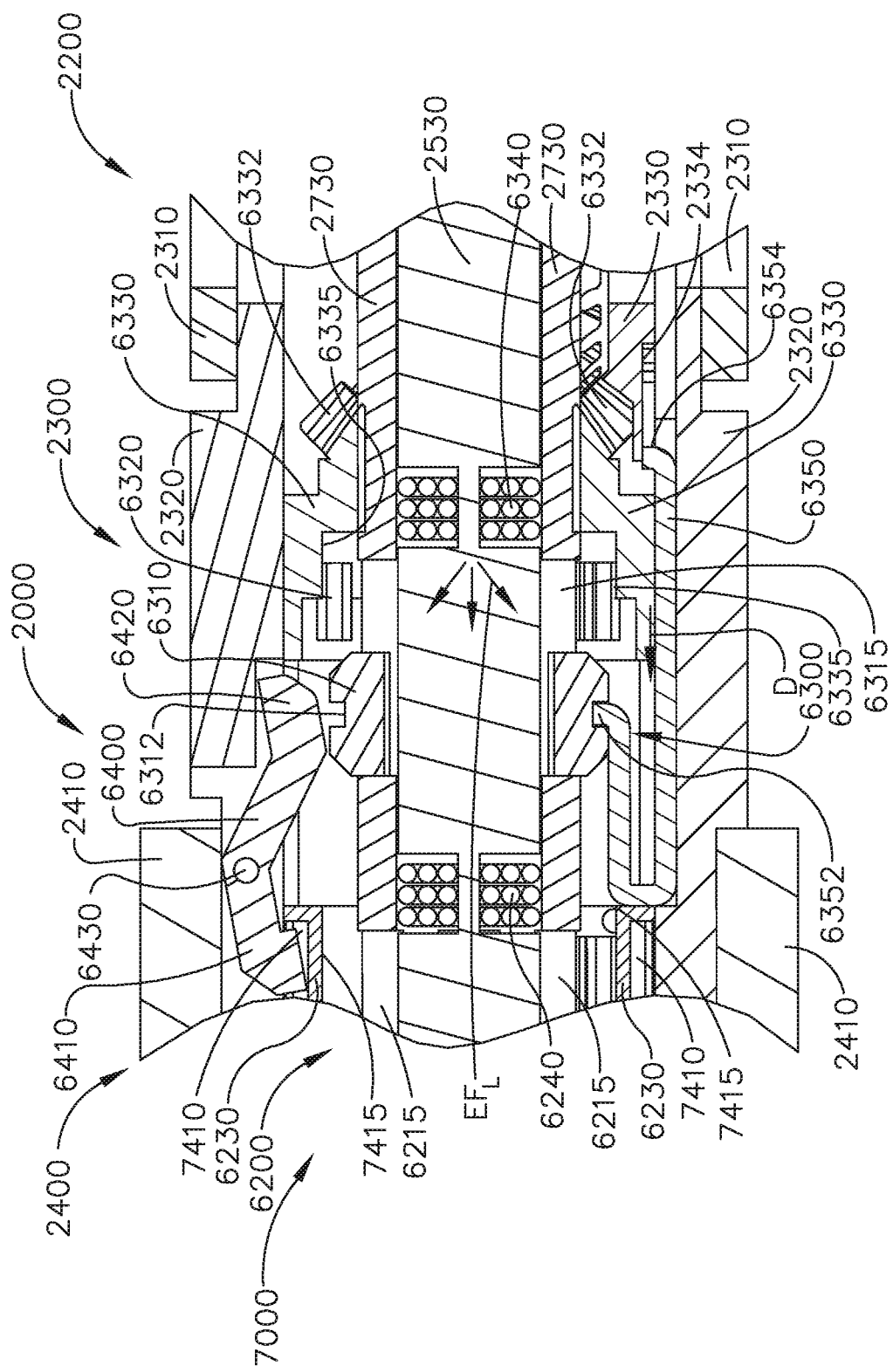
FIG. 32 depicts the third clutch of FIG. 27 in an unactuated condition.

Referring primarily to FIG. 32, the third clutch system 6300 comprises a third clutch 6310, an expandable third drive ring 6320, and a third electromagnetic actuator 6340. The third clutch 6310 comprises an annular ring and is slideably disposed on the drive shaft 2730. The third clutch 6310 is comprised of a magnetic material and is movable between a disengaged, or unactuated, position (FIG. 32) and an engaged, or actuated, position (FIG. 33) by electromagnetic fields EF generated by the third electromagnetic actuator 6340. In various instances, the third clutch 6310 is at least partially comprised of iron and/or nickel, for example. In at least one instance, the third clutch 6310 comprises a permanent magnet. As illustrated in FIG. 22A, the drive shaft 2730 comprises one or more longitudinal key slots 6315 defined therein which are configured to constrain the longitudinal movement of the third clutch 6310 relative to the drive shaft 2730. More specifically, the third clutch 6310 comprises one or more keys extending into the key slots 6315 such that the distal ends of the key slots 6315 stop the distal movement of the third clutch 6310 and the proximal ends of the key slots 6315 stop the proximal movement of the third clutch 6310.

Figure 33:
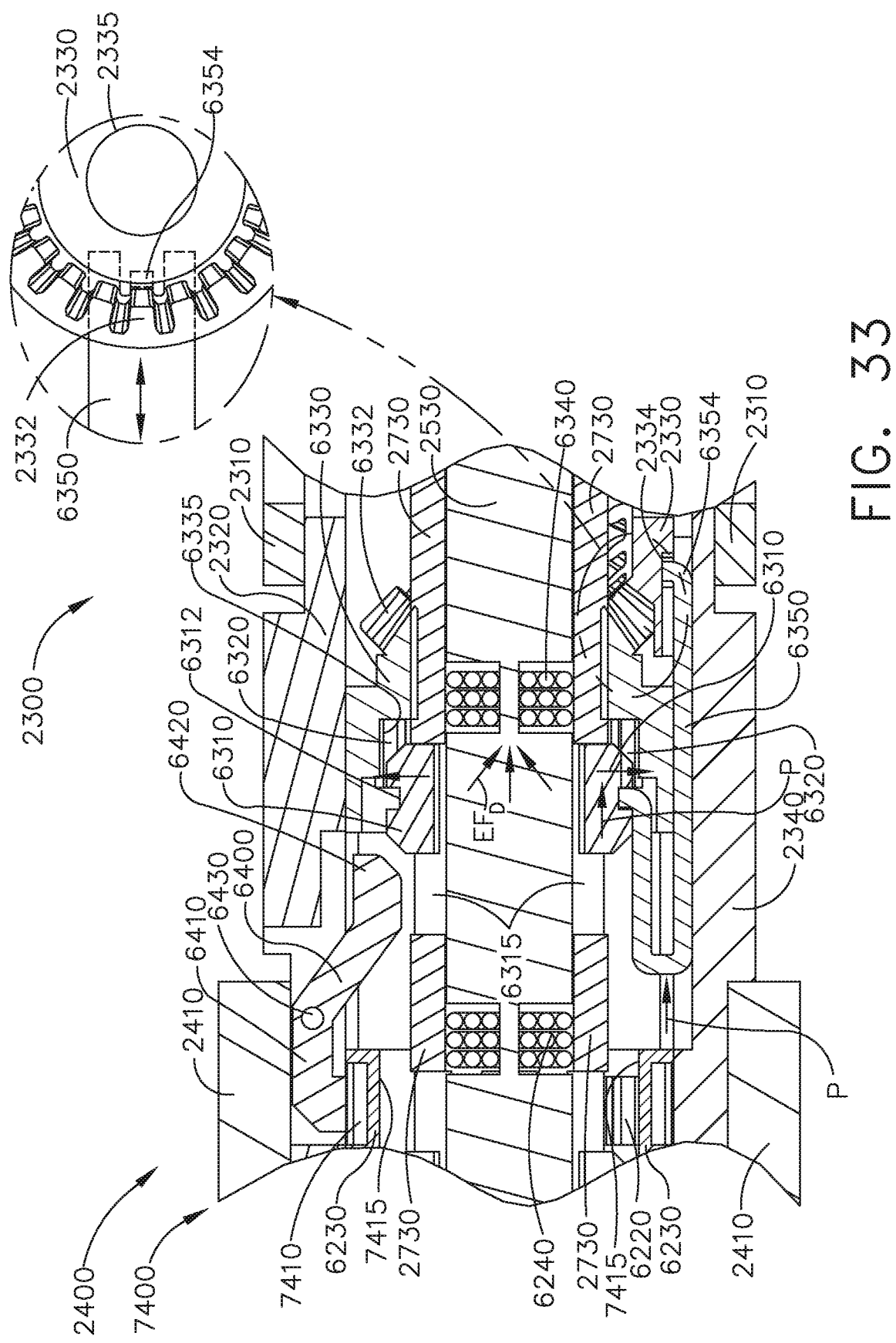
FIG. 33 depicts the third clutch of FIG. 27 in an actuated condition.

When the third clutch 6310 is in its disengaged position, referring to FIG. 32, the third clutch 6310 rotates with the drive shaft 2730 but does not transmit rotational motion to the third drive ring 6320. As can be seen in FIG. 32, the third clutch 6310 is separated from, or not in contact with, the third drive ring 6320. As a result, the rotation of the drive shaft 2730 and the third clutch 6310 is not transmitted to the articulation drive 6330 when the third clutch assembly 6300 is in its disengaged state. When the third clutch 6310 is in its engaged position, referring to FIG. 33, the third clutch 6310 is engaged with the third drive ring 6320 such that the third drive ring 6320 is expanded, or stretched, radially outwardly into contact with the articulation drive 6330. In at least one instance, the third drive ring 6320 comprises an elastomeric band, for example. As can be seen in FIG. 33, the third drive ring 6320 is compressed against an annular inner sidewall 6335 of the articulation drive 6330. As a result, the rotation of the drive shaft 2730 and the third clutch 6310 is transmitted to the articulation drive 6330 when the third clutch assembly 6300 is in its engaged state. Depending on the direction in which the drive shaft 2730 is rotated, the third clutch assembly 6300 can articulate the distal attachment portion 2400 of the shaft assembly 2000 and the end effector 7000 in a first or second direction about the articulation joint 2300.

As described above, the third electromagnetic actuator 6340 is configured to generate magnetic fields to move the third clutch 6310 between its disengaged (FIG. 32) and engaged (FIG. 33) positions. For instance, referring to FIG. 32, the third electromagnetic actuator 6340 is configured to emit a magnetic field $EF_L$ which repulses, or drives, the third clutch 6310 away from the third drive ring 6320 when the third clutch assembly 6300 is in its disengaged state. The third electromagnetic actuator 6340 comprises one or more wound coils in a cavity defined in the shaft frame 2530 which generate the magnetic field $EF_L$ when current flows in a first direction through a third electrical clutch circuit including the wound coils. The control system 1800 is configured to apply a first voltage polarity to the third electrical clutch circuit to create the current flowing in the first direction. The control system 1800 can continuously apply the first voltage polarity to the third electric clutch circuit to continuously hold the third clutch 6310 in its disengaged position. While such an arrangement can prevent the third clutch 6310 from unintentionally engaging the third drive ring 6320, such an arrangement can also consume a lot of power. Alternatively, the control system 1800 can apply the first voltage polarity to the third electrical clutch circuit for a sufficient period of time to position the third clutch 6310 in its disengaged position and then discontinue applying the first voltage polarity to the third electric clutch circuit, thereby resulting in a lower consumption of power.

Further to the above, the third electromagnetic actuator 6340 is configured to emit a magnetic field $EF_D$ which pulls, or drives, the third clutch 6310 toward the third drive ring 6320 when the third clutch assembly 6300 is in its engaged state. The coils of the third electromagnetic actuator 6340 generate the magnetic field $EF_D$ when current flows in a second, or opposite, direction through the third electrical clutch circuit. The control system 1800 is configured to apply an opposite voltage polarity to the third electrical shaft circuit to create the current flowing in the opposite direction. The control system 1800 can continuously apply the opposite voltage polarity to the third electric shaft circuit to continuously hold the third clutch 6310 in its engaged position and maintain the operable engagement between the third drive ring 6320 and the articulation drive 6330. Alternatively, the third clutch 6210 can be configured to become wedged within the third drive ring 6320 when the third clutch 6310 is in its engaged position and, in such instances, the control system 1800 may not need to continuously apply a voltage polarity to the third shaft electrical circuit to hold the third clutch assembly 6300 in its engaged state. In such instances, the control system 1800 can discontinue applying the voltage polarity once the third clutch 6310 has been sufficiently wedged in the third drive ring 6320. In any event, the end effector 7000 is articulatable in a first direction or a second direction, depending on the direction in which the drive shaft 2730 is rotated, when the third clutch assembly 6300 is in its engaged state.

Further to the above, referring to FIGS. 22, 32, and 33, the articulation drive system further comprises a lockout 6350 which prevents, or at least inhibits, the articulation of the distal attachment portion 2400 of the shaft assembly 2000 and the end effector 7000 about the articulation joint 2300 when the third clutch 6310 is in its disengaged position (FIG. 32). Referring primarily to FIG. 22, the articulation link 2340 comprises a slot, or groove, 2350 defined therein wherein the lockout 6350 is slideably positioned in the slot 2350 and extends at least partially under the stationary articulation gear 2330. The lockout 6350 comprises at attachment hook 6352 engaged with the third clutch 6310. More specifically, the third clutch 6310 comprises an annular slot, or groove, 6312 defined therein and the attachment hook 6352 is positioned in the annular slot 6312 such that the lockout 6350 translates with the third clutch 6310. Notably, however, the lockout 6350 does not rotate, or at least substantially rotate, with the third clutch 6310. Instead, the annular groove 6312 in the third clutch 6310 permits the third clutch 6310 to rotate relative to the lockout 6350. The lockout 6350 further comprises a lockout hook 6354 slideably positioned in a radially-extending lockout slot 2334 defined in the bottom of the stationary gear 2330. When the third clutch 6310 is in its disengaged position, as illustrated in FIG. 32, the lockout 6350 is in a locked position in which the lockout hook 6354 prevents the end effector 7000 from rotating about the articulation joint 2300. When the third clutch 6310 is in its engaged position, as illustrated in FIG. 33, the lockout 6350 is in an unlocked position in which the lockout hook 6354 is no longer positioned in the lockout slot 2334. Instead, the lockout hook 6354 is positioned in a clearance slot defined in the middle or body 2335 of the stationary gear 2330. In such instances, the lockout hook 6354 can rotate within the clearance slot when the end effector 7000 rotates about the articulation joint 2300.

Further to the above, the radially-extending lockout slot 2334 depicted in FIGS. 32 and 33 extends longitudinally, i.e., along an axis which is parallel to the longitudinal axis of the elongate shaft 2200. Once the end effector 7000 has been articulated, however, the lockout hook 6354 is no longer aligned with the longitudinal lockout slot 2334. With this in mind, the stationary gear 2330 comprises a plurality, or an array, of radially-extending lockout slots 2334 defined in the bottom of the stationary gear 2330 such that, when the third clutch 6310 is deactuated and the lockout 6350 is pulled distally after the end effector 7000 has been articulated, the lockout hook 6354 can enter one of the lockout slots 2334 and lock the end effector 7000 in its articulated position. Thus, as a result, the end effector 7000 can be locked in an unarticulated and an articulated position. In various instances, the lockout slots 2334 can define discrete articulated positions for the end effector 7000. For instance, the lockout slots 2334 can be defined at 10 degree intervals, for example, which can define discrete articulation orientations for the end effector 7000 at 10 degree intervals. In other instances, these orientations can be at 5 degree intervals, for example. In alternative embodiments, the lockout 6350 comprises a brake that engages a circumferential shoulder defined in the stationary gear 2330 when the third clutch 6310 is disengaged from the third drive ring 6320. In such an embodiment, the end effector 7000 can be locked in any suitable orientation. In any event, the lockout 6350 prevents, or at least reduces the possibility of, the end effector 7000 unintentionally articulating. As a result of the above, the third clutch 6310 can do things—operate the articulation drive when it is in its engaged position and lock out the articulation drive when it is in its disengaged position.

Referring primarily to FIGS. 24 and 25, the shaft frame 2530 and the drive shaft 2730 extend through the articulation joint 2300 into the distal attachment portion 2400. When the end effector 7000 is articulated, as illustrated in FIGS. 16 and 17, the shaft frame 2530 and the drive shaft 2730 bend to accommodate the articulation of the end effector 7000. Thus, the shaft frame 2530 and the drive shaft 2730 are comprised of any suitable material which accommodates the articulation of the end effector 7000. Moreover, as discussed above, the shaft frame 2530 houses the first, second, and third electromagnetic actuators 6140, 6240, and 6340. In various instances, the first, second, and third electromagnetic actuators 6140, 6240, and 6340 each comprise wound wire coils, such as copper wire coils, for example, and the shaft frame 2530 is comprised of an insulative material to prevent, or at least reduce the possibility of, short circuits between the first, second, and third electromagnetic actuators 6140, 6240, and 6340. In various instances, the first, second, and third electrical clutch circuits extending through the shaft frame 2530 are comprised of insulated electrical wires, for example. Further to the above, the first, second, and third electrical clutch circuits place the electromagnetic actuators 6140, 6240, and 6340 in communication with the control system 1800 in the drive module 1100.

As described above, the clutches 6110, 6210, and/or 6310 can be held in their disengaged positions so that they do not unintentionally move into their engaged positions. In various arrangements, the clutch system 6000 comprises a first biasing member, such as a spring, for example, configured to bias the first clutch 6110 into its disengaged position, a second biasing member, such as a spring, for example, configured to bias the second clutch 6210 into its disengaged position, and/or a third biasing member, such as a spring, for example, configured to bias the third clutch 6110 into its disengaged position. In such arrangements, the biasing forces of the springs can be selectively overcome by the electromagnetic forces generated by the electromagnetic actuators when energized by an electrical current. Further to the above, the clutches 6110, 6210, and/or 6310 can be retained in their engaged positions by the drive rings 6120, 6220, and/or 6320, respectively. More specifically, in at least one instance, the drive rings 6120, 6220, and/or 6320 are comprised of an elastic material which grips or frictionally holds the clutches 6110, 6210, and/or 6310, respectively, in their engaged positions. In various alternative embodiments, the clutch system 6000 comprises a first biasing member, such as a spring, for example, configured to bias the first clutch 6110 into its engaged position, a second biasing member, such as a spring, for example, configured to bias the second clutch 6210 into its engaged position, and/or a third biasing member, such as a spring, for example, configured to bias the third clutch 6110 into its engaged position. In such arrangements, the biasing forces of the springs can be overcome by the electromagnetic forces applied by the electromagnetic actuators 6140, 6240, and/or 6340, respectively, as needed to selectively hold the clutches 6110, 6210, and 6310 in their disengaged positions. In any one operational mode of the surgical system, the control assembly 1800 can energize one of the electromagnetic actuators to engage one of the clutches while energizing the other two electromagnetic actuators to disengage the other two clutches.

Although the clutch system 6000 comprises three clutches to control three drive systems of the surgical system, a clutch system can comprise any suitable number of clutches to control any suitable number of systems. Moreover, although the clutches of the clutch system 6000 slide proximally and distally between their engaged and disengaged positions, the clutches of a clutch system can move in any suitable manner. In addition, although the clutches of the clutch system 6000 are engaged one at a time to control one drive motion at a time, various instances are envisioned in which more than one clutch can be engaged to control more than one drive motion at a time.

In view of the above, the reader should appreciate that the control system 1800 is configured to, one, operate the motor system 1600 to rotate the drive shaft system 2700 in an appropriate direction and, two, operate the clutch system 6000 to transfer the rotation of the drive shaft system 2700 to the appropriate function of the end effector 7000. Moreover, as discussed above, the control system 1800 is responsive to inputs from the clamping trigger system 2600 of the shaft assembly 2000 and the input system 1400 of the handle 1000. When the clamping trigger system 2600 is actuated, as discussed above, the control system 1800 activates the first clutch assembly 6100 and deactivates the second clutch assembly 6200 and the third clutch assembly 6300. In such instances, the control system 1800 also supplies power to the motor system 1600 to rotate the drive shaft system 2700 in a first direction to clamp the jaw assembly 7100 of the end effector 7000. When the control system 1800 detects that the jaw assembly 7100 is in its clamped configuration, the control system 1800 stops the motor assembly 1600 and deactivates the first clutch assembly 6100. When the control system 1800 detects that the clamping trigger system 2600 has been moved to, or is being moved to, its unactuated position, the control system 1800 activates, or maintains the activation of, the first clutch assembly 6100 and deactivates, or maintains the deactivation of, the second clutch assembly 6200 and the third clutch assembly 6300. In such instances, the control system 1800 also supplies power to the motor system 1600 to rotate the drive shaft system 2700 in a second direction to open the jaw assembly 7100 of the end effector 7000.

When the rotation actuator 1420 is actuated in a first direction, further to the above, the control system 1800 activates the second clutch assembly 6200 and deactivates the first clutch assembly 6100 and the third clutch assembly 6300. In such instances, the control system 1800 also supplies power to the motor system 1600 to rotate the drive shaft system 2700 in a first direction to rotate the end effector 7000 in a first direction. When the control system 1800 detects that the rotation actuator 1420 has been actuated in a second direction, the control system 1800 activates, or maintains the activation of, the second clutch assembly 6200 and deactivates, or maintains the deactivation of, the first clutch assembly 6100 and the third clutch assembly 6300. In such instances, the control system 1800 also supplies power to the motor system 1600 to rotate the drive shaft system 2700 in a second direction to rotate the drive shaft system 2700 in a second direction to rotate the end effector 7000 in a second direction. When the control system 1800 detects that the rotation actuator 1420 is not actuated, the control system 1800 deactivates the second clutch assembly 6200.

When the first articulation actuator 1432 is depressed, further to the above, the control system 1800 activates the third clutch assembly 6300 and deactivates the first clutch assembly 6100 and the second clutch assembly 6200. In such instances, the control system 1800 also supplies power to the motor system 1600 to rotate the drive shaft system 2700 in a first direction to articulate the end effector 7000 in a first direction. When the control system 1800 detects that the second articulation actuator 1434 is depressed, the control system 1800 activates, or maintains the activation of, the third clutch assembly 6200 and deactivates, or maintains the deactivation of, the first clutch assembly 6100 and the second clutch assembly 6200. In such instances, the control system 1800 also supplies power to the motor system 1600 to rotate the drive shaft system 2700 in a second direction to articulate the end effector 7000 in a second direction. When the control system 1800 detects that neither the first articulation actuator 1432 nor the second articulation actuator 1434 are actuated, the control system 1800 deactivates the third clutch assembly 6200.

Further to the above, the control system 1800 is configured to change the operating mode of the stapling system based on the inputs it receives from the clamping trigger system 2600 of the shaft assembly 2000 and the input system 1400 of the handle 1000. The control system 1800 is configured to shift the clutch system 6000 before rotating the shaft drive system 2700 to perform the corresponding end effector function. Moreover, the control system 1800 is configured to stop the rotation of the shaft drive system 2700 before shifting the clutch system 6000. Such an arrangement can prevent the sudden movements in the end effector 7000. Alternatively, the control system 1800 can shift the clutch system 600 while the shaft drive system 2700 is rotating. Such an arrangement can allow the control system 1800 to shift quickly between operating modes.

Figure 34:
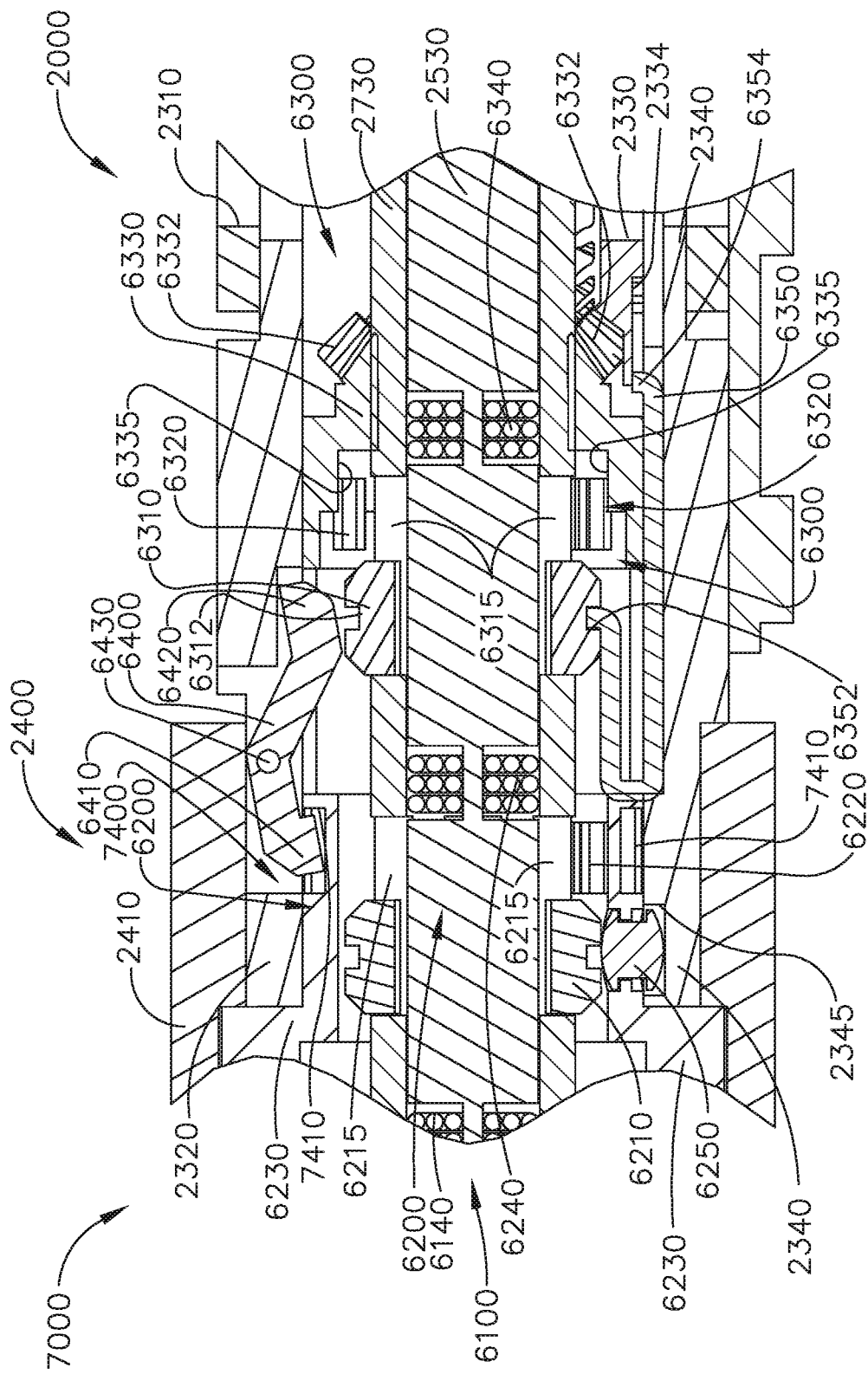
FIG. 34 depicts the second and third clutches of FIG. 27 in their unactuated conditions and the end effector of FIG. 14 locked to the shaft assembly of FIG. 2.
Figure 35:
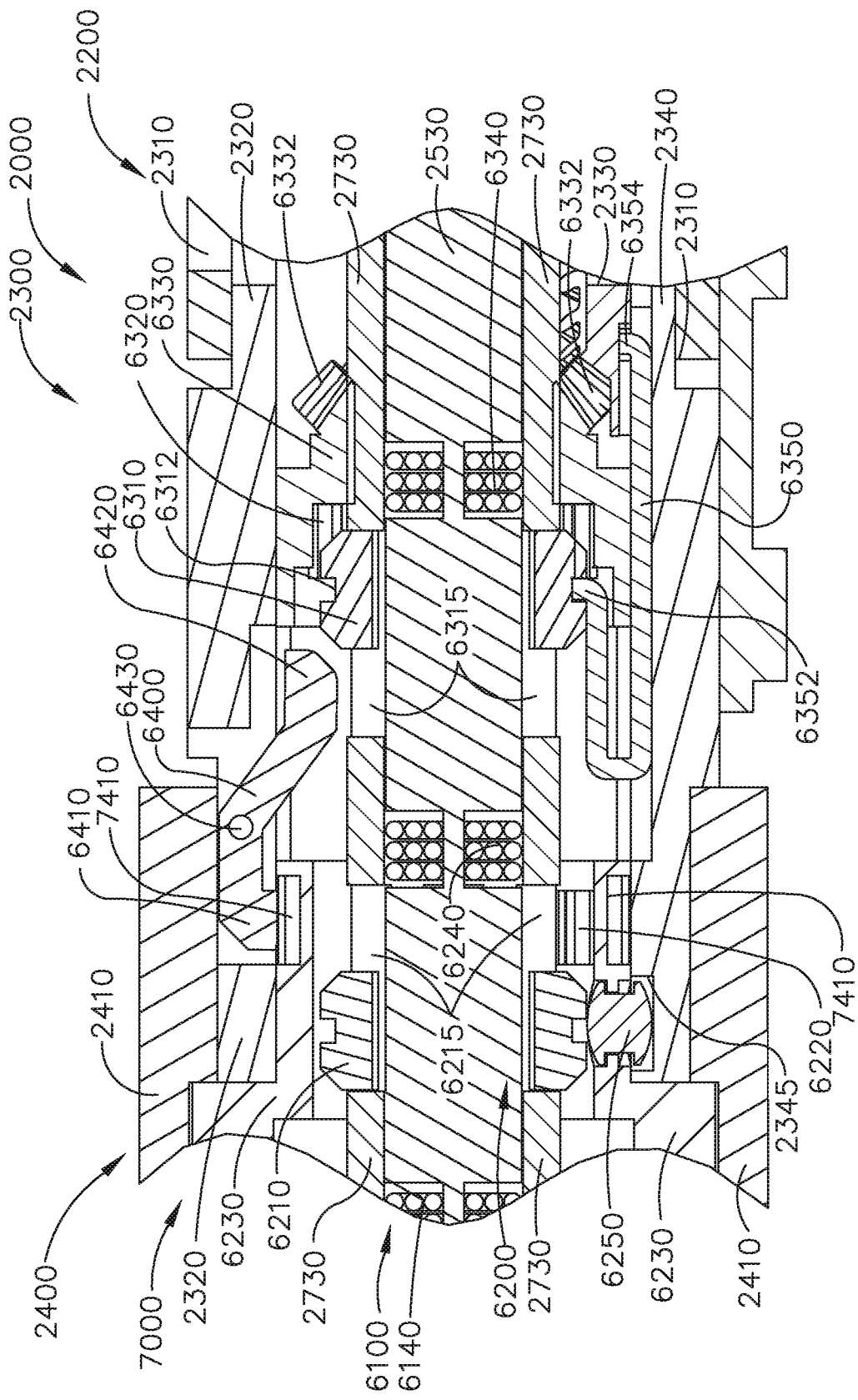
FIG. 35 depicts the second clutch of FIG. 27 in its unactuated condition and the third clutch of FIG. 27 in its actuated condition.
Figure 36:
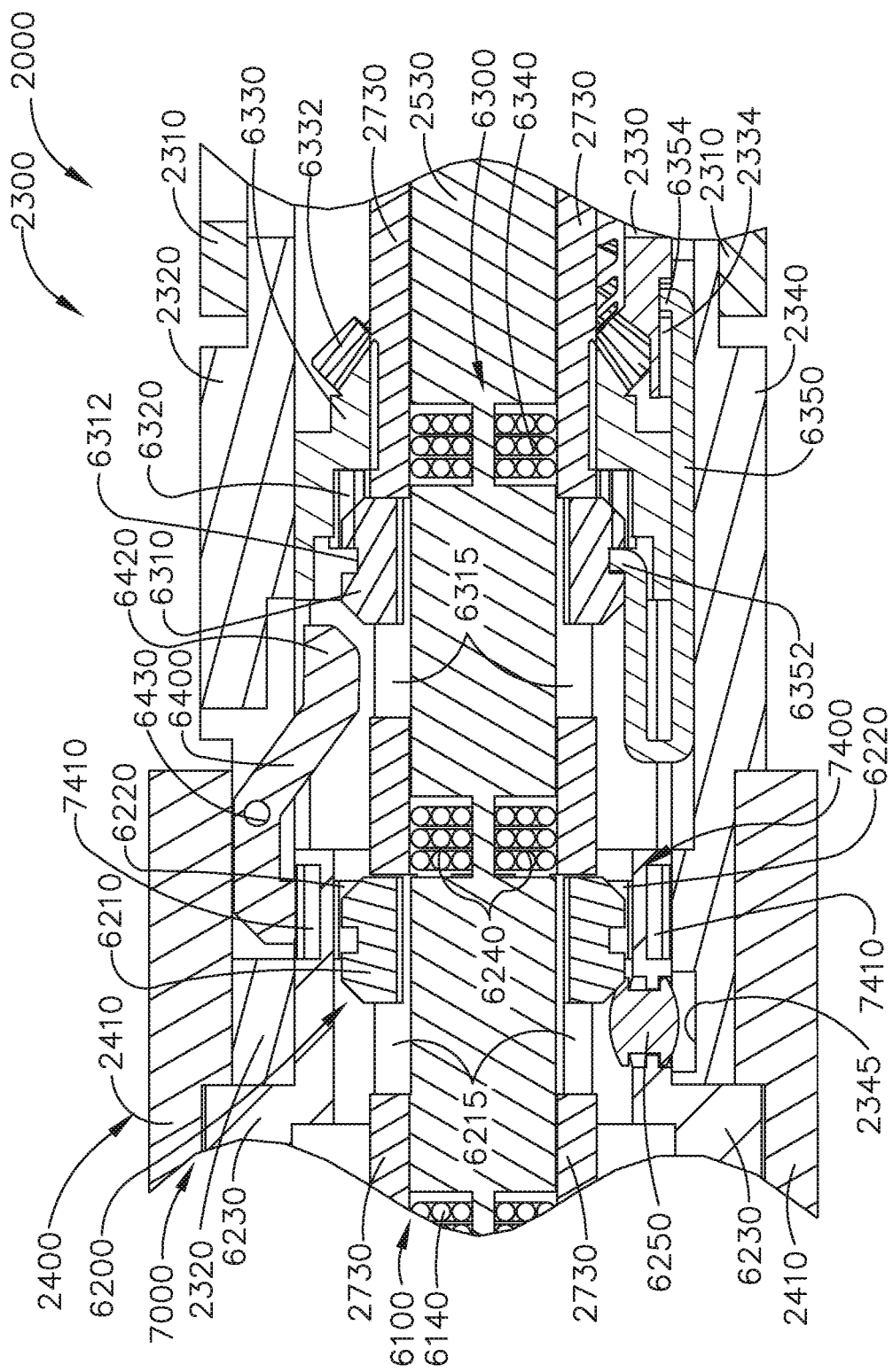
FIG. 36 depicts the second and third clutches of FIG. 27 in their actuated conditions and the end effector of FIG. 14 unlocked from the shaft assembly of FIG. 2.

As discussed above, referring to FIG. 34, the distal attachment portion 2400 of the shaft assembly 2000 comprises an end effector lock 6400 configured to prevent the end effector 7000 from being unintentionally decoupled from the shaft assembly 2000. The end effector lock 6400 comprises a lock end 6410 selectively engageable with the annular array of lock notches 7410 defined on the proximal attachment portion 7400 of the end effector 7000, a proximal end 6420, and a pivot 6430 rotatably connecting the end effector lock 6400 to the articulation link 2320. When the third clutch 6310 of the third clutch assembly 6300 is in its disengaged position, as illustrated in FIG. 34, the third clutch 6310 is contact with the proximal end 6420 of the end effector lock 6400 such that the lock end 6410 of the end effector lock 6400 is engaged with the array of lock notches 7410. In such instances, the end effector 7000 can rotate relative to the end effector lock 6400 but cannot translate relative to the distal attachment portion 2400. When the third clutch 6310 is moved into its engaged position, as illustrated in FIG. 35, the third clutch 6310 is no longer engaged with the proximal end 6420 of the end effector lock 6400. In such instances, the end effector lock 6400 is free to pivot upwardly and permit the end effector 7000 to be detached from the shaft assembly 2000.

The above being said, referring again to FIG. 34, it is possible that the second clutch 6210 of the second clutch assembly 6200 is in its disengaged position when the clinician detaches, or attempts to detach, the end effector 7000 from the shaft assembly 2000. As discussed above, the second clutch 6210 is engaged with the second clutch lock 6250 when the second clutch 6210 is in its disengaged position and, in such instances, the second clutch lock 6250 is pushed into engagement with the articulation link 2340. More specifically, the second clutch lock 6250 is positioned in the channel 2345 defined in the articulation 2340 when the second clutch 6210 is engaged with the second clutch lock 6250 which may prevent, or at least impede, the end effector 7000 from being detached from the shaft assembly 2000. To facilitate the release of the end effector 7000 from the shaft assembly 2000, the control system 1800 can move the second clutch 6210 into its engaged position in addition to moving the third clutch 6310 into its engaged position. In such instances, the end effector 7000 can clear both the end effector lock 6400 and the second clutch lock 6250 when the end effector 7000 is removed.

In at least one instance, further to the above, the drive module 1100 comprises an input switch and/or sensor in communication with the control system 1800 via the input system 1400, and/or the control system 1800 directly, which, when actuated, causes the control system 1800 to unlock the end effector 7000. In various instances, the drive module 1100 comprises an input screen 1440 in communication with the board 1410 of the input system 1400 which is configured to receive an unlock input from the clinician. In response to the unlock input, the control system 1800 can stop the motor system 1600, if it is running, and unlock the end effector 7000 as described above. The input screen 1440 is also configured to receive a lock input from the clinician in which the input system 1800 moves the second clutch assembly 6200 and/or the third clutch assembly 6300 into their unactuated states to lock the end effector 7000 to the shaft assembly 2000.

Figure 37:
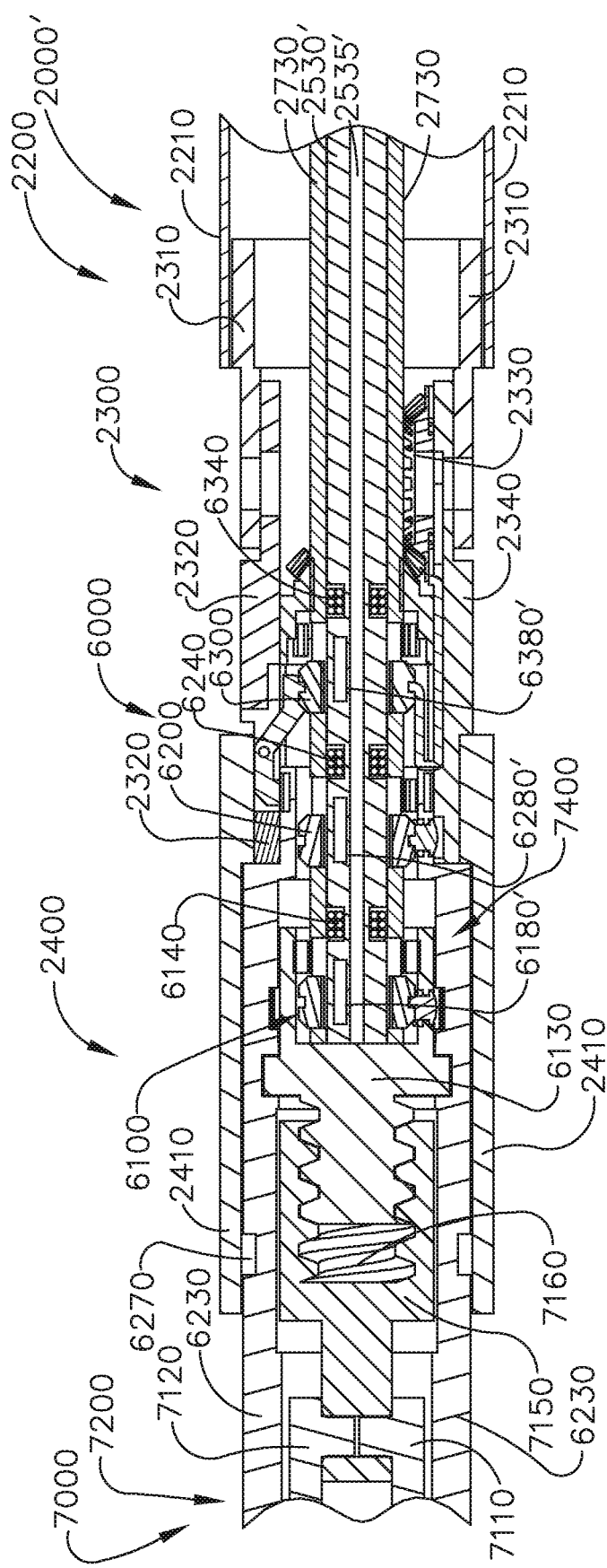
FIG. 37 is a partial cross-sectional view of a shaft assembly in accordance with at least one alternative embodiment comprising sensors configured to detect the conditions of the first, second, and third clutches of FIG. 27.

FIG. 37 depicts a shaft assembly 2000' in accordance with at least one alternative embodiment. The shaft assembly 2000' is similar to the shaft assembly 2000 in many respects, most of which will not be repeated herein for the sake of brevity. Similar to the shaft assembly 2000, the shaft assembly 2000' comprises a shaft frame, i.e., shaft frame 2530'. The shaft frame 2530' comprises a longitudinal passage 2535' and, in addition, a plurality of clutch position sensors, i.e., a first sensor 6180', a second sensor 6280', and a third sensor 6380' positioned in the shaft frame 2530'. The first sensor 6180' is in signal communication with the control system 1800 as part of a first sensing circuit. The first sensing circuit comprises signal wires extending through the longitudinal passage 2535'; however, the first sensing circuit can comprise a wireless signal transmitter and receiver to place the first sensor 6180' in signal communication with the control system 1800. The first sensor 6180' is positioned and arranged to detect the position of the first clutch 6110 of the first clutch assembly 6100. Based on data received from the first sensor 6180', the control system 1800 can determine whether the first clutch 6110 is in its engaged position, its disengaged position, or somewhere in-between. With this information, the control system 1800 can assess whether or not the first clutch 6110 is in the correct position given the operating state of the surgical instrument. For instance, if the surgical instrument is in its jaw clamping/opening operating state, the control system 1800 can verify whether the first clutch 6110 is properly positioned in its engaged position. In such instances, further to the below, the control system 1800 can also verify that the second clutch 6210 is in its disengaged position via the second sensor 6280' and that the third clutch 6310 is in its disengaged position via the third sensor 6380'. Correspondingly, the control system 1800 can verify whether the first clutch 6110 is properly positioned in its disengaged position if the surgical instrument is not in its jaw clamping/opening state. To the extent that the first clutch 6110 is not in its proper position, the control system 1800 can actuate the first electromagnetic actuator 6140 in an attempt to properly position the first clutch 6110. Likewise, the control system 1800 can actuate the electromagnetic actuators 6240 and/or 6340 to properly position the clutches 6210 and/or 6310, if necessary.

The second sensor 6280' is in signal communication with the control system 1800 as part of a second sensing circuit. The second sensing circuit comprises signal wires extending through the longitudinal passage 2535'; however, the second sensing circuit can comprise a wireless signal transmitter and receiver to place the second sensor 6280' in signal communication with the control system 1800. The second sensor 6280' is positioned and arranged to detect the position of the second clutch 6210 of the first clutch assembly 6200. Based on data received from the second sensor 6280', the control system 1800 can determine whether the second clutch 6210 is in its engaged position, its disengaged position, or somewhere in-between. With this information, the control system 1800 can assess whether or not the second clutch 6210 is in the correct position given the operating state of the surgical instrument. For instance, if the surgical instrument is in its end effector rotation operating state, the control system 1800 can verify whether the second clutch 6210 is properly positioned in its engaged position. In such instances, the control system 1800 can also verify that the first clutch 6110 is in its disengaged position via the first sensor 6180' and, further to the below, the control system 1800 can also verify that the third clutch 6310 is in its disengaged position via the third sensor 6380'. Correspondingly, the control system 1800 can verify whether the second clutch 6110 is properly positioned in its disengaged position if the surgical instrument is not in its end effector rotation state. To the extent that the second clutch 6210 is not in its proper position, the control system 1800 can actuate the second electromagnetic actuator 6240 in an attempt to properly position the second clutch 6210. Likewise, the control system 1800 can actuate the electromagnetic actuators 6140 and/or 6340 to properly position the clutches 6110 and/or 6310, if necessary.

The third sensor 6380' is in signal communication with the control system 1800 as part of a third sensing circuit. The third sensing circuit comprises signal wires extending through the longitudinal passage 2535'; however, the third sensing circuit can comprise a wireless signal transmitter and receiver to place the third sensor 6380' in signal communication with the control system 1800. The third sensor 6380' is positioned and arranged to detect the position of the third clutch 6310 of the third clutch assembly 6300. Based on data received from the third sensor 6380', the control system 1800 can determine whether the third clutch 6310 is in its engaged position, its disengaged position, or somewhere in-between. With this information, the control system 1800 can assess whether or not the third clutch 6310 is in the correct position given the operating state of the surgical instrument. For instance, if the surgical instrument is in its end effector articulation operating state, the control system 1800 can verify whether the third clutch 6310 is properly positioned in its engaged position. In such instances, the control system 1800 can also verify that the first clutch 6110 is in its disengaged position via the first sensor 6180' and that the second clutch 6210 is in its disengaged position via the second sensor 6280'. Correspondingly, the control system 1800 can verify whether the third clutch 6310 is properly positioned in its disengaged position if the surgical instrument is not in its end effector articulation state. To the extent that the third clutch 6310 is not in its proper position, the control system 1800 can actuate the third electromagnetic actuator 6340 in an attempt to properly position the third clutch 6310. Likewise, the control system 1800 can actuate the electromagnetic actuators 6140 and/or 6240 to properly position the clutches 6110 and/or 6210, if necessary.

Further to the above, the clutch position sensors, i.e., the first sensor 6180', the second sensor 6280', and the third sensor 6380' can comprise any suitable type of sensor. In various instances, the first sensor 6180', the second sensor 6280', and the third sensor 6380' each comprise a proximity sensor. In such an arrangement, the sensors 6180', 6280', and 6380' are configured to detect whether or not the clutches 6110, 6210, and 6310, respectively, are in their engaged positions. In various instances, the first sensor 6180', the second sensor 6280', and the third sensor 6380' each comprise a Hall Effect sensor, for example. In such an arrangement, the sensors 6180', 6280', and 6380' can not only detect whether or not the clutches 6110, 6210, and 6310, respectively, are in their engaged positions but the sensors 6180', 6280', and 6380' can also detect how close the clutches 6110, 6210, and 6310 are with respect to their engaged or disengaged positions.

Figure 38:
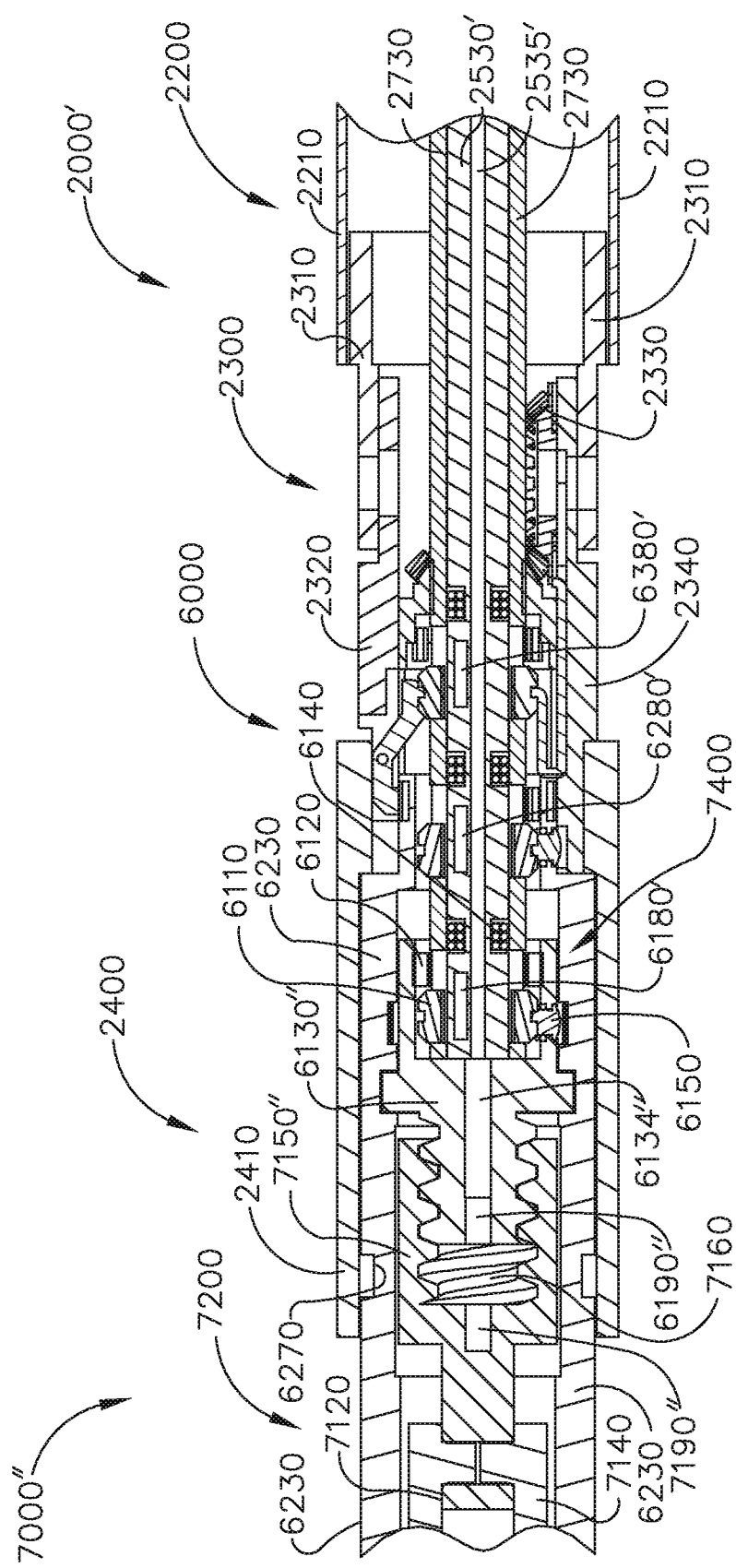
FIG. 38 is a partial cross-sectional view of a shaft assembly in accordance with at least one alternative embodiment comprising sensors configured to detect the conditions of the first, second, and third clutches of FIG. 27.

FIG. 38 depicts the shaft assembly 2000' and an end effector 7000" in accordance with at least one alternative embodiment. The end effector 7000" is similar to the end effector 7000 in many respects, most of which will not be repeated herein for the sake of brevity. Similar to the end effector 7000, the shaft assembly 7000" comprises a jaw assembly 7100 and a jaw assembly drive configured to move the jaw assembly 7100 between its open and closed configurations. The jaw assembly drive comprises drive links 7140, a drive nut 7150", and a drive screw 6130". The drive nut 7150" comprises a sensor 7190" positioned therein which is configured to detect the position of a magnetic element 6190" positioned in the drive screw 6130". The magnetic element 6190" is positioned in an elongate aperture 6134" defined in the drive screw 6130" and can comprise a permanent magnet and/or can be comprised of iron, nickel, and/or any suitable metal, for example. In various instances, the sensor 7190" comprises a proximity sensor, for example, which is in signal communication with the control system 1800. In certain instances, the sensor 7190" comprises a Hall Effect sensor, for example, in signal communication with the control system 1800. In certain instances, the sensor 7190" comprises an optical sensor, for example, and the detectable element 6190" comprises an optically detectable element, such as a reflective element, for example. In either event, the sensor 7190" is configured to communicate wirelessly with the control system 1800 via a wireless signal transmitter and receiver and/or via a wired connection extending through the shaft frame passage 2532', for example.

The sensor 7190", further to the above, is configured to detect when the magnetic element 6190" is adjacent to the sensor 7190" such that the control system 1800 can use this data to determine that the jaw assembly 7100 has reached the end of its clamping stroke. At such point, the control system 1800 can stop the motor assembly 1600. The sensor 7190" and the control system 1800 are also configured to determine the distance between where the drive screw 6130" is currently positioned and where the drive screw 6130" should be positioned at the end of its closure stroke in order to calculate the amount of closure stroke of the drive screw 6130" that is still needed to close the jaw assembly 7100. Moreover, such information can be used by the control system 1800 to assess the current configuration of the jaw assembly 7100, i.e., whether the jaw assembly 7100 is in its open configuration, its closed configuration, or a partially closed configuration. The sensor system could be used to determine when the jaw assembly 7100 has reached its fully open position and stop the motor assembly 1600 at that point. In various instances, the control system 1800 could use this sensor system to confirm that the first clutch assembly 6100 is in its actuated state by confirming that the jaw assembly 7100 is moving while the motor assembly 1600 is turning. Similarly, the control system 1800 could use this sensor system to confirm that the first clutch assembly 6100 is in its unactuated state by confirming that the jaw assembly 7100 is not moving while the motor assembly 1600 is turning.

Figure 39:
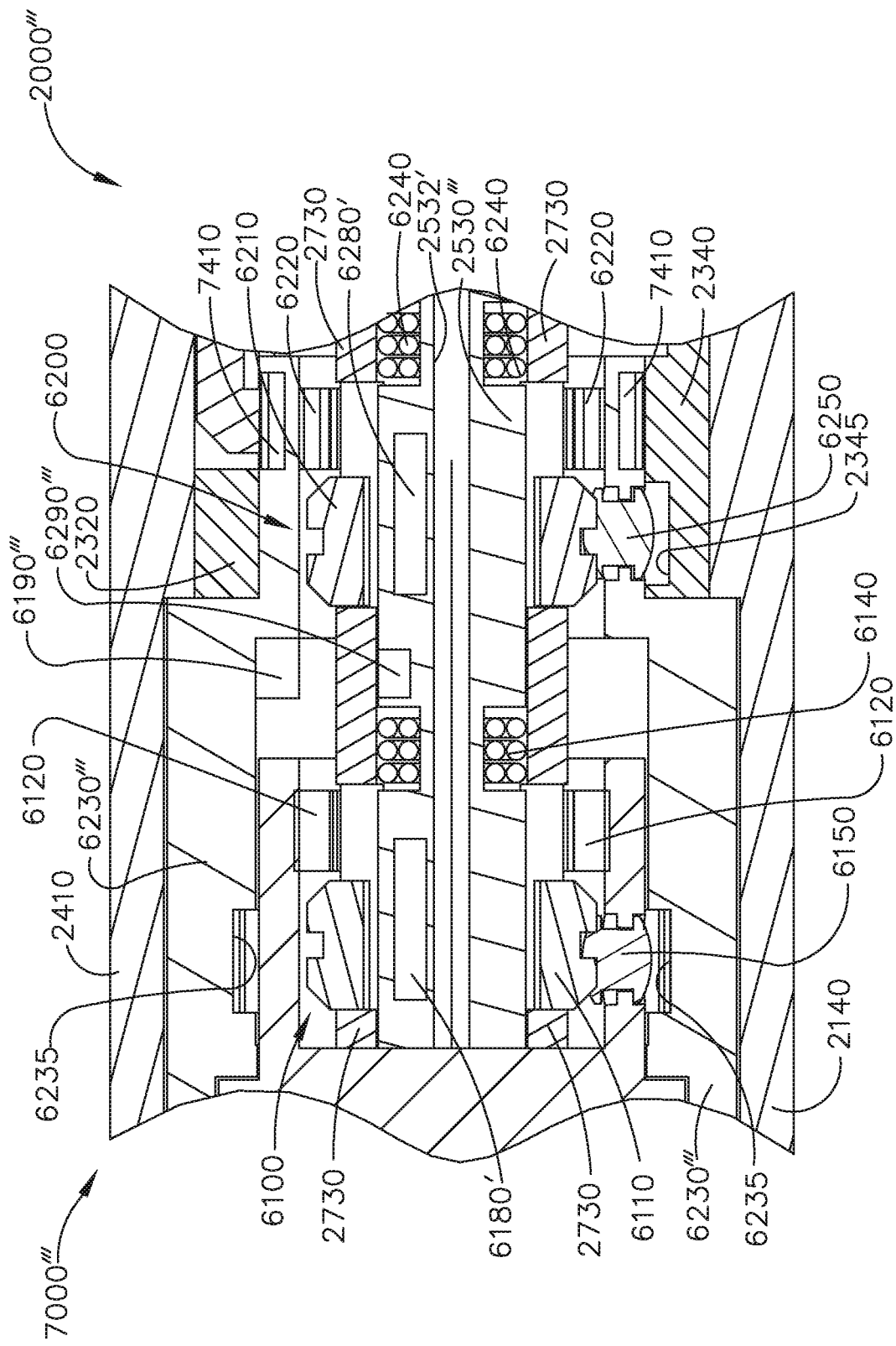
FIG. 39 depicts the first and second clutches of FIG. 38 in their unactuated conditions and a sensor in accordance with at least one alternative embodiment.

FIG. 39 depicts a shaft assembly 2000''' and an end effector 7000''' in accordance with at least one alternative embodiment. The shaft assembly 2000''' is similar to the shaft assemblies 2000 and 2000' in many respects, most of which will not be repeated herein for the sake of brevity. The end effector 7000''' is similar to the end effectors 7000 and 7000'' in many respects, most of which will not be repeated herein for the sake of brevity. Similar to the end effector 7000, the end effector 7000''' comprises a jaw assembly 7100 and a jaw assembly drive configured to move the jaw assembly 7100 between its open and closed configurations and, in addition, an end effector rotation drive that rotates the end effector 7000''' relative to the distal attachment portion 2400 of the shaft assembly 2000'. The end effector rotation drive comprises an outer housing 6230''' that is rotated relative to a shaft frame 2530''' of the end effector 7000''' by the second clutch assembly 6200. The shaft frame 2530''' comprises a sensor 6290''' positioned therein which is configured to detect the position of a magnetic element 6190''' positioned in and/or on the outer housing 6230'''. The magnetic element 6190''' can comprise a permanent magnet and/or can be comprised of iron, nickel, and/or any suitable metal, for example. In various instances, the sensor 6290''' comprises a proximity sensor, for example, in signal communication with the control system 1800. In certain instances, the sensor 6290''' comprises a Hall Effect sensor, for example, in signal communication with the control system 1800. In either event, the sensor 6290''' is configured to communicate wirelessly with the control system 1800 via a wireless signal transmitter and receiver and/or via a wired connection extending through the shaft frame passage 2532', for example. In various instances, the control system 1800 can use the sensor 6290''' to confirm whether the magnetic element 6190''' is rotating and, thus, confirm that the second clutch assembly 6200 is in its actuated state. Similarly, the control system 1800 can use the sensor 6290''' to confirm whether the magnetic element 6190''' is not rotating and, thus, confirm that the second clutch assembly 6200 is in its unactuated state. The control system 1800 can also use the sensor 6290''' to confirm that the second clutch assembly 6200 is in its unactuated state by confirming that the second clutch 6210 is positioned adjacent the sensor 6290'''.

Figure 40:
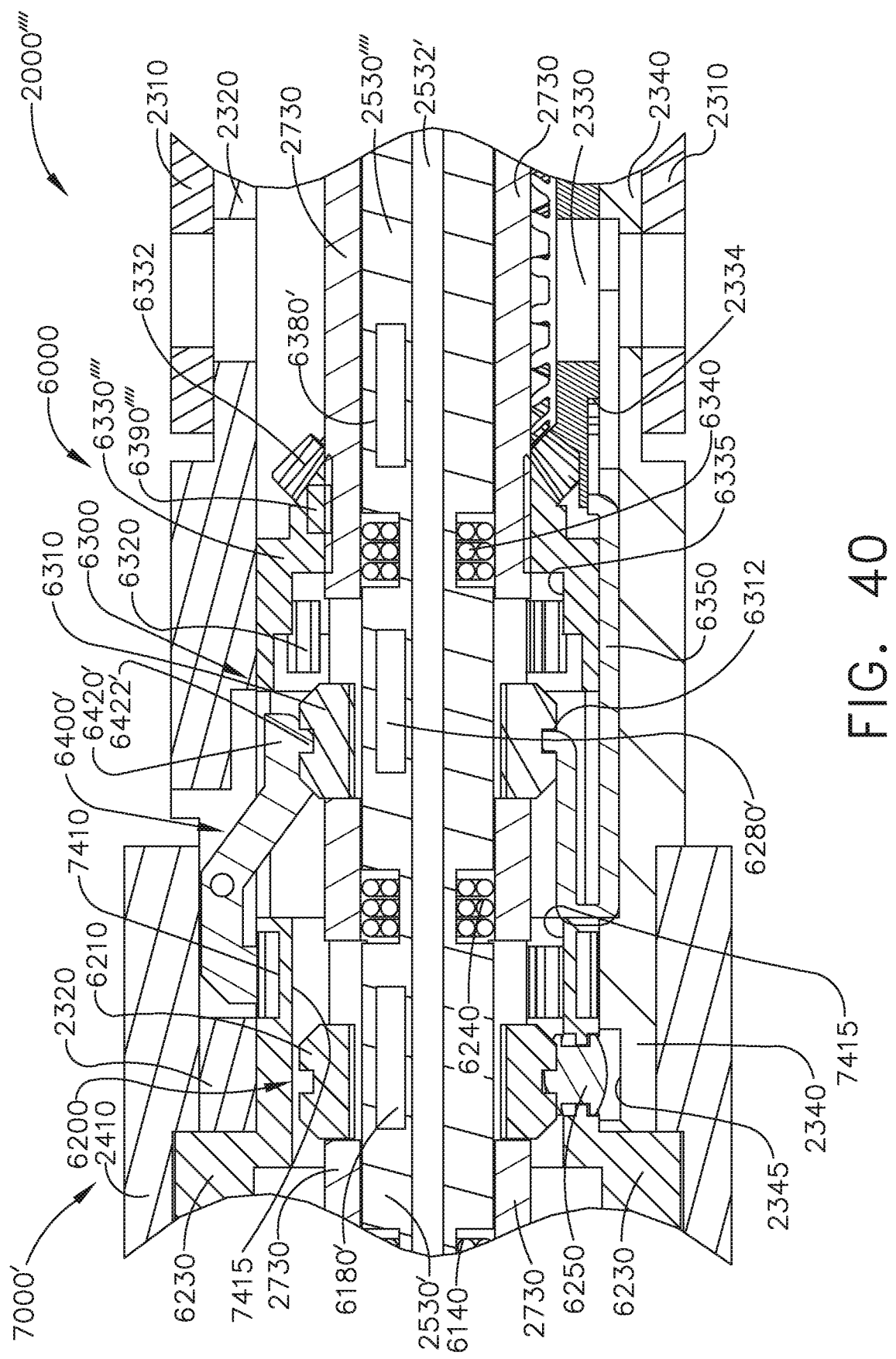
FIG. 40 depicts the second and third clutches of FIG. 38 in their unactuated conditions and a sensor in accordance with at least one alternative embodiment.

FIG. 40 depicts a shaft assembly 2000'''' in accordance with at least one alternative embodiment. The shaft assembly 2000'''' is similar to the shaft assemblies 2000, 2000', and 2000''' in many respects, most of which will not be repeated herein for the sake of brevity. Similar to the shaft assembly 2000, the shaft assembly 2000'''' comprises, among other things, an elongate shaft 2200, an articulation joint 2300, and a distal attachment portion 2400 configured to receive an end effector, such as end effector 7000', for example. Similar to the shaft assembly 2000, the shaft assembly 2000'''' comprises an articulation drive, i.e., articulation drive 6330'''' configured to rotate the distal attachment portion 2400 and the end effector 7000' about the articulation joint 2300. Similar to the above, a shaft frame 2530'''' comprises a sensor positioned therein configured to detect the position, and/or rotation, of a magnetic element 6390'''' positioned in and/or on the articulation drive 6330''''. The magnetic element 6390'''' can comprise a permanent magnet and/or can be comprised of iron, nickel, and/or any suitable metal, for example. In various instances, the sensor comprises a proximity sensor, for example, in signal communication with the control system 1800. In certain instances, the sensor comprises a Hall Effect sensor, for example, in signal communication with the control system 1800. In either event, the sensor is configured to communicate wirelessly with the control system 1800 via a wireless signal transmitter and receiver and/or via a wired connection extending through the shaft frame passage 2532', for example. In various instances, the control system 1800 can use the sensor to confirm whether the magnetic element 6390'''' is rotating and, thus, confirm that the third clutch assembly 6300 is in its actuated state. Similarly, the control system 1800 can use the sensor to confirm whether the magnetic element 6390'''' is not rotating and, thus, confirm that the third clutch assembly 6300 is in its unactuated state. In certain instances, the control system 1800 can use the sensor to confirm that the third clutch assembly 6300 is in its unactuated state by confirming that the third clutch 6310 is positioned adjacent the sensor.

Referring to FIG. 40 once again, the shaft assembly 2000'''' comprises an end effector lock 6400' configured to releasably lock the end effector 7000', for example, to the shaft assembly 2000''''. The end effector lock 6400' is similar to the end effector lock 6400 in many respects, most of which will not be discussed herein for the sake of brevity. Notably, though, a proximal end 6420' of the lock 6400' comprises a tooth 6422' configured to engage the annular slot 6312 of the third clutch 6310 and releasably hold the third clutch 6310 in its disengaged position. That said, the actuation of the third electromagnetic assembly 6340 can disengage the third clutch 6310 from the end effector lock 6400'. Moreover, in such instances, the proximal movement of the third clutch 6310 into its engaged position rotates the end effector lock 6400' into a locked position and into engagement with the lock notches 7410 to lock the end effector 7000' to the shaft assembly 2000''''. Correspondingly, the distal movement of the third clutch 6310 into its disengaged position unlocks the end effector 7000' and allows the end effector 7000' to be disassembled from the shaft assembly 2000''''.

Further to the above, an instrument system including a handle and a shaft assembly attached thereto can be configured to perform a diagnostic check to assess the state of the clutch assemblies 6100, 6200, and 6300. In at least one instance, the control system 1800 sequentially actuates the electromagnetic actuators 6140, 6240, and/or 6340—in any suitable order—to verify the positions of the clutches 6110, 6210, and/or 6310, respectively, and/or verify that the clutches are responsive to the electromagnetic actuators and, thus, not stuck. The control system 1800 can use sensors, including any of the sensors disclosed herein, to verify the movement of the clutches 6110, 6120, and 6130 in response to the electromagnetic fields created by the electromagnetic actuators 6140, 6240, and/or 6340. In addition, the diagnostic check can also include verifying the motions of the drive systems. In at least one instance, the control system 1800 sequentially actuates the electromagnetic actuators 6140, 6240, and/or 6340—in any suitable order—to verify that the jaw drive opens and/or closes the jaw assembly 7100, the rotation drive rotates the end effector 7000, and/or the articulation drive articulates the end effector 7000, for example. The control system 1800 can use sensors to verify the motions of the jaw assembly 7100 and end effector 7000.

The control system 1800 can perform the diagnostic test at any suitable time, such as when a shaft assembly is attached to the handle and/or when the handle is powered on, for example. If the control system 1800 determines that the instrument system passed the diagnostic test, the control system 1800 can permit the ordinary operation of the instrument system. In at least one instance, the handle can comprise an indicator, such as a green LED, for example, which indicates that the diagnostic check has been passed. If the control system 1800 determines that the instrument system failed the diagnostic test, the control system 1800 can prevent and/or modify the operation of the instrument system. In at least one instance, the control system 1800 can limit the functionality of the instrument system to only the functions necessary to remove the instrument system from the patient, such as straightening the end effector 7000 and/or opening and closing the jaw assembly 7100, for example. In at least one respect, the control system 1800 enters into a limp mode. The limp mode of the control system 1800 can reduce a current rotational speed of the motor 1610 by any percentage selected from a range of about 75% to about 25%, for example. In one example, the limp mode reduces a current rotational speed of the motor 1610 by 50%. In one example, the limp mode reduces the current rotational speed of the motor 1610 by 75%. The limp mode may cause a current torque of the motor 1610 to be reduced by any percentage selected from a range of about 75% to about 25%, for example. In one example, the limp mode reduces a current torque of the motor 1610 by 50%. The handle can comprise an indicator, such as a red LED, for example, which indicates that the instrument system failed the diagnostic check and/or that the instrument system has entered into a limp mode. The above being said, any suitable feedback can be used to warn the clinician that the instrument system is not operating properly such as, for example, an audible warning and/or a tactile or vibratory warning, for example.

Figure 41:
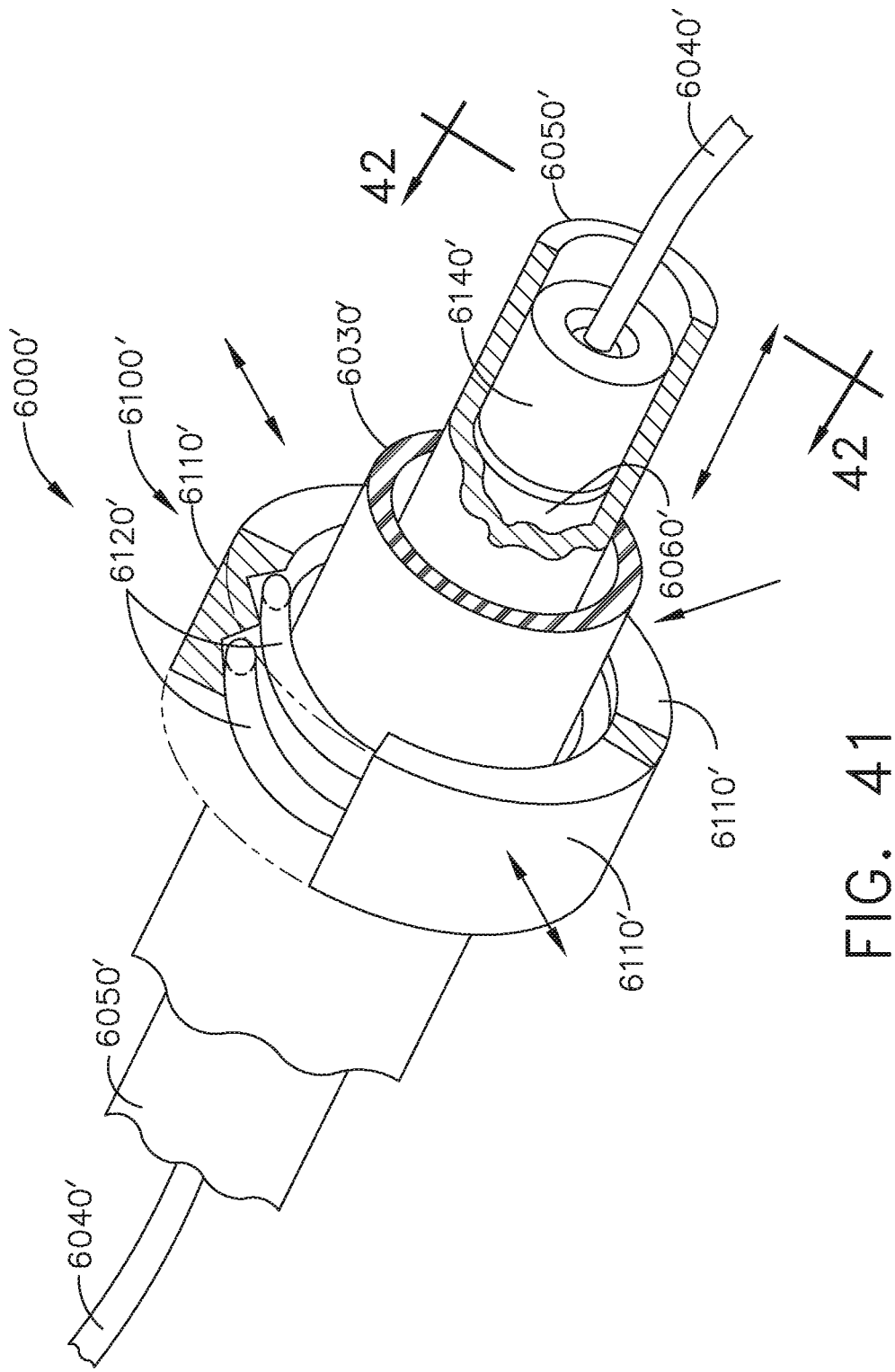
FIG. 41 is a partial cross-sectional view of a shaft assembly in accordance with at least one embodiment.
Figure 42:
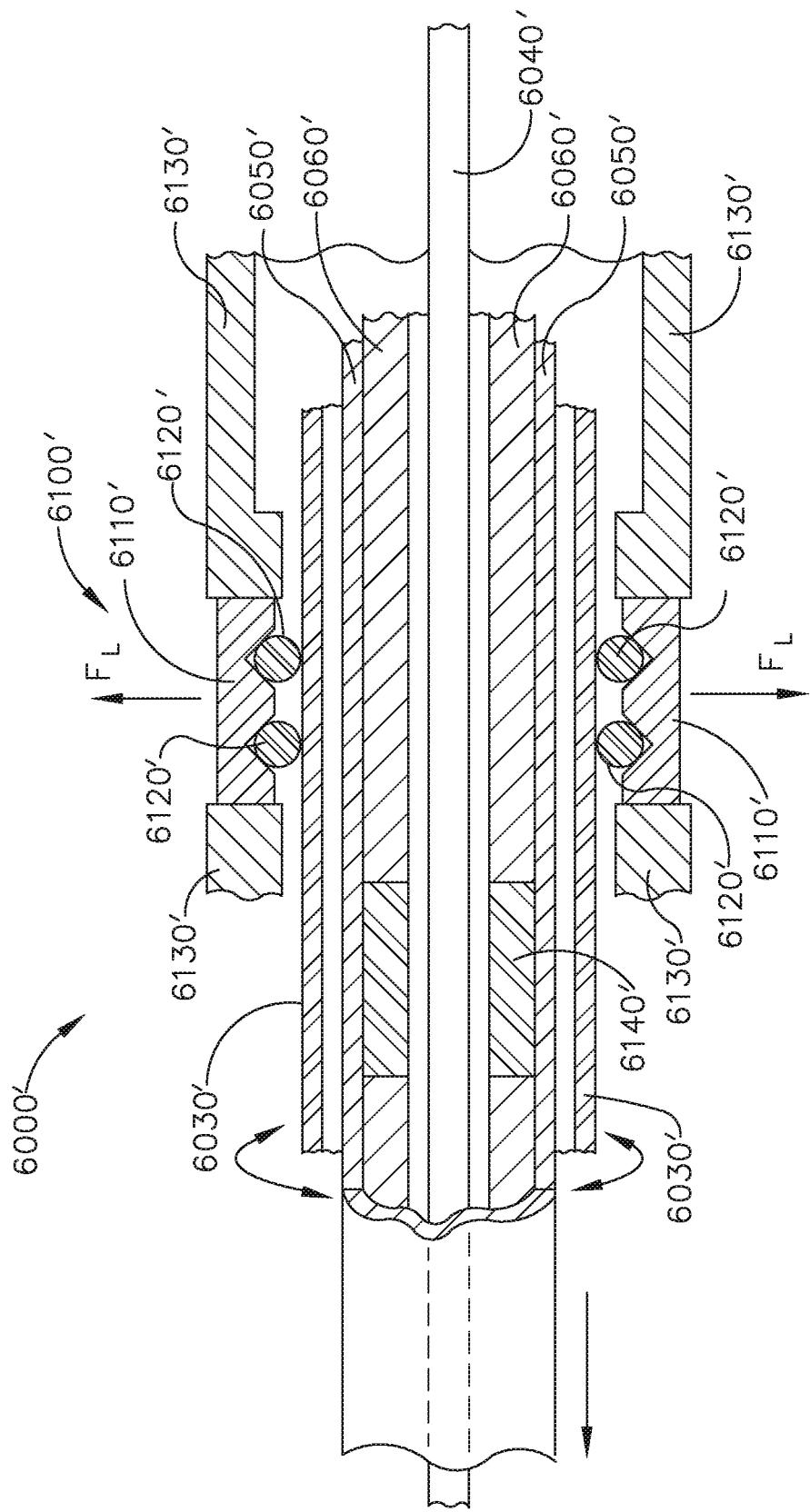
FIG. 42 is a partial cross-sectional view of the shaft assembly of FIG. 41 comprising a clutch illustrated in an unactuated condition.
Figure 43:
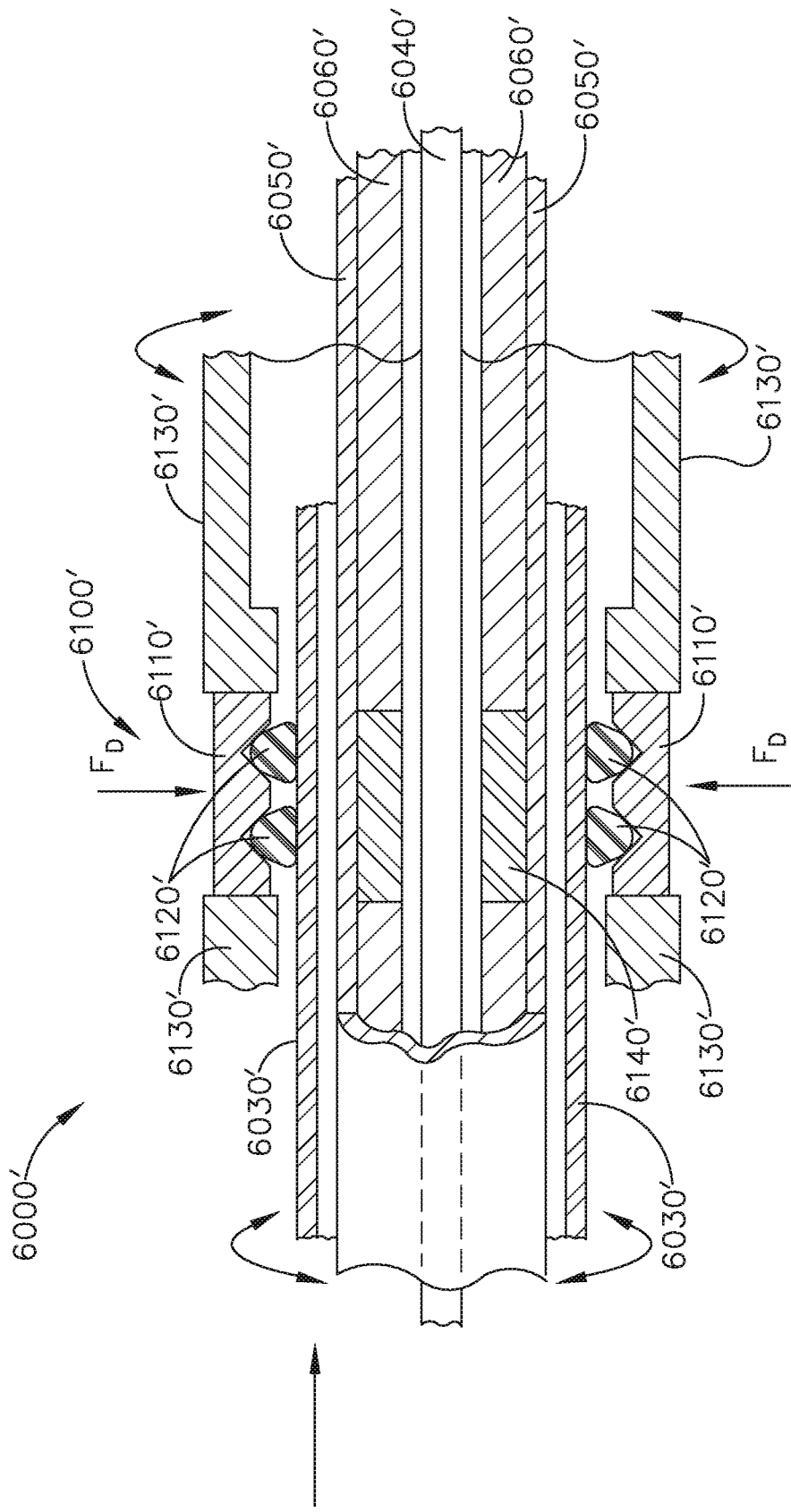
FIG. 43 is a partial cross-sectional view of the shaft assembly of FIG. 41 illustrating the clutch in an actuated condition.

FIGS. 41-43 depict a clutch system 6000' in accordance with at least one alternative embodiment. The clutch system 6000' is similar to the clutch system 6000 in many respects, most of which will not be repeated herein for the sake of brevity. Similar to the clutch system 6000, the clutch system 6000' comprises a clutch assembly 6100' which is actuatable to selectively couple a rotatable drive input 6030' with a rotatable drive output 6130'. The clutch assembly 6100' comprises clutch plates 6110' and drive rings 6120'. The clutch plates 6110' are comprised of a magnetic material, such as iron and/or nickel, for example, and can comprise a permanent magnet. As described in greater detail below, the clutch plates 6110' are movable between unactuated positions (FIG. 42) and actuated positions (FIG. 43) within the drive output 6130'. The clutch plates 6110' are slideably positioned in apertures defined in the drive output 6130' such that the clutch plates 6110' rotate with the drive output 6130' regardless of whether the clutch plates 6110' are in their unactuated or actuated positions.

When the clutch plates 6110' are in their unactuated positions, as illustrated in FIG. 42, the rotation of the drive input 6030' is not transferred to the drive output 6130'. More specifically, when the drive input 6030' is rotated, in such instances, the drive input 6030' slides past and rotates relative to the drive rings 6120' and, as a result, the drive rings 6120' do not drive the clutch plates 6110' and the drive output 6130'. When the clutch plates 6110' are in their actuated positions, as illustrated in FIG. 43, the clutch plates 6110' resiliently compress the drive rings 6120' against the drive input 6030'. The drive rings 6120' are comprised of any suitable compressible material, such as rubber, for example. In any event, in such instances, the rotation of the drive input 6030' is transferred to the drive output 6130' via the drive rings 6120' and the clutch plates 6110'. The clutch system 6000' comprises a clutch actuator 6140' configured to move the clutch plates 6110' into their actuated positions. The clutch actuator 6140' is comprised of a magnetic material such as iron and/or nickel, for example, and can comprise a permanent magnet. The clutch actuator 6140' is slideably positioned in a longitudinal shaft frame 6050' extending through the drive input 6030' and can be moved between an unactuated position (FIG. 42) and an actuated position (FIG. 43) by a clutch shaft 6060'. In at least one instance, the clutch shaft 6060' comprises a polymer cable, for example. When the clutch actuator 6140' is in its actuated position, as illustrated in FIG. 43, the clutch actuator 6140' pulls the clutch plates 6110' inwardly to compress the drive rings 6120', as discussed above. When the clutch actuator 6140' is moved into its unactuated position, as illustrated in FIG. 42, the drive rings 6120' resiliently expand and push the clutch plates 6110' away from the drive input 6030'. In various alternative embodiments, the clutch actuator 6140' can comprise an electromagnet. In such an arrangement, the clutch actuator 6140' can be actuated by an electrical circuit extending through a longitudinal aperture defined in the clutch shaft 6060', for example. In various instances, the clutch system 6000' further comprises electrical wires 6040', for example, extending through the longitudinal aperture.

Figure 44:
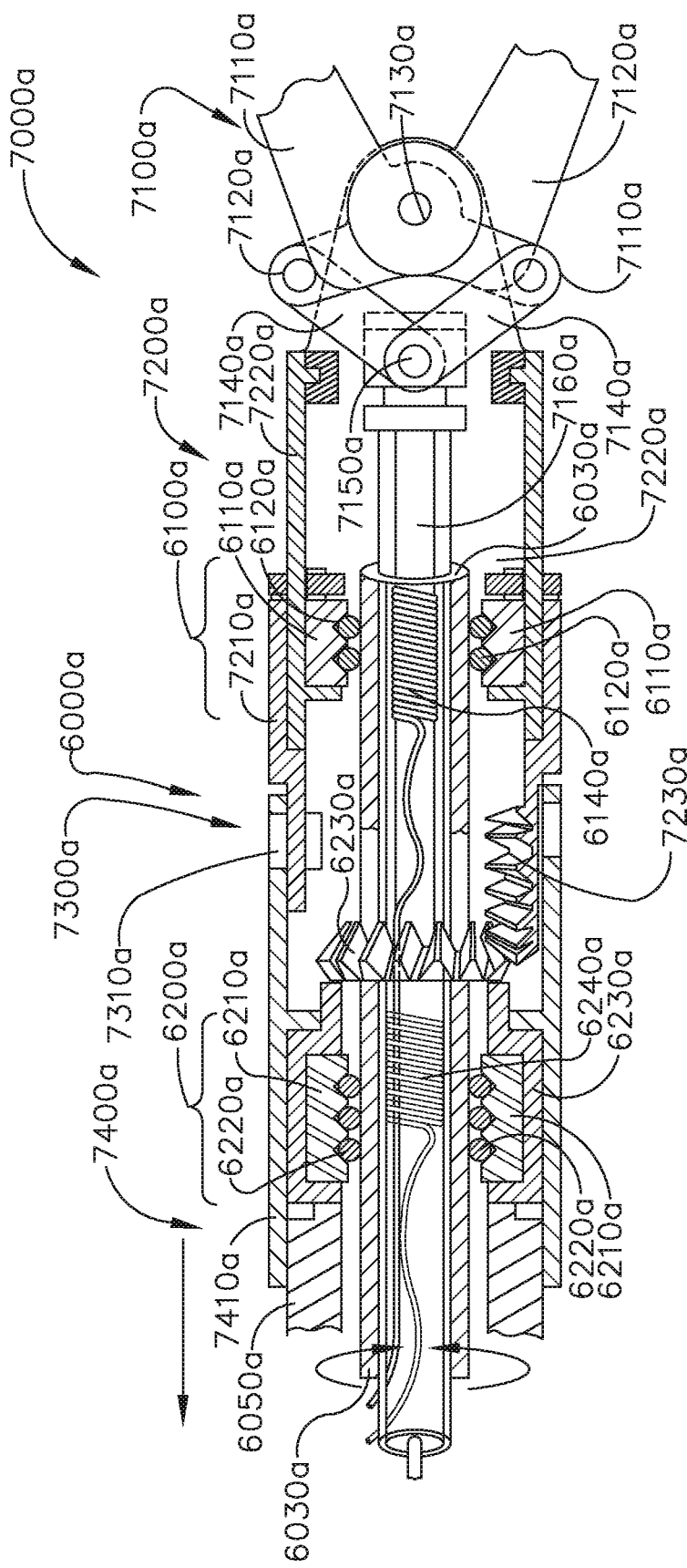
FIG. 44 is a partial cross-sectional view of a shaft assembly in accordance with at least one embodiment comprising first and second clutches illustrated in an unactuated condition.

FIG. 44 depicts an end effector 7000a including a jaw assembly 7100a, a jaw assembly drive, and a clutch system 6000a in accordance with at least one alternative embodiment. The jaw assembly 7100a comprises a first jaw 7110a and a second jaw 7120a which are selectively rotatable about a pivot 7130a. The jaw assembly drive comprises a translatable actuator rod 7160a and drive links 7140a which are pivotably coupled to the actuator rod 7160a about a pivot 7150a. The drive links 7140a are also pivotably coupled to the jaws 7110a and 7120a such that the jaws 7110a and 7120a are rotated closed when the actuator rod 7160a is pulled proximally and rotated open when the actuator rod 7160a is pushed distally. The clutch system 6000a is similar to the clutch systems 6000 and 6000' in many respects, most of which will not be repeated herein for the sake of brevity. The clutch system 6000a comprises a first clutch assembly 6100a and a second clutch assembly 6200a which are configured to selectively transmit the rotation of a drive input 6030a to rotate the jaw assembly 7100a about a longitudinal axis and articulate the jaw assembly 7100a about an articulation joint 7300a, respectively, as described in greater detail below.

The first clutch assembly 6100a comprises clutch plates 6110a and drive rings 6120a and work in a manner similar to the clutch plates 6110' and drive rings 6120' discussed above. When the clutch pates 6110a are actuated by an electromagnetic actuator 6140a, the rotation of the drive input 6030a is transferred to an outer shaft housing 7200a. More specifically, the outer shaft housing 7200a comprises a proximal outer housing 7210a and a distal outer housing 7220a which is rotatably supported by the proximal outer housing 7210a and is rotated relative to the proximal outer housing 7210a by the drive input 6030a when the clutch plates 6110a are in their actuated position. The rotation of the distal outer housing 7220a rotates the jaw assembly 7100a about the longitudinal axis owing to fact that the pivot 7130a of the jaw assembly 7100a is mounted to the distal outer housing 7220a. As a result, the outer shaft housing 7200a rotates the jaw assembly 7100a in a first direction when the outer shaft housing 7200a is rotated in a first direction by the drive input 6030a. Similarly, the outer shaft housing 7200a rotates the jaw assembly 7100a in a second direction when the outer shaft housing 7200a is rotated in a second direction by the drive input 6030a. When the electromagnetic actuator 6140a is de-energized, the drive rings 6120a expand and the clutch plates 6110a are moved into their unactuated positions, thereby decoupling the end effector rotation drive from the drive input 6030a.

The second clutch assembly 6200a comprises clutch plates 6210a and drive rings 6220a and work in a manner similar to the clutch plates 6110' and drive rings 6120' discussed above. When the clutch pates 6210a are actuated by an electromagnetic actuator 6240a, the rotation of the drive input 6030a is transferred to an articulation drive 6230a. The articulation drive 6230a is rotatably supported within an outer shaft housing 7410a of an end effector attachment portion 7400a and is rotatably supported by a shaft frame 6050a extending through the outer shaft housing 7410a. The articulation drive 6230a comprises a gear face defined thereon which is operably intermeshed with a stationary gear face 7230a defined on the proximal outer housing 7210a of the outer shaft housing 7200a. As a result, the articulation drive 6230a articulates the outer shaft housing 7200a and the jaw assembly 7100a in a first direction when the articulation drive 6230a is rotated in a first direction by the drive input 6030a. Similarly, the articulation drive 6230a articulates the outer shaft housing 7200a and the jaw assembly 7100a in a second direction when the articulation drive 6230a is rotated in a second direction by the drive input 6030a. When the electromagnetic actuator 6240a is de-energized, the drive rings 6220a expand and the clutch plates 6210a are moved into their unactuated positions, thereby decoupling the end effector articulation drive from the drive input 6030a.

Further to the above, the shaft assembly 4000 is illustrated in FIGS. 45-49. The shaft assembly 4000 is similar to the shaft assemblies 2000, 2000', 2000''', and 2000'''' in many respects, most of which will not be repeated herein for the sake of brevity. The shaft assembly 4000 comprises a proximal portion 4100, an elongate shaft 4200, a distal attachment portion 2400, and an articulate joint 2300 which rotatably connects the distal attachment portion 2040 to the elongate shaft 4200. The proximal portion 4100, similar to the proximal portion 2100, is operably attachable to the drive module 1100 of the handle 1000. The proximal portion 4100 comprises a housing 4110 including an attachment interface 4130 configured to mount the shaft assembly 4000 to the attachment interface 1130 of the handle 1000. The shaft assembly 4000 further comprises a frame 4500 including a shaft 4510 configured to be coupled to the shaft 1510 of the handle frame 1500 when the shaft assembly 4000 is attached to the handle 1000. The shaft assembly 4000 also comprises a drive system 4700 including a rotatable drive shaft 4710 configured to be operably coupled to the drive shaft 1710 of the handle drive system 1700 when the shaft assembly 4000 is attached to the handle 1000. The distal attachment portion 2400 is configured to receive an end effector, such as end effector 8000, for example. The end effector 8000 is similar to the end effector 7000 in many respects, most of which will not be repeated herein for the sake of brevity. That said, the end effector 8000 comprises a jaw assembly 8100 configured to, among other things, grasp tissue.

Figure 48:
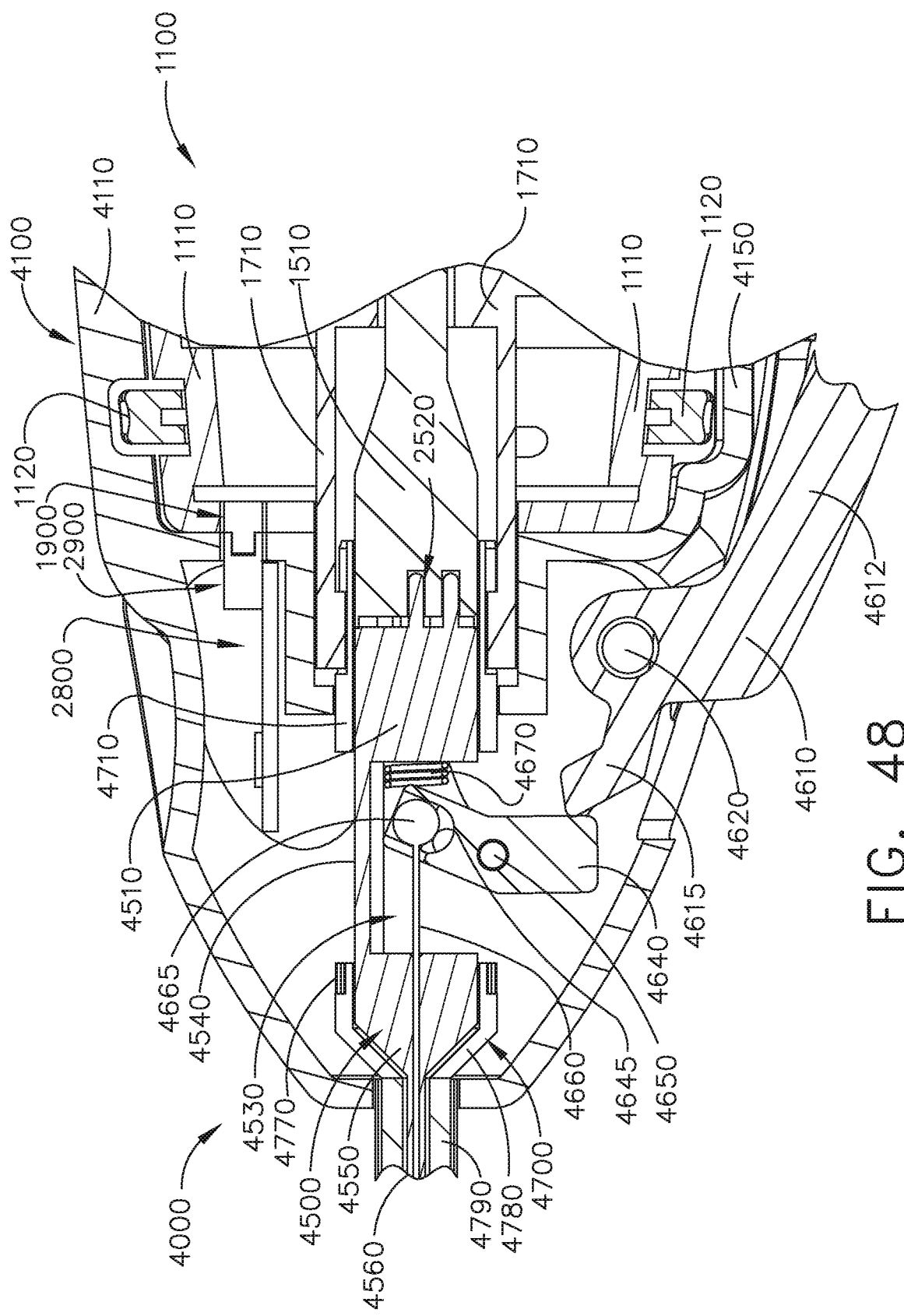
FIG. 48 is another partial cross-sectional view of the shaft assembly of FIG. 45 attached to the handle of FIG. 1.
Figure 49:
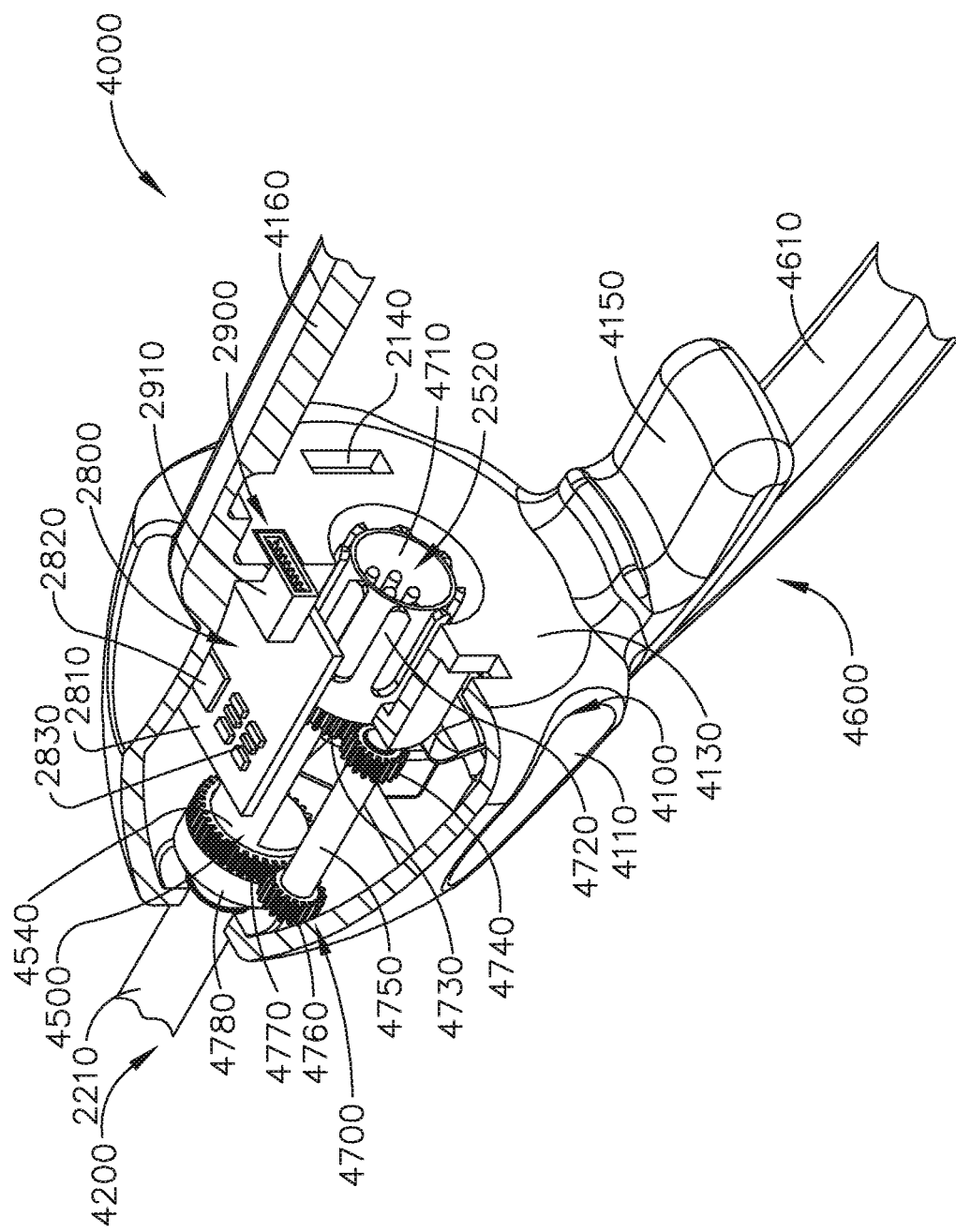
FIG. 49 is a partial cross-sectional perspective view of the shaft assembly of FIG. 45.

As discussed above, referring primarily to FIGS. 47-49, the frame 4500 of the shaft assembly 4000 comprises a frame shaft 4510. The frame shaft 4510 comprises a notch, or cut-out, 4530 defined therein. As discussed in greater detail below, the cut-out 4530 is configured to provide clearance for a jaw closure actuation system 4600. The frame 4500 further comprises a distal portion 4550 and a bridge 4540 connecting the distal portion 4550 to the frame shaft 4510. The frame 4500 further comprises a longitudinal portion 4560 extending through the elongate shaft 4200 to the distal attachment portion 2400. Similar to the above, the frame shaft 4510 comprises one or more electrical traces defined thereon and/or therein. The electrical traces extend through the longitudinal portion 4560, the distal portion 4550, the bridge 4540, and/or any suitable portion of the frame shaft 4510 to the electrical contacts 2520. Referring primarily to FIG. 48, the distal portion 4550 and longitudinal portion 4560 comprise a longitudinal aperture defined therein which is configured to receive a rod 4660 of the jaw closure actuation system 4600, as described in greater detail below.

As also discussed above, referring primarily to FIGS. 48 and 49, the drive system 4700 of the shaft assembly 4000 comprises a drive shaft 4710. The drive shaft 4710 is rotatably supported within the proximal shaft housing 4110 by the frame shaft 4510 and is rotatable about a longitudinal axis extending through the frame shaft 4510. The drive system 4700 further comprises a transfer shaft 4750 and an output shaft 4780. The transfer shaft 4750 is also rotatably supported within the proximal shaft housing 4110 and is rotatable about a longitudinal axis extending parallel to, or at least substantially parallel to, the frame shaft 4510 and the longitudinal axis defined therethrough. The transfer shaft 4750 comprises a proximal spur gear 4740 fixedly mounted thereto such that the proximal spur gear 4740 rotates with the transfer shaft 4750. The proximal spur gear 4740 is operably intermeshed with an annular gear face 4730 defined around the outer circumference of the drive shaft 4710 such that the rotation of the drive shaft 4710 is transferred to the transfer shaft 4750. The transfer shaft 4750 further comprises a distal spur gear 4760 fixedly mounted thereto such that the distal spur gear 4760 rotates with the transfer shaft 4750. The distal spur gear 4760 is operably intermeshed with an annular gear 4770 defined around the outer circumference of the output shaft 4780 such that the rotation of the transfer shaft 4750 is transferred to the output shaft 4780. Similar to the above, the output shaft 4780 is rotatably supported within the proximal shaft housing 4110 by the distal portion 4550 of the shaft frame 4500 such that the output shaft 4780 rotates about the longitudinal shaft axis. Notably, the output shaft 4780 is not directly coupled to the input shaft 4710; rather, the output shaft 4780 is operably coupled to the input shaft 4710 by the transfer shaft 4750. Such an arrangement provides room for the manually-actuated jaw closure actuation system 4600 discussed below.

Further to the above, referring primarily to FIGS. 47 and 48, the jaw closure actuation system 4600 comprises an actuation, or scissors, trigger 4610 rotatably coupled to the proximal shaft housing 4110 about a pivot 4620. The actuation trigger 4610 comprises an elongate portion 4612, a proximal end 4614, and a grip ring aperture 4616 defined in the proximal end 4614 which is configured to be gripped by the clinician. The shaft assembly 4000 further comprises a stationary grip 4160 extending from the proximal housing 4110. The stationary grip 4160 comprises an elongate portion 4162, a proximal end 4164, and a grip ring aperture 4166 defined in the proximal end 4164 which is configured to be gripped by the clinician. In use, as described in greater detail below, the actuation trigger 4610 is rotatable between an unactuated position and an actuated position (FIG. 48), i.e., toward the stationary grip 4160, to close the jaw assembly 8100 of the end effector 8000.

Referring primarily to FIG. 48, the jaw closure actuation system 4600 further comprises a drive link 4640 rotatably coupled to the proximal shaft housing 4110 about a pivot 4650 and, in addition, an actuation rod 4660 operably coupled to the drive link 4640. The actuation rod 4660 extends through an aperture defined in the longitudinal frame portion 4560 and is translatable along the longitudinal axis of the shaft frame 4500. The actuation rod 4660 comprises a distal end operably coupled to the jaw assembly 8100 and a proximal end 4665 positioned in a drive slot 4645 defined in the drive link 4640 such that the actuation rod 4660 is translated longitudinally when the drive link 4640 is rotated about the pivot 4650. Notably, the proximal end 4665 is rotatably supported within the drive slot 4645 such that the actuation rod 4660 can rotate with the end effector 8000.

Further to the above, the actuation trigger 4610 further comprises a drive arm 4615 configured to engage and rotate the drive link 4640 proximally, and translate the actuation rod 4660 proximally, when the actuation trigger 4610 is actuated, i.e., moved closer to the proximal shaft housing 4110. In such instances, the proximal rotation of the drive link 4640 resiliently compresses a biasing member, such as a coil spring 4670, for example, positioned intermediate the drive link 4640 and the frame shaft 4510. When the actuation trigger 4610 is released, the compressed coil spring 4670 re-expands and pushes the drive link 4640 and the actuation rod 4660 distally to open the jaw assembly 8100 of the end effector 8000. Moreover, the distal rotation of the drive link 4640 drives, and automatically rotates, the actuation trigger 4610 back into its unactuated position. That being said, the clinician could manually return the actuation trigger 4610 back into its unactuated position. In such instances, the actuation trigger 4610 could be opened slowly. In either event, the shaft assembly 4000 further comprises a lock configured to releasably hold the actuation trigger 4610 in its actuated position such that the clinician can use their hand to perform another task without the jaw assembly 8100 opening unintentionally.

In various alternative embodiments, further to the above, the actuation rod 4660 can be pushed distally to close the jaw assembly 8100. In at least one such instance, the actuation rod 4660 is mounted directly to the actuation trigger 4610 such that, when the actuation trigger 4610 is actuated, the actuation trigger 4610 drives the actuation rod 4660 distally. Similar to the above, the actuation trigger 4610 can compress a spring when the actuation trigger 4610 is closed such that, when the actuation trigger 4610 is released, the actuation rod 4660 is pushed proximally.

Further to the above, the shaft assembly 4000 has three functions—opening/closing the jaw assembly of an end effector, rotating the end effector about a longitudinal axis, and articulating the end effector about an articulation axis. The end effector rotation and articulation functions of the shaft assembly 4000 are driven by the motor assembly 1600 and the control system 1800 of the drive module 1100 while the jaw actuation function is manually-driven by the jaw closure actuation system 4600. The jaw closure actuation system 4600 could be a motor-driven system but, instead, the jaw closure actuation system 4600 has been kept a manually-driven system such that the clinician can have a better feel for the tissue being clamped within the end effector. While motorizing the end effector rotation and actuation systems provides certain advantages for controlling the position of the end effector, motorizing the jaw closure actuation system 4600 may cause the clinician to lose a tactile sense of the force being applied to the tissue and may not be able to assess whether the force is insufficient or excessive. Thus, the jaw closure actuation system 4600 is manually-driven even though the end effector rotation and articulation systems are motor-driven.

Figure 50:
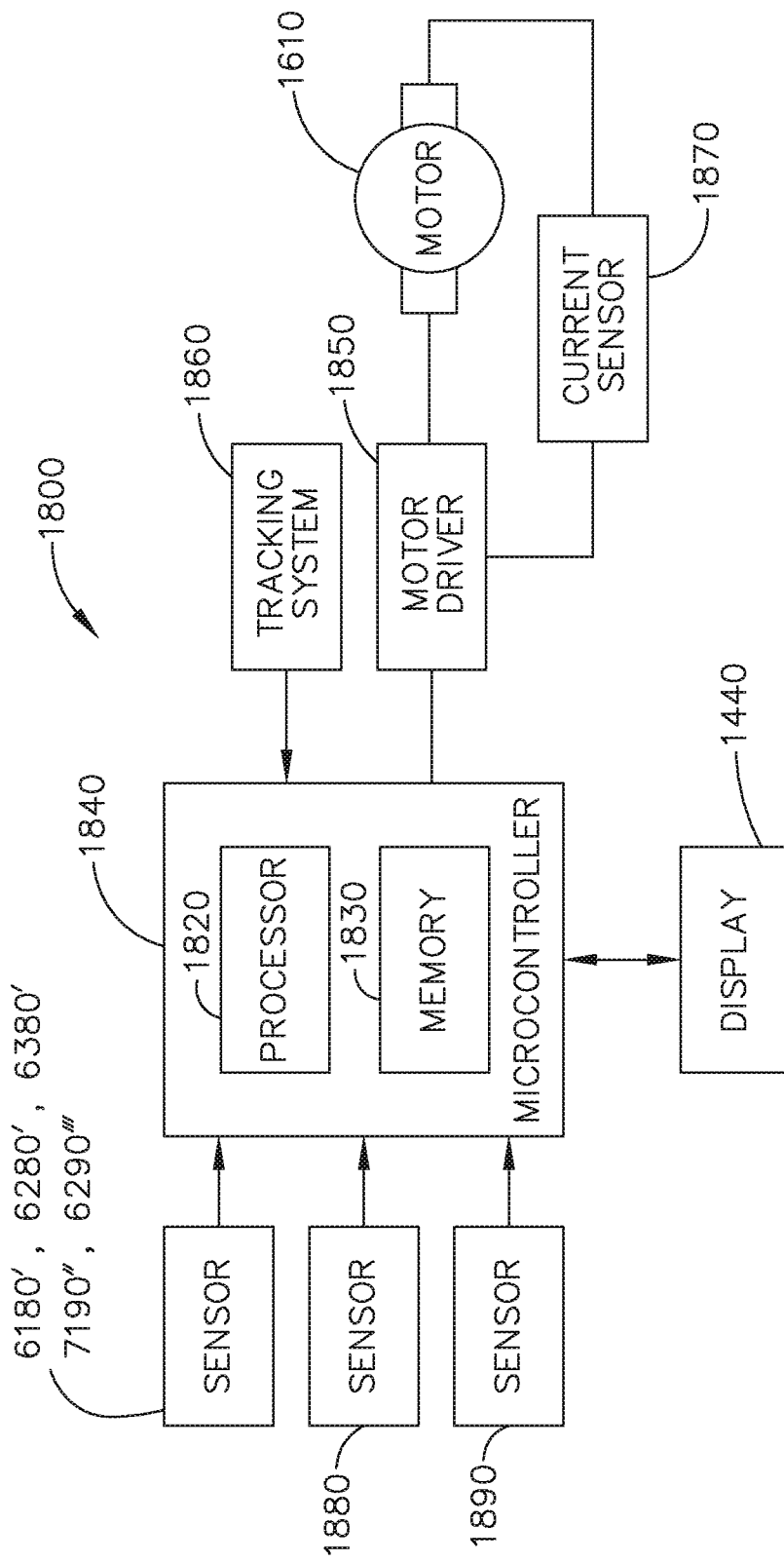
FIG. 50 is a schematic of the control system of the surgical system of FIG. 1.

FIG. 50 is a logic diagram of the control system 1800 of the surgical system depicted in FIG. 1 in accordance with at least one embodiment. The control system 1800 comprises a control circuit. The control circuit includes a microcontroller 1840 comprising a processor 1820 and a memory 1830. One or more sensors, such as sensors 1880, 1890, 6180', 6280', 6380', 7190'', and/or 6290''', for example, provide real time feedback to the processor 1820. The control system 1800 further comprises a motor driver 1850 configured to control the electric motor 1610 and a tracking system 1860 configured to determine the position of one or more longitudinally movable components in the surgical instrument, such as the clutches 6110, 6120, and 6130 and/or the longitudinally-movable drive nut 7150 of the jaw assembly drive, for example. The tracking system 1860 is also configured to determine the position of one or more rotational components in the surgical instrument, such as the drive shaft 2530, the outer shaft 6230, and/or the articulation drive 6330, for example. The tracking system 1860 provides position information to the processor 1820, which can be programmed or configured to, among other things, determine the position of the clutches 6110, 6120, and 6130 and the drive nut 7150 as well as the orientation of the jaws 7110 and 7120. The motor driver 1850 may be an A3941 available from Allegro Microsystems, Inc., for example; however, other motor drivers may be readily substituted for use in the tracking system 1860. A detailed description of an absolute positioning system is described in U.S. Patent Application Publication No. 2017/0296213, entitled SYSTEMS AND METHODS FOR CONTROLLING A SURGICAL STAPLING AND CUTTING INSTRUMENT, the entire disclosure of which is hereby incorporated herein by reference.

The microcontroller 1840 may be any single core or multicore processor such as those known under the trade name ARM Cortex by Texas Instruments, for example. In at least one instance, the microcontroller 1840 is a LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules and/or frequency modulation (FM) modules, one or more quadrature encoder inputs (QEI) analog, one or more 12-bit Analog-to-Digital Converters (ADC) with 12 analog input channels, for example, details of which are available from the product datasheet.

In various instances, the microcontroller 1840 comprises a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 1840 is programmed to perform various functions such as precisely controlling the speed and/or position of the drive nut 7150 of the jaw closure assembly, for example. The microcontroller 1840 is also programmed to precisely control the rotational speed and position of the end effector 7000 and the articulation speed and position of the end effector 7000. In various instances, the microcontroller 1840 computes a response in the software of the microcontroller 1840. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The motor 1610 is controlled by the motor driver 1850. In various forms, the motor 1610 is a DC brushed driving motor having a maximum rotational speed of approximately 25,000 RPM, for example. In other arrangements, the motor 1610 includes a brushless motor, a cordless motor, a synchronous motor, a stepper motor, or any other suitable electric motor. The motor driver 1850 may comprise an H-bridge driver comprising field-effect transistors (FETs), for example. The motor driver 1850 may be an A3941 available from Allegro Microsystems, Inc., for example. The A3941 driver 1850 is a full-bridge controller for use with external N-channel power metal oxide semiconductor field effect transistors (MOSFETs) specifically designed for inductive loads, such as brush DC motors. In various instances, the driver 1850 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted.

The tracking system 1860 comprises a controlled motor drive circuit arrangement comprising one or more position sensors, such as sensors 1880, 1890, 6180', 6280', 6380', 7190", and/or 6290''', for example. The position sensors for an absolute positioning system provide a unique position signal corresponding to the location of a displacement member. As used herein, the term displacement member is used generically to refer to any movable member of the surgical system. In various instances, the displacement member may be coupled to any position sensor suitable for measuring linear displacement. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall Effect sensors, a magnetic sensing system comprising a fixed magnet and a series of movable linearly arranged Hall Effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

The position sensors 1880, 1890, 6180', 6280', 6380', 7190", and/or 6290''', for example, may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-Effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In various instances, one or more of the position sensors of the tracking system 1860 comprise a magnetic rotary absolute positioning system. Such position sensors may be implemented as an AS5055EQFT single-chip magnetic rotary position sensor available from Austria Microsystems, AG and can be interfaced with the controller 1840 to provide an absolute positioning system. In certain instances, a position sensor comprises a low-voltage and low-power component and includes four Hall-Effect elements in an area of the position sensor that is located adjacent a magnet. A high resolution ADC and a smart power management controller are also provided on the chip. A CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface to the controller 1840. The position sensors can provide 12 or 14 bits of resolution, for example. The position sensors can be an AS5055 chip provided in a small QFN 16-pin 4×4×0.85 mm package, for example.

The tracking system 1860 may comprise and/or be programmed to implement a feedback controller, such as a PID, state feedback, and adaptive controller. A power source converts the signal from the feedback controller into a physical input to the system, in this case voltage. Other examples include pulse width modulation (PWM) and/or frequency modulation (FM) of the voltage, current, and force. Other sensor(s) may be provided to measure physical parameters of the physical system in addition to position. In various instances, the other sensor(s) can include sensor arrangements such as those described in U.S. Pat. No. 9,345,481, entitled STAPLE CARTRIDGE TISSUE THICKNESS SENSOR SYSTEM, which is hereby incorporated herein by reference in its entirety; U.S. Patent Application Publication No. 2014/0263552, entitled STAPLE CARTRIDGE TISSUE THICKNESS SENSOR SYSTEM, which is hereby incorporated herein by reference in its entirety; and U.S. patent application Ser. No. 15/628,175, entitled TECHNIQUES FOR ADAPTIVE CONTROL OF MOTOR VELOCITY OF A SURGICAL STAPLING AND CUTTING INSTRUMENT, which is hereby incorporated herein by reference in its entirety. In a digital signal processing system, absolute positioning system is coupled to a digital data acquisition system where the output of the absolute positioning system will have finite resolution and sampling frequency. The absolute positioning system may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power up of the instrument without retracting or advancing the displacement member to a reset (zero or home) position as may be required with conventional rotary encoders that merely count the number of steps forwards or backwards that the motor 1610 has taken to infer the position of a device actuator, drive bar, knife, and the like.

A sensor 1880 comprising a strain gauge or a micro-strain gauge, for example, is configured to measure one or more parameters of the end effector, such as, for example, the strain experienced by the jaws 7110 and 7120 during a clamping operation. The measured strain is converted to a digital signal and provided to the processor 1820. In addition to or in lieu of the sensor 1880, a sensor 1890 comprising a load sensor, for example, can measure the closure force applied by the closure drive system to the jaws 7110 and 7120. In various instances, a current sensor 1870 can be employed to measure the current drawn by the motor 1610. The force required to clamp the jaw assembly 7100 can correspond to the current drawn by the motor 1610, for example. The measured force is converted to a digital signal and provided to the processor 1820. A magnetic field sensor can be employed to measure the thickness of the captured tissue. The measurement of the magnetic field sensor can also be converted to a digital signal and provided to the processor 1820.

The measurements of the tissue compression, the tissue thickness, and/or the force required to close the end effector on the tissue as measured by the sensors can be used by the controller 1840 to characterize the position and/or speed of the movable member being tracked. In at least one instance, a memory 1830 may store a technique, an equation, and/or a look-up table which can be employed by the controller 1840 in the assessment. In various instances, the controller 1840 can provide the user of the surgical instrument with a choice as to the manner in which the surgical instrument should be operated. To this end, the display 1440 can display a variety of operating conditions of the instrument and can include touch screen functionality for data input. Moreover, information displayed on the display 1440 may be overlaid with images acquired via the imaging modules of one or more endoscopes and/or one or more additional surgical instruments used during the surgical procedure.

As discussed above, the drive module 1100 of the handle 1000 and/or the shaft assemblies 2000, 3000, 4000, and/or 5000, for example, attachable thereto comprise control systems. Each of the control systems can comprise a circuit board having one or more processors and/or memory devices. Among other things, the control systems are configured to store sensor data, for example. They are also configured to store data which identifies the shaft assembly to the handle 1000. Moreover, they are also configured to store data including whether or not the shaft assembly has been previously used and/or how many times the shaft assembly has been used. This information can be obtained by the handle 1000 to assess whether or not the shaft assembly is suitable for use and/or has been used less than a predetermined number of times, for example.

Figure 67:
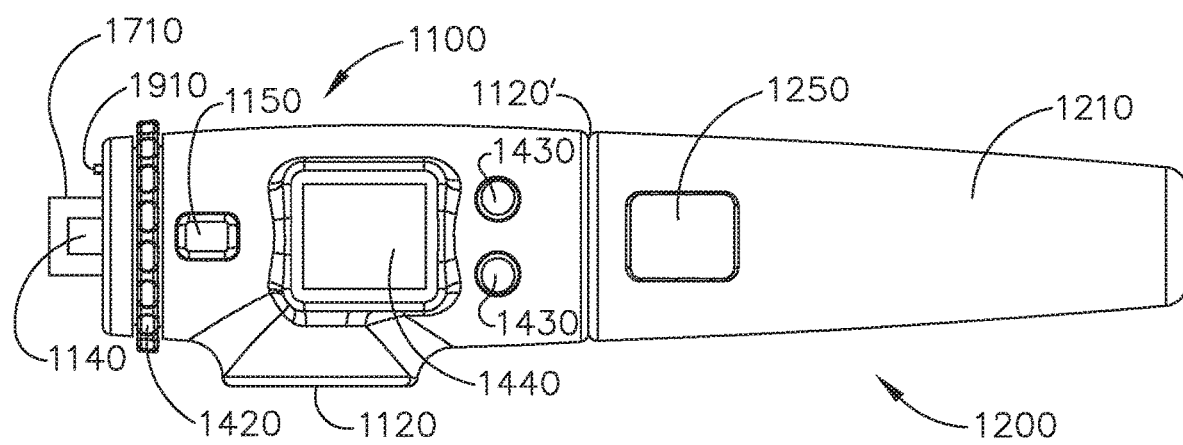
FIG. 67 is an elevational view of the power module of FIG. 55 attached to the proximal battery port of the drive module of FIG. 7.
Figure 68:
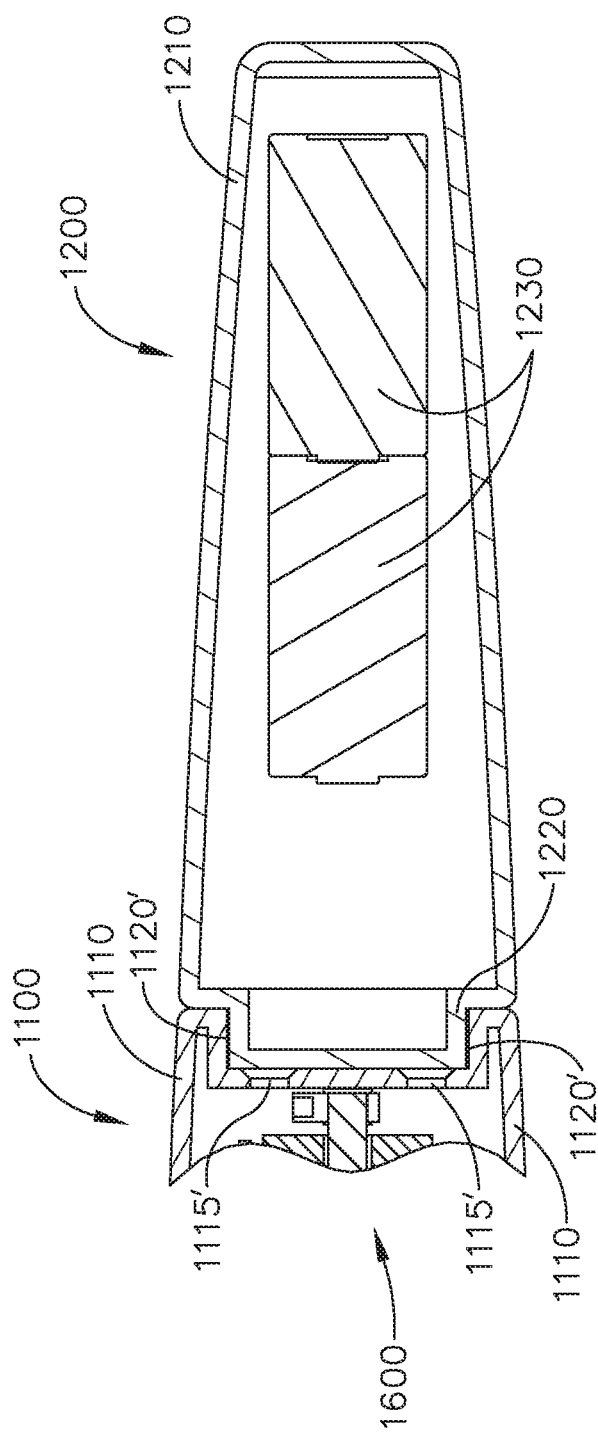
FIG. 68 is a partial cross-sectional view of the connection between the proximal battery port of the drive module of FIG. 7 and the power module of FIG. 55.

Further to the above, the first module connector 1120 of the drive module 1100 comprises a side battery port defined in the side of the drive module 1100. Similarly, the second module connector 1120' comprises a proximal battery port defined in the proximal end of the drive module 1100. That said, a drive module can comprise a battery port at any suitable location. In any event, the power module 1200 is operably attachable to the drive module 1100 at the side battery port 1120, as illustrated in FIGS. 54-58, or the proximal battery port 1120', as illustrated in FIGS. 67 and 68. This is possible because the connector 1220 of the power module 1200 is compatible with the side battery port 1120 and the proximal battery port 1120'. Among other things, the connector 1220 comprises a substantially circular, or substantially cylindrical, configuration that matches, or at least substantially matches, the substantially circular, or substantially cylindrical, configurations of the battery ports 1120 and 1120'. In various instances, the connector 1220 comprises a frustoconical, or an at least substantially frustoconical, shape having a bottom portion which is larger than the top portion and an angled, or tapered, side extending therebetween. The above being said, the connector 1220 of the power module 1200 does not comprise keys, or projections, extending therefrom which interfere with the assembly of the power module 1200 to the battery ports 1120 and 1120'.

Referring primarily to FIGS. 55 and 56, the connector 1220 comprises two latches 1240 extending therefrom. The latches 1240 are positioned on opposite sides of the connector 1220 such that they comprise opposing latch shoulders which releasably hold the power module 1200 to the handle module 1100. The side battery port 1120 comprises latch openings 1125 defined in the housing 1100 which are configured to receive the latches 1240 of the power module 1200 and, similarly, the proximal battery port 1120' comprises latch openings 1125' defined in the housing 1100 which are also configured to receive the latches 1240 of the power module 1200. While the latch openings 1125 in the side battery port 1120 and the latch openings 1125' in the proximal battery port 1120' limit the orientations in which the power module 1200 can be assembled to each battery port 1120 and 1120', i.e., two orientations for each battery port, the power module 1200 is nonetheless operably attachable to both battery ports 1120 and 1120'.

Further to the above, the latches 1240 of the power module 1200 are configured to engage the drive module 1100 in a snap-fit manner. In various instances, the latches 1240 resiliently flex radially outwardly when the power module 1200 is assembled to the drive module 1100 and then resiliently move, or snap, radially inwardly once the power module 1200 is fully seated within one of the ports 1120 and 1120' to lock the power module 1200 to the drive module 1100. In various instances, the latches 1240 comprise flexible arms which deflect radially inwardly and outwardly as described above while, in some instances, the latches 1240 comprise one or more biasing members, such as springs, for example, configured to resiliently push the latches 1240 into their inward, or locked, positions. In various embodiments, the power module 1200 can comprise members which are press-fit into apertures defined in the ports 1120 and 1120' to retain the power module 1200 to the drive module 1100.

Further to the above, the electrical contacts of the power module 1200 are defined on the top portion, or face, of the connector 1220. As discussed above, the electrical contacts of the power module 1200 engage corresponding electrical contacts defined in the ports 1120 and 1120' when the power module 1200 is attached to the drive module 1100 to place the power module 1200 in electrical communication with the drive module 1100. In various instances, the electrical contacts of the power module 1200 are compressed against the electrical contacts of the drive module 1100 when the power module 1200 is attached to the drive module 1100. In at least one such instance, the power module contacts and/or the drive module contacts comprise resilient members which are configured to elastically deflect when the power module 1200 is attached to the drive module 1100. Such resilient members, along with the latches 1240, can assure that there is an adequate electrical interface between the power module 1200 and the drive module 1100. In alternative embodiments, the power module 1200 can comprise annular electrical contacts extending around the perimeter thereof which engage electrical contacts on the sides of the ports 1120 and 1120'. Such an arrangement could permit relative rotation between the power module 1200 and the drive module 1100.

Figure 69:
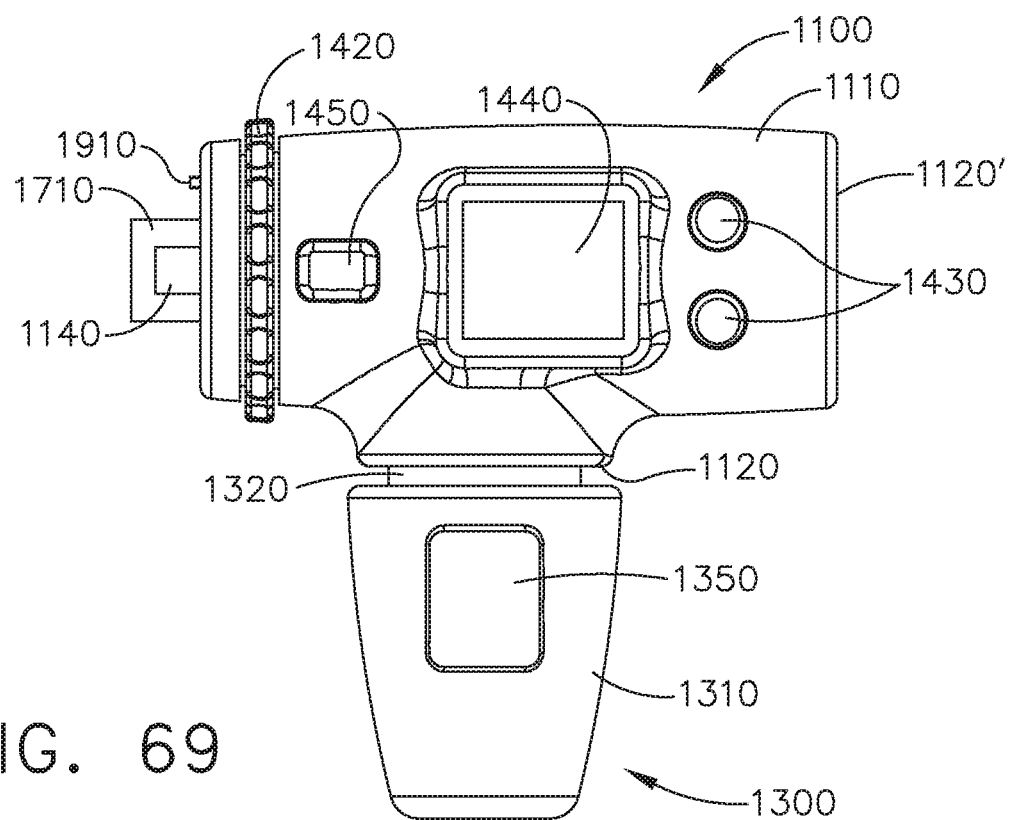
FIG. 69 is an elevational view of an attempt to connect the power module of FIG. 45 to the side battery port of the drive module of FIG. 7.
Figure 70:
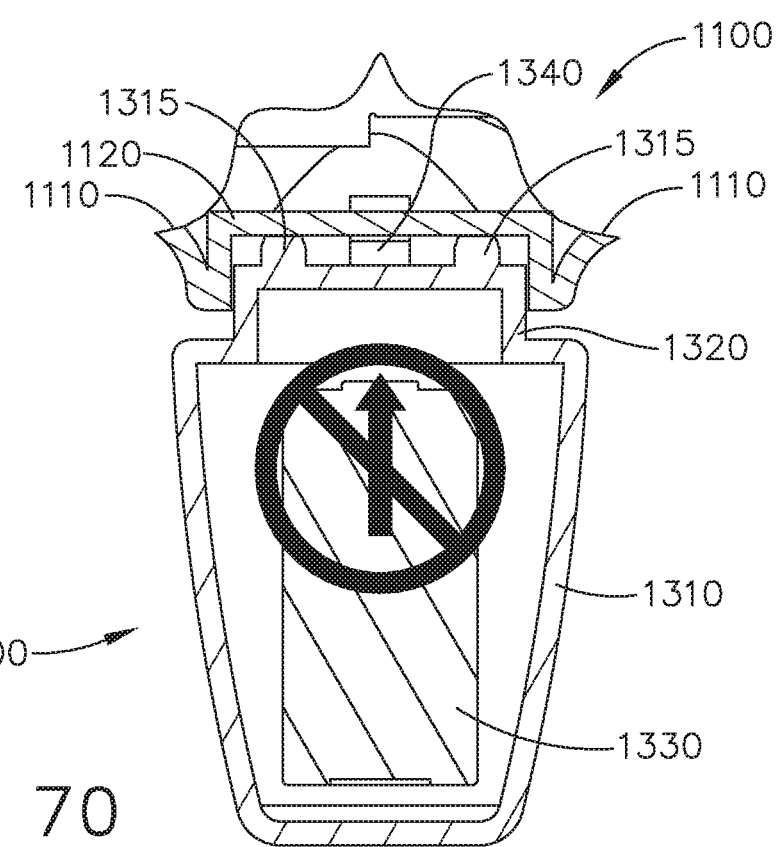
FIG. 70 is a cross-sectional detail view of an attempt to connect the power module of FIG. 45 to the side battery port of the drive module of FIG. 7.

Further to the above, the power module 1300 is operably attachable to the drive module 1100 at the proximal battery port 1120', as illustrated in FIGS. 59-66, but not the side battery port 1120, as illustrated in FIGS. 69 and 70. This is the case because the connector 1320 of the power module 1300 is compatible with the proximal battery port 1120', but not the side battery port 1120. Although the connector 1320 comprises a substantially circular, or substantially cylindrical, configuration that matches, or at least substantially matches, the substantially circular, or substantially cylindrical, configurations of the battery ports 1120 and 1120', the connector 1320 of the power module 1300 comprises keys, or projections, 1315 extending therefrom which interfere with the assembly of the power module 1300 to the side battery port 1120, but not the proximal battery port 1120'. When a clinician attempts to assembly the power module 1300 to the side battery port 1120', the projections 1315 contact the housing 1110 and prevent the latches 1340 of the power module 1300 from locking the power module 1300 to the drive module 1100 and prevent the power module 1300 from being electrically coupled to the drive module 1100. That being said, referring primarily to FIGS. 63 and 64, the proximal battery port 1120' comprises clearance apertures 1115' defined therein configured to receive the projections 1315 of the power module 1300 and permit the power module 1300 to be assembled to the proximal battery port 1120'. Similar to the above, the latch openings 1125' and the clearance apertures 1115' in the proximal battery port 1120' limit the orientations in which the power module 1300 can be assembled to the proximal battery port 1120' to two orientations.

Figure 51:
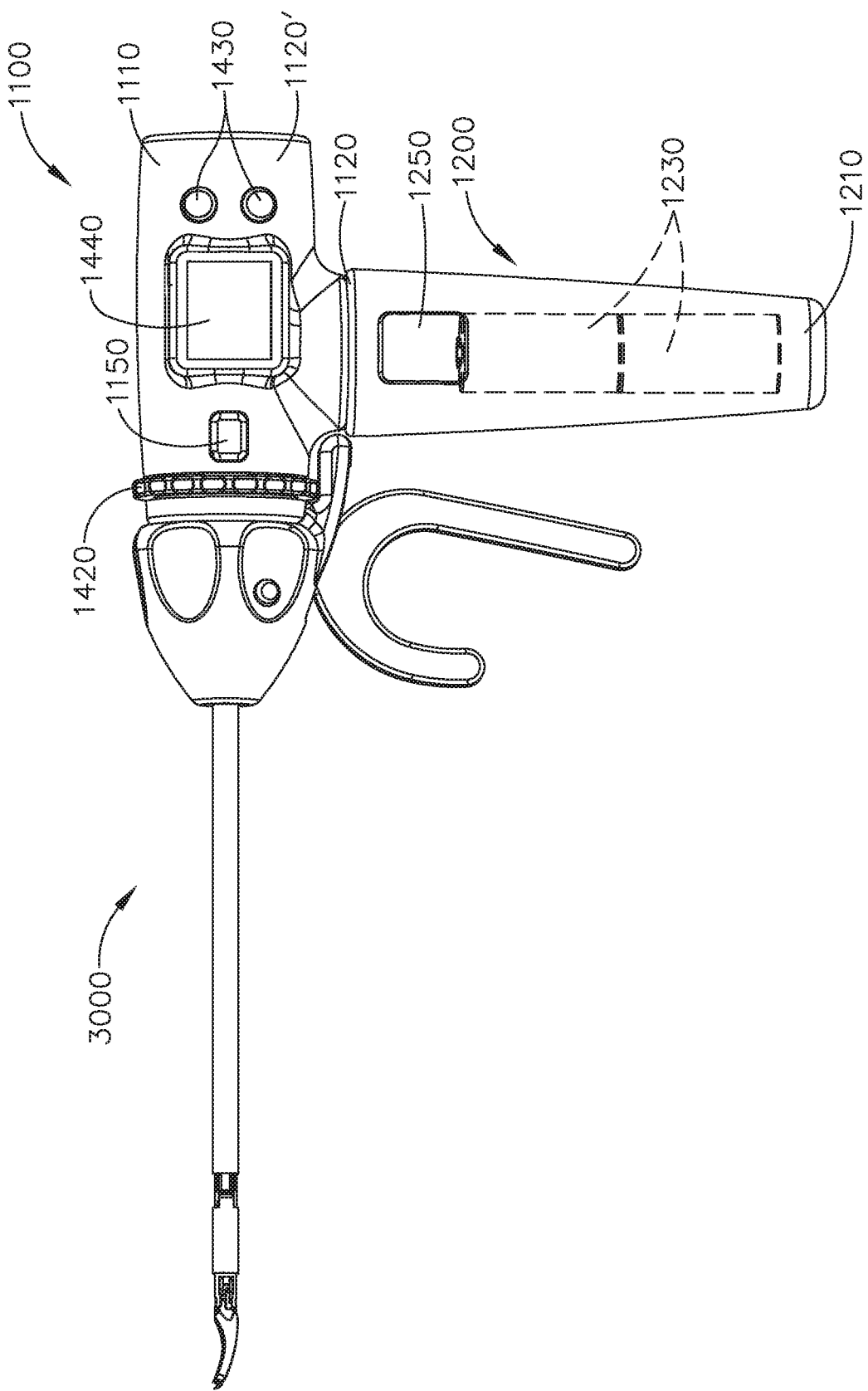
FIG. 51 is an elevational view of the handle and one of the shaft assemblies of the surgical system of FIG. 1.
Figure 52:
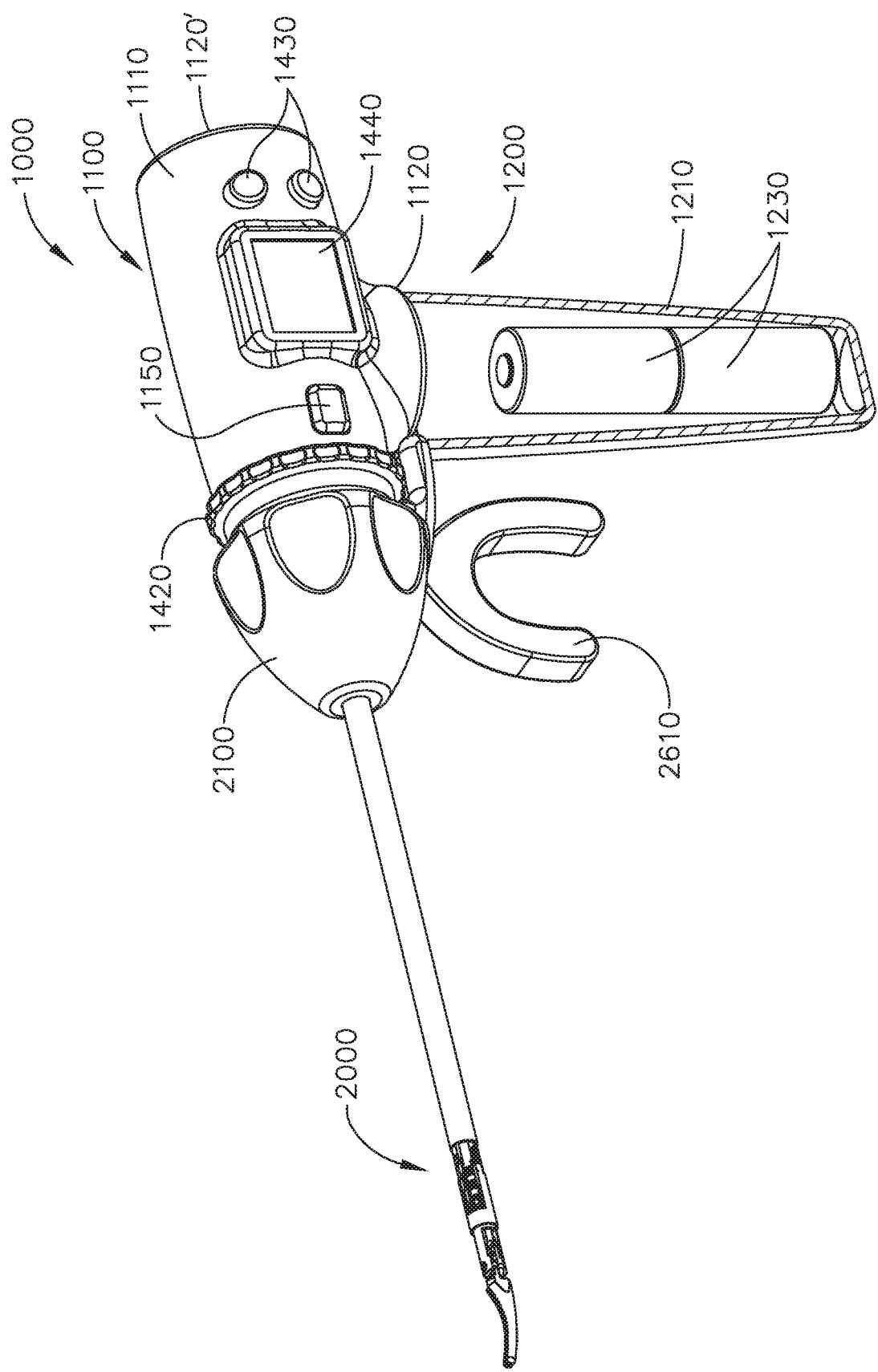
FIG. 52 is a perspective view of the handle of FIG. 1 and the shaft assembly of FIG. 2.
Figure 53:
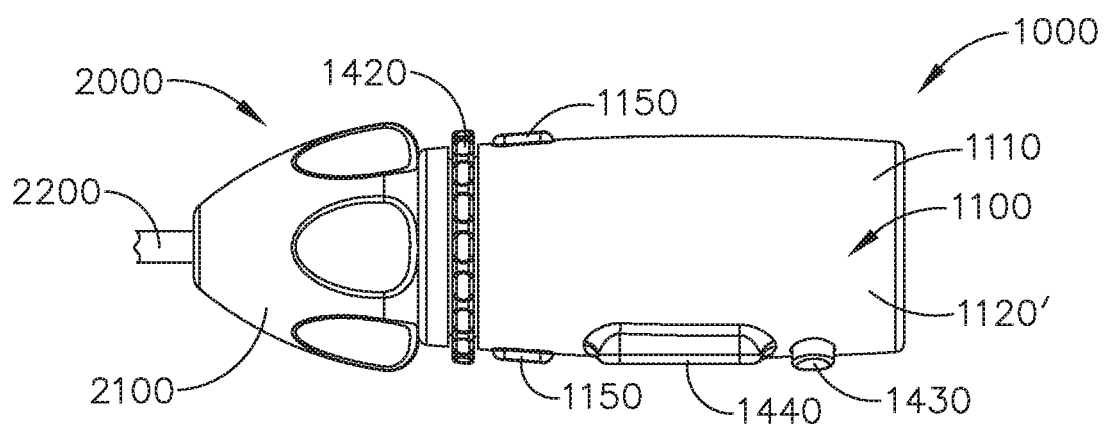
FIG. 53 is a partial top plan view of the handle of FIG. 1 and the shaft assembly of FIG. 2.
Figure 54:
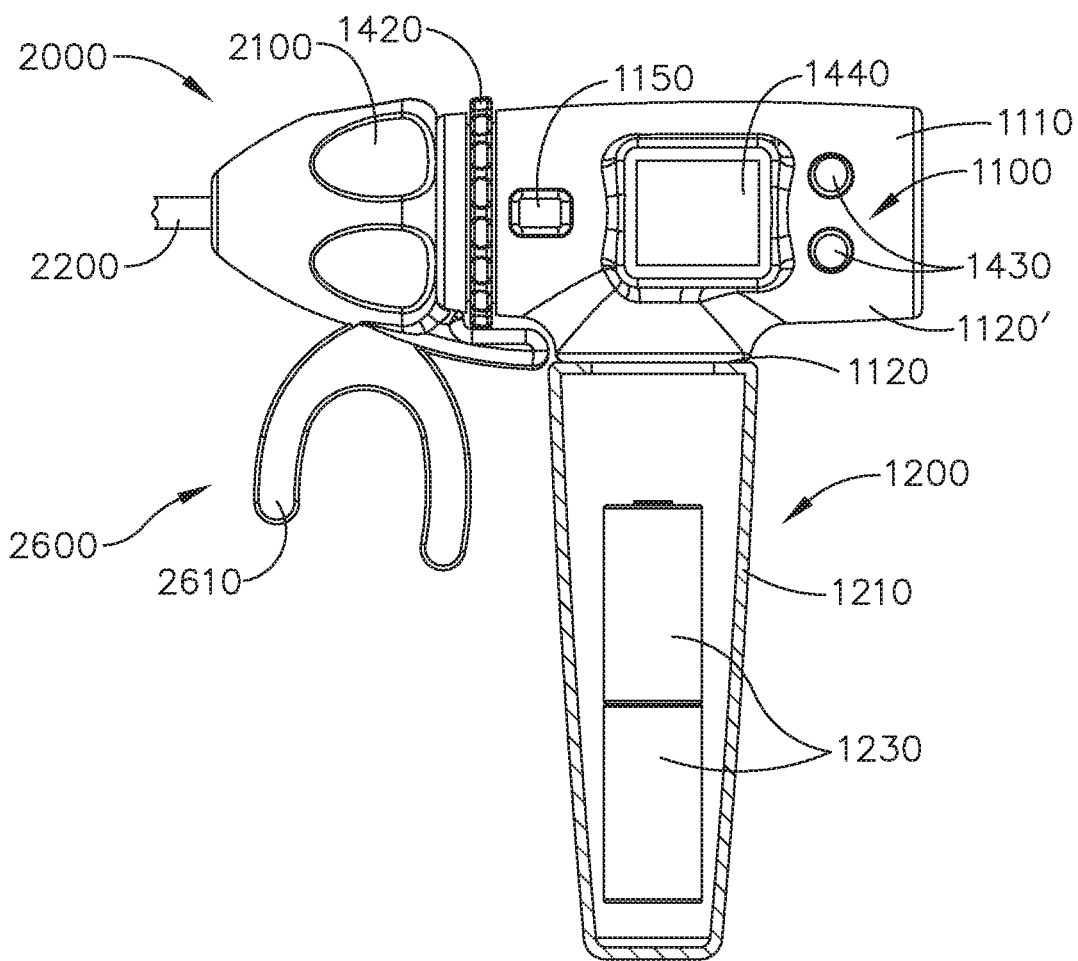
FIG. 54 is a partial elevational view of the handle of FIG. 1 and the shaft assembly of FIG. 2.
Figure 59:
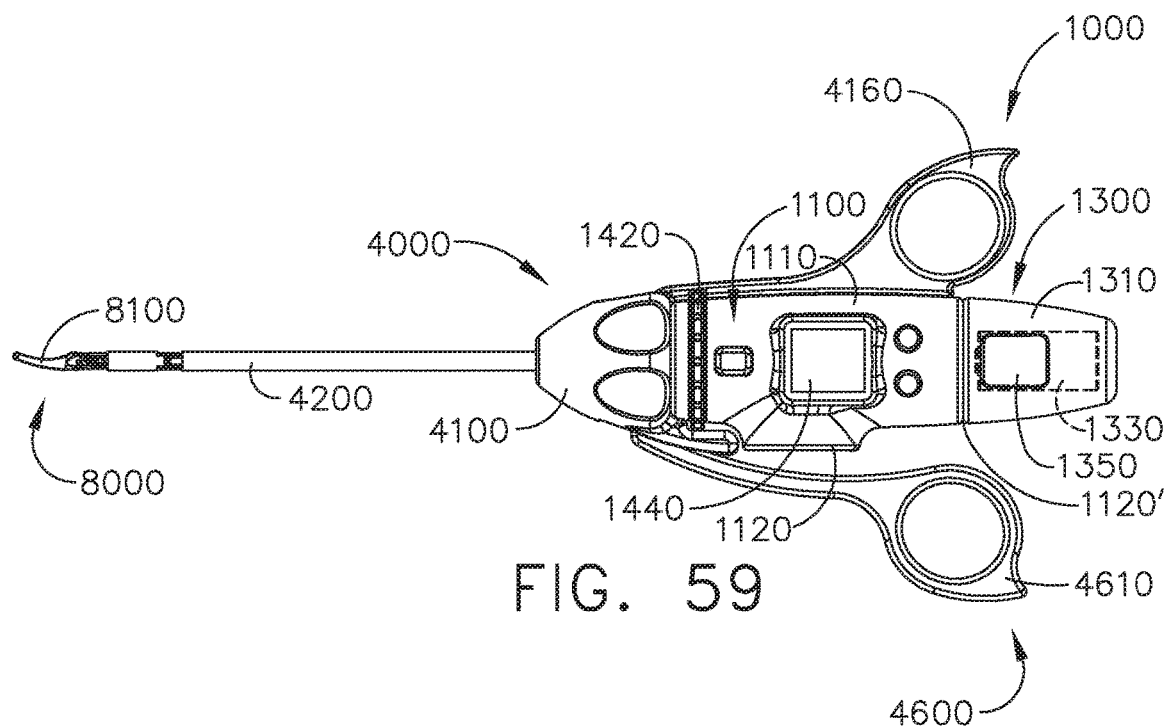
FIG. 59 is an elevational view of the handle drive module of FIG. 7, the power module of FIG. 45 attached to a proximal battery port of the handle drive module, and the shaft assembly of FIG. 45 attached to the drive module.
Figure 60:
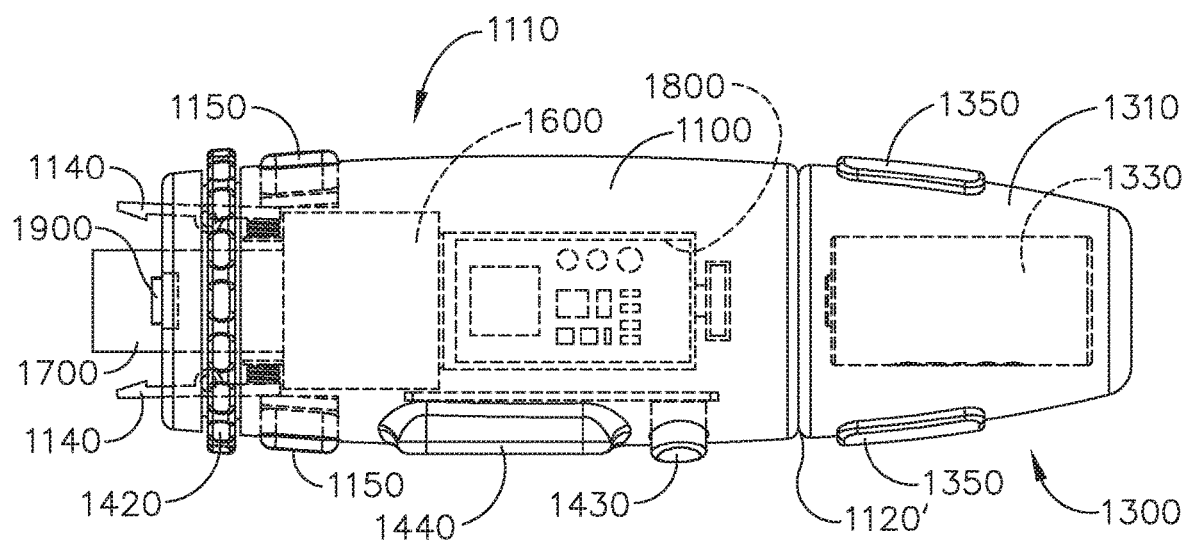
FIG. 60 is a top view of the drive module of FIG. 7 and the power module of FIG. 45 attached to the proximal battery port.
Figure 61:
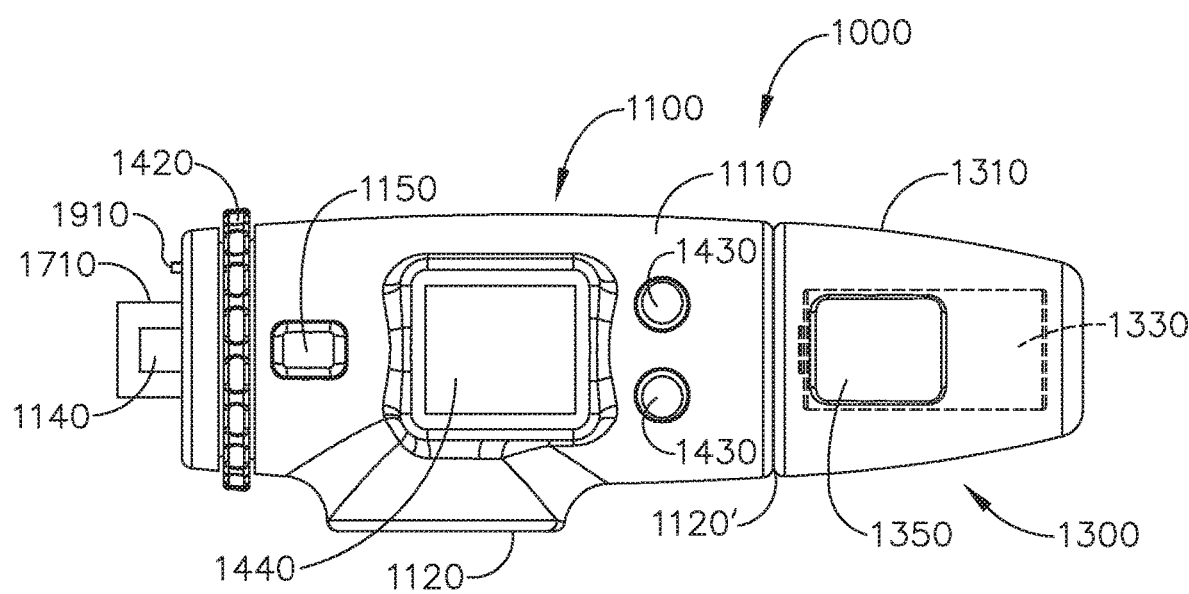
FIG. 61 is an elevational view of the drive module of FIG. 7 and the power module of FIG. 45 attached to the proximal battery port.
Figure 62:
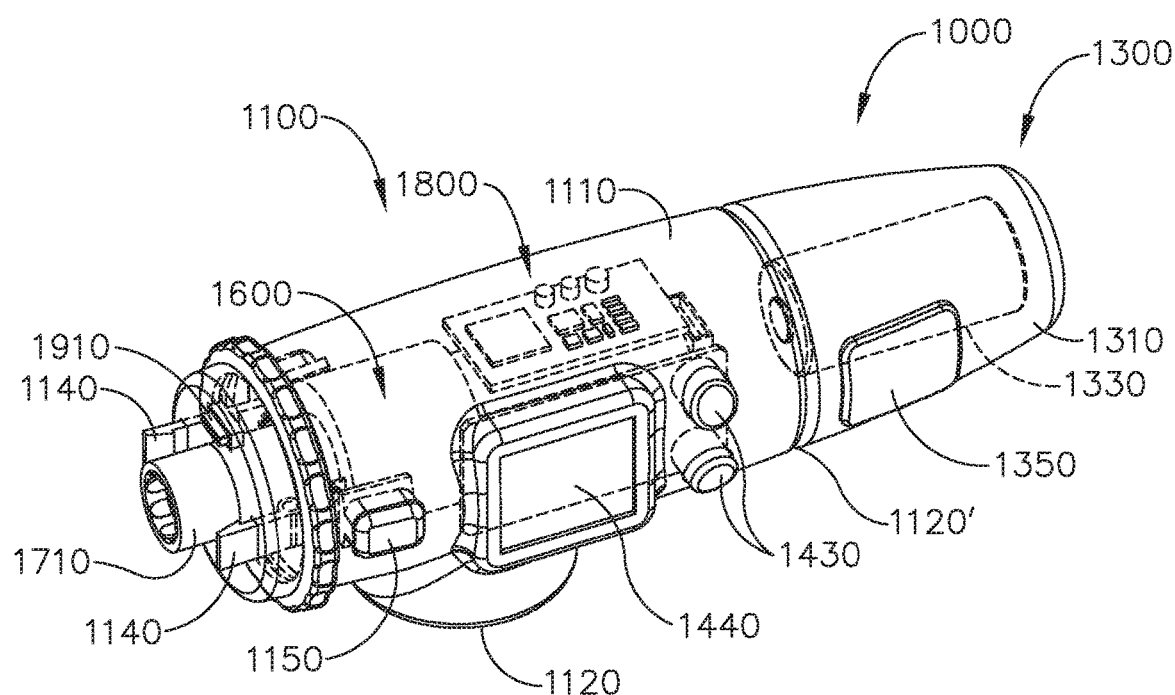
FIG. 62 is a perspective view of the drive module of FIG. 7 and the power module of FIG. 45 attached to the proximal battery port.
Figure 66:
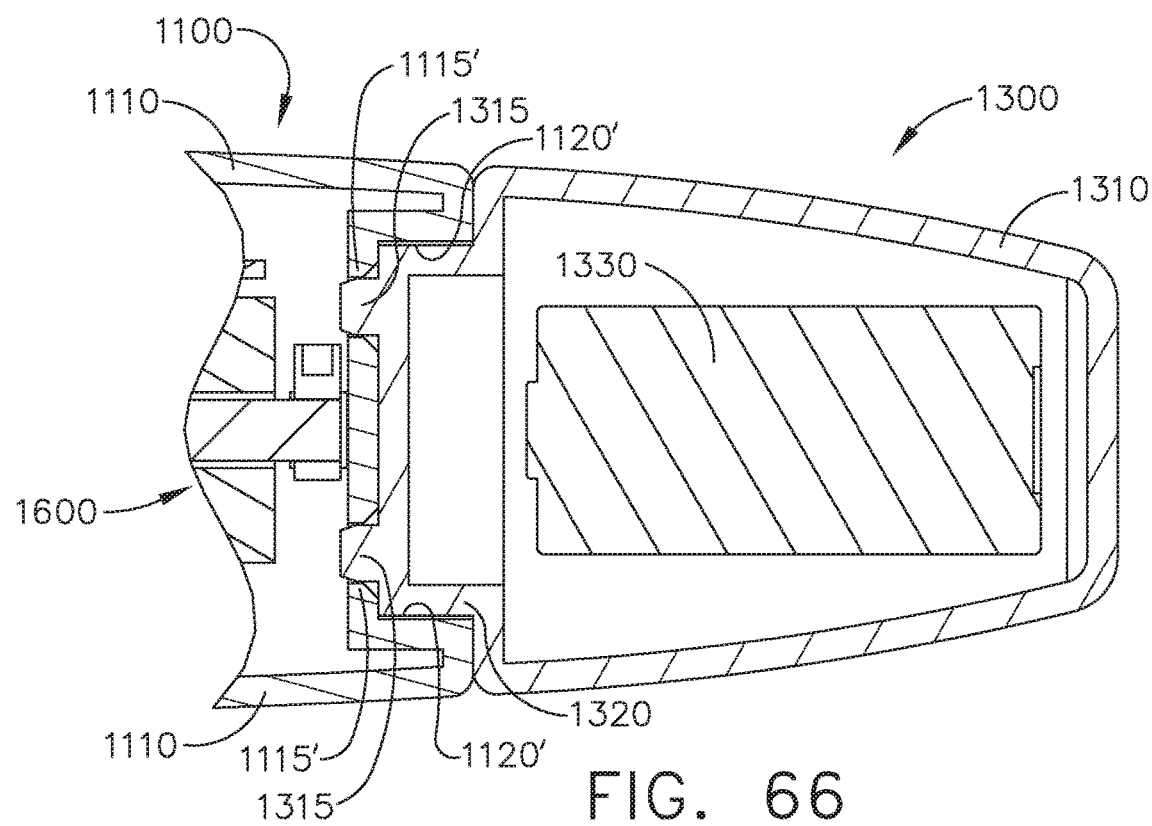
FIG. 66 is a partial cross-sectional view of the connection between proximal battery port of the drive module of FIG. 7 and the power module of FIG. 45.
Figure 71:
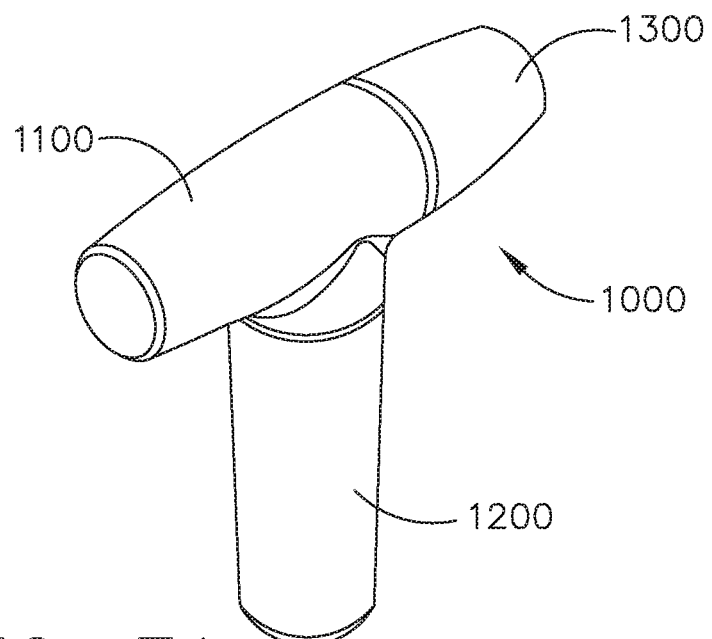
FIG. 71 is a perspective view of the power module of FIG. 45 attached to the proximal battery port of the drive module of FIG. 7 and the power module of FIG. 55 attached to the side battery port.
Figure 72:
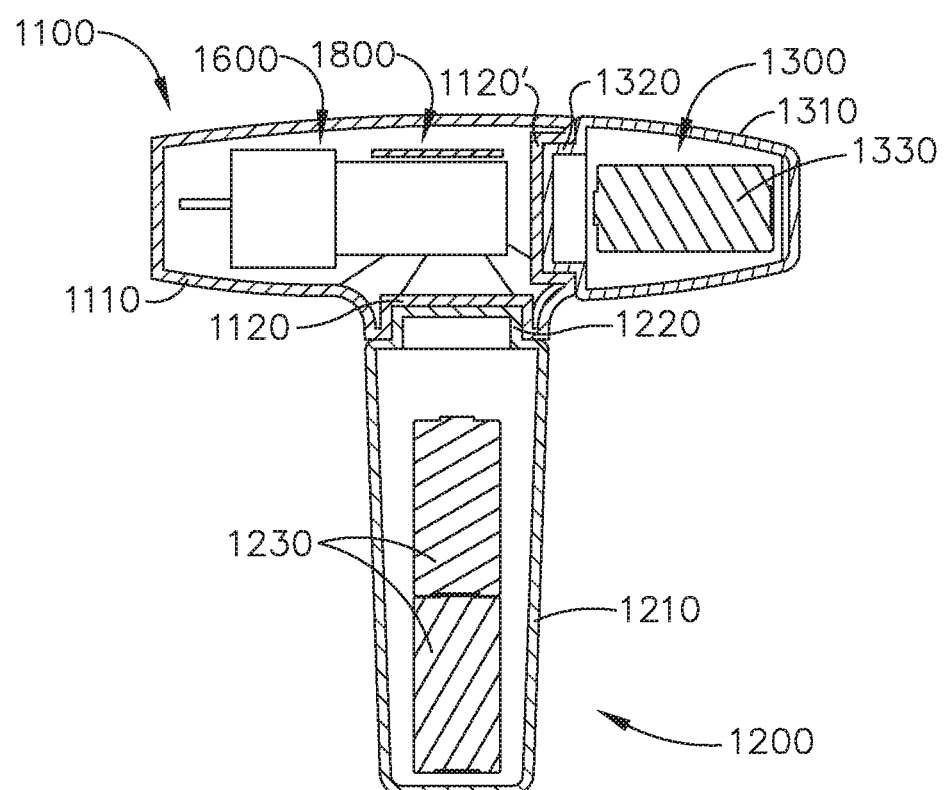
FIG. 72 is a cross-sectional view of the power module of FIG. 45 attached to the proximal battery port of the drive module of FIG. 7 and the power module of FIG. 55 attached to the side battery port.

Further to the above, other circumstances can prevent the attachment of a power module to one of the battery ports 1120 and 1120'. For instance, one of the battery ports can have an asymmetrical geometry which is configured to receive a complementary geometry of only one of the power modules. In at least one such instance, the side battery port 1120 can comprise a semicircular cavity and the proximal battery port 1120' can comprise a circular cavity, wherein the connector 1220 of the power module 1200 comprises a semicircular geometry which can be received in both of the battery ports 1120 and 1120' while the connector 1320 of the power module 1300 comprises a circular geometry which can be received in the proximal battery port 1120', but not the side battery port 1120. In some instances, the configuration of the shaft assembly attached to the drive module 1100 can prevent the assembly of one of the power modules to the drive module 1100. For instance, referring to FIG. 59, the shaft assembly 4000, for example, can prevent the assembly of the power module 1300 to the side battery port 1120 as the actuation trigger 4610 interferes with its assembly thereto. Notably, such an arrangement would also prevent the power module 1200 from being assembled to the side battery port 1120. As a result, the clinician would be required to use the proximal battery port 1120' to couple a power module to the drive module 1100 when using the shaft assembly 4000. The configuration of certain shaft assemblies, referring to FIGS. 71 and 72, would permit both of the power modules 1200 and 1300 to be assembled to the drive module 1100 at the same time. For instance, referring to FIG. 51, the shaft assembly 3000 of FIG. 1 would permit both of the power modules 1200 and 1300 to be used to supply power to the drive module 1100 simultaneously.

The power modules 1200 and 1300 are configured to supply power to the drive module 1100 at the same, or at least substantially the same, voltage. For instance, each power module 1200 and 1300 is configured to supply power to the drive module 1100 at 3 VDC, for example. The control system 1800 of the drive module 1100 comprises one or more power inverters, for example, configured to convert the DC current to AC current to the extent that AC current is needed. That said, the power modules 1200 and 1300 can be configured to deliver power to the drive module 1100 at any suitable voltage. In at least one instance, the power modules 1200 and/or 1300 are configured to deliver AC power to the drive module. In at least one such instance, the power modules 1200 and/or 1300 each comprise one or more power inverters. In alternative embodiments, the power modules 1200 and 1300 are configured to supply power to the drive module 1100 at different voltages. In such embodiments, the configurations of the ports 1120 and 1120', discussed above, can prevent a power module having a higher voltage from being attached to a lower voltage port. Likewise, the configurations of the ports 1120 and 1120' can prevent a power module having a lower voltage from being attached to a higher voltage port, if desired.

In various instances, the power modules 1200 and 1300 are configured to provide the same, or at least substantially the same, current to the drive module. In at least one instance, the power modules 1200 and 1300 supply the same, or at least substantially the same, magnitude of current to the drive module 1100. In alternative embodiments, the power modules 1200 and 1300 are configured to provide different currents to the drive module 1100. In at least one instance, the power module 1200 provides a current to the drive module 1100 having a magnitude which is twice that of the current provided by the power module 1300, for example. In at least one such instance, the battery cells of the power module 1200 are arranged in parallel to provide the same voltage as the power module 1300 but at twice the current. Similar to the above, the configurations of the ports 1120 and 1120', discussed above, can prevent a power module having a higher current from being attached to a lower current port. Likewise, the configurations of the ports 1120 and 1120' can prevent a power module having a lower current from being attached to a higher current port, if desired.

Further to the above, the control system 1800 is configured to adaptively manage the power provided by the power modules 1200 and 1300. In various instances, the control system 1800 comprises one or more transformer circuits configured to step up and/or step down the voltage provided to it by a power module. For instance, if a higher voltage power module is attached to a lower voltage port, the control system 1800 can activate, or switch on, a transformer circuit to step down the voltage from the higher voltage power module. Similarly, if a lower voltage power module is attached to a higher voltage port, the control system 1800 can activate, or switch on, a transformer circuit to step up the voltage from the lower voltage power module. In various embodiments, the control system 1800 is configured to switch a power module off if a power module having an inappropriate voltage is attached to a port in the drive module 1100. In at least one instance, the control system 1800 comprises one or more voltmeter circuits configured to evaluate the voltage of a power module attached to the drive module and, if the voltage of the power module is incorrect or outside of an appropriate voltage range, the control system 1800 can switch off the power module such that the power module does not supply power to the drive module 1100. In at least one such instance, the drive module 1100 has a voltmeter circuit for each port 1120 and 1120'. In at least one instance, the control system 1800 comprises one or more ammeter circuits configured to evaluate the current of a power module attached to the drive module and, if the current of the power module is incorrect or outside of an appropriate current range, the control system 1800 can switch off the power module such that the power module does not supply power to the drive module 1100. In at least one such instance, the drive module 1100 has a ammeter circuit for each port 1120 and 1120'. In at least one instance, each power module 1200 and 1300 comprises a switch circuit which, when opened by the control system 1800, prevents power from being supplied to the drive module 1100. If a power module comprises the correct voltage or a voltage within an appropriate voltage range for the port in which the power module is attached, the switch circuit remains closed and/or is closed by the control system 1800. In at least one such instance, the drive module 1100 has a switch circuit for each port 1120 and 1120'.

In various instances, a power module can comprise a switch which is selectively actuatable by the clinician to prevent the power module from supplying power to the drive module 1100. In at least one instance, the switch comprises a mechanical switch, for example, in the power supply circuit of the power module. A power module that has been switched off, however, can still provide other benefits. For instance, a switched-off power module 1200 can still provide a pistol grip and a switched-off power module 1300 can still provide a wand grip. Moreover, in some instances, a switched-off power module can provide a power reserve that can be selectively actuated by the clinician.

In addition to or in lieu of the above, each of the power modules 1200 and 1300 comprises an identification memory device. The identification memory devices can comprise a solid state chip, for example, having data stored thereon which can be accessed by and/or transmitted to the control system 1800 when a power module is assembled to the drive module 1100. In at least one instance, the data stored on the identification memory device can comprise data regarding the voltage that the power module is configured to supply to the drive module 1100, for example.

Further to the above, each of the shaft assemblies 2000, 3000, 4000, and/or 5000 comprise an identification memory device, such as memory device 2830, for example. The identification memory device of a shaft assembly can comprise a solid state chip, for example, having data stored thereon which can be accessed by and/or transmitted to the control system 1800 when the shaft assembly is assembled to the drive module 1100. In at least one instance, the data stored on the identification memory device can comprise data regarding the power required to operate the drive systems of the shaft assembly. The shaft assembly 2000 comprises three systems driven by the drive module 1100—the end effector articulation drive system, the end effector rotation drive system, and the jaw drive system—each of which having their own power requirement. The jaw drive system, for instance, may require more power than the end effector articulation and rotation drive systems. To this end, the control system 1800 is configured to verify that the power provided by the power module, or power modules, attached to the drive module 1100 is sufficient to power all of the drive systems—including the jaw drive system—of the shaft assembly 2000 assembled to the drive module 1100. As such, the control system 1800 is configured to assure that the power module arrangement attached to the drive module 1100 is properly paired with the shaft assembly attached to the drive module 1100. If the power provided by the power module arrangement is insufficient, or below a required power threshold, the control system 1800 can inform the clinician that a different and/or an additional power module is required. In at least one instance, the drive module 1100 comprises a low-power indicator on the housing 1110 and/or on the display screen 1440, for example. Notably, the jaw drive system of the shaft assembly 4000 is not driven by the drive module 1100; rather, it is manually powered by the clinician. As such, the power required to operate the shaft assembly 4000 can be less than the power required to operate the shaft assembly 2000, for example, and the control system 1800 can lower the required power threshold for the shaft assembly 4000 when evaluating the power module arrangement.

Further to the above, an end effector configured to grasp and/or dissect tissue may require less power than an end effector configured to clip the tissue of a patient. As a result, an end effector and/or shaft assembly comprising a clip applier may have a larger power requirement than an end effector and/or shaft assembly comprising grasping and/or dissecting jaws. In such instances, the control system 1800 of the drive module 1100 is configured to verify that the power module, or modules, attached to the drive module 1100 can provide sufficient power to the drive module 1100. The control system 1800 can be configured to interrogate the identification chips on the power modules attached to the drive module 1100 and/or evaluate the power sources within the power modules to assess whether the power modules comprise sufficiently-available voltage and/or current to properly power the drive module 1100 to operate the clip applier.

Further to the above, an end effector configured to grasp and/or dissect tissue may require less power than an end effector configured to suture the tissue of a patient, for example. As a result, an end effector and/or shaft assembly comprising a suturing device may have a larger power requirement than an end effector and/or shaft assembly comprising grasping and/or dissecting jaws. In such instances, the control system 1800 of the drive module 1100 is configured to verify that the power module, or modules, attached to the drive module 1100 can provide sufficient power to the drive module 1100 based on the shaft assembly attached to the drive module 1100. The control system 1800 can be configured to interrogate the identification chips on the power modules attached to the drive module 1100 and/or evaluate the power sources within the power modules to assess whether the power modules comprise sufficiently-available voltage and/or current to properly power the drive module 1100 to operate the suturing device.

In addition to or in lieu of the above, an end effector, such as end effector 7000, for example, comprises an identification memory device. The identification memory device of an end effector can comprise a solid state chip, for example, having data stored thereon which can be accessed by and/or transmitted to the control system 1800 when the end effector is assembled to the drive module 1100 by way of a shaft assembly. In at least one instance, the data stored on the identification memory device can comprise data regarding the power required to operate the drive systems of the end effector. The end effector can be in communication with the drive module 1100 through electrical pathways, or circuits, extending through the shaft assembly. Similar to the above, the end effector can identify itself to the drive module 1100 and, with this information, the drive module 1100 can adapt its operation to properly operate the end effector.

As described above, the power modules 1200 and 1300 each comprise one or more battery cells. That said, the power modules 1200 and 1300 can comprise any suitable means for storing and delivering power. In at least one instance, the power modules 1200 and 1300 comprise capacitors and/or supercapacitors configured to store energy and deliver energy to the drive module 1100. The capacitors and/or supercapacitors can be part of the same electrical circuit as the battery cells or a different electrical circuit. A supercapacitor can comprise electrostatic double-layer capacitance and/or electrochemical pseudocapacitance, both of which can contribute to the total capacitance of the supercapacitor. In various instances, electrostatic double-layer capacitors use carbon electrodes or derivatives with much higher electrostatic double-layer capacitance than electrochemical pseudocapacitance, achieving separation of charge in a Helmholtz double layer at the interface between the surface of a conductive electrode and an electrolyte. The separation of charge is often of the order of a few angstroms (0.3-0.8 nm), much smaller than in a conventional capacitor. Electrochemical pseudocapacitors use metal oxide or conducting polymer electrodes with a high amount of electrochemical pseudocapacitance additional to the double-layer capacitance. Pseudocapacitance is achieved by Faradaic electron charge-transfer with redox reactions, intercalation, and/or electrosorption. Hybrid capacitors, such as a lithium-ion capacitor, for example, could also be used which comprise electrodes with differing characteristics—one exhibiting mostly electrostatic capacitance and the other mostly electrochemical capacitance.

The power modules 1200 and 1300 can be rechargeable or non-rechargeable. When the power modules 1200 and 1300 are not rechargeable, they are disposed of after a single use. In such instances, it is desirable for the power modules 1200 and 1300 to be completely drained, or at least substantially drained, of power when they are disposed of. To this end, each power module comprises a drain which is engaged, or actuated, when the power module is assembled to the drive module 1100. In various instances, the drain comprises a resistance circuit inside the power module that includes the battery cells. Once actuated, the drain slowly discharges the battery cells of the power module, but at a rate which still permits the power module to provide sufficient power to the drive module 1100 during the surgical procedure. After the surgical procedure is completed, however, the drain continues to discharge the battery cells even though the power module may no longer be assembled to the drive module 1100. As such, the drain discharges the battery cells whether or not the power module is supplying power to, or attached to, the drive module 1100. The entire disclosures of U.S. Pat. No. 8,632,525, entitled POWER CONTROL ARRANGEMENTS FOR SURGICAL INSTRUMENTS AND BATTERIES, which issued on Jan. 21, 2014, and U.S. Pat. No. 9,289,212, entitled SURGICAL INSTRUMENTS AND BATTERIES FOR SURGICAL INSTRUMENTS, which issued on Mar. 22, 2016, are incorporated by reference herein.

Multiple surgical instruments, including various handheld instruments, are used by a clinician during a particular surgical procedure to perform different functions. Each surgical instrument may comprise different handle and/or grip configurations in addition to different user control mechanisms. Switching between various handheld instruments may cause delay and/or discomfort, as the clinician regains control over the surgical instrument and actuates the user control mechanism(s). The use of numerous powered surgical instruments may require a user to ensure that, prior to the start of every surgical procedure, numerous power sources are charged and/or functional, as power sources may vary and/or may not be compatible with all powered surgical instruments.

A modular surgical instrument comprising a universal handle and power source may provide a clinician with a sense of familiarity in using a universal handle configuration. The modular surgical instrument is configured for use with numerous surgical tool attachments. Instead of having to charge a plurality of different power sources, the modular surgical instrument is configured for use with a replaceable power source that can be discarded after each surgical procedure. Furthermore, the use of one universal handle with a plurality of surgical tool attachments may reduce the clutter and/or volume of surgical instruments within the surgical arena.

Figure 73:
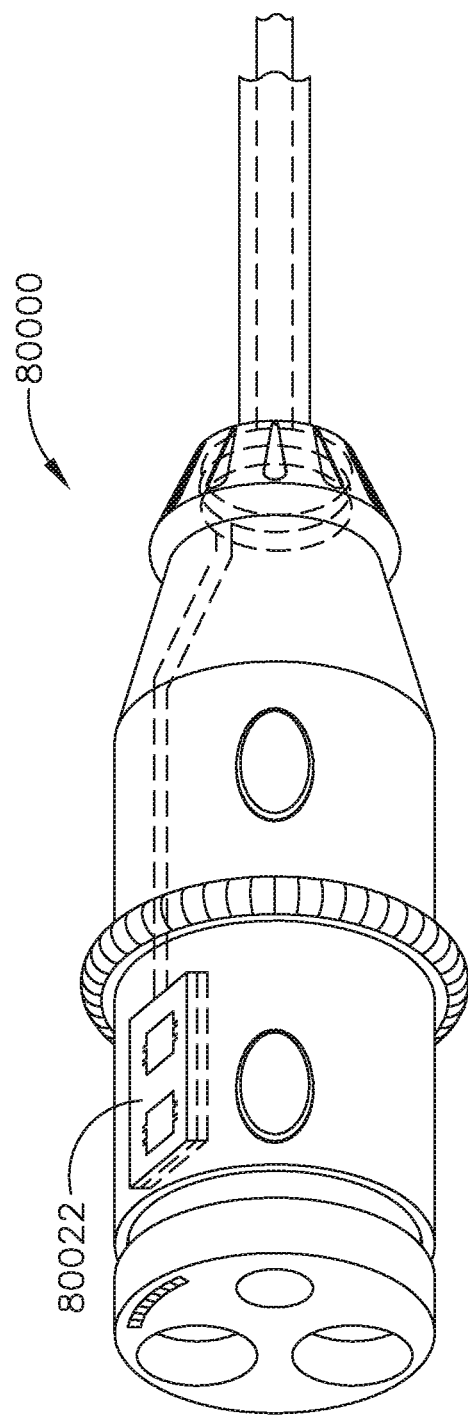
FIG. 73 is a perspective view of a portion of a surgical instrument comprising selectively attachable modular components in accordance with at least one aspect of the present disclosure.
Figure 74:
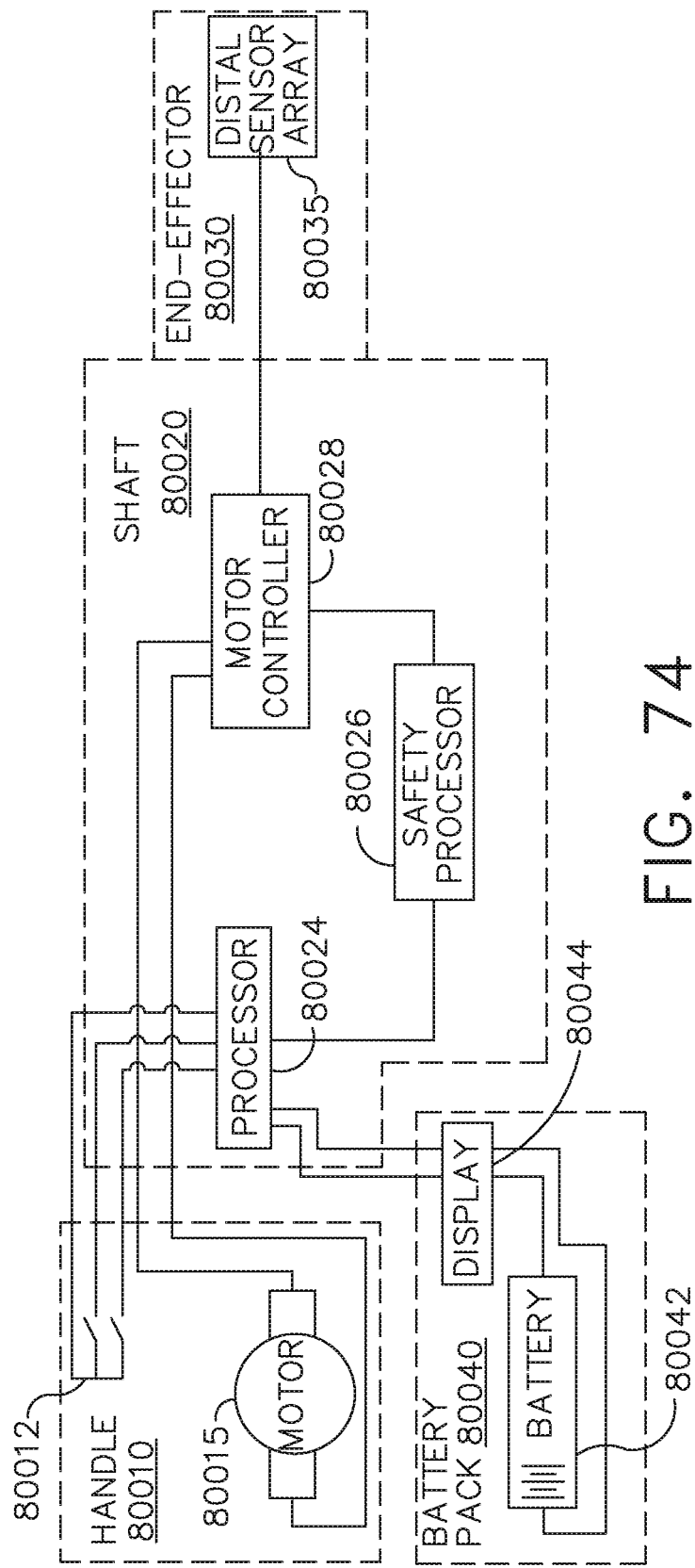
FIG. 74 illustrates an electrical architecture of the surgical instrument of FIG. 73 in accordance with at least one aspect of the present disclosure.

FIG. 73 illustrates a portion of a modular surgical instrument 80000 and FIG. 74 illustrates an electrical architecture of the modular surgical instrument 80000. The configuration of the modular surgical instrument 80000 is similar in many respects to the surgical instrument 1000 in FIG. 1 discussed above. The modular surgical instrument 80000 comprises a plurality of modular components, including, for example: a drive module 80010, a shaft 80020, an end effector 80030, and a power source 80040. In various instances, the drive module 80010 comprises a handle. The drive module 80010 comprises one or more control switches 80012 and a motor 80015.

The shaft 80020 comprises a control circuit 80022 configured to facilitate communication between the modular components 80010, 80020, 80030, 80040 of the surgical instrument 80000. The operation and functionality of the modular components 80010, 80020, 80030, 80040 of the surgical instrument 80000 are described in greater detail above in connection with other surgical instruments.

In various instances, the one or more control switches 80012 correspond to the rotation actuator 1420 and the articulation actuator 1430 of the input system 1400 as described in greater detail with respect to FIGS. 7 and 8 above. As shown in FIGS. 7 and 8, the articulation actuator 1430 comprises a first push button 1432 and a second push button 1434. The first push button 1432 comprises a first switch that is closed when the first push button 1434 is depressed. Similar in many aspects to the articulation actuator 1430 and the rotation actuator 1420 shown in FIGS. 7 and 8, the one or more control switches 80012 may comprise push buttons. When a user input depresses the push button, a switch is closed that sends a signal to the control circuit 80022 indicative of a user command. In various instances, a first push button can initiate articulation or rotation in a first direction while a second push button can initiate articulation or rotation in a second direction. The operation and functionality of these control switches 80012 are described in greater detail above.

In various instances, the shaft 80020 is configured to be disposable after being used to treat a patient. In such instances, the shaft 80020 is usable more than once on the same patient. As discussed in more detail below, the shaft 80020 comprises a processor 80024 and a memory storing instructions for one or more control programs. The disposable shaft 80020 comprises any signal processing circuits required to interface with the end effector 80030, the power source 80040, and/or the drive module 80010 when the modular surgical instrument 80000 is fully configured, or assembled. The end effector 80030 comprises a sensor array 80035 configured to monitor a parameter of the end effector 80030. Such a sensor array 80035 can detect, for example, information pertaining to the identity of the end effector 80030, an operating status of the end effector 80030, and/or information regarding the environment of the surgical site, such as tissue properties, for example. In various instances, the power source 80040 comprises a replaceable battery pack configured to be attached directly to the drive module 80010 to supply power to the surgical instrument 80000. The power source 80040 comprises a battery 80042 and a display 80044. In various instances the display 80044 comprises a touch-sensitive display, for example, wherein a user input is sent to the processor 80024.

In various instances, the drive module 80010 comprises a power source interface for attaching the modular power source 80040 thereto. The replaceable connection between the power source 80040 and the drive module 80010 allows for a user to readily change out the power source 80040 without having to disassemble a housing of the drive module 80010. The battery 80042 within the modular power source 80040 comprises a primary cell, but can also include secondary cells. The primary cell battery 80042 is configured to be fully charged once. In other words, the primary cell battery 80042 is configured to be discarded after each surgical procedure. Use of a disposable power supply may, among other things, provide assurance to the clinician that the battery 80042 is fully charged at the beginning of each surgical procedure.

The power source interface supplies the interconnection between the battery 80042 and the connection of the display 80044 upon the attachment of the power source 80040 to the drive module 80010. In other words, no continuous circuits are present within the power source 80040 until the power source 80040 is replaceably attached to the power source interface on the drive module 80010. As such, the power source 80040 can be distributed and sterilized in an uncoupled state. The ability to be in an uncoupled state permits each power source 80040 to be easily sterilized. For example, the modular power source 80040 is compatible with both ethylene oxide and gamma sterilization as no continuous circuits are present in the unattached power source 80040.

Similar to the power source 80040, the drive module 80010 does not have any continuous circuits while unattached to the shaft 80020 and the power source 80040. For at least this reason, the drive module 80010 is able to be sterilized using any desired sterilization protocol following each use. In its unattached configuration, the drive module 80010 is configured to be tolerant of full immersion during the cleaning process.

Further to the above, the control circuit 80022 of the shaft 80020 comprises a processor 80024 configured to receive a user input from the one or more control switches 80012 on the drive module 80010. The shaft 80020 further comprises a motor controller 80028 configured to control the motor 80015 within the drive module 80010 when the shaft 80020 is assembled to the drive module 80010. In various instances, the control circuit 80022 further comprises a safety processor 80024 comprising two controller-based families such as, for example, TMS570 and RM4x known under the trade name Hercules ARM Cortex R4, by Texas Instruments. The safety processor 80026 may be configured specifically for IEC 61508 and ISO 26262 safety critical applications, among others, to provide advanced integrated safety features while delivering scalable performance, connectivity, and memory options. The safety processor 80026 is configured to be in signal communication with the processor 80024 and the motor controller 80028. The motor controller 80028 is configured to be in signal communication with the sensor array 80035 of the end effector 80030 and the motor 80015 within the handle 80010. The motor controller 80028 is configured to send an electrical signal, such as, for example, a voltage signal, indicative of the voltage (or power) to be supplied to the motor 80015. The electrical signal may be determined based off of, for example, user input from the one or more control switches 80012, input received from the sensor array 80035, user input from the display 80044, and/or feedback from the motor 80015. In various instances, the motor controller 80028 may output a PWM control signal to the motor 80015 in order to control the motor 80015.

The shaft 80020 further comprises a memory configured to store control programs which, when executed, prompt the processor to, among other things, command the motor controller 80028 to activate the motor 80015 at a predetermined level. The memory within the control circuit 80022 of each shaft 80020 is configured to store one or more control programs to permit the modular surgical instrument 80000, when fully configured, to perform a desired function. In various instances, the shaft 80020 may comprise a default control program for when the attached shaft 80020 does not comprise a control program and/or a stored control program cannot be read or detected. Such a default control program permits the motor 80015 to be run at a minimum level to allow a clinician to perform basic functions of the modular surgical instrument 80000. In various instances, only basic functions of the modular surgical instrument 80000 are available in the default control program and are performed in a manner that minimizes harm to the tissue in and/or surrounding the surgical site. Storing control program(s) specific to an intended function in each replaceable shaft 80020 minimizes the amount of information that needs to be stored and, thus, relieves the drive module 80010 of the burden of storing all possible control programs, many of which go unused. In various instances, the modular components 80010, 80020, 80030, 80040 of the surgical instrument 80000 can be designed, manufactured, programmed, and/or updated at different times and/or in accordance with different software and/or firmware revisions and updates. Furthermore, individual control programs can be updated more quickly than a collection of numerous control programs. The faster update time makes it more likely that clinicians and/or assistants will update the control program(s) to utilize the most up-to-date program in each surgical procedure. In various instances, the drive module 80010 may not comprise any control programs. In other instances, the drive module 80010 may comprise a default control program as discussed above. In other words, if a clinician intends to perform a first function, the clinician may attach a first shaft comprising a stored first control program to the modular surgical instrument. If the clinician intends to perform a second function that is different from the first function, the clinician may remove the first shaft from the universal drive module and attach a second shaft comprising a stored second control program to the modular surgical instrument. In various instances, if the clinician attaches a shaft without a detectable and/or functional stored control program, the drive module 80010 may comprise a memory storing a default control program to operate the modular surgical instrument 80000 at minimum levels and/or at any suitable level of functionality. The operation and functionality of the stored control programs are described in greater detail in U.S. patent application Ser. No. 14/226,133, now U.S. Patent Application Publication No. 2015/0272557, entitled MODULAR SURGICAL INSTRUMENT SYSTEM, which is incorporated in its entirety herein.

Figure 75:
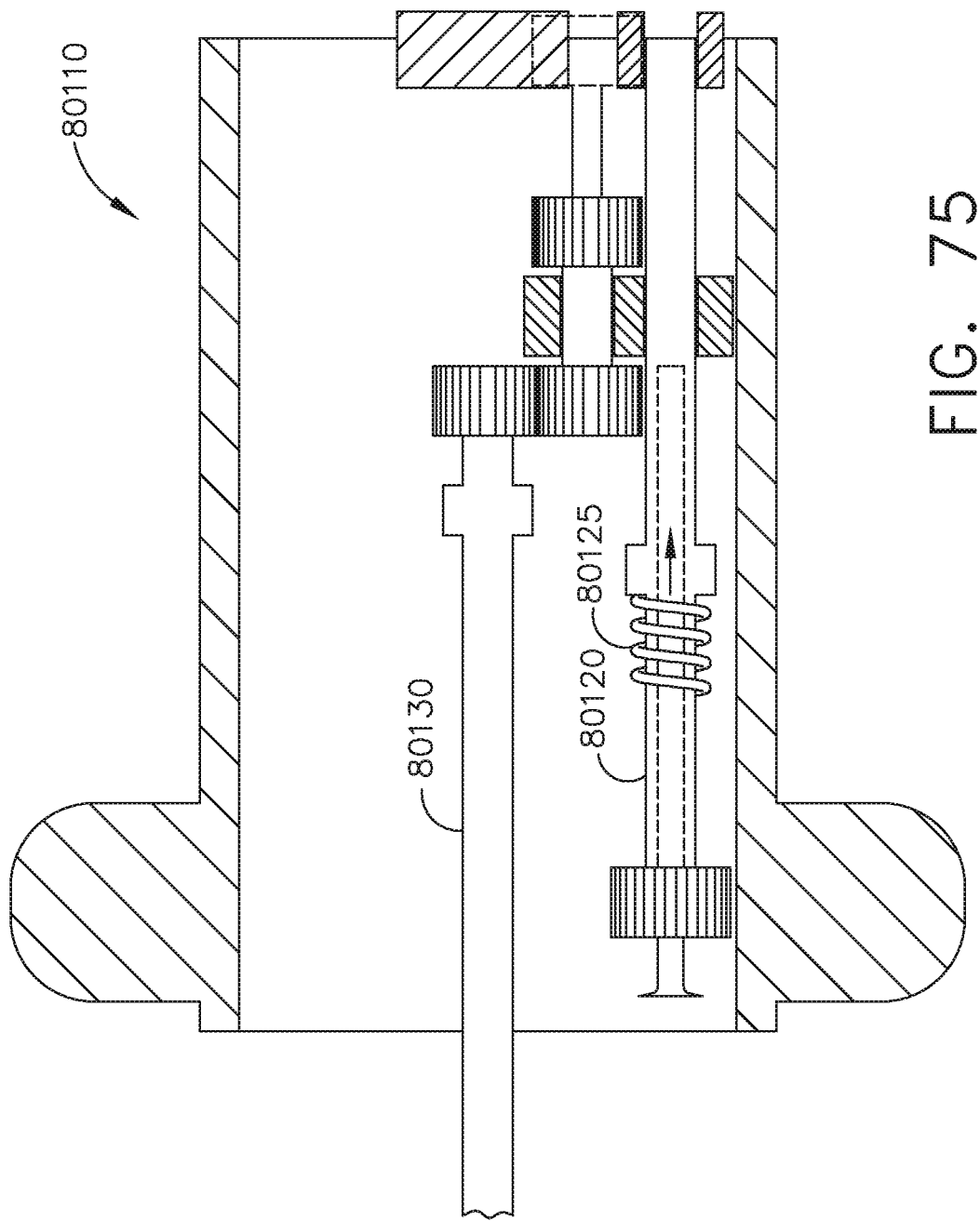
FIG. 75 is a partial cross-sectional perspective view of a handle of the surgical instrument of FIG. 73 in accordance with at least one aspect of the present disclosure.

FIG. 75 depicts a drive module 80110 comprising a plurality of drives configured to interact with corresponding drives in an attached shaft to produce a desired function, such as, for example, rotation and/or articulation of an end effector. For example, the drive module 80110 comprises a rotation drive 80120 configured to rotate an end effector upon actuation. The drive module 80110 of FIG. 75 is configured to operate based on the type of handle attached to the modular shaft. One or more of the plurality of drives is decoupled when a low-functionality handle, such as, for example, a scissor grip handle, is attached to the modular shaft. For example, during the attachment of a low-functionality handle to the modular shaft, an extending lug on the low-functionality handle may cause the rotation drive 80120 to advance distally out of engagement with the low-functionality handle. Such distal advancement results in a decoupling of the rotation drive 80120 from the handle, effectively locking out the functionality of the rotation drive 80120. Upon detachment of the scissor grip handle from the modular shaft, a resilient member 80125, such as, for example, a spring, biases the rotation drive 80120 proximally into its original position. In various instances, all of the drives are decoupled upon the attachment of the low-functionality handle to the modular shaft. In other instances, a first drive, such as, for example, the rotation drive 80120, may be decoupled upon the attachment of the low-functionality handle to the modular shaft, while a second drive 80130 remains in engagement for use with the low-functionality handle.

In various instances, the rotation drive 80120 is in communication with a manual rotation actuator, such as the rotation actuator 1420 described in more detail above with respect to FIGS. 8, 10, and 11. As a clinician rotates the rotation actuator, the position of the rotation actuator can be monitored. For instance, the surgical instrument can comprise an encoder system configured to monitor the position of the rotation actuator. In addition to or in lieu of the encoder system, the drive module 80110 can comprise a sensor system configured to detect a degree of rotation of the rotation actuator. In any event, the detected position of the rotation actuator is communicated to a processor and a motor controller, such as processor 80024 and motor controller 80028 within the shaft 80020. In various instances, the drive module 80110 comprises a handle.

The processor 80024 and the motor controller 80028 are configured to drive a system of the shaft 80020 other than the system being manually driven by the rotation drive 80120 in response to the movement of the rotation drive 80120. In at least one instance, a surgical instrument has a first rotation joint and a second rotation joint where the rotation of the surgical instrument about the first rotation joint is manually driven and the rotation of the surgical instrument about the second rotation joint is driven by an electric motor. In such an instance, the processor 80024 can monitor the rotation of the surgical instrument about the first rotation joint using the encoder and rotate the surgical instrument about the second rotation joint using the motor controller 80028 in order to keep the rotatable components of the surgical instrument aligned, for example.

Figure 76:
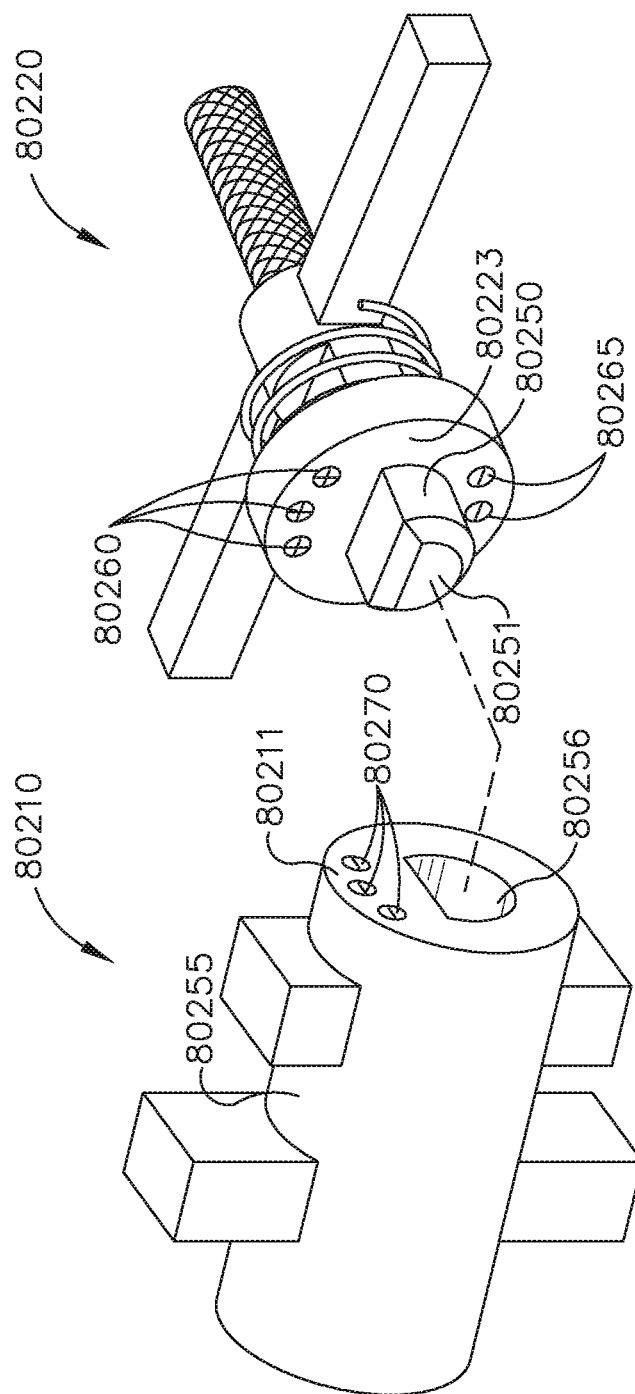
FIG. 76 is a perspective view of a system of magnetic elements arranged on the handle and a shaft of the surgical instrument of FIG. 73 in accordance with at least one aspect of the present disclosure.

FIG. 76 depicts a handle 80210 prior to engagement with an interchangeable shaft 80220. The handle 80210 is usable with several interchangeable shafts and can be referred to as a universal handle. The shaft 80220 comprises a drive rod 80250 configured to mechanically engage a distal nut 80255 of the handle 80210. A proximal end 80251 of the drive rod 80250 comprises a specific geometry configured to fit within a recess 80256 defined in the distal end of the distal nut 80255. The recess 80256 within the distal nut 80255 comprises a geometry that is complementary of the geometry of the proximal end 80251 of the drive rod 80250. In other words, once the clinician and/or the assistant has oriented the shaft 80220 in a manner that allows for the drive rod 80250 to fit within the recess on the distal nut 80255 of the handle 80210, the interchangeable shaft 80220 is successfully aligned with the universal handle 80210 such that there is little, if any, relative lateral movement between the distal nut 80255 and the drive rod 80250.

In various instances, the distal end 80211 of the drive nut 80255 and the proximal end 80223 of the drive rod 80250 comprise a plurality of magnetic elements 80260, 80265, 80270 configured to facilitate alignment of the shaft 80220 with the handle 80210 in addition to or in lieu of the mechanical alignment system described above. The system of magnetic elements 80260, 80265, 80270 allows for self-alignment of the shaft 80220 with the handle 80210. In various instances, the plurality of magnetic elements 80260, 80265, 80270 are permanent magnets. As seen in FIG. 75, the proximal end 80223 of the shaft 80220 comprises a plurality of magnetic elements 80260, 80265 that are oriented asymmetrically, although the magnetic elements 80260, 80265 may be arranged in any suitable manner. The magnetic elements 80260, 80265 are positioned with opposing poles facing outward from the proximal end 80223 of the shaft 80220. More specifically, the magnetic elements 80260 positioned on a first portion of the shaft 80220 are positioned with their positive poles facing outward from the proximal end 80223, while the magnetic elements 80265 positioned on a second, or opposite, portion of the shaft 80220 are positioned with their negative poles facing outward from the proximal end 80223. The distal end 80211 of the drive nut 80255 comprises a plurality of magnetic elements 80270 positioned with their negative poles facing outward from the distal end 80211 of the handle 80210. Such an asymmetric pattern of magnetic elements 80260, 80265 on the shaft 80220 can permit the shaft 80220 and the handle 80210 to be aligned at one or more predefined locations, as described in greater detail below. The use of magnetic elements 80260, 80265, 80270 eliminates the need for a spring mechanism to shift the handle 80210 and the shaft 80220 into predetermined positions.

Further to the above, if the clinician attempts to align the handle 80210 with the shaft 80220 such that the magnetic elements 80270 positioned on the handle 80210 are within the vicinity of the magnetic elements 80260 positioned on a first portion of the shaft 80220, the magnetic elements 80260, 80270 produce an attractive magnetic force, thereby pulling the modular components 80210, 80220 into alignment. However, if the clinician attempts to align the handle 80210 with the shaft 80220 such that the magnetic elements 80270 positioned on the handle 80210 are closer in vicinity to the magnetic elements 80265 positioned on a second portion of the shaft 80220, a repulsive magnetic force will push the modular components 80210, 80220 apart, thereby preventing an improper connection between the handle 80210 and the shaft 80220.

In certain instances, further to the above, only one stable position will exist between the modular components. In various instances, a plurality of magnetic elements are positioned so that their poles alternate in a repeating pattern along the outer circumferences of the distal end of the handle 80210 and the proximal end of the shaft 80220. Such a pattern can be created in order to provide for a plurality of stable alignment positions. The repeating pattern of magnetic elements allows for a series of stable alignments between the shaft and the handle, as an attractive magnetic force draws the modular components 80210, 80220 together at numerous positions. In various instances, the plurality of magnetic elements are oriented in a way to create a bi-stable magnetic network. Such a bi-stable network ensures that the modular components 80210, 80220 end in a stable alignment even when the modular components 80210, 80220 are initially misaligned. In other words, when the handle 80210 and the shaft 80220 are misaligned, the magnetic fields created by the plurality of magnetic elements interact with one another to initiate rotation out of the misaligned position and into the next closest stable alignment. Thus, the repulsive magnetic force experienced by misaligned modular components 80210, 80220 assists in transitioning the modular components 80210, 80220 into alignment. As the modular components 80210, 80220 are pushed apart by the repulsive magnetic force, they rotate into an attractive magnetic field thereby aligning the handle 80210 and the shaft 80220. In various instances, the repulsive magnetic force initiates rotation of the handle with respect to the shaft and vice versa. The pattern of the orientation of the magnetic elements can direct the modular components 80210, 80220 to rotate in a particular direction with respect to one another while also preventing rotation in the opposite direction. For example, in various instances, the magnetic elements are oriented in a pattern that allows for the shaft 80220 and the handle 80210 to achieve alignment by rotating with respect to one another only in a clockwise direction when a repulsive magnetic force is experienced. In other instances, the magnetic elements are oriented in a pattern that allows for the shaft 80220 and the handle 80210 to reach alignment by rotating with respect to one another only in a counterclockwise direction when a repulsive magnetic force is experienced. In various instances, the magnetic elements can impact the speed with which the modular components are brought into alignment. For example, magnetic elements can be arranged based on the strength of their magnetic fields in order to cause acceleration or deceleration into or out of alignment. While the plurality of magnetic elements 80260, 80265, 80270 are described above as being permanent magnets, in certain instances, the plurality of magnetic elements 80260, 80265, 80270 are electromagnets. In such instances, magnetic repulsive and attractive forces can be created by selectively energizing the plurality of magnetic elements 80260, 80265, 80270.

In various instances, the handle 80210 and the shaft 80220 comprise a dominant magnetic element that provides an initial attractive magnetic force, wherein the dominant magnetic elements are configured to pull the modular components 80210, 80220 closer together. After the modular components 80210, 80220 are drawn together by the dominant magnetic elements, the plurality of magnetic elements 80260, 80265, 80270 are configured to finely adjust the orientations of the handle 80210 and the shaft 80220.

Figure 77:
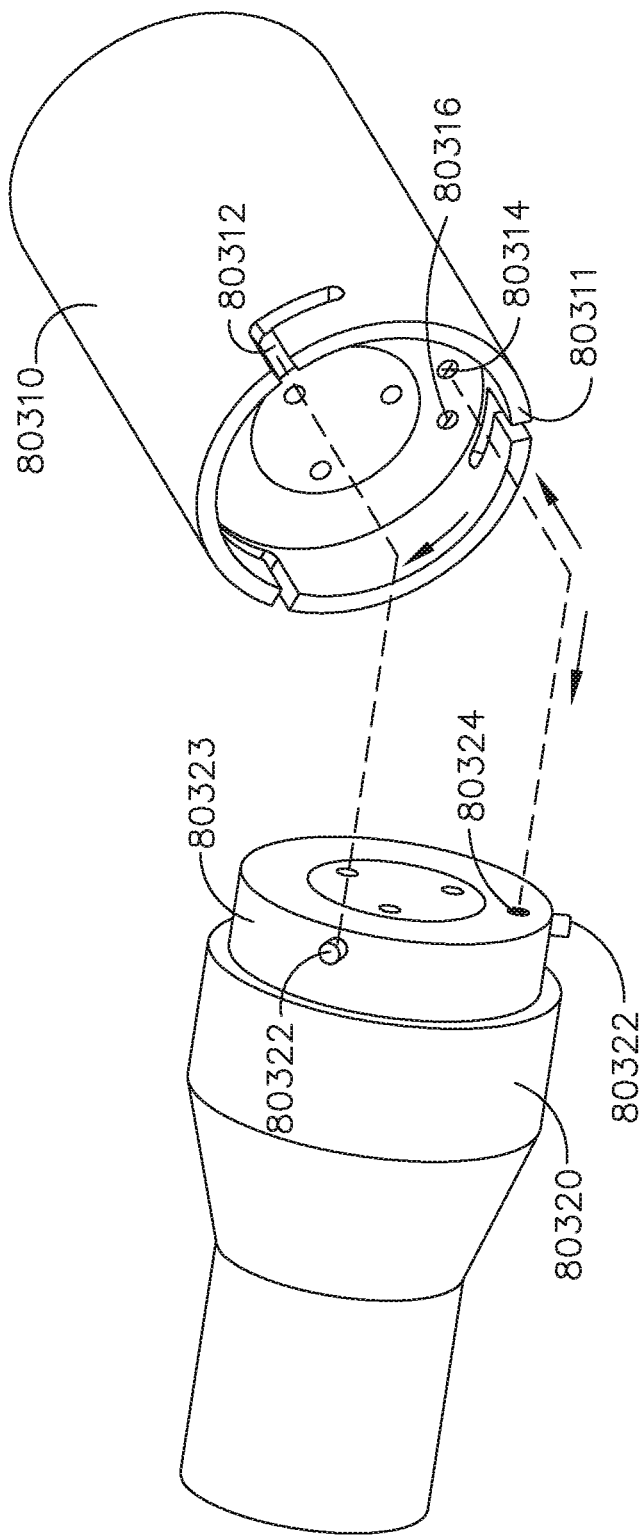
FIG. 77 is a perspective view of a system of magnetic elements arranged on the handle and the shaft of the surgical instrument of FIG. 73 in accordance with at least one aspect of the present disclosure.
Figure 78:
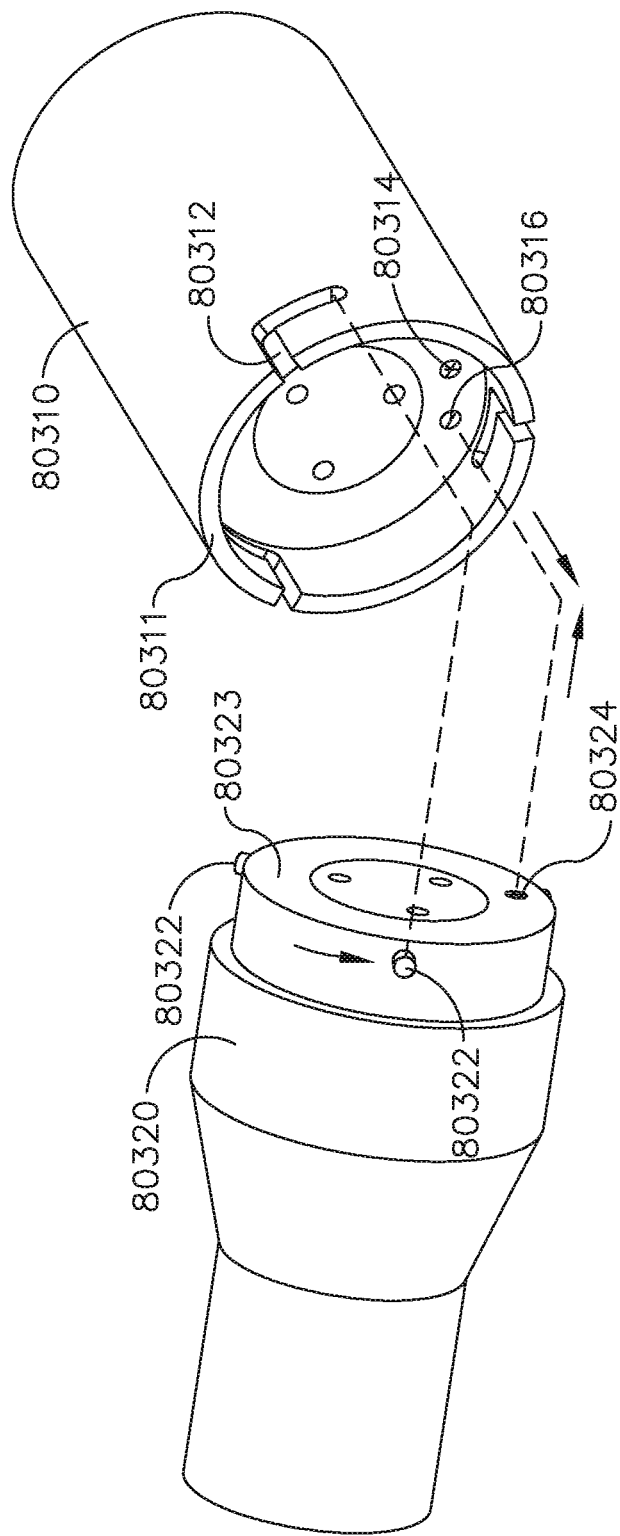
FIG. 78 is a perspective view of the system of magnetic elements of FIG. 77 aligning the shaft with the handle of the surgical instrument in accordance with at least one aspect of the present disclosure.

FIG. 77 depicts a universal handle 80310 prior to being aligned with and attached to a shaft 80320. The proximal end 80323 of the shaft 80320 comprises a pin 80322 configured to engage an L-shaped, or bayonet, slot 80312 cut into the distal end 80311 of the handle 80310. In various instances, a plurality of L-shaped slots 80312 may be cut around the circumference of the distal end 80311 to provide additional attachment support for additional pins 80322. The proximal end 80323 of the shaft 80320 further comprises a frame and a shaft magnetic element 80324 positioned in the frame with its positive pole facing outward. The distal end 80311 of the handle 80310 further comprises a first magnetic element 80314 and a second magnetic element 80316. The first magnetic element 80314 is oriented with its positive pole facing outwardly, and the second magnetic element 80316 is oriented with its negative pole facing outwardly. As the clinician begins aligning the pin 80322 of the shaft 80320 with its corresponding L-shaped slot 80312 in the handle 80310, the first magnetic element 80314 and the shaft magnetic element 80324 interact to produce a repulsive magnetic force. The clinician must overcome this force in order to engage the pin 80322 with the L-shaped slot 80312. Once the pin 80322 is within the L-shaped slot 80312 and/or once the shaft magnetic element 80324 is moved past a threshold distance with respect to the first magnetic element and the second magnetic element 80314 and 80324, the clinician can begin to manually rotate the modular components 80310, 80320 with respect to one another. In addition, as shown in FIG. 78, once the clinician has overcome the repulsive magnetic force to position the pin 80322 within the L-shaped slot 80312, the magnetic elements 80324, 80316 can react to create an attractive magnetic force once the shaft magnetic element 80324 is past the threshold. The attractive magnetic force results in rotation of the shaft 80320 with respect to the handle 80310 and full engagement of the pin 80322 into the L-shaped slot 80312. In such instances, the interaction between the magnetic fields of the shaft magnetic element 80324 and the second magnetic element 80316 on the handle 80310 is strong enough to pull and/or hold the modular components 80310, 80320 together. In various instances, such interaction results in an attractive magnetic force between the shaft magnetic element 80324 and the second magnetic element 80316, resulting in alignment of the modular components 80310, 80320 and full engagement of the pin 80322 within the L-shaped slot 80312. While the orientations of the magnetic elements are specifically described, it is envisioned that the magnetic elements can be oriented in any suitable manner. While the plurality of magnetic elements 80314, 80316, 80324 are described above as being permanent magnets, in certain instances, the plurality of magnetic elements 80314, 80316, 80324 are electromagnets. In such instances, magnetic repulsive and attractive forces can be created by selectively energizing the plurality of magnetic elements 80314, 80316, 80324.

The magnetic elements described above can comprise electromagnets, permanent magnets, or a combination thereof. In instances, such as those described above, a system of permanent magnetic elements may align the shaft and the handle in a plurality of positions. In such instances, an electromagnet can be added to the system of permanent magnetic elements. When activated, the electromagnet is configured to exert a stronger magnetic field than the magnetic fields within the system of permanent magnetic elements. In other words, an electromagnet may be incorporated in order to interrupt, thwart, and/or change the cooperation between the system of permanent magnets. Such an interruption results in the ability to exert selective control over the alignment of the modular components of the surgical instrument. For example, when a system of magnetic elements, such as the magnetic elements 80260, 80265, 82070 in FIG. 76, have drawn the shaft 80220 and the handle 80210 together in a suitably aligned position, a clinician may selectively activate an electromagnet to produce a magnetic field strong enough to overcome the attractive magnetic forces of the permanent magnets and repel the shaft away from the handle. In various instances, activation of the electromagnet repels the handle away from the shaft to release or unlock the shaft from the handle. In various instances, the activation of the electromagnet is configured to not only disrupt the attraction created by the permanent magnets but also to decouple the modular components 80210, 80220.

A modular surgical instrument, such as the surgical instrument 80000 shown in FIG. 73, for example, comprises a plurality of components configured to communicate with one another in order to perform an intended function of the surgical instrument. The communication pathways between the components of the modular surgical instrument are described in detail above. While such communication pathways can be wireless in nature, wired connections are also suitable. In various instances, the end effector and/or shaft of the surgical instrument are configured to be inserted into a patient through a trocar, or cannula, and can have any suitable diameter, such as approximately 5 mm, 8 mm, and/or 12 mm, for example. In addition to size constraints, various modular surgical instruments, such as, for example, a clip applier, comprise end effectors and/or shafts that are configured to rotate and/or articulate, for example. Thus, any wired communication pathway must be compact and have flexibility in order to maintain functionality as the end effector and/or shaft is rotated and/or articulated. In an effort to reduce the size of operational elements within a shaft and/or end effector of a surgical instrument, various micro electro-mechanical functional elements may be utilized. Incorporating micro-electronics such as, for example, a piezo inchworm actuator or a squiggle motor into a surgical instrument assists in reducing the space needed for operational elements, as a squiggle motor, for example, is configured to deliver linear movement without gears or cams.

In various instances, flexibility is built into the wired communication pathway(s) by mounting various electrical traces on a flexible substrate. In various instances, the electrical traces are supported on the flexible substrate in any suitable manner. FIG. 79 depicts a flex circuit 80400 for use in a modular surgical instrument, such as the surgical instrument 1000, for example. The flex circuit 80400 is configured to extend within a housing of a shaft, such as the shaft 80020 of FIG. 73. A distal end 80401 of the flex circuit 80400 is configured to be electrically coupled with conductive electrical traces within an end effector. In at least one instance, the electrical traces are comprised of copper and/or silver, for example. The distal end 80401 is wrapped into a first ring 80402, and the electrical traces 80405 extend around the first ring 80402. A proximal end 80403 of the flex circuit 80400 is configured to be electrically coupled with electrical traces within a handle. The proximal end 80403 is wrapped into a second ring 80404, and the electrical traces 80405 extend around the second ring 80404.

Figure 79A:
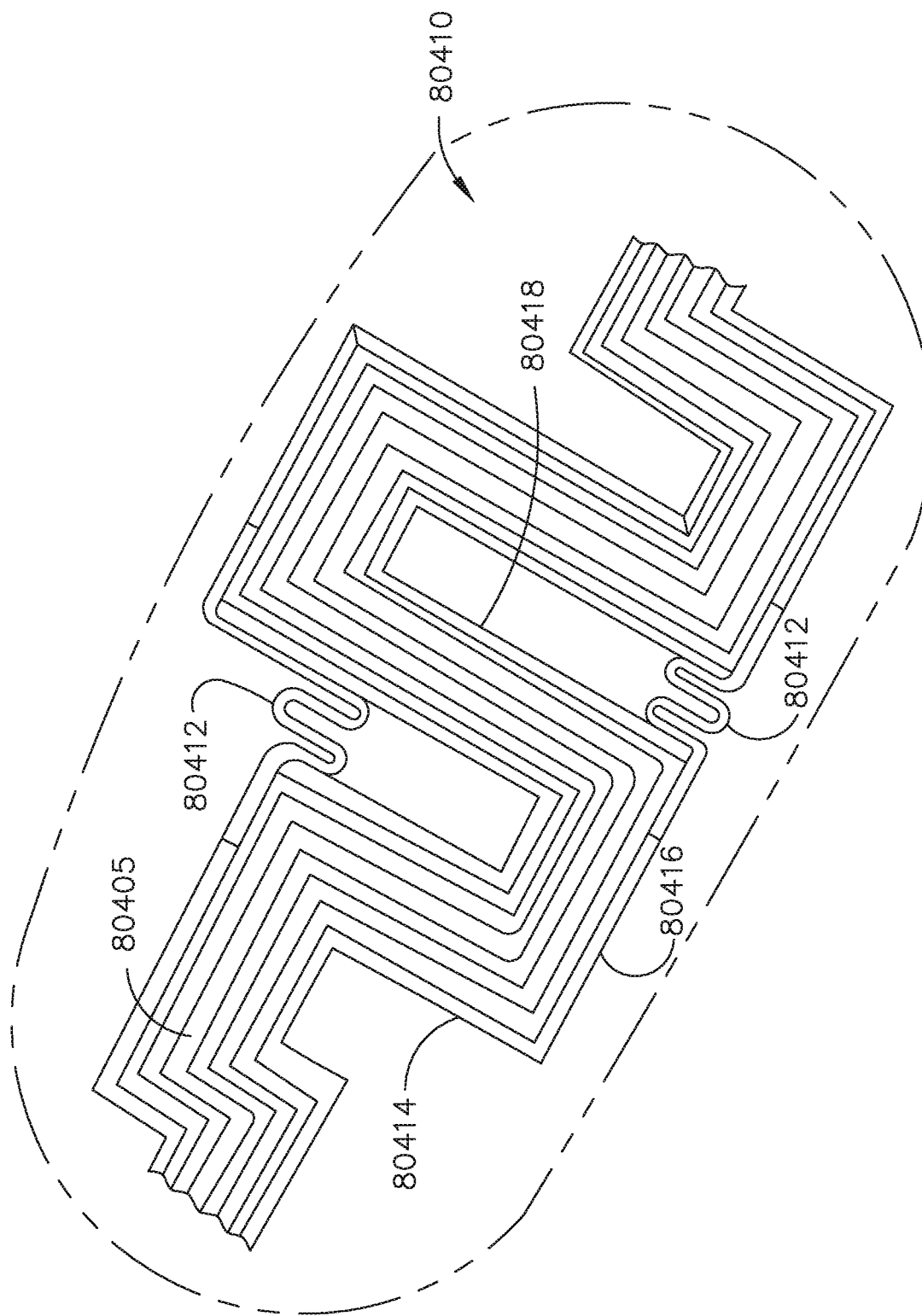
FIG. 79A is a detail perspective view of a primary strain relief portion of the flex circuit of FIG. 79 in accordance with at least one aspect of the present disclosure.

While supporting various electrical traces on the flexible substrate provides for flexibility, additional features may be added to, among other things, increase the longevity of and/or protect the integrity of the flex circuit 80400. As depicted in FIGS. 79 and 79A, a primary strain relief region 80410 is configured to be positioned proximally to an articulation joint. The primary strain relief region 80410 of the flex circuit 80400 experiences the most displacement and/or twisting in response to articulation of the surgical instrument. In an effort to, for example, relieve the strain on the flex circuit 80400 while the surgical instrument is articulated and/or assist the portion of the flex circuit 80400 within the primary strain relief region 80410 to return to its original orientation after the surgical instrument is unarticulated, one or more biasing and/or resilient members 80412 are present for resiliency and/or flexibility. The one or more biasing members 80412 are configured to transition between a flexed state and an un-flexed state, as the surgical instrument is articulated and/or rotated. In various instances, the biasing members 80412 comprise springs. The biasing members 80412 are incorporated into the substrate of the flex circuit 80400 in an effort to, for example, accommodate for motions of surrounding parts. The portion of the flex circuit 80400 within the primary strain relief region 80410 comprises a pattern comprising a first leg 80414, a base 80416, and a second leg 80418. The base 80416 extends between the first leg 80414 and the second leg 80418. The biasing member 80412 extends between and connects the first leg 80414 and the second leg 80418. The biasing member 80412, among other things, permits the first leg 80414 to be deflected relative to the second leg 80418 and then resiliently returns to its unflexed state. The biasing member 80412 is configured to flex into the flexed state when an end effector is articulated, and the biasing member 80412 is configured to resiliently return to the un-flexed state when the end effector is no longer articulated.

Figure 79B:
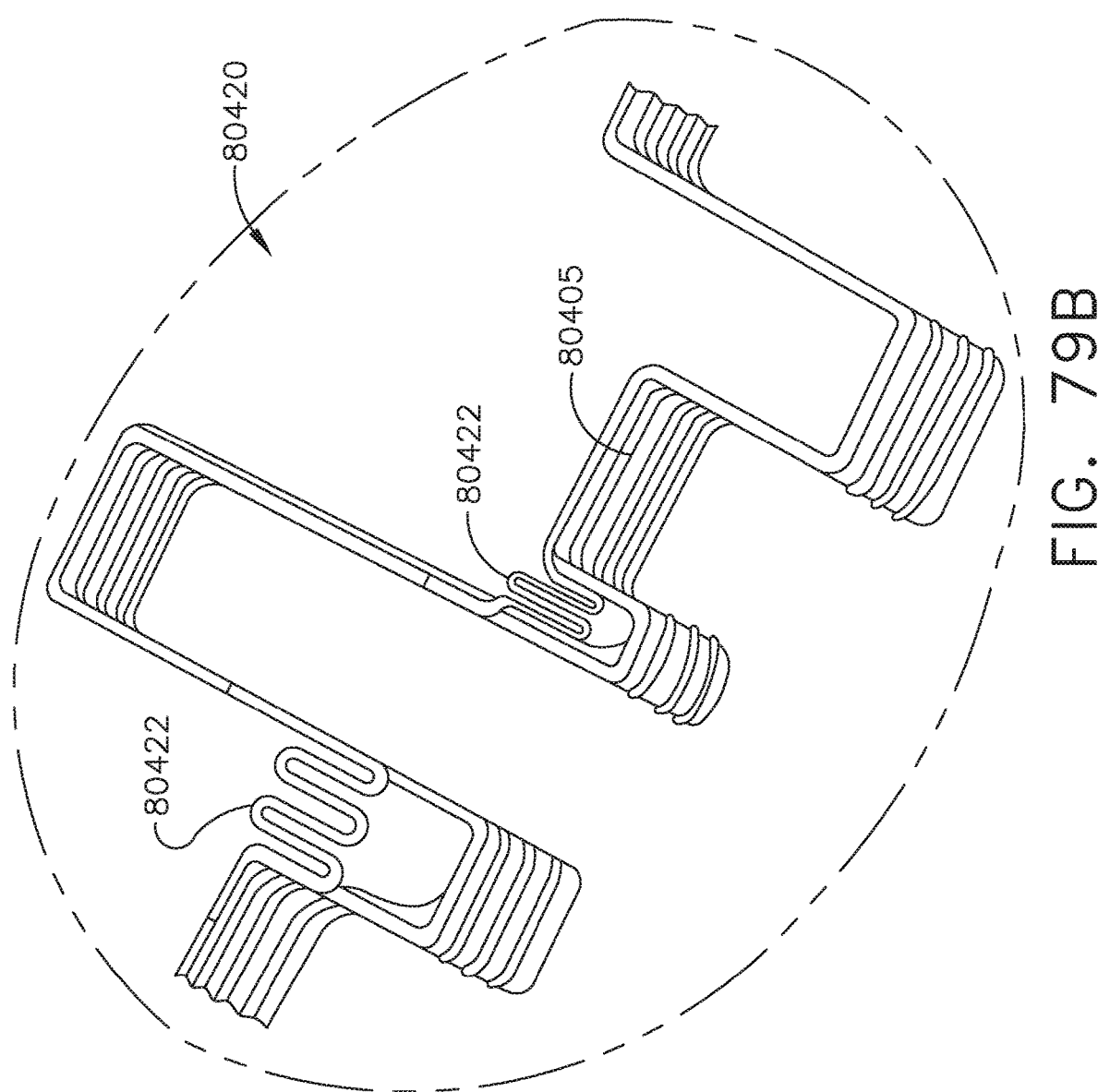
FIG. 79B is a detail perspective view of a secondary strain relief portion of the flex circuit of FIG. 79 in accordance with at least one aspect of the present disclosure.

As seen in FIGS. 79 and 79B, the flex circuit 80400 is manufactured with a secondary strain relief region 80420 whose conductive elements 80405 are separate and not interconnected. Such orientation of the conductive elements 80405 allows for the flex circuit 80400 to be folded. The non-fatiguing and flexible portions of the flex circuit 80400 are positioned perpendicular to the flex circuit 80400 within the primary strain relief region 80410. The secondary strain relief region 80420 comprises one or more biasing members 80422, similar to the biasing members 80412 described in greater detail above. The presence of biasing members 80412 within the primary strain relief region 80410 and the biasing members 80422 within the secondary strain relief portion 80320 allows the flex circuit 80400 to have a stretchable portion in at least two separate planes relative to a longitudinal axis of the shaft, such as the shaft 80020 of FIG. 73, for example. The presence of the primary strain relief portion 80410 in a first plane and a secondary strain relief portion 80320 in a second plane allows for communication between an end effector, a shaft assembly, and a handle of a surgical instrument configured to articulate the end effector, rotate the end effector, and rotate the shaft assembly. In another instance, the flex circuit 80400 can be manufactured flat and subsequently twisted in a portion, such as the primary strain relief region 80410, which correlates to the articulating or actuating portion of the surgical instrument. Such a design may mitigate the need for stress relief of the flex circuit 80400 in general.

Figure 79C:
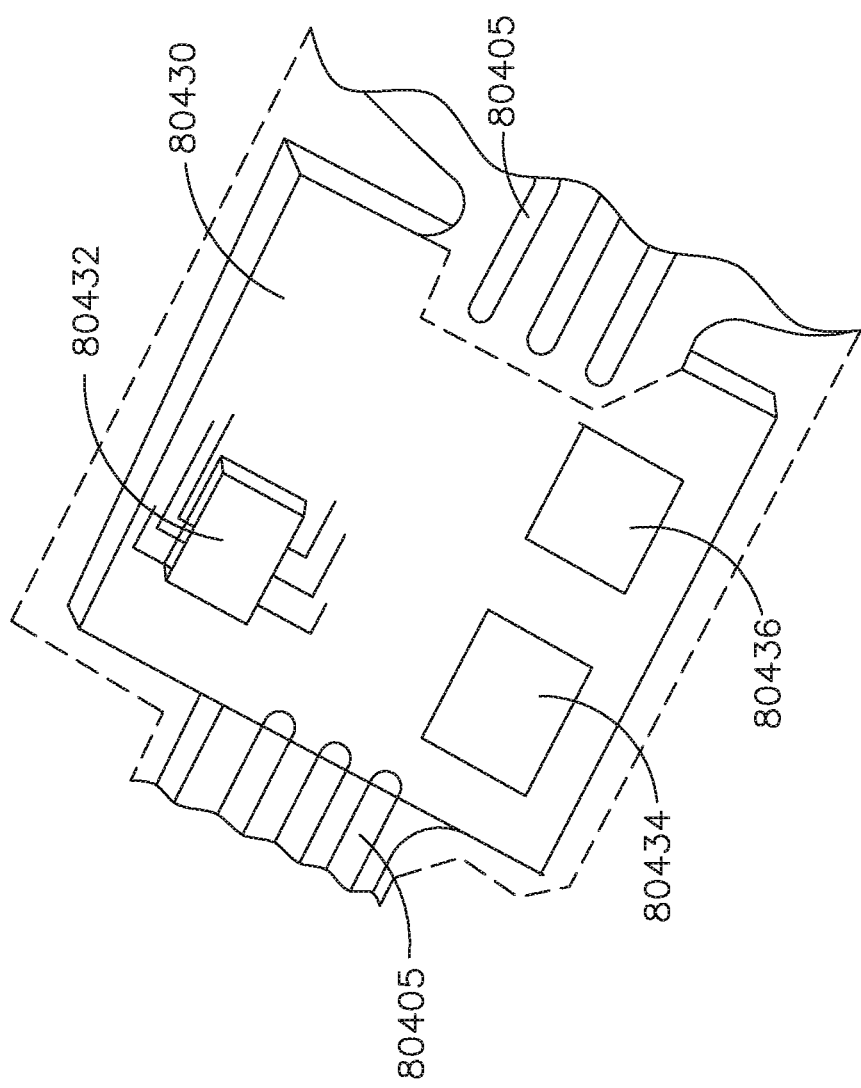
FIG. 79C is a detail perspective view of control circuit components incorporated into a flexible plastic of the flex circuit of FIG. 79 in accordance with at least one aspect of the present disclosure.

FIG. 79C depicts a portion of the flex circuit 80400 of FIG. 79 characterized by a printed circuit board (PCB) integrally formed with the flexible substrate 80430 of the flex circuit 80400. As shown in FIG. 79C, flexible plastic is over molded onto the conductive elements 80405 and various control circuit components 80432, 80434, 80436 are integrally formed with the flexible substrate 80430 of the flex circuit 80400.

Figure 80:
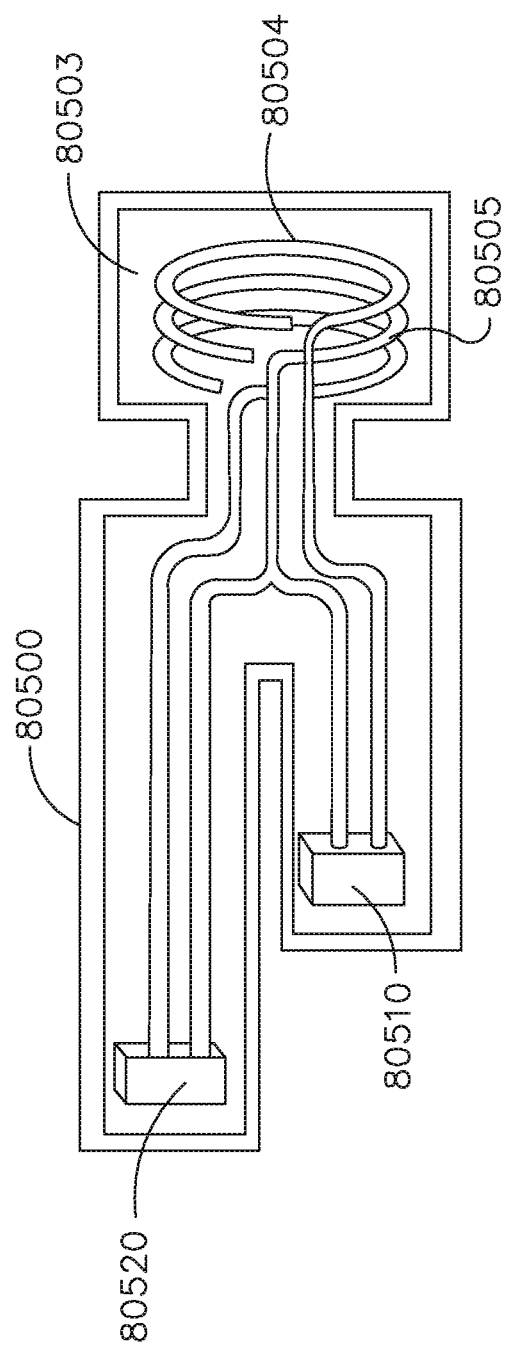
FIG. 80 is a perspective view of a flex circuit for use in combination with the flex circuit of FIG. 79 in accordance with at least one aspect of the present disclosure.

FIG. 80 depicts an end effector flex circuit 80500 configured to extend within an end effector. The end effector flex circuit 80500 is configured to be used with a shaft flex circuit, such as, for example, the flex circuit 80400 shown in FIGS. 79-79C. The end effector flex circuit 80500 comprises electrical traces 80505 supported on a flexible substrate. A distal end 80503 of the end effector flex circuit 80500 is wrapped into a ring 80504. The electrical traces 80505 extend around the ring 80504. As shown in FIGS. 81A and 81B, the ring 80504 is configured to be electrically coupled with the shaft flex circuit, for example, via the first ring 80402 on the distal end 80401 of the flex circuit 80400. One or both of the flex circuits 80400 and 80500 comprise biasing members to maintain electrical contact between the traces at the interface between the flex circuits 80400, 80500. In various instances, the end effector flex circuit 80500 comprises one or more sensors, such as, for example, a clip feed sensor 80510 and/or a clip cam form sensor 80520. Such sensors can detect a parameter of the end effector and communicate the detected parameter to the control circuit components 80432, 80434, 80436 on the shaft flex circuit 80400. In various instances, the control circuit is positioned within a handle of the surgical instrument.

Figure 82:
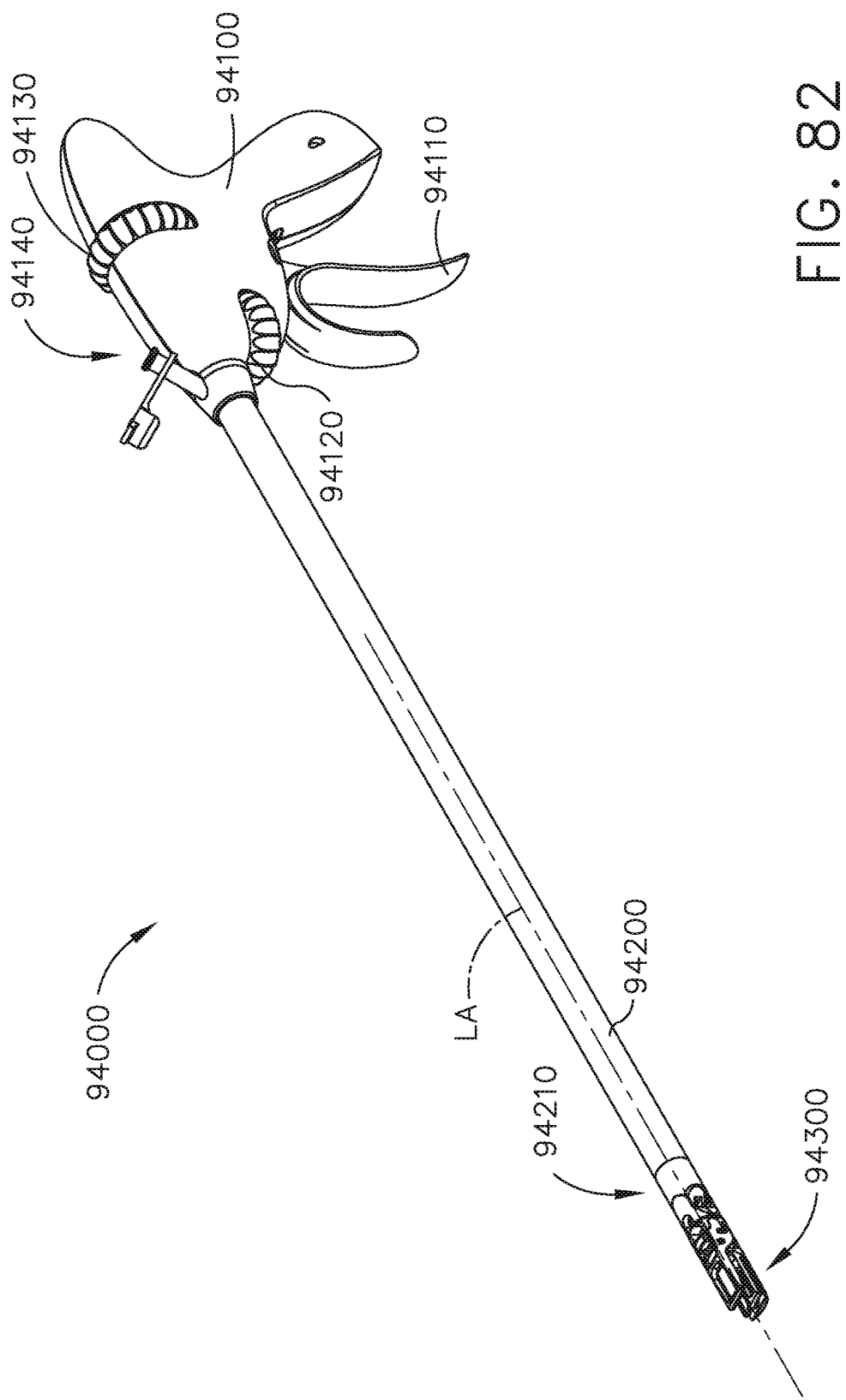
FIG. 82 is a perspective view of a surgical suturing instrument comprising a handle, a shaft, and an end effector.

FIG. 82 depicts a surgical suturing instrument 94000 configured to suture the tissue of a patient. The surgical suturing instrument 94000 comprises a handle 94100, a shaft 94200 extending distally from the handle 94100, and an end effector 94300 attached to the shaft 94200 by way of an articulation joint 94210. The handle 94100 comprises a firing trigger 94110 configured to actuate a firing drive of the surgical suturing instrument 94000, a first rotational actuator 94120 configured to articulate the end effector 94300 about an articulation axis AA defined by the articulation joint 94210, and a second rotational actuator 94130 configured to rotate the end effector 94300 about a longitudinal axis LA defined by the end effector 94300. The surgical suturing instrument 94000 further comprises a flush port 94140. Examples of surgical suturing devices, systems, and methods are disclosed in U.S. patent application Ser. No. 13/832,786, now U.S. Pat. No. 9,398,905, entitled CIRCULAR NEEDLE APPLIER WITH OFFSET NEEDLE AND CARRIER TRACKS; U.S. patent application Ser. No. 14/721,244, now U.S. Patent Application Publication No. 2016/0345958, entitled SURGICAL NEEDLE WITH RECESSED FEATURES; and U.S. patent application Ser. No. 14/740,724, now U.S. Patent Application Publication No. 2016/0367243, entitled SUTURING INSTRUMENT WITH MOTORIZED NEEDLE DRIVE, which are incorporated by reference in their entireties herein.

In various embodiments, a surgical suturing instrument can accommodate different needle and suture sizes for different suturing procedures. Such an instrument can comprise a means for detecting the size of the needle and/or suture loaded into the instrument. This information can be communicated to the instrument so that the instrument can adjust the control program accordingly. Larger diameter needles may be rotated angularly at a slower rate than smaller diameter needles. Needles with different lengths may also be used with a single instrument. In such instances, a surgical instrument can comprise means for detecting the length of the needle. This information can be communicated to a surgical instrument to modify the needle driver's path, for example. A longer needle may require a smaller stroke path from the needle driver to sufficiently advance the longer needle through its firing stroke as opposed to a smaller needle which may require a longer stroke path from the needle driver to sufficiently advance the shorter needle through its firing stroke in the same needle track.

Figure 83:
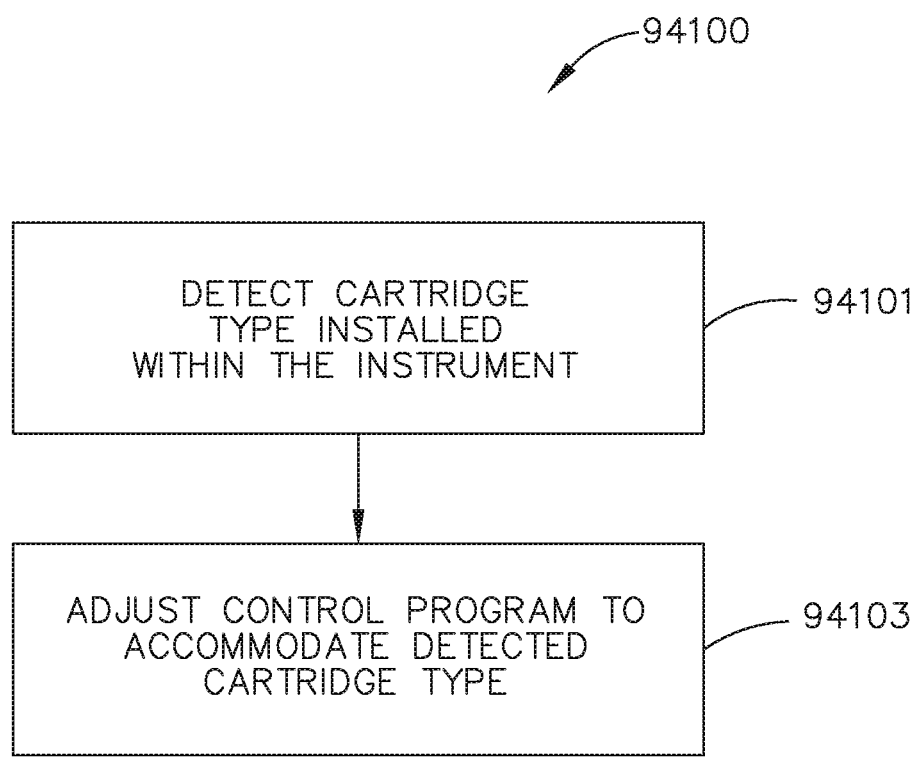
FIG. 83 is a logic flow diagram of a process depicting a control program for controlling a surgical instrument.

FIG. 83 depicts a logic diagram of a process 94100 depicting a control program for controlling a surgical instrument. The process 94100 comprises detecting 94101 the type of suturing cartridge installed within the surgical suturing instrument. In various instances, different suture cartridges may have different suture lengths, needle lengths, needle diameters, and/or suture materials, for example. The type of suture cartridge and/or its characteristics can be communicated to a control circuit by an identification chip positioned within the cartridge such that, when a suture cartridge is installed within a surgical instrument, the control circuit can identify what type of cartridge has been installed and assess the characteristics of the suture cartridge. In order to accommodate different cartridge types, a control circuit may adjust the control motions that will be applied to the suture cartridge. For example, firing speeds may differ for different sized needles. Another example may include adjusting the range of angular needle rotation based on different needle lengths, or sizes. To accommodate such differences, the process 94100 implemented by a process, for example, comprises adjusting 94103 a motor control program of the instrument based on what type of suture cartridge is installed.

In at least one embodiment, a surgical instrument is configured to apply a suture to the tissue of a patient which comprises a lockout system. The lockout system comprises a locked configuration and an unlocked configuration. The surgical instrument further comprises a control circuit and is configured to identify if a cartridge is installed or not installed within an end effector of the surgical instrument. The control circuit is configured to place the lockout system in the locked condition when a cartridge is not installed in the end effector and place the lockout system in the unlocked condition when a cartridge is installed in the end effector. Such a lockout system can include an electrical sensing circuit of which a cartridge can complete upon installation indicating that a cartridge has been installed. In at least one instance, the actuator comprises an electric motor and the lockout system can prevent power from being supplied to the electric motor. In at least one instance, the actuator comprises a mechanical trigger, and the lockout system blocks the mechanical trigger from being pulled to actuate the suture needle. When the lockout system is in the locked configuration, the lockout system prevents an actuator from being actuated. When the lockout system is in the unlocked configuration, the lockout system permits the actuator to deploy the suture positioned within the cartridge. In one embodiment, the control circuit provides haptic feedback to a user of the surgical instrument when the electrical sensing circuit places the surgical instrument in the locked configuration. In one embodiment, the control circuit prevents the actuation of an electric motor configured to actuate the actuator when the electrical sensing circuit determines that the lockout system is in the locked configuration. In one embodiment, the lockout system is in the unlocked configuration when a cartridge is positioned in the end effector and the cartridge has not been completely expended.

Figure 84:
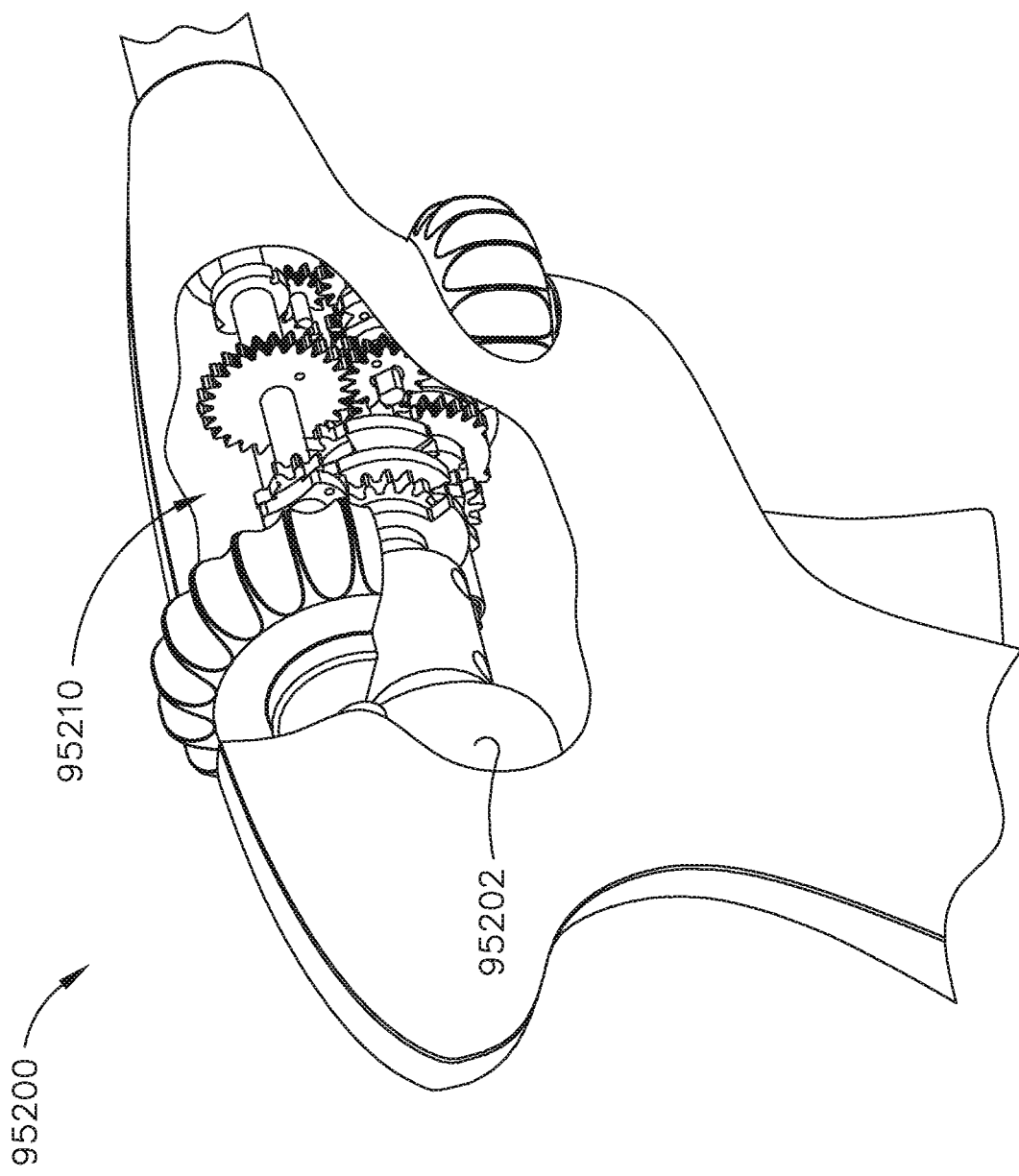
FIG. 84 is a perspective view of surgical suturing instrument handle comprising a motor.
Figure 85:
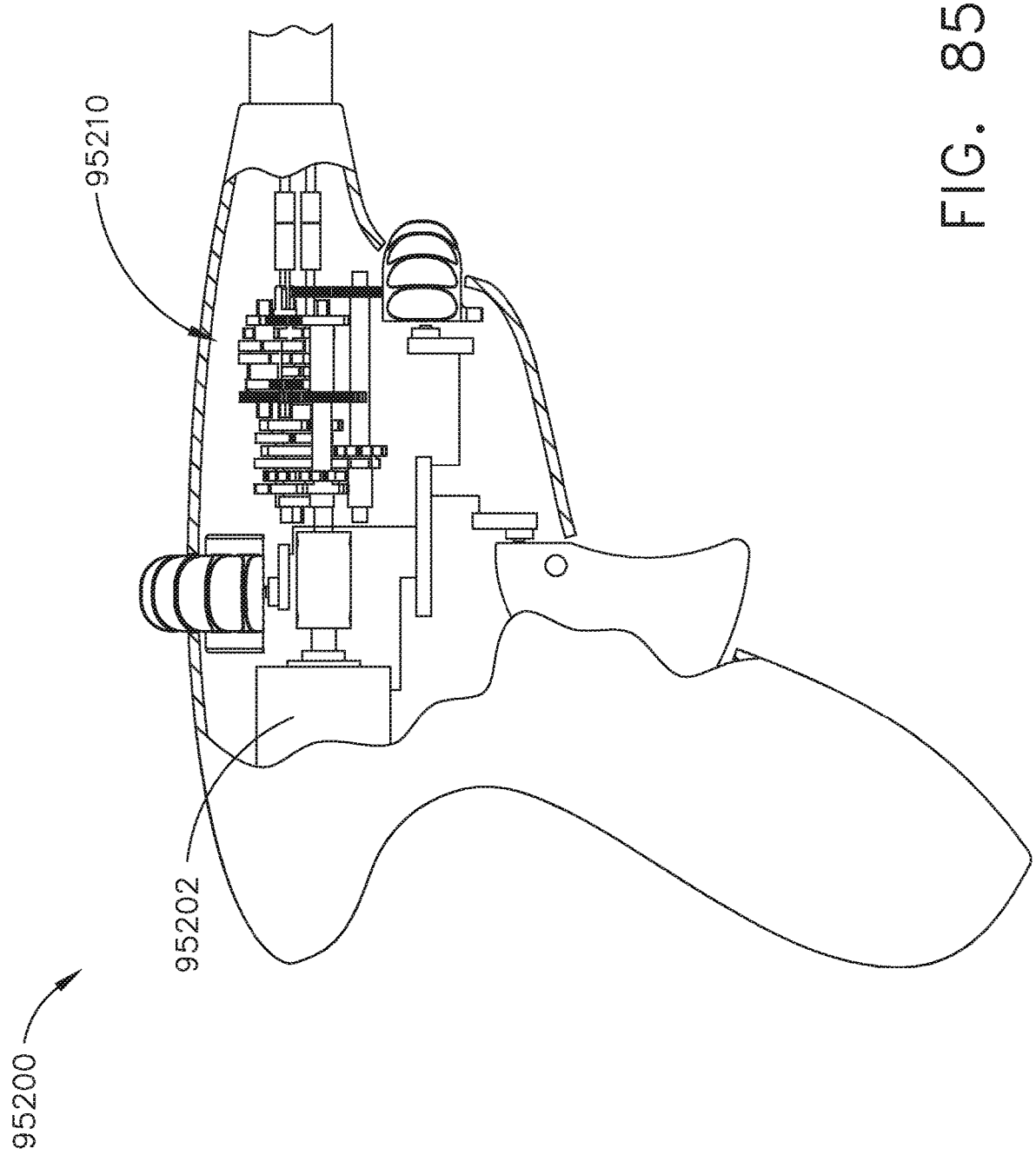
FIG. 85 is a partial cross-sectional view of the surgical suturing instrument handle of FIG. 82.

FIGS. 84 and 85 depict a handle assembly 95200 that is operable for use a surgical suturing instrument. The handle assembly 95200 is connected to a proximal end of a shaft. The handle assembly 95200 includes a motor 95202 and a transmission assembly 95210. The motor 95202 is configured to actuate a needle of a surgical suturing end effector by way of a needle driver, articulate the end effector, and rotate the end effector by way of the transmission assembly 95210. The transmission assembly 95210 is shifted between three states by a double acting solenoid, for example, so as to allow the motor 95202 to be used to actuate a needle of a surgical suturing end effector, articulate the end effector, and/or rotate the end effector. In at least one embodiment, the handle assembly 95200 could take the form of a robotic interface or a housing comprising gears, pulleys, and/or servomechanisms, for example. Such an arrangement could be used with a robotic surgical system.

Figure 86:
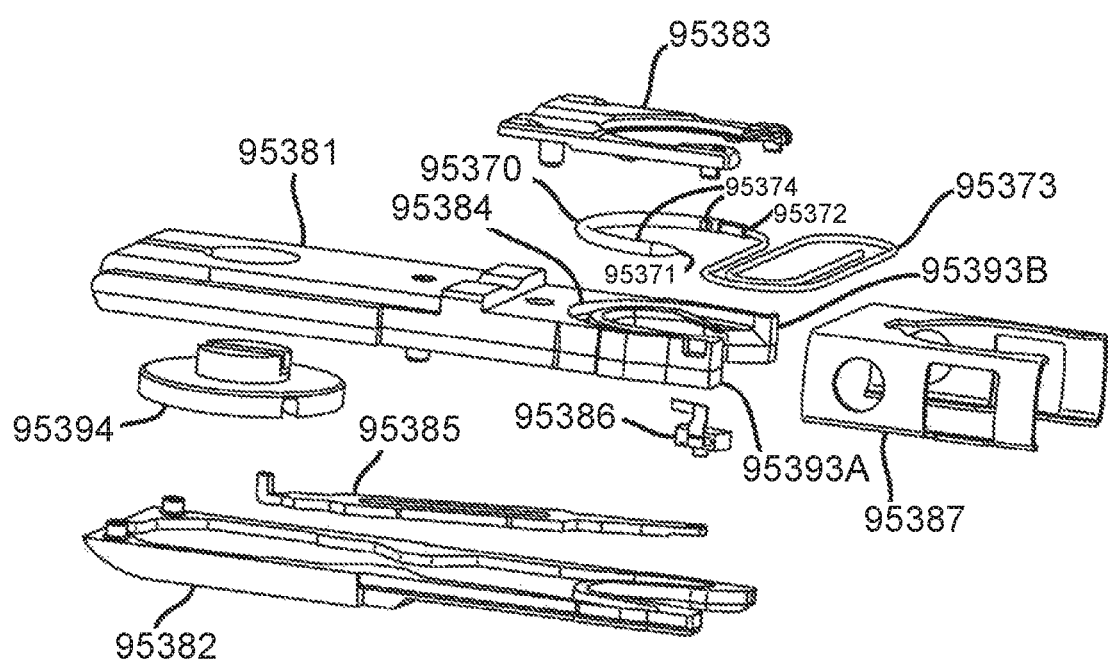
FIG. 86 is an exploded view of a suturing cartridge for use with a surgical suturing system.

FIG. 86 depicts a suturing cartridge 93590 comprising a lower body 93581, an upper body 93582, and a needle cover 93583. The cartridge 93590 further comprises a drive system comprising a needle driver 93586, a rotary input 93594, and a link 93585 connecting the needle driver 93586 and the rotary input 93594. The needle driver 93586, rotary input 93594, and link 93585 are captured between the lower body 93581 and the upper body 93582. The needle driver 93586, the link 93585, and the rotary input 93594 are configured to be actuated to drive a needle 93570 through a needle firing stroke by way of a motor-driven system, a manually-driven handheld system, and/or a robotic system, for example. The lower and upper bodies 93581, 93582 are attached to one another using any suitable technique, such as, for example, welds, pins, adhesives, and/or the like to form the cartridge body. The needle 93570 comprises a leading end 93571 configured to puncture tissue, a trailing end 93572, and a length of suture 93573 extending from and attached to the trailing end 93572. The needle 93570 is configured to rotate in a circular path defined by a needle track 93584. The needle track 93584 is defined in the cartridge body. The needle 93570 is configured to exit one of a first arm 95393A and a second arm 95393B of the cartridge body and enter the other of the first arm 95393A and the second arm 95393B during a needle firing stroke. Recessed features 93574 are provided to so that the needle driver 93586 can engage and drive the needle 93570 through the needle firing stroke in a ratchet-like motion. The needle 93570 is positioned between the needle track 93584 and the needle cover 93583. The suturing cartridge 953590 further comprises a cage 93587 that is configured to slide over the cartridge body to attach the needle cover 93583 to the lower body 93581.

The devices, systems, and methods disclosed in the Subject Applications can be used with the devices, systems, and methods disclosed in U.S. patent application Ser. No. 13/832,786, now U.S. Pat. No. 9,398,905, entitled CIRCULAR NEEDLE APPLIER WITH OFFSET NEEDLE AND CARRIER TRACKS; U.S. patent application Ser. No. 14/721,244, now U.S. Patent Application Publication No. 2016/0345958, entitled SURGICAL NEEDLE WITH RECESSED FEATURES; and U.S. patent application Ser. No. 14/740,724, now U.S. Patent Application Publication No. 2016/0367243, entitled SUTURING INSTRUMENT WITH MOTORIZED NEEDLE DRIVE, which are incorporated by reference in their entireties herein.

The devices, systems, and methods disclosed in the Subject Applications can be used with the devices, systems, and methods disclosed in U.S. Provisional Patent Application No. 62/659,900, entitled METHOD OF HUB COMMUNICATION, filed on Apr. 19, 2018, U.S. Provisional Patent Application No. 62/611,341, entitled INTERACTIVE SURGICAL PLATFORM, filed on Dec. 28, 2017, U.S. Provisional Patent Application No. 62/611,340, entitled CLOUD-BASED MEDICAL ANALYTICS, filed on Dec. 28, 2017, and U.S. Provisional Patent Application No. 62/611,339, entitled ROBOT ASSISTED SURGICAL PLATFORM, filed on Dec. 28, 2017, which are incorporated in their entireties herein. The devices, systems, and methods disclosed in the Subject Applications can also be used with the devices, systems, and methods disclosed in U.S. patent application Ser. No. 15/908,021, entitled SURGICAL INSTRUMENT WITH REMOTE RELEASE, filed on Feb. 28, 2018, U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT, filed on Feb. 28, 2018, U.S. patent application Ser. No. 15/908,040, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,057, entitled SURGICAL INSTRUMENT WITH ROTARY DRIVE SELECTIVELY ACTUATING MULTIPLE END EFFECTOR FUNCTIONS, filed on Feb. 28, 2018, U.S. patent application Ser. No. 15/908,058, entitled SURGICAL INSTRUMENT WITH MODULAR POWER SOURCES, filed on Feb. 28, 2018, and U.S. patent application Ser. No. 15/908,143, entitled SURGICAL INSTRUMENT WITH SENSOR AND/OR CONTROL SYSTEMS, filed on Feb. 28, 2018, which are incorporated in their entireties herein. The devices, systems, and methods disclosed in the Subject Applications can also be used with the devices, systems, and methods disclosed in U.S. patent application Ser. No. 14/226,133, now U.S. Patent Application Publication No. 2015/0272557, entitled MODULAR SURGICAL INSTRUMENT SYSTEM, filed on Mar. 26, 2014, which is incorporated in its entirety herein.

EXAMPLES

Example 1

A modular surgical instrument is disclosed. The modular surgical instrument comprises a handle, an elongate shaft extending distally from the handle, an end effector extending distally from the elongate shaft, and a power source. The elongate shaft comprises a processor and a memory coupled to the processor. The memory stores instructions which, when executed, cause the processor to initiate a desired function. The power source comprises a battery and a display.

Example 2

The modular surgical instrument of Example 1, wherein the power source is configured to be replaceably attached to the handle.

Example 3

The modular surgical instrument of any one of Examples 1 and 2, wherein the handle comprises a drive motor operable by a control system in the elongate shaft.

Example 4

A surgical instrument is disclosed. The surgical instrument comprises a handle comprising a motor, a battery pack replaceably attached to the handle, an elongate shaft extending distally from the handle, and an end effector extending distally from the elongate shaft. The battery pack comprises a power source couplable to the motor and a display. The elongate shaft comprises a processor and a memory coupled to the processor. The memory comprises a control program which, when executed, causes the processor to initiate a desired function. The end effector comprises a sensing circuit configured to detect a condition of the end effector, and the sensing circuit is in signal communication with the processor.

Example 5

A surgical instrument is disclosed. The surgical instrument comprises a handle, a shaft extending distally from the handle, an end effector extending distally from the shaft, an articulation joint, and a flex circuit extending within the shaft. The end effector is configured to be articulated about the articulation joint. The flex circuit comprises a first strain relief region and a second strain relief region. The first strain relief region permits expansion of the flex circuit, and the second strain relief region permits expansion of the flex circuit. The second strain relief region is substantially perpendicular to the first strain relief region.

Example 6

The surgical instrument of Example 5, wherein the shaft comprises a diameter that is less than 10 millimeters.

Example 7

The surgical instrument of any one of Examples 5 and 6, wherein the flex circuit further comprises a flexible substrate and a circuit board, wherein the circuit board is integrally formed with the flexible substrate.

Example 8

The surgical instrument of any one of Examples 5 and 6, wherein the flex circuit further comprises a flexible substrate, electrical traces supported by the flexible substrate, and a first end wrapped into a first ring, wherein the electrical traces extend around the first ring.

Example 9

The surgical instrument of Example 8, wherein the flex circuit further comprises a second end wrapped into a second ring, wherein the electrical traces extend around the second ring.

Example 10

The surgical instrument of any one of Examples 5-9, wherein the flex circuit further comprises a first leg, a second leg, a base extending between the first leg and the second leg, and a biasing member extending between the first leg and the second leg.

Example 11

The surgical instrument of Example 10, wherein the biasing member is configured to transition between a flexed state and an un-flexed state, wherein the biasing member is configured to flex into the flexed state when the end effector is articulated.

Example 12

The surgical instrument of any one of Examples 10 and 11, wherein the biasing member comprises a spring.

Example 13

A surgical instrument is disclosed. The surgical instrument comprises a housing, a shaft extending distally from the housing, and an end effector extending distally from the shaft. The surgical instrument further comprises an articulation joint, wherein the end effector is configured to articulate about the articulation joint and a flex circuit extending within the shaft. The flex circuit comprises a flexible substrate, electrical traces, a first strain relief region, wherein the first strain relief region permits expansion of the flex circuit, and a second strain relief region, wherein the second strain relief region permits expansion of the flex circuit, and wherein the second strain relief region is substantially perpendicular to the first strain relief region.

Example 14

The surgical instrument of Example 13, wherein the flex circuit further comprises a circuit board integrally formed with the flexible substrate.

Example 15

The surgical instrument of any one of Examples 13 and 14, wherein the shaft comprises a diameter that is less than 10 millimeters.

Example 16

The surgical instrument of any one of Examples 13-15, wherein the flex circuit further comprises a first leg, a second leg, a base extending between the first leg and the second leg, and a biasing member extending between the first leg and the second leg.

Example 17

The surgical instrument of Example 16, wherein the biasing member is configured to transition between a flexed state and an un-flexed state, wherein the biasing member is configured to flex into the flexed state when the end effector is articulated.

Example 18

The surgical instrument of any one of Examples 16 and 17, wherein the biasing member comprises a spring.

Example 19

A surgical instrument is disclosed. The surgical instrument comprises a handle comprising a distal end and a shaft comprising a proximal end. The distal end of the handle comprises an interface surface and a first set of magnetic elements. The proximal end of the shaft comprises a handle interface surface, a second set of magnetic elements, and a third set of magnetic elements, wherein the shaft interface surface is configured to engage the shaft at the handle interface surface, wherein an attractive magnetic force is configured to pull the handle towards the shaft when the first set of magnetic elements interact with the second magnetic elements. A repulsive magnetic force is configured to repel the handle from the shaft when the first set of magnetic elements interacts with the third set of magnetic elements.

Example 20

The surgical instrument of Example 19, wherein the first set of magnetic elements, the second set of magnetic elements, and the third set of magnetic elements comprise permanent magnets.

Example 21

The surgical instrument of Example 19, wherein the first set of magnetic elements, the second set of magnetic elements, and the third set of magnetic elements comprise electromagnets.

Example 22

The surgical instrument of Example 19, wherein the first set of magnetic elements, the second set of magnetic elements, and the third set of magnetic elements comprise permanent magnets and electromagnets.

Example 23

A surgical instrument is disclosed. The surgical instrument comprises a handle, a shaft extending distally from the handle, an end effector extending distally from the shaft, and a flex circuit. The flex circuit comprises a flexible substrate, electrical traces, and a circuit board integrally formed with said flexible substrate.

Example 24

A surgical instrument is disclosed. The surgical instrument comprises a handle, a shaft extending distally from the handle along a longitudinal shaft axis, and an end effector extending distally from the shaft, wherein the end effector comprises a sensor configured to detect a parameter of the end effector. The surgical instrument further comprises a shaft rotation system configured to rotate the shaft about the longitudinal shaft axis, an articulation joint, wherein the end effector is configured to articulation about the articulation joint, and an end effector rotation system configured to rotate the end effector with respect to the shaft about an end effector longitudinal axis. The surgical instrument further comprises a flex circuit comprising a flexible substrate, electrical traces, a proximal end wrapped into a first ring, and a distal end wrapped into a second ring. The electrical traces extend around the first ring, and the electrical traces extend around the second ring. The second ring is configured to be in signal communication with the sensor of the end effector via the distal end.

Example 25

A surgical instrument is disclosed. The surgical instrument comprises a handle, a shaft extending distally from the handle along a longitudinal axis, and an end effector extending distally from the shaft. The end effector comprises a sensor configured to detect a parameter of the end effector. The surgical instrument further comprises a shaft rotation system configured to rotate the shaft about the longitudinal axis, an articulation joint, wherein the end effector is configured to articulation about the articulation joint, and an end effector rotation system configured to rotate the end effector with respect to the shaft about the longitudinal axis. The surgical instrument further comprises a flex circuit, wherein the flex circuit comprises a flexible substrate, electrical traces, a proximal end, and a distal end, wherein the distal end is configured to be in communication with the sensor of the end effector.

Example 26

A surgical instrument is disclosed. The surgical instrument comprises a handle, a shaft extending distally from the handle, and an end effector extending distally from the shaft. The surgical instrument further comprises an articulation joint and a flex circuit. The end effector is configured to be articulated about the articulation joint. The flex circuit comprises a first leg, a second leg, a base extending between the first leg and the second leg, a flexible substrate, electrical traces supported by the flexible substrate, and a biasing member extending between the first leg and the second leg. The biasing member permits the first leg to be deflected relative to the second leg, wherein the biasing member is configured to transition between a flexed state and an un-flexed state. The biasing member is configured to flex into the flexed state when the end effector is articulated, and the biasing member is configured to resiliently return to the un-flexed state when the end effector is no longer articulated.

Example 27

The surgical instrument of Example 26, wherein the biasing member comprises a spring.

Example 28

A surgical instrument is disclosed. The surgical instrument comprises a handle comprising a distal end and a shaft comprising a proximal end. The distal end comprises a shaft interface surface and a first set of magnetic elements. The proximal end comprises a handle interface surface and a second set of magnetic elements. The shaft interface surface is configured to engage the shaft at the handle interface surface, wherein an attractive magnetic force is configured to pull the handle towards the shaft when the first set of magnetic elements interacts with the second set of magnetic elements.

Example 29

A surgical instrument is disclosed. The surgical instrument comprises a handle comprising a distal end and a shaft comprising a proximal end. The distal end of the handle comprises a frame, a shaft interface surface, and a first set of magnetic elements fixedly mounted to the frame. The proximal end of the shaft comprises a handle interface surface and a second set of magnetic elements. The shaft interface surface is configured to engage the shaft at the handle interface surface, wherein an attractive magnetic force is configured to align the handle and the shaft by rotating the first set of magnetic elements toward the second magnetic elements.

Example 30

A surgical instrument is disclosed. The surgical instrument comprises a handle comprising a distal end and a shaft comprising a proximal end. The distal end of the handle comprises a shaft interface surface and a first magnetic array. The proximal end of the shaft comprises a handle interface surface and a second magnetic array. The shaft interface surface is configured to engage the shaft at the handle interface surface, wherein the first magnetic array and the second magnetic array co-operate to produce a repulsive magnetic force when the handle and the shaft are misaligned. The first magnetic array and the second magnetic array co-operate to produce an attractive magnetic force when the handle and the shaft are aligned. The attractive magnetic force is stronger than the repulsive magnetic force, and the attractive magnetic force is configured to rotate the handle and the shaft into alignment.

Example 31

A surgical instrument is disclosed. The surgical instrument comprises a handle comprising a distal end and a shaft configured to be attached to the handle in a plurality of alignment positions. The distal end of the handle comprises a first magnetic array. The plurality of alignment positions comprises a first alignment position, a second alignment position, and a misaligned position. The misaligned position is in between the first alignment position and the second alignment position. A proximal end of the shaft comprises a second magnetic array, wherein the first magnetic array and the second magnetic array produce a repulsive magnetic force when the handle and the shaft are in the misaligned position. The first magnetic array and the second magnetic array produce an attractive magnetic force when the handle and the shaft are in the first alignment position and the second alignment position. The attractive magnetic force is configured to rotate the handle and the shaft out of the misaligned position and into one of the first alignment position and the second alignment position.

Example 32

A surgical instrument is disclosed. The surgical instrument comprises a handle comprising a first array of magnetic elements and an attachment interface. The surgical instrument further comprises a shaft assembly operably attachable to the attachment interface. The shaft assembly comprises a second array of magnetic elements, wherein the first array of magnetic elements and the second array of magnetic elements co-operate to generate a repulsive magnetic force which repulses the shaft assembly from the attachment interface when the shaft assembly is positioned on a first side of a field threshold. The first array of magnetic elements and the second array of magnetic elements co-operate to generate an attractive magnetic force which pulls the shaft assembly toward the attachment interface when the shaft assembly is positioned on a second side of a field threshold.

Example 33

A shaft assembly is disclosed. The shaft assembly comprises a shaft flex circuit, an end effector attachable to the shaft assembly, and an end effector flex circuit. The shaft flex circuit comprises a flexible substrate, electrical traces, and a distal end wrapped into a first ring, wherein the electrical traces extend around the first ring. The end effector flex circuit comprises a flexible substrate, electrical traces, and a proximal end wrapped into a second ring, wherein the electrical traces extend around the second ring, and wherein the second ring is configured to be electrically coupled to the first ring.

Example 34

A surgical instrument is disclosed. The surgical instrument comprises a handle, a shaft extending distally from the handle, an end effector extending distally from the shaft, a first flex circuit extending within the shaft, and a second flex circuit extending within the end effector. The first flex circuit comprises a distal end wrapped into a first ring, a flexible substrate, and electrical traces, wherein the electrical traces extend around the first ring. The second flex circuit comprises a proximal end wrapped into a second ring, a flexible substrate, and electrical traces, wherein the electrical traces extend around the second ring, and wherein the second ring of the second flex circuit is configured to be electrically coupled with the first ring of the first flex circuit.

Example 35

A surgical instrument is disclosed. The surgical instrument comprises a handle, a shaft extending distally from the handle along a longitudinal shaft axis, an end effector extending distally from the shaft, a shaft rotation system configured to rotate the shaft about the longitudinal shaft axis, an articulation joint, wherein the end effector is configured to articulate about the articulation joint, an end effector rotation system configured to rotate the end effector with respect to the shaft about an end effector longitudinal axis, and a flex circuit. The flex circuit comprises a flexible substrate, electrical traces, a first strain relief region, wherein the first strain relief region permits expansion of the flex circuit, and a second strain relief region, wherein the second strain relief region permits expansion of the flex circuit, and wherein the second strain relief region is substantially perpendicular to the first strain relief region.

Example 36

The surgical instrument of Example 35, wherein the flex circuit further comprises a circuit board integrally formed with the flexible substrate.

Example 37

The surgical instrument of any one of Examples 34 and 35, wherein the shaft comprises a diameter than is less than 10 millimeters.

Example 38

The surgical instrument of any one of Examples 34-36, wherein the flex circuit comprises a first leg, a second leg, a base extending between the first leg and the second leg, and a biasing member extending between the first leg and the second leg.

Example 39

The surgical instrument of Example 38, wherein the biasing member is configured to transition between a flexed state and an un-flexed state, wherein the biasing member is configured to flex into the flexed state when the end effector is articulated.

Example 40

The surgical instrument of any one of Examples 38 and 39, wherein the biasing member comprises a spring.

Example 41

A surgical instrument is disclosed. The surgical instrument comprises a housing, a first shaft attachable to said housing, a second shaft attachable to the housing, and a power source comprising a battery. The first shaft comprises a first processor and a first memory coupled to the first processor, wherein the first memory stores a first set of instructions which, when executed, cause the first processor to initiate a desired function. The second shaft comprises a second processor and a second memory coupled to the second processor, wherein the second memory stores a second set of instructions which, when executed, cause the second processor to initiate a desired function.

Example 42

The surgical instrument of Example 41, wherein the power source is configured to be directly attached to the housing.

Example 43

The surgical instrument of any one of Examples 41 and 42, wherein the housing comprises a drive motor operable by a control system in the first shaft.

Example 44

The surgical instrument of any one of Examples 41-43, wherein the first shaft comprises a diameter that is less than 10 millimeters.

Example 45

The surgical instrument of any one of Examples 41-44, wherein the first set of instructions stored by the first memory is specific to the first shaft.

Example 46

The surgical instrument of any one of Examples 41-45, wherein the second set of instructions stored by the second memory is specific to the second shaft.

Example 47

The surgical instrument of any one of Examples 41-46, wherein the first set of instructions is different than the second set of instructions.

Example 48

The surgical instrument of any one of Examples 41-47, wherein the power source further comprises a display.

Example 49

The surgical instrument of any one of Examples 41-48, wherein there are no continuous circuits within the housing while the housing is unattached to the first shaft and the power source.

Example 50

A modular surgical instrument is disclosed. The modular surgical instrument comprises a handle, an elongate shaft extending distally from the handle, an end effector extending distally from the elongate shaft, and a power source comprising a battery. The elongate shaft comprises a processor and a memory coupled to the processor. The memory stores instructions which, when executed, cause the processor to initiate a desired function.

Example 51

The modular surgical instrument of Example 50, wherein the power source is configured to be replaceably attached to the handle.

Example 52

The modular surgical instrument of any one of Examples 50 and 51, wherein the handle comprises a drive motor operable by a control system in the elongate shaft.

Example 53

The modular surgical instrument of any one of Examples 50-52, wherein the elongate shaft comprises a diameter that is less than 10 millimeters.

Example 54

The modular surgical instrument of any one of Examples 50-53, wherein the instructions stored by the memory are specific to the elongate shaft.

Example 55

The modular surgical instrument of any one of Examples 50-54, wherein the power source further comprises a display.

Example 56

The modular surgical instrument of any one of Examples 50-55, wherein there are no continuous circuits within the handle while the handle is unattached to the elongate shaft and the power source.

Example 57

The modular surgical instrument of any one of Examples 50-56, wherein there are no continuous circuits within the power source while the power source is unattached to the handle.

Example 58

A modular surgical instrument is disclosed. The modular surgical instrument comprises a handle, a first shaft assembly attachable to the handle, a second shaft assembly attachable to the handle, and a power source comprising a battery. The first shaft assembly comprises a first processor and a first memory coupled to the first processor, wherein the first memory stores a first set of instructions which, when executed, cause the first processor to initiate a desired function. The second shaft assembly comprises a second processor and a second memory coupled to the second processor, wherein the second memory stores a second set of instructions which, when executed, cause the second processor to initiate a desired function.

Example 59

The modular surgical instrument of Example 58, wherein the power source is configured to be replaceably attached directly to the handle.

Example 60

The modular surgical instrument of any one of Examples 58 and 59, wherein the handle comprises a drive motor operably by a control system in the first shaft assembly.

Example 61

A surgical system is disclosed. The surgical system comprises a surgical instrument, a first suture cartridge operably engageable with the surgical instrument, a second suture cartridge operably engageable with the surgical instrument in lieu of the first suture cartridge, and a sensor system configured to detect whether the first suture cartridge or the second suture cartridge is attached to the surgical instrument. The surgical instrument comprises a drive system including an electric motor and a control system configured to operate the electric motor using a first control program and a second control program. The first control program is different than the second control program. The first suture cartridge comprises a first cartridge body, a first needle rotatably mounted in the first cartridge body, and a first suture thread attached to the first needle. The first needle comprises a first diameter, wherein the first needle is operably coupled to the drive system when the first suture cartridge is operably engaged with the surgical instrument. The second suture cartridge comprises a second cartridge body, a second needle rotatably mounted in the second cartridge body, and a second suture thread attached to the second needle. The second needle comprises a second diameter that is different than the first diameter, wherein the second needle is operably coupled to the drive system when the second suture cartridge is operably engaged with the surgical instrument. The sensor system is in communication with the control system, wherein the control system uses the first control program and not the second control program when the first suture cartridge is operably engaged with the surgical instrument, and wherein the control system uses the second control program and not the first control program when the second suture cartridge is operably engaged with the surgical instrument.

Example 62

The surgical system of Example 61, wherein the electric motor comprises an output shaft, wherein the first control program rotates the output shaft a first number of revolutions during a first drive stroke, wherein the second control program rotates the output shaft a second number of revolutions during a second drive stroke, and wherein the first number of revolutions is different than the second number of revolutions.

Example 63

The surgical system of Example 62, wherein the first drive stroke has a first stroke length and the second drive stroke has a second stroke length, and wherein the first stroke length is different than the second stroke length.

Example 64

The surgical system of Example 61, wherein the electric motor comprises an output shaft, wherein the first control program rotates the output shaft at a first maximum speed during a drive stroke, wherein the second control program rotates the output shaft at a second maximum speed during a drive stroke, and wherein the first maximum speed is different than the second maximum speed.

Example 65

The surgical system of Example 64, wherein the control system comprises a pulse width modulation motor control circuit for controlling the speed of the electric motor.

Example 66

The surgical system of any one of Examples 64 and 65, wherein the control system comprises a frequency modulation motor control circuit for controlling the speed of the electric motor.

Example 67

The surgical system of any one of Examples 61-66, wherein the first needle has a first circumference and the second needle has a second circumference, and wherein the first circumference is different than the second circumference.

Example 68

The surgical system of any one of Examples 61-67, wherein the first needle is planar and the second needle is not planar.

Example 69

The surgical system of any one of Examples 61-68, wherein the sensor system is configured to detect when neither the first suture cartridge not the second suture cartridge is operably coupled to the surgical instrument, and wherein the control system further comprises a lockout circuit configured to prevent power from being supplied to the electric motor when neither the first suture cartridge nor the second suture cartridge is operably coupled to the surgical instrument.

Example 70

A surgical system is disclosed. The surgical system comprises a surgical instrument, a first suture cartridge operably engageable with the surgical instrument, a second suture cartridge operably engageable with the surgical instrument in lieu of the first suture cartridge, and a sensor system configured to detect whether one of the first suture cartridge and the second suture cartridge is attached to the surgical instrument. The surgical instrument comprises a drive system including an electric motor and a control system configured to operate the electric motor using a first control program and a second control program, wherein the first control program is different than the second control program. The first suture cartridge comprises a first cartridge body, a first needle rotatably mounted in the first cartridge body, and a first suture attached to the first needle. The first needle defines a first circumferential path, wherein the first needle is operably coupled to the drive system when the first suture is operably engaged with the surgical instrument. The second suture cartridge comprises a second cartridge body, a second needle rotatably mounted in the second cartridge body, and a second suture attached to the second needle. The second needle defines a second circumferential path that is different than the first circumferential path, wherein the second needle is operably coupled to the drive system when the second suture cartridge is operably engaged with the surgical instrument. The sensor system is in communication with the control system, wherein the control system uses the first control program and not the second control program when the first suture cartridge is operably engaged with the surgical instrument, and wherein the control system uses the second control program and not the first control program when the second suture cartridge is operably engaged with the surgical instrument.

Example 71

The surgical system of Example 70, wherein the electric motor comprises an output shaft, wherein the first control program rotates the output shaft a first number of revolutions during a first drive stroke, wherein the second control program rotates the output shaft a second number of revolutions during a second drive stroke, and wherein the first number of revolutions is different than the second number of revolutions.

Example 72

The surgical system of Example 71, wherein the first drive stroke has a first stroke length and the second drive stroke has a second stroke length, and wherein the first stroke length is different than the second stroke length.

Example 73

The surgical system of Example 70, wherein the electric motor comprises an output shaft, wherein the first control program rotates the output shaft at a first maximum speed during a drive stroke, wherein the second control program rotates the output shaft at a second maximum speed during a drive stroke, and wherein the first maximum speed is different than the second maximum speed.

Example 74

The surgical system of Example 73, wherein the control system comprises a pulse width modulation motor control circuit for controlling the speed of the electric motor.

Example 75

The surgical system of any one of Examples 73 and 74, wherein the control system comprises a frequency modulation motor control circuit for controlling the speed of the electric motor.

Example 76

The surgical system of any one of Examples 70-75, wherein the first needle has a first diameter and the second needle has a second diameter, wherein the first diameter is different than the second diameter.

Example 77

The surgical system of any one of Examples 70-76, wherein the first needle is planar and the second needle is not planar.

Example 78

The surgical system of any one of Examples 70-77, wherein the sensor system is configured to detect when neither the first suture cartridge nor the second suture cartridge is operably coupled to the surgical instrument, and wherein the control system further comprises a lockout circuit configured to prevent power from being supplied to the electric motor when neither the first suture cartridge nor the second suture cartridge is operably coupled to the surgical instrument.

Example 79

A surgical system is disclosed. The surgical system comprises a surgical instrument, a first expendable cartridge operably engageable with the surgical instrument, a second expendable cartridge operably engageable with the surgical instrument in lieu of the first expendable cartridge, and a sensor system configured to detect which one of the first expendable cartridge and the second expendable cartridge is attached to the surgical instrument. The surgical instrument comprises a drive system including an electric motor and a control system configured to operate the electric motor using a control program. The first expendable cartridge comprises a first cartridge body and a first drive member operably engageable with the drive system when the first cartridge is operably engaged with the surgical instrument. The second expendable cartridge comprises a second cartridge body and a second drive member operably engageable with the drive system when the second expendable cartridge is operably engaged with the surgical instrument. The sensor system is in communication with the control system, wherein the control system uses the control program when the first expendable cartridge is operably engaged with the surgical instrument, and wherein the control program is modified when the second expendable cartridge is operably engaged with the surgical instrument.

Example 80

The surgical system of Example 79, wherein the first expendable cartridge is a first suture cartridge and the second expendable cartridge is a second suture cartridge.

Example 81

A surgical suturing system is disclosed. The surgical suturing system comprises a shaft, a firing drive, an end effector extending distally from the shaft, and a control circuit. The firing drive comprises a motor. The end effector comprises a needle driver configured to be actuated by the motor, wherein the needle driver is configured to drive a needle installed within the end effector. The end effector further comprises a needle track configured to guide the needle installed within the end effector through a needle firing stroke, wherein the end effector is configured to accommodate suturing needles having different sizes. The control circuit is configured to sense the size of the suturing needle installed within the end effector and adjust the actuation stroke of the motor to accommodate the size of the suturing needle installed within the end effector.

Example 82

The surgical suturing system of Example 81, wherein the control circuit is further configured to indicate to a user the size of the needle installed within the end effector.

Example 83

The surgical suturing system of at least one of Examples 81 and 82, wherein the end effector is configured to accommodate suturing needles having different diameters.

Example 84

The surgical suturing system of at least one of Examples 81-83, wherein the end effector is configured to accommodate suturing needles having different circumference lengths.

Example 85

The surgical suturing system of at least one of Examples 81-84, wherein the control circuit is configured to adjust the actuation stroke by changing the motor speed.

Example 86

The surgical suturing system of at least one of Examples 81-85, wherein the control circuit is configured to adjust the actuation stroke by changing the amount of revolutions that the motor turns during a needle firing stroke.

Example 87

A surgical suturing system is disclosed. The surgical suturing system comprises a shaft, a firing drive, and an end effector extending distally from the shaft. The end effector comprises a needle driver configured to be actuated by the firing drive, wherein the needle driver is configured to drive a needle installed within the end effector. The end effector further comprises a needle track configured to guide the needle installed within the end effector through a needle firing stroke. The end effector is configured to receive suturing needles having different circumference lengths. The surgical suturing system further comprises a control circuit configured to sense the circumference length of the suturing needle installed within the end effector and adjust the actuation stroke of the needle driver to accommodate the circumference length of the suturing needle installed within the end effector.

Example 88

The surgical suturing system of Example 87, wherein the control circuit is further configured to indicate to a user the circumference length of the needle installed within the end effector.

Example 89

The surgical suturing system of any one of Examples 87 and 88, wherein the control circuit is configured to adjust the actuation stroke by changing the motor speed.

Example 90

The surgical suturing system of any one of Examples 87-89, wherein the control circuit is configured to adjust the actuation stroke by changing the amount of revolutions that the motor turns during a needle firing stroke.

Example 91

A surgical instrument configured to apply a suture to the tissue of a patient is disclosed. The surgical instrument comprises an end effector comprising a replaceable suture cartridge comprising a suture removably stored therein and an actuator configured to deploy the suture. The surgical instrument further comprises a lockout configurable in a locked configuration and an unlocked configuration. The lockout is in the locked configuration when the replaceable suture cartridge is not in the end effector, wherein the lockout prevents the actuator from being actuated when the lockout is in the locked configuration, wherein the lockout is in the unlocked configuration when the replaceable suture cartridge is positioned in the end effector and wherein the lockout permits the actuator to deploy the suture when the lockout is in the unlocked configuration. The surgical instrument further comprises a handle, an electric motor configured to drive the actuator, a control circuit configured to drive the electric motor, and a sensing system configured to determine when the lockout is in the locked configuration, wherein the sensing system is in communication with the control circuit.

Example 92

The surgical instrument of Example 91, wherein the control circuit prevents the actuation of the electric motor when the sensing system determines that the lockout is in the locked configuration.

Example 93

The surgical instrument of any one of Examples 91 and 92, wherein the control circuit provides haptic feedback to the user of the surgical instrument when the sensing system determines that the lockout is in the locked configuration.

Example 94

The surgical instrument of any one of Examples 91-93, wherein the lockout is in the unlocked configuration when the replaceable suture cartridge is positioned in the end effector and the replaceable suture cartridge has not been completely expended.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein.

The surgical instrument systems described herein can be used in connection with the deployment and deformation of staples. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue. In addition, various embodiments are envisioned which utilize a suitable cutting means to cut the tissue.

The entire disclosures of:

U.S. patent application Ser. No. 11/013,924, entitled TROCAR SEAL ASSEMBLY, now U.S. Pat. No. 7,371,227;

U.S. patent application Ser. No. 11/162,991, entitled ELECTROACTIVE POLYMER-BASED ARTICULATION MECHANISM FOR GRASPER, now U.S. Pat. No. 7,862,579;

U.S. patent application Ser. No. 12/364,256, entitled SURGICAL DISSECTOR, now U.S. Patent Application Publication No. 2010/0198248;

U.S. patent application Ser. No. 13/536,386, entitled EMPTY CLIP CARTRIDGE LOCKOUT, now U.S. Pat. No. 9,282,974;

U.S. patent application Ser. No. 13/832,786, entitled CIRCULAR NEEDLE APPLIER WITH OFFSET NEEDLE AND CARRIER TRACKS, now U.S. Pat. No. 9,398,905;

U.S. patent application Ser. No. 12/592,174, entitled APPARATUS AND METHOD FOR MINIMALLY INVASIVE SUTURING, now U.S. Pat. No. 8,123,764;

U.S. patent application Ser. No. 12/482,049, entitled ENDOSCOPIC STITCHING DEVICES, now U.S. Pat. No. 8,628,545;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 14/200,111, entitled CONTROL SYSTEMS FOR SURGICAL INSTRUMENTS, now U.S. Pat. No. 9,629,629;

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/813,242, entitled SURGICAL INSTRUMENT COMPRISING SYSTEMS FOR ASSURING THE PROPER SEQUENTIAL OPERATION OF THE SURGICAL INSTRUMENT, now U.S. Patent Application Publication No. 2017/0027571;

U.S. patent application Ser. No. 14/248,587, entitled POWERED SURGICAL STAPLER, now U.S. Pat. No. 9,867,612;

U.S. patent application Ser. No. 12/945,748, entitled SURGICAL TOOL WITH A TWO DEGREE OF FREEDOM WRIST, now U.S. Pat. No. 8,852,174;

U.S. patent application Ser. No. 13/297,158, entitled METHOD FOR PASSIVELY DECOUPLING TORQUE APPLIED BY A REMOTE ACTUATOR INTO AN INDEPENDENTLY ROTATING MEMBER, now U.S. Pat. No. 9,095,362;

International Application No. PCT/US2015/023636, entitled SURGICAL INSTRUMENT WITH SHIFTABLE TRANSMISSION, now International Patent Publication No. WO 2015/153642 A1;

International Application No. PCT/US2015/051837, entitled HANDHELD ELECTROMECHANICAL SURGICAL SYSTEM, now International Patent Publication No. WO 2016/057225 A1;

U.S. patent application Ser. No. 14/657,876, entitled SURGICAL GENERATOR FOR ULTRASONIC AND ELECTROSURGICAL DEVICES, U.S. Patent Application Publication No. 2015/0182277;

U.S. patent application Ser. No. 15/382,515, entitled MODULAR BATTERY POWERED HANDHELD SURGICAL INSTRUMENT AND METHODS THEREFOR, U.S. Patent Application Publication No. 2017/0202605;

U.S. patent application Ser. No. 14/683,358, entitled SURGICAL GENERATOR SYSTEMS AND RELATED METHODS, U.S. Patent Application Publication No. 2016/0296271;

U.S. patent application Ser. No. 14/149,294, entitled HARVESTING ENERGY FROM A SURGICAL GENERATOR, U.S. Pat. No. 9,795,436;

U.S. patent application Ser. No. 15/265,293, entitled TECHNIQUES FOR CIRCUIT TOPOLOGIES FOR COMBINED GENERATOR, U.S. Patent Application Publication No. 2017/0086910; and U.S. patent application Ser. No. 15/265,279, entitled TECHNIQUES FOR OPERATING GENERATOR FOR DIGITALLY GENERATING ELECTRICAL SIGNAL WAVEFORMS AND SURGICAL INSTRUMENTS, U.S. Patent Application Publication No. 2017/0086914, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical suturing system, comprising:
a shaft;
a firing drive comprising a motor;
an end effector extending distally from said shaft, wherein said end effector comprises:
   a needle driver configured to be actuated by said motor, wherein said needle driver is configured to drive a needle installed within said end effector; and
   a needle track configured to guide the needle installed within said end effector through a rotary needle firing stroke, wherein said end effector is configured to accommodate suturing needles having different sizes; and
a control circuit configured to:
   sense the size of the suturing needle installed within said end effector; and
   adjust an actuation stroke of said motor to accommodate the size of the suturing needle installed within said end effector,
wherein said control circuit is configured to adjust the actuation stroke by changing a motor speed to:
a first speed based on sensing a first needle diameter; and
a second speed based on sensing a second needle diameter, wherein the first needle diameter is different than the second needle diameter, and wherein the first speed is different than the second speed.

2. The surgical suturing system of claim 1, wherein said control circuit is further configured to indicate to a user the size of the needle installed within said end effector.

3. The surgical suturing system of claim 1, wherein said end effector is configured to accommodate suturing needles having different diameters.

4. The surgical suturing system of claim 1, wherein said end effector is configured to accommodate suturing needles having different circumference lengths.

5. The surgical suturing system of claim 1, wherein said control circuit is configured to adjust the actuation stroke by changing the amount of revolutions that the motor turns during the rotary needle firing stroke.

6. The surgical suturing system of claim 1, wherein said control circuit is configured to accommodate suturing needles having different lengths.

7. The surgical suturing system of claim 1, wherein said control circuit is configured to adjust the actuation stroke by adjusting a length of a stroke path of the rotary needle firing stroke.

8. The surgical suturing system of claim 1, wherein the first needle diameter is larger than the second needle diameter, and wherein the first speed is slower than the second speed.

9. A surgical suturing system, comprising:
a shaft;
a firing drive comprising a motor;
an end effector extending distally from said shaft, wherein said end effector comprises:
   a needle driver configured to be actuated by said motor, wherein said needle driver is configured to drive a needle installed within said end effector; and
   a needle track configured to guide the needle installed within said end effector through a rotary needle firing stroke, wherein said end effector is configured to accommodate suturing needles having different sizes; and
a control circuit configured to:
   sense the size of the suturing needle installed within said end effector; and
   adjust an actuation stroke of said motor to accommodate the size of the suturing needle installed within said end effector,
wherein said control circuit is configured to adjust the actuation stroke by adjusting a stroke path of the suturing needle to:
a first stroke path based on sensing a first circumference length of the suturing needle; and
a second stroke path based on sensing a second circumference length of the suturing needle, wherein the first circumference length is different than the second circumference length, and wherein the first stroke path is different than the second stroke path.

10. The surgical suturing system of claim 9, wherein the first circumference length is longer than the second circumference length, and wherein the first stroke path is shorter than the second stroke path.

11. A surgical suturing system, comprising:
a shaft;
a firing drive; and
an end effector extending distally from said shaft, wherein said end effector comprises:
   a needle driver configured to be actuated by said firing drive, wherein said needle driver is configured to drive a needle installed within said end effector; and
   a needle track configured to guide the needle installed within said end effector through a rotary needle firing stroke,
   wherein said end effector is configured to receive suturing needles having different circumference lengths, and wherein said surgical suturing system further comprises a control circuit configured to:
      sense the circumference length of the suturing needle installed within said end effector; and
      adjust an actuation stroke of said needle driver to accommodate the circumference length of the suturing needle installed within said end effector,
wherein said control circuit is configured to adjust the actuation stroke by adjusting a stroke length to:
a first stroke length based on sensing a first circumference length of the suturing needle; and
a second stroke length based on sensing a second circumference length of the suturing needle, wherein the first circumference length is different than the second circumference length, and wherein the first stroke length is different than the second stroke length.

12. The surgical suturing system of claim 11, wherein said control circuit is further configured to indicate to a user the circumference length of the needle installed within said end effector.

13. The surgical suturing system of claim 11, wherein said control circuit is configured to adjust the actuation stroke by changing a motor speed.

14. The surgical suturing system of claim 11, wherein said control circuit is configured to adjust the actuation stroke by changing the amount of revolutions that a motor turns during a needle firing stroke.

15. A surgical instrument configured to apply a suture to the tissue of a patient, comprising:
- an end effector, comprising:
  - a replaceable suture cartridge comprising a suture removably stored therein; and
  - an actuator configured to deploy said suture;
- a lockout configurable in a locked configuration and an unlocked configuration, wherein said lockout is in said locked configuration when said replaceable suture cartridge is not in said end effector, wherein said lockout prevents said actuator from being actuated when said lockout is in said locked configuration, wherein said lockout is in said unlocked configuration when said replaceable suture cartridge is positioned in said end effector, and wherein said lockout permits said actuator to deploy said suture when said lockout is in said unlocked configuration;
- a handle;
- an electric motor configured to drive said actuator;
- a control circuit configured to control said electric motor; and
- a sensing system configured to determine when said lockout is in said locked configuration, wherein said sensing system is in communication with said control circuit, and wherein said actuator is prevented from being actuated when said sensing system determines that said lockout is in said locked configuration,
- wherein said lockout is in the unlocked configuration upon installation of said replaceable suture cartridge when said replaceable suture cartridge is partially expended.

16. The surgical instrument of claim 15, wherein said control circuit prevents the actuation of said electric motor when said sensing system determines that said lockout is in said locked configuration.

17. The surgical instrument of claim 15, wherein said control circuit provides haptic feedback to the user of the surgical instrument when said sensing system determines that said lockout is in said locked configuration.

18. The surgical instrument of claim 15, wherein said lockout is in said unlocked configuration when said replaceable suture cartridge is positioned in said end effector and said replaceable suture cartridge has not been completely expended.

* * * * *